United States Patent
Nam et al.

(10) Patent No.: US 10,941,211 B2
(45) Date of Patent: Mar. 9, 2021

(54) ANTI-GCC ANTIBODY MOLECULES AND RELATED COMPOSITIONS AND METHODS

(71) Applicants: Millennium Pharmaceuticals, Inc., Cambridge, MA (US); Amgen British Columbia Inc., Burnaby (CA)

(72) Inventors: Samuel S. Nam, Haverhill, MA (US); Edward A. Greenfield, Stoughton, MA (US); John S. Babcook, Vancouver (CA); Theresa O'Keefe, Waltham, MA (US); Shixin Qin, Lexington, MA (US)

(73) Assignees: MILLENNIUM PHARMACEUTICALS, INC., Cambridge, MA (US); AMGEN BRITISH COLUMBIA INC., Burnaby (CA)

(*) Notice: Subject to any disclaimer, the term of this patent is extended or adjusted under 35 U.S.C. 154(b) by 188 days.

(21) Appl. No.: 16/029,101

(22) Filed: Jul. 6, 2018

(65) Prior Publication Data

US 2018/0355062 A1 Dec. 13, 2018

Related U.S. Application Data

(60) Division of application No. 14/293,802, filed on Jun. 2, 2014, now abandoned, which is a continuation of application No. 12/910,393, filed on Oct. 22, 2010, now Pat. No. 8,785,600.

(60) Provisional application No. 61/254,474, filed on Oct. 23, 2009.

(51) Int. Cl.
| | | |
|---|---|---|
| C07K 16/40 | (2006.01) | |
| C07K 16/30 | (2006.01) | |
| A61K 47/68 | (2017.01) | |
| A61P 35/00 | (2006.01) | |
| A61K 39/395 | (2006.01) | |
| G01N 33/573 | (2006.01) | |
| A61K 39/00 | (2006.01) | |

(52) U.S. Cl.
CPC ........ *C07K 16/40* (2013.01); *A61K 39/39558* (2013.01); *A61K 47/6871* (2017.08); *A61P 35/00* (2018.01); *C07K 16/30* (2013.01); *G01N 33/573* (2013.01); *A61K 2039/505* (2013.01); *C07K 2317/21* (2013.01); *C07K 2317/34* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,194,594 A | 3/1993 | Khawli et al. |
| 5,237,051 A | 8/1993 | Garbers et al. |
| 5,518,888 A | 5/1996 | Waldman |
| 5,601,990 A | 2/1997 | Waldman |
| 5,731,159 A | 3/1998 | Waldman |
| 5,879,656 A | 3/1999 | Waldman |
| 5,928,873 A | 7/1999 | Waldman |
| 6,060,037 A | 5/2000 | Waldman |
| 6,120,995 A | 9/2000 | Waldman et al. |
| 6,132,922 A | 10/2000 | Fukae et al. |
| 6,268,159 B1 | 7/2001 | Waldman |
| 6,441,163 B1 | 8/2002 | Chari et al. |
| 6,455,251 B1 | 9/2002 | Waldman |
| 6,602,659 B1 | 8/2003 | Waldman et al. |
| 6,696,550 B2 | 2/2004 | LaRosa et al. |
| 6,767,704 B2 | 7/2004 | Waldman et al. |
| 6,942,985 B2 | 9/2005 | Waldman |
| 7,041,786 B2 | 5/2006 | Shailubhai et al. |
| 7,097,839 B1 | 8/2006 | Waldman |
| 7,304,036 B2 | 12/2007 | Currie et al. |
| 7,371,727 B2 | 5/2008 | Currie et al. |
| 7,402,401 B2 | 7/2008 | Waldman |
| 7,485,422 B2 | 2/2009 | Waldman et al. |
| 7,612,181 B2 | 11/2009 | Wu et al. |
| 7,799,897 B2 | 9/2010 | Jacob et al. |
| 7,820,390 B2 | 10/2010 | Waldman |
| 7,854,933 B2 | 12/2010 | Waldman et al. |
| 7,879,802 B2 | 2/2011 | Shailubhai et al. |
| 7,910,546 B2 | 3/2011 | Currie et al. |

(Continued)

FOREIGN PATENT DOCUMENTS

| | | |
|---|---|---|
| CA | 2706633 A1 | 4/2009 |
| CN | 102573908 B | 12/2014 |

(Continued)

OTHER PUBLICATIONS

Babcook et al., (1996) "A novel strategy for generating monoclonal antibodies from single, isolated lymphocytes producing antibodies of defined specificities", *Proc. Natl. Acad. Sci. USA*, 93(15):7843-7848.

(Continued)

*Primary Examiner* — Brad Duffy
(74) *Attorney, Agent, or Firm* — Finnegan, Henderson, Farabow, Garrett & Dunner, LLP

(57) ABSTRACT

Antibodies and antigen-binding fragments of antibodies that bind GCC are disclosed. The antibodies bind an extracellular domain of GCC and can be internalized. In some embodiments, the antibodies are humanized, chimeric or human. Nucleic acids and vectors encoding the antibodies or portions thereof, recombinant cells that contain the nucleic acids, and compositions comprising the antibodies or antigen-binding fragments are also disclosed. The invention also provides therapeutic and diagnostic methods utilizing the antibodies and antigen-binding fragments provided herein.

12 Claims, 4 Drawing Sheets

Specification includes a Sequence Listing.

(56) References Cited

U.S. PATENT DOCUMENTS

| | | |
|---|---|---|
| 8,034,782 B2 | 10/2011 | Shailubhai |
| 8,067,007 B2 | 11/2011 | Waldman et al. |
| 8,114,831 B2 | 2/2012 | Shailubhai et al. |
| 8,206,704 B2 | 6/2012 | Waldman et al. |
| 8,207,295 B2 | 6/2012 | Shailubhai et al. |
| 8,357,775 B2 | 1/2013 | Shailubhai et al. |
| 8,367,800 B2 | 2/2013 | Shailubhai |
| 8,563,682 B2 | 10/2013 | Wolfe et al. |
| 8,785,600 B2 | 7/2014 | Nam et al. |
| 9,000,129 B2 | 4/2015 | Frank et al. |
| 9,273,146 B1 | 2/2016 | Frank et al. |
| 2003/0099656 A1 | 5/2003 | Patti et al. |
| 2003/0147809 A1 | 8/2003 | Gudas |
| 2003/0165496 A1 | 9/2003 | Basi et al. |
| 2003/0175310 A1 | 9/2003 | Mitchell et al. |
| 2004/0031072 A1 | 2/2004 | La Rosa et al. |
| 2004/0081651 A1 | 4/2004 | Karpusas et al. |
| 2004/0110933 A1 | 6/2004 | Rondon et al. |
| 2004/0152868 A1 | 8/2004 | Larson et al. |
| 2004/0258687 A1 | 12/2004 | Waldman et al. |
| 2005/0287067 A1 | 12/2005 | Wolfe et al. |
| 2006/0024297 A1 | 2/2006 | Wood et al. |
| 2006/0035852 A1 | 2/2006 | Sahin et al. |
| 2006/0246071 A1 | 11/2006 | Green et al. |
| 2008/0124345 A1 | 5/2008 | Rothe et al. |
| 2008/0219979 A1 | 9/2008 | Tocker et al. |
| 2009/0005257 A1 | 1/2009 | Jespers et al. |
| 2009/0041717 A1 | 2/2009 | MacDonald et al. |
| 2011/0195415 A1 | 8/2011 | Waldman et al. |
| 2011/0306055 A1 | 12/2011 | Haince et al. |
| 2012/0083503 A1 | 4/2012 | Nakagawa et al. |
| 2012/0114659 A1 | 5/2012 | Waterman et al. |
| 2012/0251509 A1 | 10/2012 | Waldman et al. |
| 2012/0308583 A1 | 12/2012 | Waldman et al. |
| 2012/0321552 A1 | 12/2012 | Waldman et al. |
| 2013/0315923 A1 | 11/2013 | Waldman et al. |
| 2014/0147380 A1 | 5/2014 | Wolfe et al. |
| 2014/0322233 A1 | 10/2014 | Nam et al. |
| 2016/0130344 A1 | 5/2016 | Frank et al. |

FOREIGN PATENT DOCUMENTS

| | | |
|---|---|---|
| EP | 1 225 844 B1 | 7/2005 |
| JP | 2010-536037 A | 11/2010 |
| JP | 2011-505145 A | 2/2011 |
| TW | 201132352 A1 | 10/2011 |
| WO | WO 95/11694 A1 | 5/1995 |
| WO | WO 97/42220 A1 | 11/1997 |
| WO | WO 97/42506 A1 | 11/1997 |
| WO | WO 01/69259 A1 | 9/2001 |
| WO | WO 01/73132 A1 | 10/2001 |
| WO | WO 2004/010957 A2 | 2/2004 |
| WO | WO 2005/010151 A2 | 2/2005 |
| WO | WO 2005/101017 A1 | 10/2005 |
| WO | WO 2006/012264 A1 | 2/2006 |
| WO | WO 2007/113648 A2 | 10/2007 |
| WO | WO 2009/023457 A1 | 2/2009 |
| WO | WO 2004/071436 A2 | 4/2009 |
| WO | WO 2009/052431 A2 | 4/2009 |
| WO | WO 2009/073540 A2 | 6/2009 |
| WO | WO 2010/065293 A1 | 6/2010 |
| WO | WO 2010/093928 A2 | 8/2010 |
| WO | WO 2010/096929 A1 | 9/2010 |
| WO | WO 2010/104035 A1 | 9/2010 |
| WO | WO 2010/147684 A1 | 12/2010 |
| WO | WO 2011/050242 A1 | 4/2011 |
| WO | WO 2011/066048 A1 | 6/2011 |
| WO | WO 2011/150454 A1 | 12/2011 |
| WO | WO 2012/020123 A9 | 2/2012 |
| WO | WO 2013/016662 A1 | 1/2013 |
| WO | WO 2013/163633 A1 | 10/2013 |
| WO | WO 2014/134311 A1 | 9/2014 |
| WO | WO 2015/084996 A1 | 6/2015 |
| WO | WO 2017/136693 A1 | 8/2017 |
| WO | WO 2017/167217 A1 | 10/2017 |

OTHER PUBLICATIONS

European Patent Application No. 19153014.6, Millennium Pharmaceuticals, Inc.: Partial European Search Report, dated Jun. 6, 2019 (18 pages).

Rudner et al., (1995) "Regulation of cell signaling by the cytoplasmic domains of the heat-stable enterotoxin receptor: identification of autoinhibitory and activating motifs", *Proc. Natl. Acad. Sci. USA*, 92(11):5169-5173.

Almenoff et al., "Ligand-based histochemical localization and capture of cells expressing heat-stable enterotoxin receptors" *Mol. Microbiol.*, 8(5):865-873 (1993).

Bakre et al., "Homologous desensitization of the human guanylate cyclase C receptor. Cell-specific regulation of catalytic activity" *Eur. J. Biochem.*, 267:179-187 (2000).

Belisle et al., "Characterization of Monoclonal Antibodies to Heat-Labile Enterotoxin Encoded by a Plasmid from a Clinical Isolate of *Escherichia coli*" *Infection and Immunity*, 43(3):1027-1032 (Mar. 1984).

Berzofsky et al., "Immunogenicity and Antigen Structure," in *Fundamental Immunology*. (Paul, W.E. ed.), New York, NY: Raven Press, 1993; Chapter 8, p. 242.

Bhandari et al., "Functional inactivation of the human guanylyl cyclase C receptor: modeling and mutation of the protein kinase-like domain" *Biochemistry*, 40:9196-9206 (2001).

Birbe et al., "Guanylyl cyclase C is a marker of intestinal metaplasia, dysplasia, and adenocarcinoma of the gastrointestinal tract" *Hum. Pathol.*, 36(2):170-179 (2005).

Bogen, S.A. et al., "Molecular mechanisms of antigen retrieval: antigen retrieval reverses steric interference caused by formalin-induced cross-links" *Biotech. Histochem.*, 84(5):207-215 (Oct. 2009).

Buc et al., "Guanylyl cyclase C as a reliable immunohistochemical marker and its ligand *Escherichia coli* heat-stable enterotoxin as a potential protein-delivering vehicle for colorectal cancer cells" *Eur. J. Cancer*, 41:1618-1627 (2005).

Camci et al., "Peripheral blood guanylyl cyclase c (GCC) expressions are associated with prognostic parameters and response to therapy in colorectal cancer patients" *Tumor Biol.*, 32:1265-1270 (2011).

Carrithers et al., "*Escherichia coli* Heat-Stable Toxin Receptors in Human Colonic Tumors" *Gastroenterology*, 107:1653-1661 (1994).

Carrithers et al., "*Escherichia coli* Heat-Stable Enterotoxin Receptors. A Novel Marker for Colorectal Tumors" *Dis. Colon Rectum*, 39:171-181 (Feb. 1996).

Carrithers et al., "Diarrhea or colorectal cancer: Can bacterial toxins serve as a treatment for colon cancer?" *Proc. Natl. Acad. Sci. USA*, 100:3018-3020 (2003).

Carrithers et al., "Guanylyl cyclase C is a selective marker for metastatic colorectal tumors in human extraintestinal tissues" *Proc. Natl. Acad. Sci. USA*, 93(25):14827-14832 (Dec. 1996).

Chang et al., "Guanylyl cyclase C as a biomarker for targeted imagining and therapy of metastatic colorectal cancer" *Biomarkers Med.*, 3(1):33-45 (2009).

*Current Protocols in Cell Biology*. Lippincott-Schwartz: 2002; pp. 16.0.1-16.0.2.

Daniel et al., "Mapping of linear antigenic sites on the S glycoprotein of a neurotropic murine coronavirus with synthetic peptides: a combination of nine prediction algorithms fails to identify relevant epitopes and peptide immunogenicity is drastically influenced by the nature of the protein carrier" *Virology*, 202(2):540-549 (1994).

De Sauvage et al., "Primary structure and functional expression of the human receptor for *Escherichia coli* heat-stable enterotoxin" *J. Biol. Chem.*, 266(27):17912-17918 (1991).

Debruyne et al., "Bile acids induce ectopic expression of intestinal guanylyl cyclase C through nuclear factor—kappaB and Cdx2 in human esophageal cells" *Gastroenterology*, 130:1191-1206 (2006).

Doronina et al., "Novel peptide linkers for highly potent antibody—auristatin conjugate" *Bioconjug. Chem.*, 19(10):1960-1963 (2008).

Eurasian Patent Application No. 201792376, by Millennium Pharmaceuticals, Inc.: Search Report, dated May 10, 2018 (3 pages).

(56) References Cited

OTHER PUBLICATIONS

European Patent Application No. 10825726, by Millennium Pharmaceuticals, Inc.: Extended European Search Report, including Supplementary Search Report and Opinion, dated May 7, 2013 (8 pages).
European Patent Application No. 13782061, by Millennium Pharmaceuticals, Inc.: Partial Supplementary Search Report, dated Jan. 28, 2016 (8 pages).
European Patent Application No. 13782061, by Millennium Pharmaceuticals, Inc.: Extended European Search Report, including Search Opinion, dated May 17, 2016 (12 pages).
European Patent Application No. 14756404, by Millennium Pharmaceuticals, Inc.: Supplementary Search Report, dated Oct. 5, 2016 (9 pages).
Fischer and Léger, "Bispecific Antibodies: Molecules That Enable Novel Therapeutic Strategies," *Pathobiology*, 74(1):3-14 (2007).
Francisco et al., "cAC10-vcMMAE, an anti-CD30—monomethyl auristatin E conjugate with potent and selective antitumor activity" *Blood*, 102:1458-1465 (2003).
Frick et al., "Guanylyl cyclase C: a molecular marker for staging and postoperative surveillance of patients with colorectal cancer" *Expert Rev. Mol. Diagn.*, 5:701-713 (2005).
Gali et al., "Chemical synthesis of *Escherichia coli* $ST_h$ analogues by regioselective disulfide bond formation: biological evaluation of an $^{111}$In-DOTA-Phe$^{19}$-$ST_h$ analogue for specific targeting of human colon cancers" *Bioconjug. Chem.*, 13:224-231 (2002).
George et al., (1998) "Differential effects of anti-$\beta_2$-glycoprotein I antibodies on endothelial cells and on the manifestations of experimental antiphospholipid syndrome" *Circulation*, 97:900-906.
Gershoni et al., (2007) "Epitope mapping—The first step in developing epitope base vaccines" *Biodrugs*, 21(3):145-156.
Greenspan and Di Cera, "Defining epitopes: It's not as easy as it seems" *Nat. Biotechnol.*, 17(10):936-937 (1999).
Guarino et al., "Binding of *E. coli* heat-stable enterotoxin to rat intestinal brush borders and to basolateral membranes" *Dig. Dis. Sci.*, 32:1017-1026 (1987).
Gussow and Seemann, "Humanization of monoclonal antibodies" *Methods in Enzymology*, 203:99-121 (1991).
Holm et al., "Functional mapping and single chain construction of the anti-cytokeratin 8 monoclonal antibody TS1" *Mol. Immunol.*, 44(6):1075-1084 (2007).
International Patent Application No. PCT/US2010/53686, filed Oct. 22, 2010, by Millennium Pharmaceuticals, Inc.: International Search Report and Written Opinion, dated Mar. 10, 2011 (10 pages).
International Patent Application No. PCT/US2010/53686, filed Oct. 22, 2010, by Millennium Pharmaceuticals, Inc.: International Preliminary Report on Patentability, dated Apr. 24, 2012 (6 pages).
International Patent Application No. PCT/US2013/038542, filed Apr. 27, 2013, by Millennium Pharmaceuticals, Inc.: International Preliminary Report on Patentability, dated Mar. 20, 2014 (8 pages).
International Patent Application No. PCT/US2013/038542, filed Apr. 27, 2013, by Millennium Pharmaceuticals, Inc.: International Search Report and Written Opinion, dated Sep. 9, 2013.
International Patent Application No. PCT/US2014/019034, filed Feb. 27, 2014, by Millennium Pharmaceuticals, Inc.: International Search Report and Written Opinion, dated May 14, 2014.
Karu et al., "Recombinant Antibody Technology" *ILAR J.*, 37(3):132-141 (1995).
Kenya Patent Application No. KE/P/2012/001534: Search Report, dated Jun. 25, 2014.
Kloeters et al., "Uroguanylin inhibits proliferation of pancreatic cancer cells" *Scand. J. Gastroenterol.*, 43:447-455 (2008).
Knoop and Owens, "Pharmacologic action of *Escherichia coli* heat-stable (STa) enterotoxin" *J. Pharmacol. Toxicol. Meth.* 28:67-72 (Sep. 1992).
Kontermann and Brinkmann, "Bispecific antibodies" *Drug Disc. Today*, 20(7):838-847 (2015).
Liu et al., "In vivo imaging of human colorectal cancer using radiolabeled analogs of the uroguanylin peptide hormone" *Anticancer Res.*, 29:3777-3784 (2009).

Maccallum et al., "Antibody-antigen Interactions: Contact Analysis and Binding Site Topography" *J. Mol. Biol.*, 262(5):732-745 (1996).
Mann et al., "Mice lacking the guanylyl cyclase C receptor are resistant to STa-induced intestinal secretion" *Biochem. Biophys. Res. Commun.*, 239:463-466 (1997).
Mao et al., "Ectopic expression of guanylyl cyclase C in gastric cancer as a potential biomarker and therapeutic target" *J. Digest. Dis.*, 10:272-285 (2009).
Mariuzza et al., "The Structural Basis of Antigen-Antibody Recognition" *Annu. Rev. Biophys. Biophys. Chem.*, 16:139-159 (1987).
McCarthy et al., "Altering the fine specificity of an anti-*Legionella* single chain antibody by a single amino acid insertion" *J. Immunol. Meth.*, 251:137-149 (2001).
Morris, "Epitope Mapping of Protein Antigens by Competition ELISA" in *The Protein Protocols Handbook*. Totowa, NJ: Humana Press, 1996; pp. 595-600.
Nandi et al., "Epitope conservation and immunohistochemical localization of the guanylin/stable toxin peptide receptor, guanylyl cyclase C" *J. Cell. Biochem.*, 66:500-511 (1997).
Nandi et al., "Expression of the extracellular domain of the human heat-stable enterotoxin receptor in *Escherichia coli* and generation of neutralizing antibodies" *Protein Expr. Purif.*, 8:151-159 (1996).
Nandi et al., "Topological mimicry and epitope duplication in the guanylyl cyclase C receptor" *Protein Sci.*, 7:2175-2183 (1998).
Nolan and O'Kennedy, "Bifunctional antibodies: concept, production and applications" *Biochimica et Biophysica Acta*, 1040(1):1-11 (1990).
Park et al., "Ectopic Expression of Guanylyl Cyclase C in Adenocarcinomas of the Esophagus and Stomach" *Cancer Epidemiol. Biomarkers Prev.*, 11:739-744 (2002).
Pitari et al., "Bacterial enterotoxins are associated with resistance to colon cancer" *Proc. Natl. Acad. Sci. USA*, 100:2695-2699 (Mar. 2003).
Pitari et al., "Interruption of homologous desensitization in cyclic guanosine 3',5'—monophosphate signaling restores colon cancer cytostasis by bacterial enterotoxins" *Cancer Res.*, 65(23):11129-11135 (2005).
Rudikoff et al., "Single Amino acid substitution altering antigen-binding specificity" *Proc. Natl. Acad. Sci., USA*, 79:1979-1983 (Mar. 1982).
Sargent et al., "Evaluation of guanylyl cyclase C lymph node status for colon cancer staging and prognosis" *Ann. Surg. Oncol.*, 18:3261-3270 (2011).
Schulz et al., "A validated quantitative assay to detect occult micrometastases by reverse transcriptase—polymerase chain reaction of guanylyl cyclase C in patients with colorectal cancer" *Clin. Cancer Res.*, 12:4545-4552 (2006).
Shahied et al., "Bispecific Minibodies Targeting HER2/neu and CD16 Exhibit Improved Tumor Lysis When Placed in a Divalent Tumor Antigen Binding Format" *J. Biol. Chem.*, 279(52):53907-53914 (2004).
Singh et al., "Isolation and expression of a guanylate cyclase-coupled heat stable enterotoxin receptor cDNA from a human colonic cell line" *Biochem. Biophys. Res. Commun.*, 179(3):1455-1463 (1991).
Snook et al., "Guanylyl Cyclase C-Induced Immunotherapeutic Responses Opposing Tumor Metastases Without Autoimmunity" *J. Natl. Cancer Inst.*, 100:950-961 (2008).
Sompuram et al., "Antibodies immunoreactive with formalin-fixed tissue antigens recognize linear protein epitopes" *Am. J. Clin. Pathol.*, 125(1):82-90 (Jan. 2006).
Suresh et al., "Bispecific monoclonal antibodies from hybrid hybridomas" *Methods in Enzymology*, 121:210-228 (1986).
Swaminathan, "Thermodynamic Analyses Reveal Role of Water Release in Epitope Recognition by a Monoclonal Antibody against the Human Guanylyl Cyclase C Receptor" *J. Biol. Chem.*, 274(44):31272-31278 (1999).
Urbanski et al., "Internalization of *E. coli* ST mediated by guanylyl cyclase C in T84 human colon carcinoma cells" *Biochim. Biophys. Acta*, 1245:29-36 (1995).
Vaandrager et al., "Guanylyl cyclase C is an N-linked glycoprotein receptor that accounts for multiple heat-stable enterotoxin-binding proteins in the intestine" *J. Biol. Chem.*, 268(3):2174-2179 (1993).

(56) References Cited

OTHER PUBLICATIONS

Vajdos et al., "Comprehensive functional maps of the antigen-binding site of an anti-ErbB2 antibody obtained with shotgun scanning mutagenesis" *J. Mol. Biol.*, 320(2):415-428 (2002).

Veiby et al., "The Investigational Drug MLN0264 First-in-human, First in Class ADC Targeting GCC: Phase I Dose-escalation Study and Supportive Scientific Rationale" *Eur. J. Cancer*, 48(6):101 (2012).

Vijayachandra et al., "Biochemical characterization of the intracellular domain of the human guanylyl cyclase C receptor provides evidence for a catalytically active homotrimer" *Biochemistry*, 39:16075-16083 (2000).

Wiegand et al., "Human guanylin: cDNA isolation, structure, and activity" *FEBS Lett.*, 311:150-154 (Oct. 1992).

Wolfe et al., "In vivo imaging of human colon cancer xenografts in immunodeficient mice using a guanylyl cyclase C-specific ligand" *J. Nucl. Med.*, 43:392-399 (2002).

Zhang et al., (Nov. 2013) "Abstract PR12: MLN0264, an investigational, first-in-class antibody-drug conjugate (ADC) targeting guanylyl cyclase C (GCC), demonstrates antitumor activity alone and in combination with gemcitabine in human pancreatic cancer xenograft models expressing GCC" *Mol Cancer Ther*, 12(11 Suppl):PR12 [online]. Retrieved from: http://mct.aacrjournals.org/content/12/11_Supplement/PR12, on Sep. 8, 2016 (4 pages).

SEQUENCE LISTING

<160> NUMBER OF SEQ ID NOS: 319

<210> SEQ ID NO 1
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tgaaggagtc aggacctggc ctggtggcgc cctcacagag cctgtccatc      60
acatgcactg tctctgggtt ctcattaagc agaaatgcta taagctgggt tcgccagcca     120
ccaggaaagg gtctggagtg gcttggagta atatggactg gtggaggcac aaattataat     180
tcagctctca aatccagact gagcatccgc aaagagaact ccaagagtca agttttctta     240
aaaatgaaca gtctacaaac tgaagacaca gccaggtact ctgtgccag aagtggttac     300 gacgggtttg attactgggg ccaagggact ctggtcactg tctctgca                  348

<210> SEQ ID NO 2
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Asn
            20                  25                  30

Ala Ile Ser Trp Val Arg Gln Pro Pro Gly Lys Gly Leu Glu Trp Leu
        35                  40                  45

Gly Val Ile Trp Thr Gly Gly Gly Thr Asn Tyr Asn Ser Ala Leu Lys
    50                  55                  60

Ser Arg Leu Ser Ile Arg Lys Glu Asn Ser Lys Ser Gln Val Phe Leu
65                  70                  75                  80

Lys Met Asn Ser Leu Gln Thr Glu Asp Thr Ala Arg Tyr Phe Cys Ala
                85                  90                  95

Arg Ser Gly Tyr Asp Gly Phe Asp Tyr Trp Gly Gln Gly Thr Leu Val
            100                 105                 110

Thr Val Ser Ala
        115
```

<210> SEQ ID NO 3
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
cagattgttc tcacccagtc tccagcaatc atgtctgcat ctccagggga gaaggtcacc    60
atgacctgca gtgccagctc aagtgtaaat tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcaccagcat ggaggctgaa   240
gatgctgcca cttattactg ccagcagtgg agtggtaacc cgtacacgtt cggagggggg   300
accaaactgg aaataaaa                                                 318
```

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Thr Ser Met Glu Ala Glu
65                  70                  75                  80
```

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys
            100                 105

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caggtccagt tgaagcagtc tggagctgaa ctggtgaagc ctggggcttc agtgaagata      60
tcctgcaagg cttctggcta caccttcact gactactata aaactgggt gaagcagagg     120 cctggacagg gccttgagtg gattggaaag attggtcctc gaagtggtaa tacttactac    180
aatgagaagt tcaagggcaa ggccacactg actgcagaca atcgtccag cacagcctac    240 atgcagctca gcagcctgac atctgaggac tctgcagtct atttctgtgc aagatgggat    300
gcttactggg gccaagggac tctggtcact gtctct                              336

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Lys Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Asp Ala Tyr Trp Gly Gln Gly Thr Leu Val Thr Val Ser
            100                 105                 110

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gatgttgtga tgacccagac tccactgtct ttgtcggtta ccattggaca accagcctct      60
atctcttgca gtcaagtca gagcctctta tatagtaatg gaaagacata tttgaattgg    120
ttacaacaga ggcctggcca ggctccaaag cacctaatgt atcaggtgtc caaactggac    180
cctggcatcc ctgacaggt cagtggcagt ggatcagaaa cagattttac acttaaaatc    240

```
agcagagtgg aggctgaaga tttgggagtt tattactgct tgcaaggtac atattatccg    300
tacacgttcg gagggggac caagctggaa ataaag                               336
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Asp Val Val Met Thr Gln Thr Pro Leu Ser Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Gln Gln Arg Pro Gly Gln Ala
        35                  40                  45

Pro Lys His Leu Met Tyr Gln Val Ser Lys Leu Asp Pro Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr Tyr Tyr Pro Tyr Thr Phe Gly Gly Gly Thr Lys Leu Glu Ile Lys
            100                 105                 110
```

<210> SEQ ID NO 9
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
caggtccaac tgcagcagcc tggggctgaa ctggtgaagc ctggggcttc agtgcagatg    60
tcctgtaagg cttctggcta tattttcacc ggctactgga tgtactgggt gaagcagagg   120
cctggccaag cccttgagtg gattggaagg attcatcctt ctgatagtaa tactaactac   180
aatcaaaagt tcaagggcaa ggccacattg actgtagaca atcctccag cacagcctac    240 atgcaactca gcagcctgac atctgaggac tctgcggtct attactgtac ccatgccctt   300
gcttactggg gccaagggac tctggtcact gtctct                              336
```

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Gln Gln Pro Gly Ala Glu Leu Val Lys Pro Gly Ala
1               5                   10                  15

Ser Val Gln Met Ser Cys Lys Ala Ser Gly Tyr Ile Phe Thr Gly Tyr
            20                  25                  30

Trp Met Tyr Trp Val Lys Gln Arg Pro Gly Gln Gly Leu Glu Trp Ile
        35                  40                  45
```

Gly Arg Ile His Pro Ser Asp Ser Asn Thr Asn Tyr Asn Gln Lys Phe
        50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr His Ala Leu Ala Tyr Trp Gly Gln Gly Thr Leu Val Thr Val Ser
            100                 105                 110

<210> SEQ ID NO 11
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatgttgtgt tgacccagac tccactcact ttgtcgatta ccattggaca accagcctct    60
atctcttgca agtcaagtca gagcctctta tatagtaatg aaaaaccta tttgagttgg   120 ttattacaga ggccaggcca gtctccaaag cgcctaatct atctggtgtc tcaactggac   180
tctggagtcc ctgacaggtt cactggcagt ggatcaggaa cagattttac actgaagatc   240
agcagagtgg aggctgagga tttgggagtg tattactgcg tgcaaggtac acatttattc   300
acgttcggct cggggacaaa gttggaaata aaa                               333

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Leu Thr Gln Thr Pro Leu Thr Leu Ser Ile Thr Ile Gly
 1               5                  10                  15

Gln Pro Ala Ser Ile Ser Cys Lys Ser Ser Gln Ser Leu Leu Tyr Ser
                 20                  25                  30

Asn Gly Lys Thr Tyr Leu Ser Trp Leu Leu Gln Arg Pro Gly Gln Ser
             35                  40                  45

Pro Lys Arg Leu Ile Tyr Leu Val Ser Gln Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Val Gln Gly
                 85                  90                  95

Thr His Leu Phe Thr Phe Gly Ser Gly Thr Lys Leu Glu Ile Lys
            100                 105                 110

<210> SEQ ID NO 13
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
caggtccagc tgaagcagtc tggagctgag ctggtgaagc tggggcttc agtgaagatg    60 tcctgcaagg cttctggcta caccttcaca gactactata taaactgggt gaagcagagg   120
cctggacagg gccttgagtg gattggaaag attggtccta gaagtggtag tacttactac   180
aatgagaagt tcaagggcaa ggccacactg actgcagaca atcctccag cacagcctac    240 atgcagctca gcagcctgac atctgaggac tctgcagtct atttctgtgc aagatgggat   300
gcttactggg gccaagggac tctggtcact gtctctgca                          339
```

```
<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

Gln Val Gln Leu Lys Gln Ser Gly Ala Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Lys Ile Gly Pro Arg Ser Gly Ser Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Asp Ala Tyr Trp Gly Gln Gly Thr Leu Val Thr Val Ser
            100                 105                 110

Ala

```
<210> SEQ ID NO 15
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gatgttgtga tgacccagac tccactgtct ttgtcggtta ccattggaca accagcctct    60
atctcttgca agtcaagtca gagcctctta tatagtaatg gaaagacata tttgaattgg   120
ttacaacaga ggcctggcca ggctccaaag cacctaatgt atcaggtgtc caaactggac   180
cctggcatcc ctgacaggtt cagtggcagt ggatcagaaa cagattttac acttaaaatc   240
agcagagtgg aggctgaaga tttgggagtt tattactgct tgcaaggtac atattatccg   300
tacacgttcg gaggggggac caagctggaa ataaaa                             336
```

```
<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

Asp Val Val Met Thr Gln Thr Pro Leu Ser Leu Ser Val Thr Ile Gly
1               5                   10                  15

Gln Pro Ala Ser Ile Ser Cys Lys Ser Gln Ser Leu Leu Tyr Ser
            20                  25                  30

Asn Gly Lys Thr Tyr Leu Asn Trp Leu Gln Gln Arg Pro Gly Gln Ala
        35                  40                  45

Pro Lys His Leu Met Tyr Gln Val Ser Lys Leu Asp Pro Gly Ile Pro
50                  55                  60

Asp Arg Phe Ser Gly Ser Gly Ser Glu Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr Tyr Tyr Pro Tyr Thr Phe Gly Gly Gly Thr Lys Leu Glu Ile Lys
                100                 105                 110

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tacagcagtg gggcgcagga ctgttgaagc cttcggagac cctgtccctc     60
acctgcgctg tctttggtgg gtccttcagt ggttactact ggagctggat ccgccagccc    120
ccagggaagg gctggagtg gattggggaa atcaatcatc gtggaaacac caacgacaac    180
ccgtccctca gagtcgagt caccatatca gtagacacgt ccaagaacca gttcgccctg    240
aagctgagtt ctgtgaccgc cgcggacacg gctgtttatt actgtgcgag agaacgtgga    300
tacacctatg gtaactttga ccactggggc cagggaaccc tggtcaccgt ctcctca       357

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
                100                 105                 110

Thr Leu Val Thr Val Ser Ser
            115

<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gaaatagtga tgacgcagtc tccagccacc ctgtctgtgt ctccagggga aagagccacc      60
ctctcctgca gggccagtca gagtgttagc agaaacttag cctggtatca gcagaaacct     120
ggccaggctc ccaggctcct catctatggt gcatccacca gggccactgg aatcccagcc     180
aggttcagtg gcagtgggtc tgggacagag ttcactctca ccatcggcag cctgcagtct     240
gaagattttg cagtttatta ctgtcagcag tataaaacct ggcctcggac gttcggccaa     300
gggaccaacg tggaaatcaa a                                                321
```

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys
            100                 105
```

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
caggtgcagc tggtggagtc tgggggaggc ttggtcaagc ctggagggtc cctgagactc      60
tcctgtgcag cctctggatt caccttcagt gactgctaca tgagctggat ccgccagtct     120
ccagggaagg ggctggagtg ggtttcatac attactacta gtggtaatac catttactac     180
gcagactctg tgaagggccg attcaccatc tccagggaca acgccaagaa ctcactgtat     240
ctgcaaatga acagcctgag agccgaggac acggccgtgt attactgtgc gagagactgg     300
ggatggttct acggtatgga cgtctggggc caagggacca cggtcaccgt ctcctca       357
```

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Cys
            20                  25                  30

Tyr Met Ser Trp Ile Arg Gln Ser Pro Gly Lys Gly Leu Glu Trp Val
        35                  40                  45

Ser Tyr Ile Thr Thr Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Trp Phe Tyr Gly Met Asp Val Trp Gly Gln Gly
            100                 105                 110

Thr Thr Val Thr Val Ser Ser
        115

<210> SEQ ID NO 23
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (216)..(217)
<223> OTHER INFORMATION: a, c, t, g, unknown or other

<400> SEQUENCE: 23
gatattgtga tgacccagac tccactctct ctgtccgtca cccctggaca gccggcctcc      60
atctcctgca agtctagtca gagcctcctg cataatgatg gaaagaccta tttgtattgg     120
tacctgcaga agccaggcca gcctccacaa ctcctgatct atgaagtttc caaccggttc     180
tctggagtgc cagataggtt cagtagcagc gggtcnnga cagatttcac actgaaaatc     240
agccgggtgg aggctgagga tgttggggtt tattactgca tgcaaagtat acagcttcct     300
cggacgttcg gccaagggac caaggtggaa atcaaa                                336

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (73)..(73)
<223> OTHER INFORMATION: Any amino acid

<400> SEQUENCE: 24

Asp Ile Val Met Thr Gln Thr Pro Leu Ser Leu Ser Val Thr Pro Gly
1               5                   10                  15

```
Gln Pro Ala Ser Ile Ser Cys Lys Ser Ser Gln Ser Leu Leu His Asn
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Ser Gly Ser Xaa Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Arg Thr Phe Gly Gln Gly Thr Lys Val Glu Ile Lys
            100                 105                 110
```

<210> SEQ ID NO 25
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagct atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagggagg     300
agcagctcgt actttgacta ttggggccag ggaaccctgg tcaccgtctc ctca           354
```

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Ser Tyr Phe Asp Tyr Trp Gly Gln Gly Thr
            100                 105                 110

Leu Val Thr Val Ser Ser
        115
```

<210> SEQ ID NO 27

<210> SEQ ID NO 27
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gatattgtga tgacccagac tccactctcc tcacctgtca cccttggaca gccggcctcc    60
atctcctgca ggtctagtca aagcctcgta cacagtgatg aaacaccta cttgagttgg    120
cttcagcaga ggccaggcca gcctccaaga ctcctaattt ataagacttc taaccgcttc   180
tctggggtcc cagacagatt cagtggcagt ggggcaggga cagatttcac actgaaaatc   240
agcagggtgg gagctgagga tgtcggggtt tattactgca tgcaagctac gcaatttcca   300
accttcggcc aagggacacg actggagatt aaa                                333
```

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Thr Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Gly Ala Glu Asp Val Gly Val Tyr Tyr Cys Met Gln Ala
                85                  90                  95
Thr Gln Phe Pro Thr Phe Gly Gln Gly Thr Arg Leu Glu Ile Lys
            100                 105                 110
```

<210> SEQ ID NO 29
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
caggtgcagc tggtggagtc tgggggaggc gtggtccagc ctgggaggtc cctgagactc    60
tcctgtgtag cgtctggatt caccttcagt agctatggca tgcactgggt ccgccaggct   120
ccaggcaagg gctggagtg gtgggagct atatggtatg atggaagtaa taatactat     180
gcagcctccg tgaagggccg attcaccatc tccagagaca attccaagaa cacgctgtat   240
ctgcaaatga acagcctgag agccgaggac acggctgtat tttactgtgc gagagggagg   300
agcagctcgt attttgacta ctggggccag ggaaccctgg tcaccgtctc ctca         354
```

<210> SEQ ID NO 30
<211> LENGTH: 118

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Gly Ala Ile Trp Tyr Asp Gly Ser Asn Lys Tyr Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Gly Arg Ser Ser Ser Tyr Phe Asp Tyr Trp Gly Gln Gly Thr
            100                 105                 110

Leu Val Thr Val Ser Ser
        115

<210> SEQ ID NO 31
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gatattgtga tgacccagac tccactctcc tcacctgtca cccttggaca gccggcctcc      60
atctcctgca ggtctagtca agcctcgta cacagtgatg gaaacaccta cttgagttgg     120
cttcagcaga ggccaggcca gcctccaaga ctcctaattt ataagacttc taaccgcttc     180
tctggggtcc cagacagatt cagtggcagt ggggcaggga cagatttcac actgaaaatc     240
agcagggtgg gagctgagga tgtcggggtt tattactgca tgcaagctac gcaatttcca     300
accttcggcc aagggacacg actggagatt aaa                                  333

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Thr Ser Asn Arg Phe Ser Gly Val Pro
    50                  55                  60

Asp Arg Phe Ser Gly Ser Gly Ala Gly Thr Asp Phe Thr Leu Lys Ile
```

```
                65                  70                  75                  80
Ser Arg Val Gly Ala Glu Asp Val Gly Val Tyr Tyr Cys Met Gln Ala
                    85                  90                  95

Thr Gln Phe Pro Thr Phe Gly Gln Gly Thr Arg Leu Glu Ile Lys
                100                 105                 110

<210> SEQ ID NO 33
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg gctggagtg gtggcagct atatggtatg atggaagtaa taaatactat      180
gcagactccg tgaagggccg attcaccatc tccagagaca attccaagaa cacgctgtat     240
ctgcaaatga acagcctgag agccgaggac acggctgtgt attactgtgc gagagggagg     300
agcagctcgt actttgacta ttggggccag ggaaccctgg tcaccgtctc ctca           354

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ala Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Tyr Phe Asp Tyr Trp Gly Gln Gly Thr
            100                 105                 110

Leu Val Thr Val Ser Ser
        115

<210> SEQ ID NO 35
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatattgtga tgacccagac tccactctcc tcacctgtca cccttggaca gccggcctcc      60
```

```
ttctcctgca ggtctagtca aagcctcgta cacagtgatg gaaacacgta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttcca    300
accttcggcc aagggacacg actggagatt aaa                                 333
```

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ile Val Met Thr Gln Thr Pro Leu Ser Ser Pro Val Thr Leu Gly
1               5                   10                  15

Gln Pro Ala Ser Phe Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Thr Phe Gly Gln Gly Thr Arg Leu Glu Ile Lys
            100                 105                 110
```

<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
caggtgcagc tggtggagtc tgggggaggc ttggtcaagc ctggagggtc cctgagactc    60
tcctgtgcag cctctggatt caccttcagt gactactaca tgagctggat ccgccaggct    120
ccagggaagg ggctggagtg gatttcatac attactagta gtggtagtac catatactac    180
tcagcctctg tgaagggccg attcaccatc tccagggaca acgccaagaa ctcactgtat    240
ctgcaaatga acagcctgag agccgaggac acggccgtgt attactgtgc gagagatttc    300
agtggctggt tcggagtcca ctttgactac tggggccagg gaaccctggt caccgtctcc    360
tcg                                                                  363
```

<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Gln Val Gln Leu Val Glu Ser Gly Gly Gly Leu Val Lys Pro Gly Gly
```

```
1               5                  10                 15
Ser Leu Arg Leu Ser Cys Ala Ala Ser Gly Phe Thr Phe Ser Asp Tyr
            20                  25                 30

Tyr Met Ser Trp Ile Arg Gln Ala Pro Gly Lys Gly Leu Glu Trp Ile
            35                  40                 45

Ser Tyr Ile Thr Ser Ser Gly Ser Thr Ile Tyr Tyr Ser Ala Ser Val
            50                  55                 60

Lys Gly Arg Phe Thr Ile Ser Arg Asp Asn Ala Lys Asn Ser Leu Tyr
65                  70                  75                 80

Leu Gln Met Asn Ser Leu Arg Ala Glu Asp Thr Ala Val Tyr Tyr Cys
            85                  90                 95

Ala Arg Asp Phe Ser Gly Trp Phe Gly Val His Phe Asp Tyr Trp Gly
            100                 105                110

Gln Gly Thr Leu Val Thr Val Ser Ser
            115                 120
```

<210> SEQ ID NO 39
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
gatattgtga tgacccagac tccactctct ctgtccgtca cccctggaca gccggcctcc      60
atctcctgta agtctagtca gagcctcctg catagtgatg aaagaccta  tttgtattgg    120
tacctgcaga agccaggcca gcctccacag ctcctgatct atgaagtttc caaccggttc    180
tctggagtgc caaataggtt cagtggcagc gggtcaggga cagatttcac actgaaaatc    240
agccgggtgg aggctgagga tgttggggtt tattactgca tgcaaagtat acaacttacg    300
tggacgttcg gccaagggac caaggtggaa atcaaa                              336
```

<210> SEQ ID NO 40
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Asp Ile Val Met Thr Gln Thr Pro Leu Ser Leu Ser Val Thr Pro Gly
1               5                  10                 15

Gln Pro Ala Ser Ile Ser Cys Lys Ser Ser Gln Ser Leu Leu His Ser
            20                  25                 30

Asp Gly Lys Thr Tyr Leu Tyr Trp Tyr Leu Gln Lys Pro Gly Gln Pro
            35                  40                 45

Pro Gln Leu Leu Ile Tyr Glu Val Ser Asn Arg Phe Ser Gly Val Pro
            50                  55                 60

Asn Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Met Gln Ser
            85                  90                 95

Ile Gln Leu Thr Trp Thr Phe Gly Gln Gly Thr Lys Val Glu Ile Lys
            100                 105                110
```

<210> SEQ ID NO 41
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggactg ggtctcagat attagtggta gtggtggtag cacatactac    180
gcagactccg tgaagggccg gttcaccatc tccagagaca attccaagaa cacgctgtat    240
ctgcaaatgc acagcctgag cgccgaggac acggccatat attactgtgc gaaacggcgg    300
tggcagggggt acttcgatct ctggggccgt ggcaccctgg tcactgtctc ctca          354
```

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Asp Trp Val
        35                  40                  45
Ser Asp Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met His Ser Leu Ser Ala Glu Asp Thr Ala Ile Tyr Tyr Cys
                85                  90                  95
Ala Lys Arg Arg Trp Gln Gly Tyr Phe Asp Leu Trp Gly Arg Gly Thr
            100                 105                 110
Leu Val Thr Val Ser Ser
        115
```

<210> SEQ ID NO 43
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gaaattgtgt tgacgcagtc tccaggcacc ctgtctttgt ctccagggga aagagccacc    60
ctctcctgca gggccaggca gcgtgttgac agcaggtact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca aggtggagat caaa                                          324
```

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Arg Gln Arg Val Asp Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 45
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaggtgcagc tgttggagtc tgggggaggc ttggtacagc ctggggggtc cctgagactc      60
tcctgtgcag cctctggatt cacctttagc cgctatgcca tgaactgggt ccgccaggct    120
ccagggaagg gctggagtg gtctcaggt attagtggga gtggtggtag gacatactac      180
gcagactccg tgaagggccg gttcaccatc tccagagaca attccaagaa cacactatat    240
ctgcaaatga acagcctgag agccgaggac acggccgtat attactgtgc gaaagatcgc    300 gattttgga gtggtccatt tgactactgg ggccagggaa ccctggtcac cgtctcctca     360

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Asp Phe Trp Ser Gly Pro Phe Asp Tyr Trp Gly Gln
            100                 105                 110

Gly Thr Leu Val Thr Val Ser Ser
        115                 120
```

<210> SEQ ID NO 47
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
gaaatagtga tgacgccgtc ttcagccacc ctgtctgtgt ctccagggga gagagccacc    60
ctctcctgca gggccagtca gagtgttagt agaaacttag cctggtacca gcagaaacct   120
ggccaggctc ccaggctcct catctatggt gcatccacca gggccactgg tatcccagcc   180
aggttcagtg gcagtgggtc tgggacagaa ttcactctca ccatcagcag cctgcagtct   240
gaagattttg cagtttatta ctgtcaccag tatagtaact ggatgtgcag ttttggccag   300
gggaccaagc tggagatcaa a                                             321
```

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Glu Ile Val Met Thr Pro Ser Ser Ala Thr Leu Ser Val Ser Pro Gly
  1               5                  10                  15

Glu Arg Ala Thr Leu Ser Cys Arg Ala Ser Gln Ser Val Ser Arg Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys His Gln Tyr Ser Asn Trp Met Cys
                 85                  90                  95

Ser Phe Gly Gln Gly Thr Lys Leu Glu Ile Lys
            100                 105
```

<210> SEQ ID NO 49
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
caggtgcagc tgcaggagtc gggcccagga ctggtgaagc cttcggagac cctgtccctc    60
```

```
acctgcactg tctctggtgg ctccatcaga agttactact ggagctggat ccggcagccc    120
gccgggaagg gactggagtg gattggacgt atttatatca gtgggaggac caccttcaac    180
ccctccctca agagtcgagt caccatatca gtggacacgt ccaagaacca gttctccctg    240
aagctgagct ctgtgaccgc cgcggacacg gccgtgtatt tctgtgcgag agatagatat    300
tatggctacc ttgactactg gggccaggga accctggtca ccgtctcctc a             351
```

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Ser Gly Arg Thr Thr Phe Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Asp Arg Tyr Tyr Gly Tyr Leu Asp Tyr Trp Gly Gln Gly Thr Leu
            100                 105                 110

Val Thr Val Ser Ser
        115
```

<210> SEQ ID NO 51
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
gaaattgtgt tgacgcagtc tccaggcacc ctgtctttgt ctccagggga aagagccacc     60
ctctcctgca gggccagtca gagtgttagc cgcagttact tagcctggta ccaacagaaa    120
cctggccagg ctcccaggct cctcatctat gatgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gttcaccgag cacccttcggc   300 caagggacac gactggagat taaa                                           324
```

<210> SEQ ID NO 52
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ser Thr Phe Gly Gln Gly Thr Arg Leu Glu Ile Lys
            100                 105
```

<210> SEQ ID NO 53
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
caggtgcagc tgcaggagtc gggcccagga ctggtgaagc cttcggagac cctgtccctc      60
acctgcactg tctctggcgg ctccatccgt cattactact ggagctggat ccggcagccc     120
ccagggaagg gactggagtg gattgggtat atctattaca gtgggagcac caactacaac     180
ctctccctca agagtcgagt caccatatca gagacacgt ccaagaatca ggtctccctg     240
aagctgagtt ctgtgaccgc tgcggacacg gccgtgtatt attgtgcggc gggtatgggc     300
tttgactact ggggccaggg aaccctggtc accgtctcct ca                       342
```

<210> SEQ ID NO 54
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Leu Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Ala Gly Met Gly Phe Asp Tyr Trp Gly Gln Gly Thr Leu Val Thr Val
            100                 105                 110

Ser Ser
```

<210> SEQ ID NO 55
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gacatccaga tgacccagtc tccttcctcc ctgtctgcat ctataggaga cagagtcacc        60
atcacttgcc gggcaagtca ggccattaga aatgatttag gctggtatca gctgaaaccg       120
gggaaagccc ctaagcgcct gatctattct gcatccagtt tgcaaagtgg ggtcccatca       180
aggttcagcg gcagtggatc tgggacagaa ttcactctca caatcagcag cctgcagcct       240
gaggattctg caacttatta ctgtctacag cataatagtt tccctccgac gttcggccaa       300
gggaccaagg tggaaatcaa a                                                 321
```

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ala Ile Arg Asn Asp
            20                  25                  30

Leu Gly Trp Tyr Gln Leu Lys Pro Gly Lys Ala Pro Lys Arg Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Leu Gln His Asn Ser Phe Pro Pro
                85                  90                  95

Thr Phe Gly Gln Gly Thr Lys Val Glu Ile Lys
            100                 105
```

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
agaaatgcta taagc                                                        15
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Asn Ala Ile Ser
1               5

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gtaatatgga ctggtggagg cacaaattat aattcagctc tcaaatcc                48

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Ile Trp Thr Gly Gly Gly Thr Asn Tyr Asn Ser Ala Leu Lys Ser
1               5                   10                  15

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
agtggttacg acgggtttga ttac                                          24

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Tyr Asp Gly Phe Asp Tyr
1               5

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agtgccagct caagtgtaaa ttacatgcac                                    30

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 64

Ser Ala Ser Ser Ser Val Asn Tyr Met His
1               5                   10

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gacacatcca aactggcttc t                                            21

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Thr Ser Lys Leu Ala Ser
1               5

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagcagtgga gtggtaaccc gtacacg                                      27

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Trp Ser Gly Asn Pro Tyr Thr
1               5

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gactactata taaac                                                   15

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 70

Asp Tyr Tyr Ile Asn
1               5

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aagattggtc ctcgaagtgg taatacttac tacaatgaga agttcaaggg c         51

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ile Gly Pro Arg Ser Gly Asn Thr Tyr Tyr Asn Glu Lys Phe Lys
1               5                   10                  15

Gly

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgggatgctt ac                                                    12

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp Asp Ala Tyr
1

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aagtcaagtc agagcctctt atatagtaat ggaaagacat atttgaat              48

<210> SEQ ID NO 76
<211> LENGTH: 16

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Ser Ser Gln Ser Leu Leu Tyr Ser Asn Gly Lys Thr Tyr Leu Asn
1               5                   10                  15

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caggtgtcca aactggaccc t                                           21

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Val Ser Lys Leu Asp Pro
1               5

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ttgcaaggta catattatcc gtacacg                                     27

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Gln Gly Thr Tyr Tyr Pro Tyr Thr
1               5

<210> SEQ ID NO 81
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggctactgga tgtac                                                  15

```
<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Tyr Trp Met Tyr
1               5

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aggattcatc cttctgatag taatactaac tacaatcaaa agttcaaggg c          51

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ile His Pro Ser Asp Ser Asn Thr Asn Tyr Asn Gln Lys Phe Lys
1               5                   10                  15
Gly

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcccttgctt ac                                                     12

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Leu Ala Tyr
1

<210> SEQ ID NO 87
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
```

```
aagtcaagtc agagcctctt atatagtaat ggaaaaacct atttgagt                48
```

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Lys Ser Ser Gln Ser Leu Leu Tyr Ser Asn Gly Lys Thr Tyr Leu Ser
1               5                   10                  15
```

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89

```
ctggtgtctc aactggactc t                                             21
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Leu Val Ser Gln Leu Asp Ser
1               5
```

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91

```
gtgcaaggta cacatttatt cacg                                          24
```

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Val Gln Gly Thr His Leu Phe Thr
1               5
```

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide <210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Tyr Tyr Ile Asn
1               5

<210> SEQ ID NO 95
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aagattggtc ctagaagtgg tagtacttac tacaatgaga gttcaaggg c            51

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Ile Gly Pro Arg Ser Gly Ser Thr Tyr Tyr Asn Glu Lys Phe Lys
1               5                   10                  15

Gly

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgggatgctt ac                                                      12

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Asp Ala Tyr
1

<210> SEQ ID NO 99
<211> LENGTH: 48
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 99
aagtcaagtc agagcctctt atatagtaat ggaaagacat atttgaat                48

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Ser Ser Gln Ser Leu Leu Tyr Ser Asn Gly Lys Thr Tyr Leu
1               5                   10                  15

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caggtgtcca aactggaccc t                                             21

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Val Ser Lys Leu Asp Pro
1               5

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ttgcaaggta catattatcc gtacacg                                       27

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Gln Gly Thr Tyr Tyr Pro Tyr Thr
1               5

<210> SEQ ID NO 105

<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggttactact ggagc                                                    15

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Tyr Tyr Trp Ser
1               5

<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gaaatcaatc atcgtggaaa caccaacgac aacccgtccc tcaag                   45

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Ile Asn His Arg Gly Asn Thr Asn Asp Asn Pro Ser Leu Lys Ser
1               5                   10                  15

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gaacgtggat acacctatgg taactttgac cac                                33

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Arg Gly Tyr Thr Tyr Gly Asn Phe Asp His
1               5                   10

<210> SEQ ID NO 111
<211> LENGTH: 33
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 111
agggccagtc agagtgttag cagaaactta gcc                                    33

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 112

Arg Ala Ser Gln Ser Val Ser Arg Asn Leu Ala
1               5                   10

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 113
ggtgcatcca ccagggccac t                                                 21

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 114

Gly Ala Ser Thr Arg Ala Thr
1               5

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 115
cagcagtata aaacctggcc tcggacg                                           27

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 116

Gln Gln Tyr Lys Thr Trp Pro Arg Thr

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gactgctaca tgagc                                                      15

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Cys Tyr Met Ser
1               5

<210> SEQ ID NO 119
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tacattacta ctagtggtaa taccatttac tacgcagact ctgtgaaggg c               51

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Tyr Ile Thr Thr Ser Gly Asn Thr Ile Tyr Tyr Ala Asp Ser Val Lys
1               5                   10                  15
Gly

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gactggggat ggttctacgg tatggacgtc                                      30

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Trp Gly Trp Phe Tyr Gly Met Asp Val
1               5                   10

<210> SEQ ID NO 123
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aagtctagtc agagcctcct gcataatgat ggaaagacct atttg             45

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Ser Ser Gln Ser Leu Leu His Asn Asp Gly Lys Thr Tyr Leu Tyr
1               5                   10                  15

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gaagtttcca accggttctc t                                       21

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Val Ser Asn Arg Phe Ser
1               5

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atgcaaagta tacagcttcc tcggacg                                 27

<210> SEQ ID NO 128
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 128

Met Gln Ser Ile Gln Leu Pro Arg Thr
1               5

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agctatggca tgcac                                                    15

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Tyr Gly Met His
1               5

<210> SEQ ID NO 131
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gctatatggt atgatggaag taataaatac tatgcagact ccgtgaaggg c            51

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Ile Trp Tyr Asp Gly Ser Asn Lys Tyr Tyr Ala Asp Ser Val Lys
1               5                   10                  15

Gly

<210> SEQ ID NO 133
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gggaggagca gctcgtactt tgactat                                       27

<210> SEQ ID NO 134

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Arg Ser Ser Ser Tyr Phe Asp Tyr
1               5

<210> SEQ ID NO 135
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aggtctagtc aaagcctcgt acacagtgat ggaaacacct acttgagt              48

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Arg Ser Ser Gln Ser Leu Val His Ser Asp Gly Asn Thr Tyr Leu Ser
1               5                   10                  15

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aagacttcta accgcttctc t                                            21

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Thr Ser Asn Arg Phe Ser
1               5

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atgcaagcta cgcaatttcc aacc                                         24
```

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Gln Ala Thr Gln Phe Pro Thr
1               5

<210> SEQ ID NO 141
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agctatggca tgcac                                                    15

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Tyr Gly Met His
1               5

<210> SEQ ID NO 143
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gctatatggt atgatggaag taataaatac tatgcagcct ccgtgaaggg c            51

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile Trp Tyr Asp Gly Ser Asn Lys Tyr Tyr Ala Ala Ser Val Lys
1               5                   10                  15

Gly

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gggaggagca gctcgtattt tgactac                                      27

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Arg Ser Ser Ser Tyr Phe Asp Tyr
1               5

<210> SEQ ID NO 147
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
aggtctagtc aaagcctcgt acacagtgat ggaaacacct acttgagt               48

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ser Ser Gln Ser Leu Val His Ser Asp Gly Asn Thr Tyr Leu Ser
1               5                   10                  15

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aagacttcta accgcttctc t                                            21

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Lys Thr Ser Asn Arg Phe Ser
1               5

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
atgcaagcta cgcaatttcc a                                              21

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Met Gln Ala Thr Gln Phe Pro Thr
1               5

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
agctatggca tgcac                                                     15

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Tyr Gly Met His
1               5

<210> SEQ ID NO 155
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gctatatggt atgatggaag taataaatac tatgcagact ccgtgaaggg c              51

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ile Trp Tyr Asp Gly Ser Asn Lys Tyr Tyr Ala Asp Ser Val Lys
1               5                   10                  15

Gly

<210> SEQ ID NO 157
<211> LENGTH: 27

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gggaggagca gctcgtactt tgactat                                          27

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Arg Ser Ser Ser Tyr Phe Asp Tyr
1               5

<210> SEQ ID NO 159
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aggtctagtc aaagcctcgt acacagtgat ggaaacacgt acttgagt                   48

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ser Ser Gln Ser Leu Val His Ser Asp Gly Asn Thr Tyr Leu Ser
1               5                   10                  15

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aagatttcta accggttctc t                                                21

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Lys Ile Ser Asn Arg Phe Ser
1               5
```

```
<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
atgcaagcta cacaatttcc aacc                                           24

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Met Gln Ala Thr Gln Phe Pro Thr
1               5

<210> SEQ ID NO 165
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gactactaca tgagc                                                     15

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Tyr Tyr Met Ser
1               5

<210> SEQ ID NO 167
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tacattacta gtagtggtag taccatatac tactcagcct ctgtgaaggg c              51

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Tyr Ile Thr Ser Ser Gly Ser Thr Ile Tyr Tyr Ser Ala Ser Val Lys
1               5                   10                  15
```

Gly

<210> SEQ ID NO 169
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gatttcagtg gctggttcgg agtccacttt gactac                                 36

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Phe Ser Gly Trp Phe Gly Val His Phe Asp Tyr
1               5                   10

<210> SEQ ID NO 171
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aagtctagtc agagcctcct gcatagtgat ggaaagacct atttgtat                   48

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Lys Ser Ser Gln Ser Leu Leu His Ser Asp Gly Lys Thr Tyr Leu Tyr
1               5                   10                  15

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gaagtttcca accggttctc t                                                21

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Glu Val Ser Asn Arg Phe Ser
1               5

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
atgcaaagta tacaacttac gtggacg                                      27

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Met Gln Ser Ile Gln Leu Thr Trp Thr
1               5

<210> SEQ ID NO 177
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
agctatgcca tgagc                                                    15

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Tyr Ala Met Ser
1               5

<210> SEQ ID NO 179
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gatattagtg gtagtggtgg tagcacatac tacgcagact ccgtgaaggg c            51

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 180

Asp Ile Ser Gly Ser Gly Gly Ser Thr Tyr Tyr Ala Asp Ser Val Lys
1               5                   10                  15

Gly

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 181
cggcggtggc agggggtactt cgatctc                                        27

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 182

Arg Arg Trp Gln Gly Tyr Phe Asp Leu
1               5

<210> SEQ ID NO 183
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 183
agggccaggc agcgtgttga cagcaggtac ttagcc                            36

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 184

Arg Ala Arg Gln Arg Val Asp Ser Arg Tyr Leu Ala
1               5                   10

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 185
ggtgcatcca gcagggccac t                                                      21

<210> SEQ ID NO 186
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Ala Ser Ser Arg Ala Thr
1               5

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cagcagtatg gtagctcacc gctcact                                          27

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Tyr Gly Ser Ser Pro Leu Thr
1               5

<210> SEQ ID NO 189
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cgctatgcca tgaac                                                       15

<210> SEQ ID NO 190
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Tyr Ala Met Asn
1               5

<210> SEQ ID NO 191
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggtattagtg ggagtggtgg taggacatac tacgcagact ccgtgaaggg c               51
```

-continued

```
<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Ile Ser Gly Ser Gly Gly Arg Thr Tyr Tyr Ala Asp Ser Val Lys
1               5                   10                  15

Gly

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gatcgcgatt tttggagtgg tccatttgac tac                                33

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Arg Asp Phe Trp Ser Gly Pro Phe Asp Tyr
1               5                   10

<210> SEQ ID NO 195
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
agggccagtc agagtgttag tagaaactta gcc                                33

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Ala Ser Gln Ser Val Ser Arg Asn Leu Ala
1               5                   10

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
```

```
ggtgcatcca ccagggccac t                                              21
```

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Ala Ser Thr Arg Ala Thr
1               5

<210> SEQ ID NO 199
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199

```
caccagtata gtaactggat gtgcagt                                        27
```

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

His Gln Tyr Ser Asn Trp Met Cys Ser
1               5

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201

```
agttactact ggagc                                                     15
```

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Tyr Tyr Trp Ser
1               5

<210> SEQ ID NO 203
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 203
cgtatttata tcagtgggag gaccaccttc aacccctccc tcaagagt                    48

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Ile Tyr Ile Ser Gly Arg Thr Thr Phe Asn Pro Ser Leu Lys Ser
1               5                   10                  15

<210> SEQ ID NO 205
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gatagatatt atggctacct tgactac                                            27

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Arg Tyr Tyr Gly Tyr Leu Asp Tyr
1               5

<210> SEQ ID NO 207
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
agggccagtc agagtgttag ccgcagttac ttagcc                                  36

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Arg Ala Ser Gln Ser Val Ser Arg Ser Tyr Leu Ala
1               5                   10

<210> SEQ ID NO 209
<211> LENGTH: 21
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 209
gatgcatcca gcagggccac t                                              21

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 210

Asp Ala Ser Ser Arg Ala Thr
1               5

<210> SEQ ID NO 211
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
cagcagtatg gtagttcacc gagcacc                                        27

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

Gln Gln Tyr Gly Ser Ser Pro Ser Thr
1               5

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
cattactact ggagc                                                     15

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

His Tyr Tyr Trp Ser
1               5

<210> SEQ ID NO 215
<211> LENGTH: 48
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 215
tatatctatt acagtgggag caccaactac aacctctccc tcaagagt              48

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Tyr Ile Tyr Tyr Ser Gly Ser Thr Asn Tyr Asn Leu Ser Leu Lys Ser
1               5                   10                  15

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ggtatgggct ttgactac                                               18

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Met Gly Phe Asp Tyr
1               5

<210> SEQ ID NO 219
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cgggcaagtc aggccattag aaatgattta ggc                              33

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Arg Ala Ser Gln Ala Ile Arg Asn Asp Leu Gly
1               5                   10

<210> SEQ ID NO 221
```

<210> SEQ ID NO 221 (implied continuation)
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tctgcatcca gtttgcaaag t                                              21

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ala Ser Ser Leu Gln Ser
1               5

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ctacagcata atagtttccc tccgacg                                        27

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Leu Gln His Asn Ser Phe Pro Pro Thr
1               5

<210> SEQ ID NO 225
<211> LENGTH: 30
<212> TYPE: PRT
<213> ORGANISM: Homo sapiens

<400> SEQUENCE: 225

Ile Leu Val Asp Leu Phe Asn Asp Gln Tyr Leu Glu Asp Asn Val Thr
1               5                   10                  15

Ala Pro Asp Tyr Met Lys Asn Val Leu Val Leu Thr Leu Ser
            20                  25                  30

<210> SEQ ID NO 226
<211> LENGTH: 25
<212> TYPE: PRT
<213> ORGANISM: Homo sapien

<400> SEQUENCE: 226

Phe Ala His Ala Phe Arg Asn Leu Thr Phe Glu Gly Tyr Asp Gly Pro
1               5                   10                  15

Val Thr Leu Asp Asp Trp Gly Asp Val
            20                  25

<210> SEQ ID NO 227
<211> LENGTH: 3222
<212> TYPE: DNA
<213> ORGANISM: Homo sapiens

<400> SEQUENCE: 227

| | | | | | |
|---|---|---|---|---|---|
| atgaagacgt | tgctgttgga | cttggctttg | tggtcactgc | tcttccagcc | cgggtggctg | 60 |
| tcctttagtt | cccaggtgag | tcagaactgc | cacaatggca | gctatgaaat | cagcgtcctg | 120 |
| atgatgggca | actcagcctt | tgcagagccc | ctgaaaaact | ggaagatgc | ggtgaatgag | 180 |
| gggctggaaa | tagtgagagg | acgtctgcaa | aatgctggcc | taaatgtgac | tgtgaacgct | 240 |
| actttcatgt | attcggatgg | tctgattcat | aactcaggcg | actgccggag | tagcacctgt | 300 |
| gaaggcctcg | acctactcag | gaaaatttca | atgcacaac | ggatgggctg | tgtcctcata | 360 |
| gggccctcat | gtacatactc | caccttccag | atgtaccttg | acacagaatt | gagctacccc | 420 |
| atgatctcag | ctggaagttt | tggattgtca | tgtgactata | agaaaccctt | aaccaggctg | 480 |
| atgtctccag | ctagaaagtt | gatgtacttc | ttggttaact | tttggaaaac | caacgatctg | 540 |
| cccttcaaaa | cttattcctg | gagcacttcg | tatgtttaca | gaatggtac | agaaactgag | 600 |
| gactgtttct | ggtaccttaa | tgctctggag | gctagcgttt | cctatttctc | ccacgaactc | 660 |
| ggctttaagg | tggtgttaag | acaagataag | gagtttcagg | atatcttaat | ggaccacaac | 720 |
| aggaaaagca | atgtgattat | tatgtgtggt | ggtccagagt | tcctctacaa | gctgaagggt | 780 |
| gaccgagcag | tggctgaaga | cattgtcatt | attctagtgg | atcttttcaa | tgaccagtac | 840 |
| tttgaggaca | atgtcacagc | ccctgactat | atgaaaaatg | tccttgttct | gacgctgtct | 900 |
| cctgggaatt | cccttctaaa | tagctctttc | tccaggaatc | tatcaccaac | aaaacgagac | 960 |
| tttgctcttg | cctatttgaa | tggaatcctg | ctctttggac | atatgctgaa | gatatttctt | 1020 |
| gaaaatggag | aaaatattac | cacccccaaa | tttgctcatg | ctttcaggaa | tctcactttt | 1080 |
| gaagggtatg | acggtccagt | gaccttggat | gactggggg | atgttgacag | taccatggtg | 1140 |
| cttctgtata | cctctgtgga | caccaagaaa | tacaaggttc | ttttgaccta | tgataccac | 1200 |
| gtaaataaga | cctatcctgt | ggatatgagc | cccacattca | cttggaagaa | ctctaaactt | 1260 |
| cctaatgata | ttacaggccg | gggccctcag | atcctgatga | ttgcagtctt | caccctcact | 1320 |
| ggagctgtgg | tgctgctcct | gctcgtcgct | ctcctgatgc | tcagaaaata | tagaaaagat | 1380 |
| tatgaacttc | gtcagaaaaa | atggtcccac | attcctcctg | aaaatatctt | tcctctggag | 1440 |
| accaatgaga | ccaatcatgt | tagcctcaag | atcgatgatg | acaaaagacg | agatacaatc | 1500 |
| cagagactac | gacagtgcaa | atacgacaaa | aagcgagtga | ttctcaaaga | tctcaagcac | 1560 |
| aatgatggta | atttcactga | aaaacagaag | atagaattga | acaagttgct | tcagattgac | 1620 |
| tattacaacc | tgaccaagtt | ctacggcaca | gtgaaacttg | ataccatgat | cttcggggtg | 1680 |
| atagaatact | gtgagagagg | atcctccgg | gaagttttaa | atgacacaat | ttcctacccct | 1740 |
| gatggcacat | tcatggattg | ggagtttaag | atctctgtct | tgtatgacat | tgctaaggga | 1800 |
| atgtcatatc | tgcactccag | taagacagaa | gtccatggtc | gtctgaaatc | taccaactgc | 1860 |
| gtagtggaca | gtagaatggt | ggtgaagatc | actgattttg | gctgcaattc | cattttacct | 1920 |
| ccaaaaaagg | acctgtggac | agctccagag | cacctccgcc | aagccaacat | ctctcagaaa | 1980 |
| ggagatgtgt | acagctatgg | gatcatcgca | caggagatca | tcctgcggaa | agaaaccttc | 2040 |
| tacactttga | gctgtcggga | ccggaatgag | aagattttca | gagtggaaaa | ttccaatgga | 2100 |

-continued

```
atgaaaccct tccgcccaga tttattcttg gaaacagcag aggaaaaaga gctagaagtg      2160
tacctacttg taaaaaactg ttgggaggaa gatccagaaa agagaccaga tttcaaaaaa      2220
attgagacta cacttgccaa gatatttgga cttttt catg accaaaaaaa tgaaagctat     2280
atggatacct tgatccgacg tctacagcta tattctcgaa acctggaaca tctggtagag      2340
gaaaggacac agctgtacaa ggcagagagg gacagggctg acagacttaa ctttatgttg      2400
cttccaaggc tagtggtaaa gtctctgaag gagaaaggct ttgtggagcc ggaactatat      2460
gaggaagtta caatctactt cagtgacatt gtaggtttca ctactatctg caaatacagc      2520
acccccatgg aagtggtgga catgcttaat gacatctata agagttttga ccacattgtt      2580
gatcatcatg atgtctacaa ggtggaaacc atcggtgatg cgtacatggt ggctagtggt      2640
ttgcctaaga gaatggcaa tcggcatgca atagacattg ccaagatggc cttgaaaatc      2700
ctcagcttca tggggacctt tgagctggag catcttcctg gcctcccaat atggattcgc      2760
attggagttc actctggtcc ctgtgctgct ggagttgtgg gaatcaagat gcctcgttat      2820
tgtctatttg gagatacggt caacacagcc tctaggatgg aatccactgg cctcccttg      2880 agaattcacg tgagtggctc caccatagcc atcctgaaga gaactgagtg ccagttcctt      2940
tatgaagtga gaggagaaac atacttaaag gaagaggaa atgagactac ctactggctg      3000
actgggatga aggaccagaa attcaacctg ccaacccctc ctactgtgga gaatcaacag      3060
cgtttgcaag cagaattttc agacatgatt gccaactctt tacagaaaag acaggcagca      3120
gggataagaa gccaaaaacc cagacgggta gccagctata aaaaggcac tctggaatac      3180 ttgcagctga ataccacaga caaggagagc acctattttt aa                        3222
```

<210> SEQ ID NO 228
<211> LENGTH: 1073
<212> TYPE: PRT
<213> ORGANISM: Homo sapiens

<400> SEQUENCE: 228

```
Met Lys Thr Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
                20                  25                  30

Gly Ser Tyr Glu Ile Ser Val Leu Met Met Gly Asn Ser Ala Phe Ala
            35                  40                  45

Glu Pro Leu Lys Asn Leu Glu Asp Ala Val Asn Glu Gly Leu Glu Ile
        50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175
```

```
Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser
    290                 295                 300

Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Leu Phe Gly His Met Leu
                325                 330                 335

Lys Ile Phe Leu Glu Asn Gly Glu Asn Ile Thr Thr Pro Lys Phe Ala
            340                 345                 350

His Ala Phe Arg Asn Leu Thr Phe Glu Gly Tyr Asp Gly Pro Val Thr
        355                 360                 365

Leu Asp Asp Trp Gly Asp Val Asp Ser Thr Met Val Leu Leu Tyr Thr
    370                 375                 380

Ser Val Asp Thr Lys Lys Tyr Lys Val Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu Pro Asn Asp Ile Thr Gly Arg Gly Pro Gln Ile Leu
            420                 425                 430

Met Ile Ala Val Phe Thr Leu Thr Gly Ala Val Val Leu Leu Leu Leu
            435                 440                 445

Val Ala Leu Leu Met Leu Arg Lys Tyr Arg Lys Asp Tyr Glu Leu Arg
450                 455                 460

Gln Lys Lys Trp Ser His Ile Pro Pro Glu Asn Ile Phe Pro Leu Glu
465                 470                 475                 480

Thr Asn Glu Thr Asn His Val Ser Leu Lys Ile Asp Asp Asp Lys Arg
                485                 490                 495

Arg Asp Thr Ile Gln Arg Leu Arg Gln Cys Lys Tyr Asp Lys Lys Arg
            500                 505                 510

Val Ile Leu Lys Asp Leu Lys His Asn Asp Gly Asn Phe Thr Glu Lys
        515                 520                 525

Gln Lys Ile Glu Leu Asn Lys Leu Leu Gln Ile Asp Tyr Tyr Asn Leu
    530                 535                 540

Thr Lys Phe Tyr Gly Thr Val Lys Leu Asp Thr Met Ile Phe Gly Val
545                 550                 555                 560

Ile Glu Tyr Cys Glu Arg Gly Ser Leu Arg Glu Val Leu Asn Asp Thr
                565                 570                 575

Ile Ser Tyr Pro Asp Gly Thr Phe Met Asp Trp Glu Phe Lys Ile Ser
            580                 585                 590

Val Leu Tyr Asp Ile Ala Lys Gly Met Ser Tyr Leu His Ser Ser Lys
```

-continued

```
            595                 600                 605
Thr Glu Val His Gly Arg Leu Lys Ser Thr Asn Cys Val Val Asp Ser
610                 615                 620

Arg Met Val Val Lys Ile Thr Asp Phe Gly Cys Asn Ser Ile Leu Pro
625                 630                 635                 640

Pro Lys Lys Asp Leu Trp Thr Ala Pro Glu His Leu Arg Gln Ala Asn
                645                 650                 655

Ile Ser Gln Lys Gly Asp Val Tyr Ser Tyr Gly Ile Ile Ala Gln Glu
                660                 665                 670

Ile Ile Leu Arg Lys Glu Thr Phe Tyr Thr Leu Ser Cys Arg Asp Arg
                675                 680                 685

Asn Glu Lys Ile Phe Arg Val Glu Asn Ser Asn Gly Met Lys Pro Phe
690                 695                 700

Arg Pro Asp Leu Phe Leu Glu Thr Ala Glu Lys Glu Leu Glu Val
705                 710                 715                 720

Tyr Leu Leu Val Lys Asn Cys Trp Glu Glu Asp Pro Glu Lys Arg Pro
                725                 730                 735

Asp Phe Lys Lys Ile Glu Thr Thr Leu Ala Lys Ile Phe Gly Leu Phe
                740                 745                 750

His Asp Gln Lys Asn Glu Ser Tyr Met Asp Thr Leu Ile Arg Arg Leu
                755                 760                 765

Gln Leu Tyr Ser Arg Asn Leu Glu His Leu Val Glu Glu Arg Thr Gln
770                 775                 780

Leu Tyr Lys Ala Glu Arg Asp Arg Ala Asp Arg Leu Asn Phe Met Leu
785                 790                 795                 800

Leu Pro Arg Leu Val Val Lys Ser Leu Lys Glu Lys Gly Phe Val Glu
                805                 810                 815

Pro Glu Leu Tyr Glu Glu Val Thr Ile Tyr Phe Ser Asp Ile Val Gly
                820                 825                 830

Phe Thr Thr Ile Cys Lys Tyr Ser Thr Pro Met Glu Val Val Asp Met
                835                 840                 845

Leu Asn Asp Ile Tyr Lys Ser Phe Asp His Ile Val Asp His His Asp
850                 855                 860

Val Tyr Lys Val Glu Thr Ile Gly Asp Ala Tyr Met Val Ala Ser Gly
865                 870                 875                 880

Leu Pro Lys Arg Asn Gly Asn Arg His Ala Ile Asp Ile Ala Lys Met
                885                 890                 895

Ala Leu Glu Ile Leu Ser Phe Met Gly Thr Phe Glu Leu Glu His Leu
                900                 905                 910

Pro Gly Leu Pro Ile Trp Ile Arg Ile Gly Val His Ser Gly Pro Cys
                915                 920                 925

Ala Ala Gly Val Val Gly Ile Lys Met Pro Arg Tyr Cys Leu Phe Gly
                930                 935                 940

Asp Thr Val Asn Thr Ala Ser Arg Met Glu Ser Thr Gly Leu Pro Leu
945                 950                 955                 960

Arg Ile His Val Ser Gly Ser Thr Ile Ala Ile Leu Lys Arg Thr Glu
                965                 970                 975

Cys Gln Phe Leu Tyr Glu Val Arg Gly Glu Thr Tyr Leu Lys Gly Arg
                980                 985                 990

Gly Asn Glu Thr Thr Tyr Trp Leu  Thr Gly Met Lys Asp  Gln Lys Phe
                995                 1000                1005

Asn Leu  Pro Thr Pro Pro Thr  Val Glu Asn Gln Gln  Arg Leu Gln
            1010                1015                1020
```

Ala Glu Phe Ser Asp Met Ile Ala Asn Ser Leu Gln Lys Arg Gln
       1025                1030                1035

Ala Ala Gly Ile Arg Ser Gln Lys Pro Arg Arg Val Ala Ser Tyr
    1040                1045                1050

Lys Lys Gly Thr Leu Glu Tyr Leu Gln Leu Asn Thr Thr Asp Lys
    1055                1060                1065

Glu Ser Thr Tyr Phe
    1070

<210> SEQ ID NO 229
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Lys Thr Leu Leu Leu Asp Leu Ala Leu Trp Ser Leu Leu Phe Gln
1               5                   10                  15

Pro Gly Trp Leu Ser Phe Ser Ser Gln Val Ser Gln Asn Cys His Asn
            20                  25                  30

Gly Ser Tyr Glu Ile Ser Val Leu Met Met Gly Asn Ser Ala Phe Ala
        35                  40                  45

Glu Pro Leu Lys Asn Leu Glu Asp Ala Val Asn Glu Gly Leu Glu Ile
    50                  55                  60

Val Arg Gly Arg Leu Gln Asn Ala Gly Leu Asn Val Thr Val Asn Ala
65                  70                  75                  80

Thr Phe Met Tyr Ser Asp Gly Leu Ile His Asn Ser Gly Asp Cys Arg
                85                  90                  95

Ser Ser Thr Cys Glu Gly Leu Asp Leu Leu Arg Lys Ile Ser Asn Ala
            100                 105                 110

Gln Arg Met Gly Cys Val Leu Ile Gly Pro Ser Cys Thr Tyr Ser Thr
        115                 120                 125

Phe Gln Met Tyr Leu Asp Thr Glu Leu Ser Tyr Pro Met Ile Ser Ala
    130                 135                 140

Gly Ser Phe Gly Leu Ser Cys Asp Tyr Lys Glu Thr Leu Thr Arg Leu
145                 150                 155                 160

Met Ser Pro Ala Arg Lys Leu Met Tyr Phe Leu Val Asn Phe Trp Lys
                165                 170                 175

Thr Asn Asp Leu Pro Phe Lys Thr Tyr Ser Trp Ser Thr Ser Tyr Val
            180                 185                 190

Tyr Lys Asn Gly Thr Glu Thr Glu Asp Cys Phe Trp Tyr Leu Asn Ala
        195                 200                 205

Leu Glu Ala Ser Val Ser Tyr Phe Ser His Glu Leu Gly Phe Lys Val
    210                 215                 220

Val Leu Arg Gln Asp Lys Glu Phe Gln Asp Ile Leu Met Asp His Asn
225                 230                 235                 240

Arg Lys Ser Asn Val Ile Ile Met Cys Gly Gly Pro Glu Phe Leu Tyr
                245                 250                 255

Lys Leu Lys Gly Asp Arg Ala Val Ala Glu Asp Ile Val Ile Ile Leu
            260                 265                 270

Val Asp Leu Phe Asn Asp Gln Tyr Phe Glu Asp Asn Val Thr Ala Pro
        275                 280                 285

Asp Tyr Met Lys Asn Val Leu Val Leu Thr Leu Ser Pro Gly Asn Ser

```
                     290                 295                 300
Leu Leu Asn Ser Ser Phe Ser Arg Asn Leu Ser Pro Thr Lys Arg Asp
305                 310                 315                 320

Phe Ala Leu Ala Tyr Leu Asn Gly Ile Leu Phe Gly His Met Leu
                325                 330                 335

Lys Ile Phe Leu Glu Asn Gly Glu Asn Ile Thr Thr Pro Lys Phe Ala
                340                 345                 350

His Ala Phe Arg Asn Leu Thr Phe Glu Gly Tyr Asp Gly Pro Val Thr
                355                 360                 365

Leu Asp Asp Trp Gly Asp Val Asp Ser Thr Met Val Leu Leu Tyr Thr
            370                 375                 380

Ser Val Asp Thr Lys Lys Tyr Lys Val Leu Leu Thr Tyr Asp Thr His
385                 390                 395                 400

Val Asn Lys Thr Tyr Pro Val Asp Met Ser Pro Thr Phe Thr Trp Lys
                405                 410                 415

Asn Ser Lys Leu
            420

<210> SEQ ID NO 230
<211> LENGTH: 1444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gaattcctca ccatgggatg gagctgtatc atcctcttct tggtagcaac agctacaggt    60
gtccactccc aggtgcagct acagcagtgg ggcgcaggac tgttgaagcc ttcggagacc   120
ctgtccctca cctgcgctgt ctttggtggg tctttcagtg ttactactg gagctggatc    180 cgccagcccc cagggaaggg gctggagtgg attggggaaa tcaatcatcg tggaaacacc   240
aacgacaacc cgtccctcaa gagtcgagtc accatatcag tagacacgtc caagaaccag   300
ttcgccctga gctgagttc tgtgaccgcc gcggacacgg ctgtttatta ctgtgcgaga   360
gaacgtggat acacctatgg taactttgac cactggggcc agggaaccct ggtcaccgtc    420
agctcagcct ccaccaaggg cccatcggtc ttccccctgg cacctcctc caagagcacc    480 tctggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
```

-continued

```
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaataat agggataaca gggtaatact    1440
agag                                                                 1444

<210> SEQ ID NO 231
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Gly Trp Ser Cys Ile Ile Leu Phe Leu Val Ala Thr Ala Thr Gly
1               5                   10                  15

Val His Ser Gln Val Gln Leu Gln Gln Trp Gly Ala Gly Leu Leu Lys
                20                  25                  30

Pro Ser Glu Thr Leu Ser Leu Thr Cys Ala Val Phe Gly Gly Ser Phe
            35                  40                  45

Ser Gly Tyr Tyr Trp Ser Trp Ile Arg Gln Pro Pro Gly Lys Gly Leu
        50                  55                  60

Glu Trp Ile Gly Glu Ile Asn His Arg Gly Asn Thr Asn Asp Asn Pro
65                  70                  75                  80

Ser Leu Lys Ser Arg Val Thr Ile Ser Val Asp Thr Ser Lys Asn Gln
                85                  90                  95

Phe Ala Leu Lys Leu Ser Ser Val Thr Ala Ala Asp Thr Ala Val Tyr
            100                 105                 110

Tyr Cys Ala Arg Glu Arg Gly Tyr Thr Tyr Gly Asn Phe Asp His Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320
```

```
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465

<210> SEQ ID NO 232
<211> LENGTH: 722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
gcggccgcct caccatggga tggagctgta tcatcctctt cttggtagca acagctacag      60
gtgtccactc cgaaatagtg atgacgcagt ctccagccac cctgtctgtg tctccagggg     120
aaagagccac cctctcctgc agggccagtc agagtgttag cagaaactta gcctggtatc     180
agcagaaacc tggccaggct cccaggctcc tcatctatgg tgcatccacc agggccactg     240
gaatcccagc caggttcagt ggcagtgggt ctgggacaga gttcactctc accatcggca     300
gcctgcagtc tgaagatttt gcagtttatt actgtcagca gtataaaacc tggcctcgga     360
cgttcggcca agggaccaac gtggaaatca aacgtacggt ggctgcacca tctgtcttca     420
tcttcccgcc atctgatgag cagttgaaat ctggaactgc ctctgttgtg tgcctgctga     480
ataacttcta tcccagagag gccaaagtac agtggaaggt ggataacgcc ctccaatcgg     540
gtaactccca ggagagtgtc acagagcagg acagcaagga cagcacctac agcctcagca     600
gcaccctgac cctgagcaaa gcagactacg agaaacacaa agtctacgcc tgcgaagtca     660
cccatcaggg cctgagctcg cccgtcacaa agagcttcaa caggggagag tgttagtcta     720
ga                                                                    722

<210> SEQ ID NO 233
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Met Gly Trp Ser Cys Ile Ile Leu Phe Leu Val Ala Thr Ala Thr Gly
```

```
              1               5                  10                 15
Val His Ser Glu Ile Val Met Thr Gln Ser Pro Ala Thr Leu Ser Val
              20                 25                 30

Ser Pro Gly Glu Arg Ala Thr Leu Ser Cys Arg Ala Ser Gln Ser Val
              35                 40                 45

Ser Arg Asn Leu Ala Trp Tyr Gln Gln Lys Pro Gly Gln Ala Pro Arg
 50                 55                 60

Leu Leu Ile Tyr Gly Ala Ser Thr Arg Ala Thr Gly Ile Pro Ala Arg
 65                 70                 75                 80

Phe Ser Gly Ser Gly Ser Gly Thr Glu Phe Thr Leu Thr Ile Gly Ser
              85                 90                 95

Leu Gln Ser Glu Asp Phe Ala Val Tyr Tyr Cys Gln Gln Tyr Lys Thr
              100                105                110

Trp Pro Arg Thr Phe Gly Gln Gly Thr Asn Val Glu Ile Lys Arg Thr
              115                120                125

Val Ala Ala Pro Ser Val Phe Ile Phe Pro Pro Ser Asp Glu Gln Leu
 130                135                140

Lys Ser Gly Thr Ala Ser Val Val Cys Leu Leu Asn Asn Phe Tyr Pro
145                 150                155                160

Arg Glu Ala Lys Val Gln Trp Lys Val Asp Asn Ala Leu Gln Ser Gly
              165                170                175

Asn Ser Gln Glu Ser Val Thr Glu Gln Asp Ser Lys Asp Ser Thr Tyr
              180                185                190

Ser Leu Ser Ser Thr Leu Thr Leu Ser Lys Ala Asp Tyr Glu Lys His
              195                200                205

Lys Val Tyr Ala Cys Glu Val Thr His Gln Gly Leu Ser Ser Pro Val
 210                215                220

Thr Lys Ser Phe Asn Arg Gly Glu Cys
225                 230

<210> SEQ ID NO 234
<211> LENGTH: 112
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ataagaatgc ggccgcctca ccatgggatg gagctgtatc atcctcttct tggtagcaac      60
agctacaggt gtccactccg aaatagtgat gacgcagtct ccagccaccc tg             112

<210> SEQ ID NO 235
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gccaccgtac gtttgatttc cacgttggtc ccttggccga acgtc                      45

<210> SEQ ID NO 236
<211> LENGTH: 103
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 236
ccggaattcc tcaccatggg atggagctgt atcatcctct tcttggtagc aacagctaca     60
ggtgtccact cccaggtgca gctacagcag tggggcgcag gac                      103

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ggaggctgag ctgacggtga ccagggttcc ctggccccag tggtc                     45

<210> SEQ ID NO 238
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
caggtgcagt tgcaggagtc gggcccagga ctggtgaagc cttcggagac cctgtccctc     60
acctgcactg tctctggtgc ctccatcagt cattactact ggagctggat ccggcagccc    120
gccgggaagg gactggaatg gattgggcgt atctatatca gtggggaggac cagctacaac    180 ccctccctca agagtcgagt caccgtgtca gtagacacgt ccaagaacca gttctccctg    240
aagctgagct ctgtgaccgc cgcggacacg gccgtgtatt actgtgcgag agatcggcta    300
actgggtact ttgactactg gggccaggga accctggtca ccgtctcctc ag           352

<210> SEQ ID NO 239
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser His Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Ser Gly Arg Thr Ser Tyr Asn Pro Ser Leu Lys
    50                  55                  60

Ser Arg Val Thr Val Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Leu Thr Gly Tyr Phe Asp Tyr Trp Gly Gln Gly Thr Leu
            100                 105                 110

Val Thr Val Ser Ser
        115
```

<210> SEQ ID NO 240
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccgc tggcatccca     180
gacaggttca gtggcagtgg gtctgggaca gacttcactc tcaccatcag cagactggag     240
cctgaagatt ttgcagtgta ttactgtcag cagtatggta gctccctcac tttcggcgga     300
gggaccaagg tggagatcaa ac                                              322

<210> SEQ ID NO 241
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 242
<211> LENGTH: 353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242
caggtgcagt tgcaggagtc gggcccagga ctggtgaagc cttcggagac cctgtccctc      60
acctgcactg tctctggtgc ctccatcagt cattactact ggagctggat ccggcagccc     120
gccgggaagg gactggaatg gattgggcgt atctatatca gtgggaggac cagctacaac     180
ccctccctca agagtcgagt caccgtgtca gtagacacgt ccaagaacca gttctccctg     240
aagctgagct ctgtgaccgc cgcggacacg gccgtgtatt actgtgcgag agatcggcta     300
actgggtact ttgactactg gggccaggga accctggtca ccgtctcctc agc            353

-continued

```
<210> SEQ ID NO 243
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser His Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Ser Gly Arg Thr Ser Tyr Asn Pro Ser Leu Lys
    50                  55                  60

Ser Arg Val Thr Val Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Leu Thr Gly Tyr Phe Asp Tyr Trp Gly Gln Gly Thr Leu
            100                 105                 110

Val Thr Val Ser Ser
        115

<210> SEQ ID NO 244
<211> LENGTH: 329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtacatcca gcagggccac tggcatccca     180
gacaggttca gtggcagtgg gtctgggaca gacttcactc tcaccatcag cagactggag     240
cctgaagact ttgcagtgta ttactgtcag cagtatggta gctcacccat gtgcagtttt     300
ggccagggga ccaagctgga gatcaaacg                                         329

<210> SEQ ID NO 245
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Met Cys Ser Phe Gly Gln Gly Thr Lys Leu Glu Ile Lys
            100                 105

<210> SEQ ID NO 246
<211> LENGTH: 362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
gaggtgcagc tgttggagtc tgggggaggc ttggtacagc ctgggggggtc cctgagactc      60 tcctgtgcag cctctggatt cacctttagc cgctatgcca tgaactgggt ccgccaggct     120
ccagggaagg ggctggagtg ggtctcaggt attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatcgc     300 gattttttgga gtggtccatt tgactactgg ggccagggaa ccctggtcac cgtctcctca     360
gc                                                                    362

<210> SEQ ID NO 247
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Asp Phe Trp Ser Gly Pro Phe Asp Tyr Trp Gly Gln
            100                 105                 110

Gly Thr Leu Val Thr Val Ser Ser
        115                 120

<210> SEQ ID NO 248
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248

```
gaaatagtga tgacgccgtc ttcagccacc ctgtctgtgt ctccagggga aagagccacc    60
ctctcctgta gggccagtca gagtgttagt agaagcttag cctggtacca gcagaaacct   120
ggccaggctc ccaggctcct catctacggt gcatccacca gggccactgg gatcccagcc   180
aggttcagtg gcagtgggtc tgggacagaa ttcactctca ccatcagcag cctgcagtct   240
gaagatgttg cagtttatta ctgtcagcag tataataact ggatgtgcag ttttggccag   300
gggaccaagc tggagatcaa acg                                          323
```

<210> SEQ ID NO 249
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Glu Ile Val Met Thr Pro Ser Ser Ala Thr Leu Ser Val Ser Pro Gly
1               5                   10                  15

Glu Arg Ala Thr Leu Ser Cys Arg Ala Ser Gln Ser Val Ser Arg Ser
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Val Ala Val Tyr Tyr Cys Gln Gln Tyr Asn Asn Trp Met Cys
                85                  90                  95

Ser Phe Gly Gln Gly Thr Lys Leu Glu Ile Lys
            100                 105
```

<210> SEQ ID NO 250
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250

```
cattactact ggagc                                                    15
```

<210> SEQ ID NO 251
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

```
His Tyr Tyr Trp Ser
1               5
```

<210> SEQ ID NO 252
<211> LENGTH: 48
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 252
cgtatctata tcagtgggag gaccagctac aacccctccc tcaagagt                    48

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Arg Ile Tyr Ile Ser Gly Arg Thr Ser Tyr Asn Pro Ser Leu Lys Ser
1               5                   10                  15

<210> SEQ ID NO 254
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gatcggctaa ctgggtactt tgactac                                           27

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asp Arg Leu Thr Gly Tyr Phe Asp Tyr
1               5

<210> SEQ ID NO 256
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
agggccagtc agagtgttag cagcagctac ttagcc                                 36

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Gln Ser Val Ser Ser Ser Tyr Leu Ala
1               5                   10

<210> SEQ ID NO 258
<211> LENGTH: 21
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 258
ggtgcatcca gcagggccgc t  21

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Gly Ala Ser Ser Arg Ala Ala
1     5

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 260
cagcagtatg gtagctccct cact  24

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Gln Gln Tyr Gly Ser Ser Leu Thr
1     5

<210> SEQ ID NO 262
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
cattactact ggagc  15

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

His Tyr Tyr Trp Ser
1     5

<210> SEQ ID NO 264

```
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
cgtatctata tcagtgggag gaccagctac aacccctccc tcaagagt                   48

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Ile Tyr Ile Ser Gly Arg Thr Ser Tyr Asn Pro Ser Leu Lys Ser
1               5                   10                  15

<210> SEQ ID NO 266
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gatcggctaa ctgggtactt tgactac                                          27

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asp Arg Leu Thr Gly Tyr Phe Asp Tyr
1               5

<210> SEQ ID NO 268
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
agggccagtc agagtgttag cagcagctac ttagcc                                36

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Ala Ser Gln Ser Val Ser Ser Ser Tyr Leu Ala
1               5                   10
```

```
<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ggtacatcca gcagggccac t                                              21

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gly Thr Ser Ser Arg Ala Thr
1               5

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cagcagtatg gtagctcacc catgtgcagt                                     30

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Gln Tyr Gly Ser Ser Pro Met Cys Ser
1               5                   10

<210> SEQ ID NO 274
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
cgctatgcca tgaac                                                     15

<210> SEQ ID NO 275
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Tyr Ala Met Asn
```

<210> SEQ ID NO 276
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggtattagtg gtagtggtgg tagcacatac tacgcagact ccgtgaaggg c         51

<210> SEQ ID NO 277
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gly Ile Ser Gly Ser Gly Gly Ser Thr Tyr Tyr Ala Asp Ser Val Lys
1               5                   10                  15
Gly

<210> SEQ ID NO 278
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gatcgcgatt tttggagtgg tccatttgac tac                              33

<210> SEQ ID NO 279
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Arg Asp Phe Trp Ser Gly Pro Phe Asp Tyr
1               5                   10

<210> SEQ ID NO 280
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
agggccagtc agagtgttag tagaagctta gcc                              33

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Ala Ser Gln Ser Val Ser Arg Ser Leu Ala
1               5                   10

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ggtgcatcca ccagggccac t                                             21

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Ala Ser Thr Arg Ala Thr
1               5

<210> SEQ ID NO 284
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
cagcagtata ataactggat gtgcagt                                       27

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Gln Tyr Asn Asn Trp Met Cys Ser
1               5

<210> SEQ ID NO 286
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286
caggtgcagc tacagcagtg gggcgcagga ctgttgaagc cttcggagac cctgtccctc    60
acctgcgctg tctttggtgg gtccttcagt ggttactact ggagctggat ccgccagccc   120
ccagggaagg ggctggagtg gattggggaa atcaatcatc gtggaaacac caacgacaac   180
ccgtccctca agagtcgagt caccatatca gtagacacgt ccaagaacca gttcgccctg   240

```
aagctgagtt ctgtgaccgc cgcggacacg gctgtttatt actgtgcgag agaacgtgga    300
tacacctatg gtaactttga ccactggggc cagggaaccc tggtcaccgt ctcctca      357
```

<210> SEQ ID NO 287
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser
        115

<210> SEQ ID NO 288
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288

```
gaaattgtgt tgacgcagtc tccaggcacc ctgtctttgt ctccagggga aagagccacc    60
ctctcctgca gggccagtca gagtgttagc agcaggtact tagcctggta ccagcagaaa   120
cctggccagg ctcccaggct cctcatctat ggtgcatcca gcagggccac tggcacccca   180
gacaggttca gtggcagtgg gtctgggaca gacttcactc tcaccatcag cagactggag   240
cctgaagatt ttgcagtgta tttctgtcag cagtatgaaa ggtcattcac tttcggccct   300
gggaccaaag tggat                                                    315
```

<210> SEQ ID NO 289
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

```
Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Thr Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Glu Arg Ser Phe
                 85                  90                  95

Thr Phe Gly Pro Gly Thr Lys Val Asp
            100                 105

<210> SEQ ID NO 290
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ggttactact ggagc                                                          15

<210> SEQ ID NO 291
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Tyr Tyr Trp Ser
 1               5

<210> SEQ ID NO 292
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gaaatcaatc atcgtggaaa caccaacgac aacccgtccc tcaag                         45

<210> SEQ ID NO 293
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Glu Ile Asn His Arg Gly Asn Thr Asn Asp Asn Pro Ser Leu Lys Ser
 1               5                  10                  15

<210> SEQ ID NO 294
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
```

-continued

```
gaacgtggat acacctatgg taactttgac cac                                    33

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Glu Arg Gly Tyr Thr Tyr Gly Asn Phe Asp His
1               5                   10

<210> SEQ ID NO 296
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
agggccagtc agagtgttag cagcaggtac ttagcct                                37

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Arg Ala Ser Gln Ser Val Ser Ser Arg Tyr Leu Ala
1               5                   10

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ggtgcatcca gcagggccac tg                                                22

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Ala Ser Ser Arg Ala Thr
1               5

<210> SEQ ID NO 300
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 300
cagcagtatg aaaggtcatt cactt                                    25

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Gln Tyr Glu Arg Ser Phe Thr
1               5

<210> SEQ ID NO 302
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (4)..(4)
<223> OTHER INFORMATION: Met or Trp
<220> FEATURE:
<221> NAME/KEY: MOD_RES
<222> LOCATION: (5)..(5)
<223> OTHER INFORMATION: Ser or Asn

<400> SEQUENCE: 302

Xaa Xaa Xaa Xaa Xaa
1               5

<210> SEQ ID NO 303
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid or not present
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Thr or Ile
<220> FEATURE:
<221> NAME/KEY: MOD_RES
<222> LOCATION: (10)..(10)
<223> OTHER INFORMATION: Tyr, Thr, or Ser
<220> FEATURE:
<221> NAME/KEY: MOD_RES

```
<222> LOCATION: (11)..(12)
<223> OTHER INFORMATION: Any amino acid
<220> FEATURE:
<221> NAME/KEY: MOD_RES
<222> LOCATION: (13)..(13)
<223> OTHER INFORMATION: Leu or Val
<220> FEATURE:
<221> NAME/KEY: MOD_RES
<222> LOCATION: (15)..(15)
<223> OTHER INFORMATION: Ser or Gly

<400> SEQUENCE: 303

Xaa Ile Xaa Xaa Ser Gly Xaa Xaa Xaa Xaa Xaa Xaa Xaa Lys Xaa
1               5                   10                  15

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(6)
<223> OTHER INFORMATION: Any amino acid and this region may encompass 4
      to 6 residues
<220> FEATURE:
<221> NAME/KEY: MOD_RES
<222> LOCATION: (8)..(10)
<223> OTHER INFORMATION: Any amino acid and this region may encompass 2
      to 3 residues

<400> SEQUENCE: 304

Xaa Xaa Xaa Xaa Xaa Xaa Gly Xaa Xaa Xaa Asp Tyr
1               5                   10

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (6)..(6)
<223> OTHER INFORMATION: Val or Leu
<220> FEATURE:
<221> NAME/KEY: MOD_RES
<222> LOCATION: (7)..(7)
<223> OTHER INFORMATION: Ser or Leu
<220> FEATURE:
<221> NAME/KEY: MOD_RES
<222> LOCATION: (8)..(16)
<223> OTHER INFORMATION: Any amino acid and this region may encompass 5
      to 9 residues

<400> SEQUENCE: 305

Xaa Xaa Ser Gln Ser Xaa Xaa Xaa Xaa Xaa Xaa Xaa Xaa Xaa Xaa
1               5                   10                  15

<210> SEQ ID NO 306
<211> LENGTH: 7
<212> TYPE: PRT
```

<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 306

Xaa Xaa Ser Xaa Arg Xaa Xaa
1               5

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic consensus sequence
<220> FEATURE:
<221> NAME/KEY: MOD_RES
<222> LOCATION: (1)..(1)
<223> OTHER INFORMATION: Gln, His, or Met
<220> FEATURE:
<221> NAME/KEY: MOD_RES
<222> LOCATION: (3)..(3)
<223> OTHER INFORMATION: Tyr or Ser
<220> FEATURE:
<221> NAME/KEY: MOD_RES
<222> LOCATION: (4)..(10)
<223> OTHER INFORMATION: Any amino acid and this region may encompass 5 to 7 residues

<400> SEQUENCE: 307

Xaa Gln Xaa Xaa Xaa Xaa Xaa Xaa Xaa Xaa
1               5                   10

<210> SEQ ID NO 308
<211> LENGTH: 702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 308
atgggatgga gctgtatcat cctcttcttg gtagcaacag ctacaggtgt ccactccgaa 60
atagtgatga cgcagtctcc agccaccctg tctgtgtctc caggggaaag agccaccctc 120
tcctgcaggg ccagtcagag tgttagcaga aacttagcct ggtatcagca gaaacctggc 180
caggctccca ggctcctcat ctatggtgca tccaccaggg ccactggaat cccagccagg 240
ttcagtggca gtgggtctgg gacagagttc actctcacca tcggcagcct gcagtctgaa 300
gattttgcag tttattactg tcagcagtat aaaacctggc ctcggacgtt cggccaaggg 360
accaacgtgg aaatcaaacg tacggtggct gcaccatctg tcttcatctt cccgccatct 420
gatgagcagt tgaaatctgg aactgcctct gttgtgtgcc tgctgaataa cttctatccc 480
agagaggcca aagtacagtg gaaggtggat aacgccctcc aatcgggtaa ctcccaggag 540
agtgtcacag agcaggacag caaggacagc acctacagcc tcagcagcac cctgaccctg 600

| | |
|---|---|
| agcaaagcag actacgagaa acacaaagtc tacgcctgcg aagtcaccca tcagggcctg | 660 |
| agctcgcccg tcacaaagag cttcaacagg ggagagtgtt ag | 702 |

<210> SEQ ID NO 309
<211> LENGTH: 1407
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 309

| | |
|---|---|
| atgggatgga gctgtatcat cctcttcttg gtagcaacag ctacaggtgt ccactcccag | 60 |
| gtgcagctac agcagtgggg cgcaggactg ttgaagcctt cggagaccct gtccctcacc | 120 |
| tgcgctgtct ttggtgggtc tttcagtggt tactactgga gctggatccg ccagccccca | 180 |
| gggaaggggc tggagtggat tgggaaatc aatcatcgtg aaacaccaa cgacaacccg | 240 |
| tccctcaaga gtcgagtcac catatcagta gacacgtcca agaaccagtt cgccctgaag | 300 |
| ctgagttctg tgaccgccgc ggacacggct gtttattact gtgcgagaga acgtggatac | 360 |
| acctatggta actttgacca ctggggccag ggaaccctgg tcaccgtcag ctcagcctcc | 420 |
| accaagggcc catcggtctt ccccctggca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcaccca gacctacatc | 660 |
| tgcaacgtga atcacaagcc cagcaacacc aaggtggaca agaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

<210> SEQ ID NO 310
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 310

| | |
|---|---|
| atggagtttg ggctgagctg gcttttcct gtggctattt taaaaggtgt ccagtgtgag | 60 |
| gtgcagctgt tggagtctgg gggaggcttg gtacagcctg gggggtccct gagactctcc | 120 |

```
tgtgcagcct ctggattcac ctttagccgc tatgccatga actgggtccg ccaggctcca    180
gggaaggggc tggagtgggt ctcaggtatt agtgggagtg gtggtaggac atactacgca    240
gactccgtga agggccggtt caccatctcc agagacaatt ccaagaacac actatatctg    300
caaatgaaca gcctgagagc cgaggacacg gccgtatatt actgtgcgaa agatcgcgat    360
ttttggagtg gtccatttga ctactggggc cagggaaccc tggtcaccgt cagctcagcc    420
tccaccaagg gcccatcggt cttccccctg gcaccctcct ccaagagcac ctctggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttccccc aaacccaag gacaccctca tgatctcccg gacccctgag     840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggatgagctg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaataa                                    1410
```

<210> SEQ ID NO 311
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311

```
atgaggctcc ctgctcagct tctcttcctc ctgctactct ggctcccaga taccactgga     60
gaaatagtga tgacgccgtc ttcagccacc ctgtctgtgt ctccagggga gagagccacc    120
ctctcctgca gggccagtca gagtgttagt agaaacttag cctggtacca gcagaaacct    180
ggccaggctc ccaggctcct catctatggt gcatccacca gggccactgg tatcccagcc    240
aggttcagtg gcagtgggtc tgggacagaa ttcactctca ccatcagcag cctgcagtct    300
gaagattttg cagtttatta ctgtcaccag tatagtaact ggatgtgcag ttttggccag    360
gggaccaagc tggagatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag cacccctgacc   600
ctgagcaaag cagactacga gaaacacaaa gtctacgcct gcgaagtcac ccatcagggc    660
ctgagctcgc ccgtcacaaa gagcttcaac aggggagagt gttag                    705
```

```
<210> SEQ ID NO 312
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Val
<220> FEATURE:
<221> NAME/KEY: MOD_RES
<222> LOCATION: (4)..(4)
<223> OTHER INFORMATION: Ser or Gly

<400> SEQUENCE: 312

Ser Xaa Lys Xaa
1

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (6)..(6)
<223> OTHER INFORMATION: Val or Leu
<220> FEATURE:
<221> NAME/KEY: MOD_RES
<222> LOCATION: (7)..(7)
<223> OTHER INFORMATION: Ser or Leu

<400> SEQUENCE: 313

Xaa Xaa Ser Gln Ser Xaa Xaa
1               5

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Leu Glu Asp Asn Val Thr Ala Pro Asp Tyr
1               5                   10

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Arg Asn Leu Thr Phe Glu Gly Tyr Asp Gly Pro Val Thr Leu Asp
1               5                   10                  15
```

<210> SEQ ID NO 316
<211> LENGTH: 18
<212> TYPE: PRT
<213> ORGANISM: Escherichia coli

<400> SEQUENCE: 316

Asn Thr Phe Tyr Cys Cys Glu Leu Cys Cys Asn Pro Ala Cys Ala Gly
1               5                   10                  15

Cys Tyr

<210> SEQ ID NO 317
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Ser Gln Val Ser Gln Asn Cys His Asn Gly Ser Tyr Glu Ile Ser Val
1               5                   10                  15

Leu Met Met Gly Asn Ser Ala Phe Ala Glu Pro Leu Lys Asn Leu Glu
            20                  25                  30

Asp Ala Val Asn Glu Gly Leu Glu Ile Val Arg Gly Arg Leu Gln Asn
        35                  40                  45

Ala Gly Leu Asn Val Thr Val Asn Ala Thr Phe Met Tyr Ser Asp Gly
    50                  55                  60

Leu Ile His Asn Ser Gly Asp Cys Arg Ser Ser Thr Cys Glu Gly Leu
65                  70                  75                  80

Asp Leu Leu Arg Lys Ile Ser Asn Ala Gln Arg Met Gly Cys Val Leu
                85                  90                  95

Ile Gly Pro Ser Cys Thr Tyr Ser Thr Phe Gln Met Tyr Leu Asp Thr
            100                 105                 110

Glu Leu Ser Tyr Pro Met Ile Ser Ala Gly Ser Phe Gly Leu Ser Cys
        115                 120                 125

Asp Tyr Lys Glu Thr Leu Thr Arg Leu Met Ser Pro Ala Arg Lys Leu
    130                 135                 140

Met Tyr Phe Leu Val Asn Phe Trp Lys Thr Asn Asp Leu Pro Phe Lys
145                 150                 155                 160

Thr Tyr Ser Trp Ser Thr Ser Tyr Val Tyr Lys Asn Gly Thr Glu Thr
                165                 170                 175

Glu Asp Cys Phe Trp Tyr Leu Asn Ala Leu Glu Ala Ser Val Ser Tyr
            180                 185                 190

Phe Ser His Glu Leu Gly Phe Lys Val Val Leu Arg Gln Asp Lys Glu
        195                 200                 205

Phe Gln Asp Ile Leu Met Asp His Asn Arg Lys Ser Asn Val Ile Ile
    210                 215                 220

Met Cys Gly Gly Pro Glu Phe Leu Tyr Lys Leu Lys Gly Asp Arg Ala
225                 230                 235                 240

Val Ala Glu Asp Ile Val Ile Leu Val Asp Leu Phe Asn Asp Gln
                245                 250                 255

Tyr Leu Glu Asp Asn Val Thr Ala Pro Asp Tyr Met Lys Asn Val Leu
            260                 265                 270

Val Leu Thr Leu Ser Pro Gly Asn Ser Leu Leu Asn Ser Ser Phe Ser
        275                 280                 285

Arg Asn Leu Ser Pro Thr Lys Arg Asp Phe Ala Leu Ala Tyr Leu Asn
290                 295                 300

Gly Ile Leu Leu Phe Gly His Met Leu Lys Ile Phe Leu Glu Asn Gly
305                 310                 315                 320

Glu Asn Ile Thr Thr Pro Lys Phe Ala His Ala Phe Arg Asn Leu Thr
                325                 330                 335

Phe Glu Gly Tyr Asp Gly Pro Val Thr Leu Asp Asp Trp Gly Asp Val
            340                 345                 350

Asp Ser Thr Met Val Leu Leu Tyr Thr Ser Val Asp Thr Lys Lys Tyr
        355                 360                 365

Lys Val Leu Leu Thr Tyr Asp Thr His Val Asn Lys Thr Tyr Pro Val
370                 375                 380

Asp Met Ser Pro Thr Phe Thr Trp Lys Asn Ser Lys Leu Pro Asn Asp
385                 390                 395                 400

Ile Thr Gly Arg Gly Pro Gln Pro Lys Ser Ser Asp Lys Thr His Thr
                405                 410                 415

Cys Pro Pro Cys Pro Ala Pro Glu Leu Ala Gly Ala Pro Ser Val Phe
            420                 425                 430

Leu Phe Pro Pro Lys Pro Lys Asp Thr Leu Met Ile Ser Arg Thr Pro
        435                 440                 445

Glu Val Thr Cys Val Val Val Asp Val Ser His Glu Asp Pro Glu Val
450                 455                 460

Lys Phe Asn Trp Tyr Val Asp Gly Val Glu Val His Asn Ala Lys Thr
465                 470                 475                 480

Lys Pro Arg Glu Glu Gln Tyr Asn Ser Thr Tyr Arg Val Val Ser Val
                485                 490                 495

Leu Thr Val Leu His Gln Asp Trp Leu Asn Gly Lys Glu Tyr Lys Cys
            500                 505                 510

Lys Val Ser Asn Lys Ala Leu Pro Ala Pro Ile Glu Lys Thr Ile Ser
        515                 520                 525

Lys Ala Lys Gly Gln Pro Arg Glu Pro Gln Val Tyr Thr Leu Pro Pro
530                 535                 540

Ser Arg Asp Glu Leu Thr Lys Asn Gln Val Ser Leu Thr Cys Leu Val
545                 550                 555                 560

Lys Gly Phe Tyr Pro Ser Asp Ile Ala Val Glu Trp Glu Ser Asn Gly
                565                 570                 575

Gln Pro Glu Asn Asn Tyr Lys Thr Thr Pro Pro Val Leu Asp Ser Asp
            580                 585                 590

Gly Ser Phe Phe Leu Tyr Ser Lys Leu Thr Val Asp Lys Ser Arg Trp
        595                 600                 605

Gln Gln Gly Asn Val Phe Ser Cys Ser Val Met His Glu Ala Leu His
610                 615                 620

Asn His Tyr Thr Gln Lys Ser Leu Ser Leu Ser Pro Gly Lys
625                 630                 635

<210> SEQ ID NO 318
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Ser Gln Val Ser Gln Asn Cys His Asn Gly Ser Tyr Glu Ile Ser Val
1               5                   10                  15

-continued

```
Leu Met Met Gly Asn Ser Ala Phe Ala Glu Pro Leu Lys Asn Leu Glu
         20                  25                  30

Asp Ala Val Asn Glu Gly Leu Glu Ile Val Arg Gly Arg Leu Gln Asn
             35                  40                  45

Ala Gly Leu Asn Val Thr Val Asn Ala Thr Phe Met Tyr Ser Asp Gly
 50                  55                  60

Leu Ile His Asn Ser Gly Asp Cys Arg Ser Thr Cys Glu Gly Leu
 65                  70                  75                  80

Asp Leu Leu Arg Lys Ile Ser Asn Ala Gln Arg Met Gly Cys Val Leu
                 85                  90                  95

Ile Gly Pro Ser Cys Thr Tyr Ser Thr Phe Gln Met Tyr Leu Asp Thr
                100                 105                 110

Glu Leu Ser Tyr Pro Met Ile Ser Ala Gly Ser Phe Gly Leu Ser Cys
            115                 120                 125

Asp Tyr Lys Glu Thr Leu Thr Arg Leu Met Ser Pro Ala Arg Lys Leu
130                 135                 140

Met Tyr Phe Leu Val Asn Phe Trp Lys Thr Asn Asp Leu Pro Phe Lys
145                 150                 155                 160

Thr Tyr Ser Trp Ser Thr Ser Tyr Val Tyr Lys Asn Gly Thr Glu Thr
                165                 170                 175

Glu Asp Cys Phe Trp Tyr Leu Asn Ala Leu Glu Ala Ser Val Ser Tyr
            180                 185                 190

Phe Ser His Glu Leu Gly Phe Lys Val Val Leu Arg Gln Asp Lys Glu
        195                 200                 205

Phe Gln Asp Ile Leu Met Asp His Asn Arg Lys Ser Asn Val Ile Ile
    210                 215                 220

Met Cys Gly Gly Pro Glu Phe Leu Tyr Lys Leu Lys Gly Asp Arg Ala
225                 230                 235                 240

Val Ala Glu Asp Ile Val Ile Leu Val Asp Leu Phe Asn Asp Gln
                245                 250                 255

Tyr Leu Glu Asp Asn Val Thr Ala Pro Asp Tyr Met Lys Asn Val Leu
            260                 265                 270

Val Leu Thr Leu Ser Pro Gly Asn Ser Leu Leu Asn Ser Ser Phe Ser
        275                 280                 285

Arg Asn Leu Ser Pro Thr Lys Arg Asp Phe Ala Leu Ala Tyr Leu Asn
    290                 295                 300

Gly Ile Leu Leu Phe Gly His Met Leu Lys Ile Phe Leu Glu Asn Gly
305                 310                 315                 320

Glu Asn Ile Thr Thr Pro Lys Phe Ala His Ala Phe Arg Asn Leu Thr
                325                 330                 335

Phe Glu Gly Tyr Asp Gly Pro Val Thr Leu Asp Asp Trp Gly Asp Val
            340                 345                 350

Asp Ser Thr Met Val Leu Leu Tyr Thr Ser Val Asp Thr Lys Lys Tyr
        355                 360                 365

Lys Val Leu Leu Thr Tyr Asp Thr His Val Asn Lys Thr Tyr Pro Val
    370                 375                 380

Asp Met Ser Pro Thr Phe Thr Trp Lys Asn Ser Lys Leu Pro Asn Asp
385                 390                 395                 400

Ile Thr Gly Arg Gly Pro Gln Pro Lys Ser Ser Asp Lys Thr His Thr
                405                 410                 415

Cys Pro Pro Cys Pro Ala Pro Glu Leu Ala Gly Ala Pro Ser Val Phe
            420                 425                 430
```

Leu Phe Pro Pro Lys Pro Lys Asp Thr Leu Met Ile Ser Arg Thr Pro
            435                 440                 445

Glu Val Thr Cys Val Val Val Asp Val Ser His Glu Asp Pro Glu Val
        450                 455                 460

Lys Phe Asn Trp Tyr Val Asp Gly Val Glu Val His Asn Ala Lys Thr
465                 470                 475                 480

Lys Pro Arg Glu Glu Gln Tyr Asn Ser Thr Tyr Arg Val Val Ser Val
                485                 490                 495

Leu Thr Val Leu His Gln Asp Trp Leu Asn Gly Lys Glu Tyr Lys Cys
            500                 505                 510

Lys Val Ser Asn Lys Ala Leu Pro Ala Pro Ile Glu Lys Thr Ile Ser
        515                 520                 525

Lys Ala Lys Gly Gln Pro Arg Glu Pro Gln Val Tyr Thr Leu Pro Pro
530                 535                 540

Ser Arg Asp Glu Leu Thr Lys Asn Gln Val Ser Leu Thr Cys Leu Val
545                 550                 555                 560

Lys Gly Phe Tyr Pro Ser Asp Ile Ala Val Glu Trp Glu Ser Asn Gly
                565                 570                 575

Gln Pro Glu Asn Asn Tyr Lys Thr Thr Pro Pro Val Leu Asp Ser Asp
            580                 585                 590

Gly Ser Phe Phe Leu Tyr Ser Lys Leu Thr Val Asp Lys Ser Arg Trp
        595                 600                 605

Gln Gln Gly Asn Val Phe Ser Cys Ser Val Met His Glu Ala Leu His
610                 615                 620

Asn His Tyr Thr Gln Lys Ser Leu Ser Leu Ser Pro Gly Leu Asp Leu
625                 630                 635                 640

Asp Asp Val Cys Ala Glu Ala Gln Asp Gly Glu Leu Asp Gly Leu Trp
                645                 650                 655

Thr Thr Ile Thr Ile Phe Ile Ser Leu Phe Leu Leu Ser Val Cys Tyr
            660                 665                 670

Ser Ala Ser Val Thr Leu Phe Lys Val Lys Trp Ile Phe Ser Ser Val
        675                 680                 685

Val Glu Leu Lys Gln Thr Ile Ser Pro Asp Tyr Arg Asn Met Ile Gly
690                 695                 700

Gln Gly Ala
705

<210> SEQ ID NO 319
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Phe Leu Gly
1

ANTI-GCC ANTIBODY MOLECULES AND RELATED COMPOSITIONS AND METHODS

RELATED APPLICATIONS

The present application is a divisional of U.S. patent application Ser. No. 14/293,802, filed Jun. 2, 2014, which is a continuation of U.S. patent application Ser. No. 12/910,393, filed Oct. 22, 2010 (now U.S. Pat. No. 8,785,600), which claims the benefit of U.S. Provisional Application Ser. No. 61/254,474, filed Oct. 23, 2009. The contents of the prior applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 21, 2010, is named M2051702.txt and is 165,791 bytes in size.

FIELD OF INVENTION

The invention relates to antibody molecules which bind GCC, as well as to related molecules, e.g., nucleic acids which encode such antibody molecules, compositions, and related methods, e.g., therapeutic and diagnostic methods.

BACKGROUND

Guanylyl cyclase C (GCC) is a transmembrane cell surface receptor that functions in the maintenance of intestinal fluid, electrolyte homeostasis and cell proliferation, see, e.g., Carrithers et al., *Proc. Natl. Acad. Sci. USA* 100:3018-3020 (2003). GCC is expressed at the mucosal cells lining the small intestine, large intestine and rectum (Carrithers et al., *Dis Colon Rectum* 39: 171-181 (1996)). GCC expression is maintained upon neoplastic transformation of intestinal epithelial cells, with expression in all primary and metastatic colorectal tumors (Carrithers et al., *Dis Colon Rectum* 39: 171-181 (1996); Buc et al. *Eur J Cancer* 41: 1618-1627 (2005); Carrithers et al., *Gastroenterology* 107: 1653-1661 (1994)).

SUMMARY

The inventors have discovered numerous anti-GCC antibodies, including both human and murine antibodies. Accordingly, in one aspect, the invention features an anti-GCC antibody molecule, as disclosed herein. The anti-GCC antibody molecules are useful as naked antibody molecules and as components of immunoconjugates. Accordingly, in another aspect, the invention features immunoconjugates comprising an anti-GCC antibody molecule and a therapeutic agent or label. The invention also features pharmaceutical compositions comprising the anti-GCC antibody molecules and immunoconjugates described herein. The invention also features methods of using the anti-GCC antibody molecules and immunoconjugates described herein for detection of GCC and of cells or tissues that express GCC; for diagnosis, prognosis, imaging, or staging of a GCC-mediated disease; for modulating an activity or function of a GCC protein; and for treatment of a GCC-mediated disease, as described herein. In another aspect, the invention also features isolated and/or recombinant nucleic acids encoding anti-GCC antibody molecule amino acid sequences, as well as vectors and host cells comprising such nucleic acids, and methods for producing anti-GCC antibody molecules.

All publications, patent applications, patents and other references mentioned herein are incorporated by references in their entirety.

Other features, objects, and advantages of the invention(s) disclosed herein will be apparent from the description and drawings, and from the claims.

DETAILED DESCRIPTION

Guanylyl Cyclase C

Figure 1:
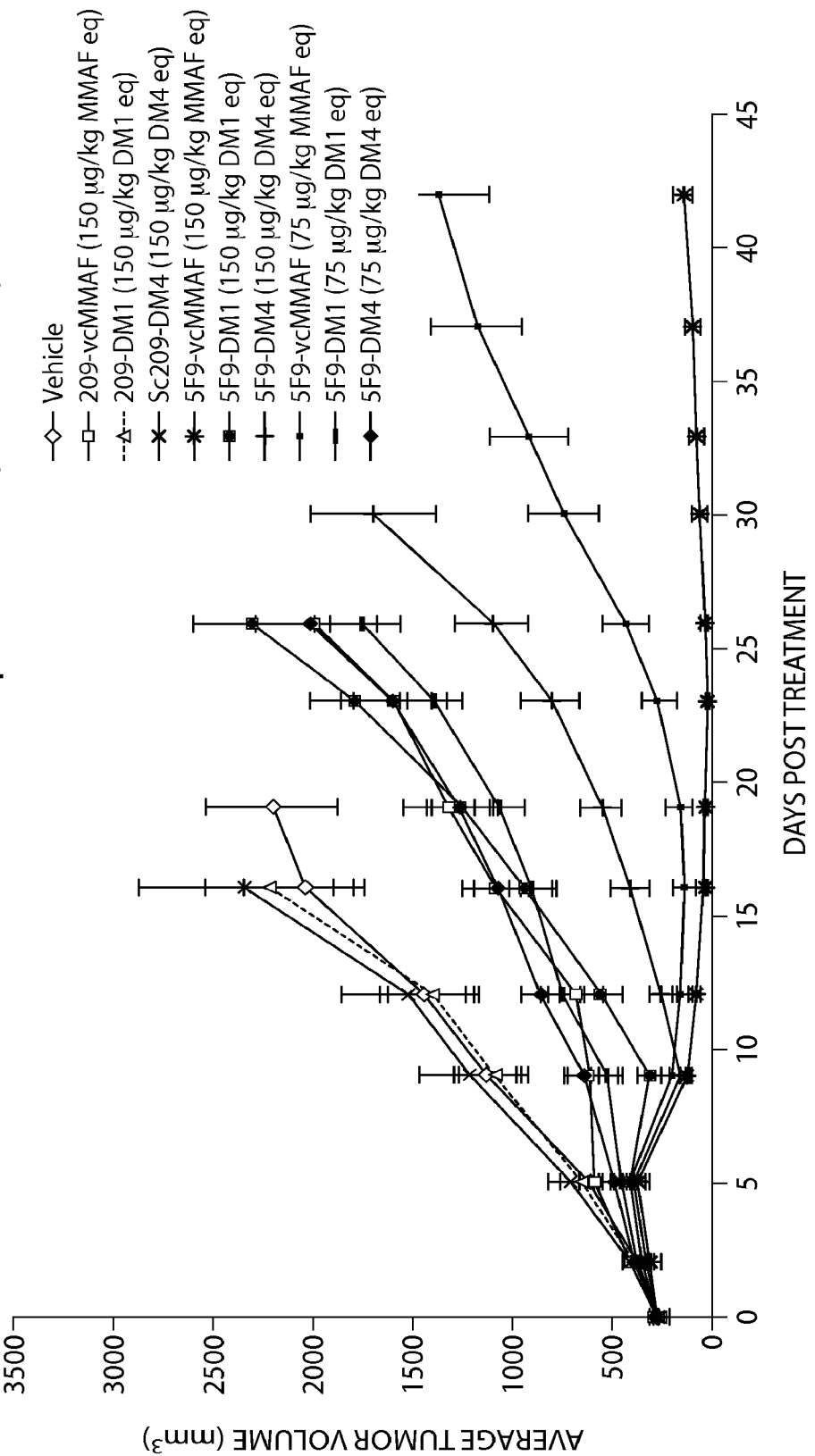
FIG. 1 depicts tumor growth in 293-GCC #2 bearing SCID mice treated with 5F9vc-MMAF, -DM1, and -DM4 on a q14d schedule.

Guanylyl cyclase C (GCC) (also known as STAR, ST Receptor, GUC2C, and GUCY2C) is a transmembrane cell surface receptor that functions in the maintenance of intestinal fluid, electrolyte homeostasis and cell proliferation (Carrithers et al., *Proc Natl Acad Sci USA* 100: 3018-3020 (2003); Mann et al., *Biochem Biophys Res Commun* 239: 463-466 (1997); Pitari et al., *Proc Natl Acad Sci USA* 100: 2695-2699 (2003)); GenBank Accession No. NM_004963, each of which is incorporated herein by reference). This function is mediated through binding of guanylin (Wiegand et al. FEBS Lett. 311:150-154 (1992)). GCC also is a receptor for heat-stable enterotoxin (ST, e.g., having an amino acid sequence of NTFYCCELCCNPACAGCY, SEQ ID NO:316) which is a peptide produced by *E. coli*, as well as other infectious organisms (Rao, M. C. *Ciba Found. Symp.* 112:74-93 (1985); Knoop F. C. and Owens, M. *J. Pharmacol. Toxicol. Methods* 28:67-72 (1992)). Binding of ST to GCC activates a signal cascade that results in enteric disease, e.g., diarrhea.

```
Nucleotide sequence for human GCC (GenBank Accession No.
NM_004963):
                                                      (SEQ ID NO: 227)
   1 atgaagacgt tgctgttgga cttggctttg tggtcactgc tcttccagcc cgggtggctg 61 tcctttagtt cccaggtgag tcagaactgc cacaatggca gctatgaaat cagcgtcctg 121 atgatgggca actcagcctt tgcagagccc ctgaaaaact tggaagatgc ggtgaatgag 181 gggctggaaa tagtgagagg acgtctgcaa aatgctggcc taaatgtgac tgtgaacgct
```

-continued

```
 241 actttcatgt attcggatgg tctgattcat aactcaggcg actgccggag tagcacctgt
 301 gaaggcctcg acctactcag gaaaatttca aatgcacaac ggatgggctg tgtcctcata
 361 gggccctcat gtacatactc caccttccag atgtaccttg acacagaatt gagctacccc
 421 atgatctcag ctggaagttt tggattgtca tgtgactata agaaacctt aaccaggctg
 481 atgtctccag ctagaaagtt gatgtacttc ttggttaact tttggaaaac caacgatctg
 541 cccttcaaaa cttattcctg gagcacttcg tatgtttaca agaatggtac agaaactgag
 601 gactgtttct ggtaccttaa tgctctggag ctagcgtttt cctatttctc ccacgaactc
 661 ggctttaagg tggtgttaag acaagataag gagtttcagg atatcttaat ggaccacaac
 721 aggaaaagca atgtgattat tatgtgtggt ggtccagagt tcctctacaa gctgaagggt
 781 gaccgagcag tggctgaaga cattgtcatt attctagtgg atcttttcaa tgaccagtac
 841 tttgaggaca atgtcacagc ccctgactat atgaaaaatg tccttgttct gacgctgtct
 901 cctgggaatt cccttctaaa tagctctttc tccaggaatc tatcaccaac aaaacgagac
 961 tttgctcttg cctatttgaa tggaatcctg ctctttggac atatgctgaa gatatttctt
1021 gaaaatggag aaaatattac cacccccaaa tttgctcatg ctttcaggaa tctcactttt
1081 gaagggtatg acggtccagt gaccttggat gactgggggg atgttgacag taccatggtg
1141 cttctgtata cctctgtgga caccaagaaa tacaaggttc ttttgaccta tgatacccac
1201 gtaaataaga cctatcctgt ggatatgagc cccacattca cttggaagaa ctctaaactt
1261 cctaatgata ttacaggccg gggccctcag atcctgatga ttgcagtctt caccctcact
1321 ggagctgtgg tgctgctcct gctcgtcgct cctgatgc tcagaaaata tagaaaagat
1381 tatgaacttc gtcagaaaaa atggtcccac attcctcctg aaaatatctt tcctctggag
1441 accaatgaga ccaatcatgt tagcctcaag atcgatgatg acaaaagacg agatacaatc
1501 cagagactac gacagtgcaa atacgacaaa aagcgagtga ttctcaaaga tctcaagcac
1561 aatgatggta atttcactga aaaacagaag atagaattga caagttgct tcagattgac
1621 tattacaacc tgaccaagtt ctacggcaca gtgaaacttg ataccatgat cttcggggtg
1681 atagaatact gtgagagagg atccctccgg gaagttttaa atgacacaat ttcctaccct
1741 gatggcacat tcatggattg ggagtttaag atctctgtct tgtatgacat tgctaaggga
1801 atgtcatatc tgcactccag taagacagaa gtccatggtc gtctgaaatc taccaactgc
1861 gtagtggaca gtagaatggt ggtgaagatc actgattttg gctgcaattc cattttacct
1921 ccaaaaaagg acctgtggac agctccagag cacctccgcc aagccaacat ctctcagaaa
1981 ggagatgtgt acagctatgg gatcatcgca caggagatca tcctgcggaa agaaaccttc
2041 tacactttga gctgtcggga ccggaatgag aagattttca gagtgaaaaa ttccaatgga
2101 atgaaaccct tccgcccaga tttattcttg gaaacagcag aggaaaaaga gctagaagtg
2161 tacctacttg taaaaaactg ttgggaggaa gatccagaaa agagaccaga tttcaaaaaa
2221 attgagacta cacttgccaa gatatttgga cttttcatg accaaaaaaa tgaaagctat
2281 atggatacct tgatccgacg tctacagcta tattctcgaa acctggaaca tctggtagag
2341 gaaaggacac agctgtacaa ggcagagagg gacagggctg cagagcttaa ctttatgttg
2401 cttccaaggc tagtggtaaa gtctctgaag gagaaaggct tgtggagcc ggaactatat
2461 gaggaagtta caatctactt cagtgacatt gtaggtttca ctactatctg caaatacagc
2521 accccccatgg aagtggtgga catgcttaat gacatctata agagttttga ccacattgtt
2581 gatcatcatg atgtctacaa ggtggaaacc atcggtgatc gtacatggt ggctagtggt
2641 ttgcctaaga gaaatggcaa tcggcatgca atagacattg ccaagatggc cttggaaatc
```

-continued

```
2701 ctcagcttca tggggacctt tgagctggag catcttcctg gcctcccaat atggattcgc 2761 attggagttc actctggtcc ctgtgctgct ggagttgtgg gaatcaagat gcctcgttat 2821 tgtctatttg gagatacggt caacacagcc tctaggatgg aatccactgg cctccctttg 2881 agaattcacg tgagtggctc caccatagcc atcctgaaga gaactgagtg ccagttcctt 2941 tatgaagtga gaggagaaac atacttaaag ggaagaggaa atgagactac ctactggctg 3001 actgggatga aggaccagaa attcaacctg ccaaccoctc ctactgtgga gaatcaacag 3061 cgtttgcaag cagaattttc agacatgatt gccaactctt tacagaaaag acaggcagca 3121 gggataagaa gccaaaaacc cagacgggta gccagctata aaaaaggcac tctggaatac 3181 ttgcagctga ataccacaga caaggagagc acctattttt aa
```

Amino acid sequence for human GCC (GenPept Accession No. NP_004954):

(SEQ ID NO: 228)

```
   1 mktllldlal wsllfqpgwl sfssqvsqnc hngsyeisvl mmgnsafaep lknledavne 61 gleivrgrlq naglnvtvna tfmysdglih nsgdcrsstc egldllrkis naqrmgcvli 121 gpsctystfq myldtelsyp misagsfgls cdyketltrl msparklmyf lvnfwktndl 181 pfktyswsts yvykngtete dcfwylnale asvsyfshel gfkvvlrqdk efqdilmdhn 241 rksnviimcg gpeflyklkg dravaedivi ilvdlfndqy fednvtapdy mknvlvltls 301 pgnsllnssf srnlsptkrd falaylngil lfghmlkifl engenittpk fahafrnltf 361 egydgpvtld dwgdvdstmv llytsvdtkk ykvlltydth vnktypvdms ptftwknskl 421 pnditgrgpq ilmiavftlt gavvllllva llmlrkyrkd yelrqkkwsh ippenifple 481 tnetnhvslk idddkrrdti qrlrqckydk krvilkdlkh ndgnftekqk ielnkllqid 541 yynltkfygt vkldtmifgv ieycergslr evlndtisyp dgtfmdwefk isvlydiakg 601 msylhsskte vhgrlkstnc vvdsrmvvki tdfgcnsilp pkkdlwtape hlrqanisqk 661 gdvysygiia qeiilrketf ytlscrdrne kifrvensng mkpfrpdlfl etaeekelev 721 yllvkncwee dpekrpdfkk iettlakifg lfhdqknesy mdtlirrlql ysrnlehlve 781 ertqlykaer dradrlnfml lprlvvkslk ekgfvepely eevtiyfsdi vgfttickys 841 tpmevvdmln diyksfdhiv dhhdvykvet igdaymvasg lpkrngnrha idiakmalei 901 lsfmgtfele hlpglpiwir igvhsgpcaa gvvgikmpry clfgdtvnta srmestglpl 961 rihvsgstia ilkrtecqfl yevrgetylk grgnettywl tgmkdqkfnl ptpptvenqq 1021 rlqaefsdmi anslqkrqaa girsqkprrv asykkgtley lqlnttdkes tyf
```

The GCC protein has some generally accepted domains each of which contributes a separable function to the GCC molecule. The portions of GCC include a signal sequence (for directing the protein to the cell surface) from amino acid residue 1 to about residue 23, or residue 1 to about residue 21 of SEQ ID NO:228 (excised for maturation to yield functional mature protein from about amino acid residues 22 or 24 to 1073 of SEQ ID NO:228), an extracellular domain for ligand, e.g., guanylin or ST, binding from about amino acid residue 24 to about residue 420, or about residue 54 to about residue 384 of SEQ ID NO:228, a transmembrane domain from about amino acid residue 431 to about residue 454, or about residue 436 to about residue 452 of SEQ ID NO:228, a kinase homology domain, predicted to have tyrosine kinase activity from about amino acid residue 489 to about residue 749, or about residue 508 to about residue 745 of SEQ ID NO:228 and a guanylyl cyclase catalytic domain from about residue 750 to about residue 1007, or about residue 816 to about residue 1002 of SEQ ID NO:228.

In normal human tissues, GCC is expressed at the mucosal cells, e.g., at the apical brush border membranes, lining the small intestine, large intestine and rectum (Carrithers et al., *Dis Colon Rectum* 39: 171-181 (1996)). GCC expression is maintained upon neoplastic transformation of intestinal epithelial cells, with expression in all primary and metastatic colorectal tumors (Carrithers et al., *Dis Colon Rectum* 39: 171-181 (1996); Buc et al. *Eur J Cancer* 41: 1618-1627 (2005); Carrithers et al., *Gastroenterology* 107: 1653-1661 (1994)). Neoplastic cells from the stomach, esophagus and the gastroesophageal junction also express GCC (see, e.g., U.S. Pat. No. 6,767,704; Debruyne et al. *Gastroenterology* 130:1191-1206 (2006)). The tissue-specific expression and association with cancer, e.g., of gastrointestinal origin, (e.g., colon cancer, stomach cancer, or esophageal cancer), can be exploited for the use of GCC as a diagnostic marker for this disease (Carrithers et al., *Dis Colon Rectum* 39: 171-181 (1996); Buc et al. *Eur J Cancer* 41: 1618-1627 (2005)).

As a cell surface protein, GCC can also serve as a therapeutic target for receptor binding proteins such as antibodies or ligands. In normal intestinal tissue, GCC is expressed on the apical side of epithelial cell tight junctions that form an impermeable barrier between the luminal environment and vascular compartment (Almenoff et al., *Mol Microbiol* 8: 865-873); Guarino et al., *Dig Dis Sci* 32: 1017-1026 (1987)). As such, systemic intravenous administration of a GCC-binding protein therapeutic will have minimal effect on intestinal GCC receptors, while having access to neoplastic cells of the gastrointestinal system, including invasive or metastatic colon cancer cells, extraintestinal or metastatic colon tumors, esophageal tumors or stomach tumors, adenocarcinoma at the gastroesophageal junction. Additionally, GCC internalizes through receptor mediated endocytosis upon ligand binding (Buc et al. *Eur J Cancer* 41: 1618-1627 (2005); Urbanski et al., *Biochem Biophys Acta* 1245: 29-36 (1995)).

Polyclonal antibodies raised against the extracellular domain of GCC (Nandi et al. *Protein Expr. Purif* 8:151-159 (1996)) were able to inhibit the ST peptide binding to human and rat GCC and inhibit ST-mediated cGMP production by human GCC.

GCC has been characterized as a protein involved in cancers, including colon cancers. See also, Carrithers et al., *Dis Colon Rectum* 39: 171-181 (1996); Buc et al. *Eur J Cancer* 41: 1618-1627 (2005); Carrithers et al., *Gastroenterology* 107: 1653-1661 (1994); Urbanski et al., *Biochem Biophys Acta* 1245: 29-36 (1995). Antibody molecule therapeutics directed to GCC can be used alone in unconjugated form to thereby inhibit the GCC-expressing cancerous cells. Anti-GCC antibody molecules of the invention can bind human GCC. In some embodiments, an anti-GCC antibody molecule of the invention can inhibit the binding of a ligand, e.g., guanylin or heat-stable enterotoxin to GCC. In other embodiments, an anti-GCC antibody molecule of the invention does not inhibit the binding of a ligand, e.g., guanylin or heat-stable enterotoxin to GCC.

Monoclonal antibodies specific for GCC include GCC:B10 (Nandi et al., *J. Cell. Biochem.* 66:500-511 (1997)), GCC:4D7 (Vijayachandra et al. *Biochemistry* 39:16075-16083 (2000)) and GCC:C8 (Bakre et al. *Eur. J. Biochem.* 267:179-187 (2000)). GCC:B10 has a kappa light chain and an IgG2a isotype and cross-reacts to rat, pig and monkey GCC. GCC:B10 binds to the first 63 amino acids of the intracellular domain of GCC, specifically to residues 470-480 of SEQ ID NO:228 (Nandi et al. *Protein Sci.* 7:2175-2183 (1998)). GCC:4D7 binds to the kinase homology domain, within residues 491-568 of GCC (Bhandari et al. *Biochemistry* 40:9196-9206 (2001)). GCC:C8 binds to the protein kinase-like domain in the cytoplasmic portion of GCC.

Definitions and Methods

Unless otherwise defined herein, scientific and technical terms used in connection with the present invention have the meanings that are commonly understood by those of ordinary skill in the art. Generally, nomenclature utilized in connection with, and techniques of, cell and tissue culture, molecular biology, and protein and oligo- or polynucleotide chemistry and hybridization described herein are those known in the art. GenBank or GenPept accession numbers and useful nucleic acid and peptide sequences can be found at the website maintained by the National Center for Biotechnological Information, Bethesda Md. Standard techniques are used for recombinant DNA, oligonucleotide synthesis, and tissue culture and transformation and transfection (e.g., electroporation, lipofection). Enzymatic reactions and purification techniques are performed according to manufacturer's specifications or as commonly accomplished in the art or as described herein. The foregoing techniques and procedures are generally performed according to methods known in the art, e.g., as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2000)) or see generally, Harlow, E. and Lane, D. (1988) *Antibodies: A Laboratory Manual*, Cold Spring Harbor Laboratory Press, Cold Spring Harbor, N.Y. The nomenclatures utilized in connection with, and the laboratory procedures and techniques of, analytical chemistry, synthetic organic chemistry, and medicinal and pharmaceutical chemistry described herein are known in the art. Standard techniques are used for chemical syntheses, chemical analyses, pharmaceutical preparation, formulation, and delivery, and treatment of patients. Furthermore, unless otherwise required by context, singular terms shall include pluralities and plural terms shall include the singular.

As used herein, the term "antibody molecule" refers to an antibody, antibody peptide(s) or immunoglobulin, or an antigen binding fragment of any of the foregoing, e.g., of an antibody. Antibody molecules include single chain antibody molecules, e.g., scFv, see. e.g., Bird et al. (1988) *Science* 242:423-426; and Huston et al. (1988) *Proc. Natl. Acad. Sci. USA* 85:5879-5883), and single domain antibody molecules, see, e.g., WO9404678. Although not within the term "antibody molecules," the invention also includes "antibody analog(s)," other non-antibody molecule protein-based scaffolds, e.g., fusion proteins and/or immunoconjugates that use CDRs to provide specific antigen binding.

An "anti-GCC antibody molecule" refers to an antibody molecule (i.e., an antibody, antigen-binding fragment of an antibody or antibody analog) which interacts with or recognizes, e.g., binds (e.g., binds specifically) to GCC, e.g., human GCC. Exemplary anti-GCC antibody molecules are such as those summarized in Tables 1 and 2.

As used herein, the term "antibody," "antibody peptide(s)" or "immunoglobulin" refers to single chain, two-chain, and multi-chain proteins and glycoproteins. The term antibody includes polyclonal, monoclonal, chimeric, CDR-grafted and human or humanized antibodies, all of which are discussed in more detail elsewhere herein. Also included within the term are camelid antibodies, see, e.g., US2005/0037421, and nanobodies, e.g., IgNARs (shark antibodies), see, e.g., WO03/014161. The term "antibody" also includes synthetic and genetically engineered variants.

As used herein, the term "antibody fragment" or "antigen binding fragment" of an antibody refers, e.g., to Fab, Fab', F(ab')$_2$, and Fv fragments, single chain antibodies, functional heavy chain antibodies (nanobodies), as well as any portion of an antibody having specificity toward at least one desired epitope, that competes with the intact antibody for specific binding (e.g., a fragment having sufficient CDR sequences and having sufficient framework sequences so as to bind specifically to an epitope). E.g., an antigen binding fragment can compete for binding to an epitope which binds the antibody from which the fragment was derived. Derived, as used in this and similar contexts, does not imply any particular method or process of derivation, but can refer merely to sequence similarity. Antigen binding fragments can be produced by recombinant techniques, or by enzymatic or chemical cleavage of an intact antibody. The term, antigen binding fragment, when used with a single chain, e.g., a heavy chain, of an antibody having a light and heavy chain means that the fragment of the chain is sufficient such that when paired with a complete variable region of the other chain, e.g., the light chain, it will allow binding of at least 25, 50, 75, 85 or 90% of that seen with the whole heavy and light variable region.)

The term, "antigen binding constellation of CDRs" or "a number of CDRs sufficient to allow binding" (and similar language), as used herein, refers to sufficient CDRs of a chain, e.g., the heavy chain, such that when placed in a framework and paired with a complete variable region of the other chain, or with a portion of the other chain's variable region of similar length and having the same number of CDRs, e.g., the light chain, will allow binding, e.g., of at least 25, 50, 75, 85 or 90% of that seen with the whole heavy and light variable region.

As used herein, the term "human antibody" includes an antibody that possesses a sequence that is derived from a human germ-line immunoglobulin sequence, such as an antibody derived from transgenic mice having human immunoglobulin genes (e.g., XENOMOUSE™ genetically engineered mice (Abgenix, Fremont, Calif.)), human phage display libraries, human myeloma cells, or human B cells.

As used herein, the term "humanized antibody" refers to an antibody that is derived from a non-human antibody e.g., rodent (e.g., murine) that retains or substantially retains the antigen-binding properties of the parent antibody but is less immunogenic in humans. Humanized as used herein is intended to include deimmunized antibodies. Typically humanized antibodies include non-human CDRs and human or human derived framework and constant regions.

The term "modified" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse, sheep or goat) that is transgenic for human immunoglobulin genes or antibodies prepared, expressed, created or isolated by any other means that involves splicing of human immunoglobulin gene sequences to other DNA sequences. Such modified antibodies include humanized, CDR grafted (e.g., an antibody having CDRs from a first antibody and a framework region from a different source, e.g., a second antibody or a consensus framework), chimeric, in vitro generated (e.g., by phage display) antibodies, and may optionally include variable or constant regions derived from human germline immunoglobulin sequences or human immunoglobulin genes or antibodies which have been prepared, expressed, created or isolated by any means that involves splicing of human immunoglobulin gene sequences to alternative immunoglobulin sequences. In embodiments a modified antibody molecule includes an antibody molecule having a sequence change from a reference antibody.

The term "monospecific antibody" refers to an antibody or antibody preparation that displays a single binding specificity and affinity for a particular epitope. This term includes a "monoclonal antibody" or "monoclonal antibody composition."

The term "bispecific antibody" or "bifunctional antibody" refers to an antibody that displays dual binding specificity for two epitopes, where each binding site differs and recognizes a different epitope.

The terms "non-conjugated antibody" and "naked antibody" are used interchangeably to refer to an antibody molecule that is not conjugated to a non-antibody moiety, e.g., a therapeutic agent or a label.

The terms "immunoconjugate", "antibody conjugate", "antibody drug conjugate", and "ADC" are used interchangeably and refer to an antibody that is conjugated to a non-antibody moiety, e.g., a therapeutic agent or a label.

The term "agent" is used herein to denote a chemical compound, a mixture of chemical compounds, a biological macromolecule, or an extract made from biological materials. The term "therapeutic agent" refers to an agent that has biological activity.

The term "anti-cancer agent" or "chemotherapeutic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis or angiogenesis is frequently a property of anti-cancer or chemotherapeutic agents. A chemotherapeutic agent may be a cytotoxic or cytostatic agent. The term "cytostatic agent" refers to an agent which inhibits or suppresses cell growth and/or multiplication of cells.

"Cytotoxic agents" refer to compounds which cause cell death primarily by interfering directly with the cell's functioning, including, but not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment of the invention and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment of the invention.

As used herein the phrase, a sequence "derived from" or "specific for a designated sequence" refers to a sequence that comprises a contiguous sequence of approximately at least 6 nucleotides or at least 2 amino acids, at least about 9 nucleotides or at least 3 amino acids, at least about 10-12 nucleotides or 4 amino acids, or at least about 15-21 nucleotides or 5-7 amino acids corresponding, i.e., identical or complementary to, e.g., a contiguous region of the designated sequence. In certain embodiments, the sequence comprises all of a designated nucleotide or amino acid sequence. The sequence may be complementary (in the case of a polynucleotide sequence) or identical to a sequence region that is unique to a particular sequence as determined by techniques known in the art. Regions from which sequences may be derived, include but are not limited to, regions encoding specific epitopes, regions encoding CDRs, regions encoding framework sequences, regions encoding constant domain regions, regions encoding variable domain regions, as well as non-translated and/or non-transcribed regions. The derived sequence will not necessarily be derived physically from the sequence of interest under study, but may be generated in any manner, including, but not limited to, chemical synthesis, replication, reverse transcription or transcription, that is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified or combined in ways known in the art to be consistent with the intended use. For example, a sequence may comprise two or more contiguous sequences which each comprise part of a designated sequence, and are interrupted with a region which is not identical to the designated sequence but is intended to represent a sequence derived from the designated sequence. With regard to antibody molecules, "derived therefrom" includes an antibody molecule which is functionally or structurally related to a comparison antibody, e.g., "derived therefrom" includes an antibody molecule having similar or substantially the same sequence or structure, e.g., having the same or similar CDRs, framework or variable regions. "Derived therefrom" for an antibody also includes residues, e.g., one or more, e.g., 2, 3, 4, 5, 6 or more residues, which may or may not be contiguous, but are defined or identified according to a numbering scheme or homology to general antibody structure or three-dimensional proximity, i.e., within a CDR or a framework region, of a comparison sequence. The term "derived therefrom" is not limited to physically derived therefrom but includes generation by any manner, e.g., by use of sequence information from a comparison antibody to design another antibody.

As used herein, the phrase "encoded by" refers to a nucleic acid sequence that codes for a polypeptide sequence, wherein the polypeptide sequence or a portion thereof contains an amino acid sequence of at least 3 to 5 amino acids, at least 8 to 10 amino acids, or at least 15 to 20 amino acids from a polypeptide encoded by the nucleic acid sequence.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 30%, 40%, or 50%, at least 60%, or at least 70%, 80%, 90%, 95%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences can be determined using any method known in the art. For example, the Needleman and Wunsch, *J. Mol. Biol.* 48:444-453 (1970), algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. The percent homology between two nucleotide sequences can also be determined using the GAP program in the GCG software package (Accelerys, Inc. San Diego, Calif.), using an NWSgapdna.CMP matrix and a gap weight of 40, 50, 60, 70, or 80 and a length weight of 1, 2, 3, 4, 5, or 6. An exemplary set of parameters for determination of homology are a Blossum 62 scoring matrix with a gap penalty of 12, a gap extend penalty of 4, and a frameshift gap penalty of 5.

As used herein, the term "hybridizes under stringent conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C. Very high stringency conditions (4) are often the preferred conditions and the ones that should be used unless otherwise specified.

It is understood that the antibodies and antigen binding fragment thereof of the invention may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie, J U et al. *Science* 247:1306-1310 (1990) or Padlan et al. *FASEB J.* 9:133-139 (1995). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or, without substantially altering a biological activity, whereas an "essential" amino acid residue results in such a change. In an antibody, an essential amino acid residue can be a specificity determining residue (SDR).

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, e.g., a mixture, solution or suspension or comprising an isolated cell or a cultured cell which comprises the polynucleotide or polypeptide, and still be isolated in that the vector or composition is not part of its natural environment.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

As used herein, the term "vector" refers to a replicon in which another polynucleotide segment is attached, such as to bring about the replication and/or expression of the attached segment.

As used herein, the term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

As used herein, the term "purified product" refers to a preparation of the product which has been isolated from the cellular constituents with which the product is normally associated and/or from other types of cells that may be present in the sample of interest.

As used herein, the term "epitope" refers to a protein determinate capable of binding specifically to an antibody. Epitopic determinants usually consist of chemically active surface groupings of molecules such as amino acids or sugar side chains and usually have specific three dimensional structural characteristics, as well as specific charge characteristics. Some epitopes are linear epitopes while others are conformational epitopes. A linear epitope is an epitope wherein a contiguous amino acid primary sequence comprises the epitope recognized. A linear epitope typically includes at least 3, and more usually, at least 5, for example, about 8 to about 10 contiguous amino acids. A conformational epitope can result from at least two situations, such as: a) a linear sequence which is only exposed to antibody binding in certain protein conformations, e.g., dependent on ligand binding, or dependent on modification (e.g., phosphorylation) by signaling molecules; or b) a combination of structural features from more than one part of the protein, or in multisubunit proteins, from more than one subunit, wherein the features are in sufficiently close proximity in 3-dimensional space to participate in binding.

As used herein, "isotype" refers to the antibody class (e.g., IgM or IgG1) that is encoded by heavy chain constant region genes.

As used herein, the terms "detectable agent," "label" or "labeled" are used to refer to incorporation of a detectable marker on a polypeptide or glycoprotein. Various methods of labeling polypeptides and glycoproteins are known in the art and may be used. Examples of labels for polypeptides include, but are not limited to, the following: radioisotopes or radionuclides (e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99}$mTc), praseodymium, or phosphorous ($^{32}$P) or a positron-emitting radionuclide, e.g., carbon 11 ($^{11}$C), potassium-40 ($^{40}$K), nitrogen-13 ($^{13}$N), oxygen-15 ($^{15}$O), fluorine-18 ($^{18}$F), and iodine-121 ($^{121}$I)), fluorescent labels (e.g., FITC, rhodamine, lanthanide phosphors), enzymatic labels (e.g., horseradish peroxidase, beta-galactosidase, luciferase, alkaline phosphatase), chemiluminescent, biotinyl groups (which can be detected by a marked avidin, e.g., a molecule containing a streptavidin moiety and a fluorescent marker or an enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "specific binding," "bind(s) specifically" or "binding specificity" means, for an anti-GCC antibody molecule, that the antibody molecule binds to GCC, e.g., human GCC protein, with greater affinity than it does to a non-GCC protein, e.g., BSA. Typically an anti-GCC molecule will have a $K_d$ for the non-GCC protein, e.g., BSA, which is greater than 2, greater than 10, greater than 100, greater than 1,000 times, greater than $10^4$, greater than $10^5$, or greater than $10^6$ times its $K_d$ for GCC, e.g., human GCC protein. In determination of $K_d$, the $K_d$ for GCC and the non-GCC protein, e.g., BSA, should be done under the same conditions.

As used herein, the term "treat" or "treatment" is defined as the administration of an anti-GCC antibody molecule to a subject, e.g., a patient, or administration, e.g., by application, to an isolated tissue or cell from a subject which is returned to the subject. The anti-GCC antibody molecule can be administered alone or in combination with a second agent. The treatment can be to cure, heal, alleviate, relieve, alter, remedy, ameliorate, palliate, improve or affect the disorder, the symptoms of the disorder or the predisposition toward the disorder, e.g., a cancer. While not wishing to be bound by theory, treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a cancer).

As used herein, the term "subject" is intended to include mammals, primates, humans and non-human animals. For example, a subject can be a patient (e.g., a human patient or a veterinary patient), having a cancer, e.g., of gastrointestinal origin (e.g., colon cancer), a symptom of a cancer, e.g., of gastrointestinal origin (e.g., colon cancer), in which at least some of the cells express GCC, or a predisposition toward a cancer, e.g., of gastrointestinal origin (e.g., colon cancer), in which at least some of the cells express GCC. The term "non-human animals" of the invention includes all non-human vertebrates, e.g., non-human mammals and non-mammals, such as non-human primates, sheep, dog, cow, chickens, amphibians, reptiles, etc, unless otherwise noted. In an embodiment subject excludes one or more or all of a mouse, rat, rabbit or goat.

As used herein, an amount of an anti-GCC antibody molecule "effective" or "sufficient" to treat a disorder, or a "therapeutically effective amount" or "therapeutically sufficient amount" refers to an amount of the antibody molecule which is effective, upon single or multiple dose administration to a subject, in treating a cell, e.g., cancer cell (e.g., a GCC-expressing tumor cell), or in prolonging curing, alleviating, relieving or improving a subject with a disorder as described herein beyond that expected in the absence of such treatment. As used herein, "inhibiting the growth" of the tumor or cancer refers to slowing, interrupting, arresting or stopping its growth and/or metastases and does not necessarily indicate a total elimination of the tumor growth.

As used herein, "GCC," also known as "STAR", "GUC2C", "GUCY2C" or "ST receptor" protein refers to mammalian GCC, preferably human GCC protein. Human GCC refers to the protein shown in SEQ ID NO:228 and naturally occurring allelic protein variants thereof. The allele in SEQ ID NO: 228 can be encoded by the nucleic acid sequence of GCC shown in SEQ ID NO:227. Other variants are known in the art. See, e.g., accession number Ensp0000261170, Ensembl Database, European Bioinformatics Institute and Wellcome Trust Sanger Institute, which has a leucine at residue 281; SEQ ID NO: 14 of published US patent application number US 20060035852; or GenBank accession number AAB19934. Typically, a naturally occurring allelic variant has an amino acid sequence at least 95%, 97% or 99% identical to the GCC sequence of SEQ ID NO:228. The transcript encodes a protein product of 1073 amino acids, and is described in GenBank accession no.: NM_004963. GCC protein is characterized as a transmembrane cell surface receptor protein, and is believed to play a critical role in the maintenance of intestinal fluid, electrolyte homeostasis and cell proliferation.

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, may be referred to as "substituted." A substituted alkyl group is an alkyl group that is substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

As with alkyl groups, alkenyl and alkynyl groups, can be substituted. A "substituted" alkenyl or alkynyl group is one that is substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_5$ alkyl, —C$_2$-C$_8$ alkenyl, —C$_2$-C$_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CH—CH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —C$_1$-C$_8$ alkyl, —C$_2$-C$_8$ alkenyl, —C$_2$-C$_8$ alkynyl, O—(C$_1$-C$_8$ alkyl), —O—(C$_2$-C$_8$ alkenyl), —O—(C$_2$-C$_8$ alkynyl), and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group:

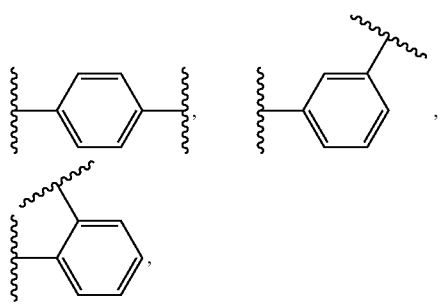

Typical "—(C$_1$-C$_8$ alkylene)aryl," "—(C$_2$-C$_8$ alkenylene)aryl", "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 82:5566 (1960).

Unless otherwise noted, the term "heterocyclo" refers to an optionally substituted heterocycle group as defined above that is divalent (i.e., derived by the removal of two hydrogen atoms from the same or two different carbon atoms of a parent heterocyclic ring system).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), —$C_1$-$C_8$ alkyl, —$C_2$-$C_8$ alkenyl, —$C_2$-$C_8$ alkynyl, and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo[4,5], [5,5], [5,6] or [6,6] system, or 9 or 10 ring atoms arranged as a bicyclo[5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Examples of monocyclic carbocylic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl, -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention are pharmaceutically acceptable and may or may not need to be cleaved from the parent compound after administration to a subject in order for the compound to be active. Cleavage is through normal metabolic processes within the body. Hydroxy protecting groups are well known in the art, see, PROTECTIVE GROUPS IN ORGANIC SYNTHESIS by T. W. Greene and P. G. M. Wuts (John Wiley & sons, $3^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-chloro-4-methyl)phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphneylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1,-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —R, —Si(R)(R)(R), —C(O)R, —C(O)OR, —C(O)NH(R), —S(O)$_2$R, —S(O)$_2$OH, P(O)(OH)$_2$, and —P(O)(OH)OR, wherein R is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, alkynylene, aryl, carbocycle, and heterocycle radicals whether alone or as part of another group are optionally substituted.

The abbreviation "AFP" refers to dimethylvaline-valine-dolaisoleuine-dolaproine-phenylalanine-p-phenylenediamine (see Formula (XVIII) infra).

The abbreviation "MMAE" refers to monomethyl auristatin E (see Formula (XIII) infra).

The abbreviation "AEB" refers to an ester produced by reacting auristatin E with paraacetyl benzoic acid (see Formula (XXII) infra).

The abbreviation "AEVB" refers to an ester produced by reacting auristatin E with benzoylvaleric acid (see Formula (XXIII) infra).

The abbreviation "MMAF" refers to monomethyl auristatin F (see Formula (XXI) infra).

Antibodies

In certain aspects, the invention relates to anti-GCC antibody molecules with features such as those summarized in Tables 1 and 2. In other aspects, the invention relates to anti-GCC antibody molecules with features such as those summarized in Tables 3, 4, 5 and/or 6.

In an embodiment, the anti-GCC antibody molecule is a human hybridoma antibody and is one of antibody 5F9, 5H3, 6H8, 8C2, 10C10, 10D3 and 1D3. In an embodiment, the anti-GCC antibody molecule is derived from antibody 5F9, 5H3, 6H8, 8C2, 10C10, 10D3, or 1D3. In an embodiment, the anti-GCC antibody molecule is produced by hybridoma 5F9 (PTA-8132).

In an embodiment the anti-GCC antibody molecule is a selected lymphocyte antibody and is one of antibody Abx-12, Abx-020, Abx-106, Abx-198, Abx-221, Abx-229, Abx-338, and Abx-393. In an embodiment, the anti-GCC antibody molecule is derived from antibody Abx-12, Abx-020, Abx-106, Abx-198, Abx-221, Abx-229, Abx-338, and Abx-393.

In an embodiment the anti-GCC antibody molecule is a murine antibody and is one of antibody mAb 3G1, mAb 8E12, mAb10B8, and mAb 8F1. In an embodiment, the anti-GCC antibody molecule is derived from antibody mAb 3G1, mAb 8E12, and mAb 8F1.

In an embodiment an anti-GCC antibody molecule will have an affinity for GCC, e.g., as measured by direct binding or competition binding assays, in a range described herein. In an embodiment the anti-GCC antibody molecule has a $K_d$ of less than $1\times10^{-6}$ M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In an embodiment the antibody molecule is an IgG, or antigen-binding fragment thereof, and has a $K_d$ of less than $1\times10^{-6}$M, less than $1\times10^{-7}$ M, less than $1\times10^{-8}$ M, or less than $1\times10^{-9}$ M. In an embodiment, an anti-GCC antibody molecule, e.g., a 5F9 antibody or antibody derived therefrom has a $K_d$ of about 80 to about 200 pM, preferably about 100 to about 150 pM or about 120 pM. In an embodiment, an anti-GCC antibody molecule, e.g., a 5F9 antibody or antibody derived therefrom has a $k_a$ of about 0.9 to about $1.25\times10^5$ $M^{-1}s^{-1}$, preferably about $1.1\times10^5$ $M^{-1}s^{-1}$. In an embodiment the antibody molecule is an ScFv and has a $K_d$ of less than $1\times10^{-6}$M, less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M.

In embodiments, the antibody molecules are not immunoconjugates, i.e., are "naked" and in embodiments cause a cellular reaction upon binding to GCC. In related embodiments, the cellular reaction is performed by the GCC-expressing cell to which the antibody binds. Such a cellular reaction can be signal transduction mediated by GCC, e.g., if the antibody molecule is an agonist of GCC (see, e.g., US Patent Application publication no. US20040258687. In other embodiments, the cellular reaction is performed by a second cell, e.g., an immune effector cell (e.g., a natural killer cell) which recognizes the antibody molecule bound to GCC on the first cell. In some embodiments, surveillance molecules, e.g., complement molecules, contact the GCC-bound antibody molecule prior to the cellular reaction. The cellular reactions in these embodiments can cause death of the GCC-expressing cell.

In further embodiments, antibody molecules which are immunoconjugates can both cause a cellular reaction upon binding to GCC and internalize to deliver an agent to the GCC-expressing cell to which it binds.

In some embodiments, an anti-GCC antibody molecule of the invention can block ligand binding to GCC.

In an embodiment, the anti-GCC antibody molecule fails to show substantial cross reaction with one or both of rat GCC and mouse GCC.

In an embodiment, the antibody molecule is not GCC:B10, GCC:4D7 or GCC:C8. In another embodiment, an anti-GCC antibody molecule does not bind an intracellular domain of GCC, about amino acid residue 455 to 1073 of SEQ ID NO:228. For example, in this embodiment, an anti-GCC antibody molecule does not bind the kinase homology domain or the guanylyl cyclase domain of GCC.

The naturally occurring mammalian antibody structural unit is typified by a tetramer. Each tetramer is composed of two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains can be classified as kappa and lambda light chains. Heavy chains can be classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site. Preferred isotypes for the anti-GCC antibody molecules are IgG immunoglobulins, which can be classified into four subclasses, IgG1, IgG2, IgG3 and IgG4, having different gamma heavy chains. Most therapeutic antibodies are human, chimeric, or humanized antibodies of the IgG1 type. In a particular embodiment, the anti-GCC antibody molecule has the IgG1 isotype.

The variable regions of each heavy and light chain pair form the antigen binding site. Thus, an intact IgG antibody has two binding sites which are the same. However, bifunctional or bispecific antibodies are artificial hybrid constructs which have two different heavy/light chain pairs, resulting in two different binding sites.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

An anti-GCC antibody molecule can comprise all, or an antigen binding subset of the CDRs, of one or both, the heavy and light chain, of one of the above-referenced human hybridoma, selected lymphocyte, or murine antibodies Amino acid sequences of human hybridoma, selected lymphocyte, and murine antibody portions, including variable regions and CDRs, can be found in Table 3 and Table 5.

Thus, in an embodiment the antibody molecule includes one or both of:

(a) one, two, three, or an antigen binding number of, light chain CDRs (LCDR1, LCDR2 and/or LCDR3) of one of the above-referenced human hybridoma, selected lymphocyte, or murine antibodies. In embodiments the CDR(s) may comprise an amino acid sequence of one or more or all of LCDR1-3 as follows: LCDR1, or modified LCDR1 wherein one to seven amino acids are conservatively substituted) LCDR2, or modified LCDR2 wherein one or two amino acids are conservatively substituted); or LCDR3, or modified LCDR3 wherein one or two amino acids are conservatively substituted; and (b) one, two, three, or an antigen binding number of, heavy chain CDRs (HCDR1, HCDR2 and/or HCDR3) of one of the above-referenced human hybridoma, selected lymphocyte, or murine antibodies. In embodiments the CDR(s) may comprise an amino acid sequence of one or more or all of HCDR1-3 as follows: HCDR1, or modified HCDR1 wherein one or two amino acids are conservatively substituted; HCDR2, or modified HCDR2 wherein one to four amino acids are conservatively substituted; or HCDR3, or modified HCDR3 wherein one or two amino acids are conservatively substituted.

Useful immunogens for production of anti-GCC antibodies include GCC e.g., human GCC-expressing cells (e.g., a tumor cell line, e.g., T84 cells, or fresh or frozen colon tumor cells, recombinant cells expressing GCC); membrane fractions of GCC-expressing cells (e.g., a colon tumor cell line, e.g., T84 cells, or fresh or frozen colonic tumor cells, recombinant cells expressing GCC, e.g., HT-29-GCC #2 cells, which express full-length GCC, or a portion thereof, e.g., CHO GCC #27 cells which express a portion comprising the GCC extracellular domain, e.g., SEQ ID NO:318); isolated or purified GCC, e.g., human GCC protein (e.g., biochemically isolated GCC, e.g., isolated from gastrointestinal tumor cells or recombinant cells expressing GCC or a variant thereof), or a portion thereof (e.g., the extracellular domain of GCC, the kinase homology domain of GCC or the guanylyl cyclase catalytic domain of GCC or peptide corresponding to a portion thereof, e.g., comprising at least about 8, 10, 12, 14, 16, 20, 24, 28 or 32 amino acid residues of SEQ ID NO:228); or an immunogen comprising SEQ ID NO:229 or comprising a mature portion thereof without the signal sequence (i.e., without amino acid residues 1 to about 21 or 23 of SEQ ID NO:229), e.g., the mature TOK107-hIgG protein, SEQ ID NO:317.

Immunogens can be fused to heterologous sequences to aid in biochemical manipulation, purification, immunization or antibody titer measurement. Such immunogens can comprise a portion of GCC, e.g., the extracellular domain, and a portion comprising a non-GCC polypeptide. Many options exist for constructing a fusion protein for ease of purification or immobilization onto a solid support, e.g., an affinity column or a microtiter plate or other suitable assay substrate/chip. For example, a fusion moiety can add a domain, e.g., glutathione-S-transferase/kinase (GST), which can bind glutathione; an Fc region of an immunoglobulin, which can bind to protein A or protein G; amino acid residues, e.g., two, three, four, five, preferably six histidine residues which can bind nickel or cobalt on an affinity column; an epitope tag, e.g., a portion of c-myc oncogene (myc-tag), a FLAG tag (U.S. Pat. No. 4,703,004), a hemagglutinin (HA) tag, a T7 gene 10 tag, a V5 tag, an HSV tag, or a VSV-G tag which can bind a tag-specific antibody; or a cofactor, e.g., biotin, which can bind streptavidin.

Immunogens which comprise the Fc portion of an immunoglobulin can hold the GCC, either in solution or attached to a cell, in a configuration which allows structural access to GCC epitopes by the host immune surveillance components for efficient antibody generation. Because immunoglobulin heavy chains comprising the Fc regions associate into dimers through interchain disulfide bonds, immunogens resulting from fusion with Fc regions are dimers. Valency of fusion proteins can reflect the type of immunoglobulin contributing an Fc region. For example, fusions with IgG proteins can be dimers, IgA fusions can make tetrameric immunogens, and IgM fusions can make decameric immunogens, the latter two is facilitated with co-transfection of the J chain. An exemplary immunoglobulin for an Fc fusion protein is IgG1. The portion used typically has the IgG1 hinge, CH2 and CH3 domains encoded by a single exon. Because this exon also has a portion of the CH1 region, which has a cysteine oriented to disulfide bond with a cysteine from the light chain, a useful modification is to mutate the CH1 cysteine, e.g., to a serine, to ensure there is no unpaired cysteine in the fusion protein. Such a mutation also increases flexibility of the hinge.

An Fc portion derived from a non-host species, e.g., human Ig Fc region, for fusing to an immunogen for immunization in a host species, e.g., mouse, rat, rabbit, goat, acts as an adjuvant. This adjuvant function can trigger specific antibodies against both Fc and GCC epitopes. Fc-reactive antibodies can be identified and discarded during screening. The Fc portion can have a wild type sequence or a sequence which is mutated to modify effector function. For example, a mutated constant region (variant) can be incorporated into a fusion protein to minimize binding to Fc receptors and/or ability to fix complement (see e.g. Winter et al, GB 2,209,757 B; Morrison et al., WO 89/07142; Morgan et al., WO 94/29351). In a preferred example, lysine 235 and glycine 237, numbered according to Fc region standards, are mutated, e.g., to alanine. An immunogen/fusion protein with Fc-mutated IgG can have reduced interaction with Fc receptors in the host. A preferred soluble immunogen fusion protein (after maturation to cleave the signal peptide and secretion) is TOK-107-hIgG (alt. name hGCC-ECD/hIgG1 Fc), which consists of amino acid residues 24 to 430 of SEQ ID NO:228 fused to mutated human IgG1 immunoglobulin Fc (SEQ ID NO:317).

To prepare a cell-expressed immunogen, the immunoglobulin portion can be structured to mimic an immunoglobulin portion of the B cell receptor. For example, the immunoglobulin Fc region can be further fused to a polypeptide comprising a transmembrane region from an immune receptor, such as Fcγ receptors, Fcα receptors, Fcα/μ receptor or Fcε receptors. Proper orientation of such an Fc receptor cell-bound immunogen with adequate exposure on the cell surface may be improved if the cell expressing the immunogen fusion protein further comprises additional components of the antigen receptor complex, e.g., B cell IgM receptor or IgD receptor. Suitable components of the complex include immunoglobulin (Ig) sheath proteins, such as MB-1 and B29 (CD79A and CD79B; Hombach et al. *Eur. J. Immunol.* 20:2795-2799 (1990) for IgM receptor), which form a heterodimer. The Ig sheath proteins can be provided endogenously by the transfected cell, e.g., if transfecting a B cell lymphoma cell line; or by co-transfection of the immunogen with sheath proteins, e.g., in a separate vector or in the same vector. Preferred IgG sheath proteins for immunization in mouse are mouse CD79a and CD79b (GenBank Accession Nos. NM_007655 and NM_008339, respectively). A preferred cell-bound immunogen fusion protein (after maturation to cleave the signal peptide and translocation to the cell surface) is the TOK111 product, consisting of the TOK-107hIgG (hGCC-ECD/hIgG1 Fc) fused to the mouse IgG2a (e.g., GenPept Accession No. AAB59661) transmembrane and intracellular domains (SEQ ID NO:318).

Useful epitopes, e.g., reference epitopes, from the GCC molecule, to which the anti-GCC antibody molecules, e.g., monoclonal antibodies, human antibodies or humanized antibodies, as described herein, can bind, can be found on the extracellular portion of GCC. Such GCC epitopes can bind antibody molecules on the surface of cells, e.g., on the cell exterior.

For example, an epitope for an anti-GCC antibody molecule can reside within, or include a residue(s) from, residues 1-50 of SEQ ID NO:228, or a fragment thereof that binds an anti-GCC antibody molecule of the invention, e.g., a 5F9-binding fragment thereof. Such fragments can comprise residues 1-25, 5-30, 10-35, 15-40, 20-45, 25-50, 5-45, 10-40, 15-35, 20-30 or 33-50 of SEQ ID NO:228. In some embodiments, an epitope for an anti-GCC antibody molecule, e.g., a 5F9 antibody, is a conformational epitope further comprising one or more additional amino acid residues in the GCC amino acid sequence beyond residue 50, i.e., selected from about residue 50 to 1073 of SEQ ID NO:228.

In another example, an epitope for an anti-GCC antibody molecule can reside within, or include a residue(s) from, SEQ ID NO:225, or residues 271-300 of SEQ ID NO:228, or a fragment thereof that binds an anti-GCC antibody molecule of the invention, e.g., an ABX-198-, a 3G1-, an 8F1-, or a 10B8-binding fragment thereof. Such fragments can comprise residues 281-290 of SEQ ID NO:228, or residues 281-290 of SEQ ID NO:228 wherein residue 281 is leucine, or residues 281-300 or residues 271-290 of SEQ ID NO:228. In some embodiments, an epitope for an anti-GCC antibody molecule, e.g., an ABX-198-, a 3G1-, an 8F1-, or a 10B8 antibody, is a conformational epitope further comprising one or more additional amino acid residues, i.e., non-SEQ ID NO:225 residues in the GCC amino acid sequence e.g., selected from about residue 1 to 270 and/or about 301 to 1073 of SEQ ID NO:228.

In another example, an epitope for the anti-GCC antibody molecule can reside within, or include a residue(s) from SEQ ID NO:226, or residues 351-375 of SEQ ID NO:228, or a fragment thereof that binds an anti-GCC antibody molecule of the invention, e.g., an ABX-012-, ABX-338-, or ABX-106-binding fragment thereof. Such fragments can comprise 356-370 of SEQ ID NO:228, or residues 351-370 of SEQ ID NO:228, or residues 356-375 of SEQ ID NO:228. In some embodiments, an epitope for an anti-GCC antibody molecule, e.g., an ABX-012-, an ABX-338-, or an ABX-106 antibody, is a conformational epitope further comprising one or more additional amino acid residues, i.e., non-SEQ ID NO:226 residues in the GCC amino acid sequence e.g., selected from about residue 1 to 350 and/or about 376 to 1073 of SEQ ID NO:228.

Antibodies raised against such epitopes or the extracellular domain, e.g., epitopes that reside within, or include a residue(s) from amino acid residues 24 to 420 of SEQ ID NO:228, or a reference portion thereof, e.g., residues 24 to 75, 75 to 150, 150 to 225, 225 to 300, 300 to 375 or 375 to 420 of GCC, or antibody molecules derived therefrom, can be useful as therapeutic or diagnostic antibodies, as described herein.

In an embodiment, the anti-GCC antibody molecule has one or more of the following properties:

a) it competes for binding, e.g., binding to cell surface GCC or purified GCC, with one of the above-referenced anti-GCC antibody molecules summarized in Tables 1 and 2 e.g., human hybridoma antibodies (e.g., 5F9), selected lymphocyte antibodies (e.g., Abx-229), or murine antibodies (e.g., 3G1);

b) it binds to the same, or substantially the same, epitope on GCC as one of the above-referenced anti-GCC antibody molecules summarized in Tables 1 and 2, e.g., human hybridoma antibodies (e.g., 5F9), selected lymphocyte antibodies (e.g., Abx-229), or murine antibodies (e.g., 3G1). In an embodiment, the antibody binds the same epitope, as determined by one or more of a peptide array assay or by binding to truncation mutants, chimeras or point mutants expressed on the cell surface or membrane preparations, e.g., as those assays are described herein;

c) it binds to an epitope which has at least 1, 2, 3, 4, 5, 8, 10, 15 or 20 contiguous amino acid residues in common with the epitope of one of the above-referenced anti-GCC antibody molecules summarized in Tables 1 and 2, e.g., human hybridoma antibodies (e.g., 5F9), selected lymphocyte antibodies (e.g., Abx-229) or murine antibodies (e.g., 3G1);

d) it binds a region of human GCC that is bound by an anti-GCC antibody of the invention, wherein the region e.g., an extracellular or cytoplasmic region, is 10-15, 10-20, 20-30, or 20-40 residues in length, and binding is determined, e.g., by binding to truncation mutants; In an embodiment the anti-GCC antibody molecule binds the extracellular region of human GCC. In an embodiment an anti-GCC antibody molecule can bind the human GCC portion of the extracellular domain defined by amino acid residues 24 to 420 of SEQ ID NO:228. In an embodiment an anti-GCC antibody molecule can bind the guanylate cyclase signature site at amino acid residues 931 to 954 of SEQ ID NO:228; or e) it binds to a reference epitope described herein.

In an embodiment the anti-GCC antibody molecule binds the GCC sequence ILVDLFNDQYFEDNVTAPDYMKNVLVLTLS (SEQ ID NO:225).

In an embodiment the anti-GCC antibody molecule binds the GCC sequence FAHAFRNLTF-EGYDGPVTLDDWGDV (SEQ ID NO:226).

In an embodiment the antibody molecule binds a conformational epitope. In other embodiments an antibody molecule binds a linear epitope.

The anti-GCC antibody molecules can be polyclonal antibodies, monoclonal antibodies, monospecific antibodies, chimeric antibodies (See U.S. Pat. No. 6,020,153) or human or humanized antibodies or antibody fragments or derivatives thereof. Synthetic and genetically engineered variants (See U.S. Pat. No. 6,331,415) of any of the foregoing are also contemplated by the present invention. Monoclonal antibodies can be produced by a variety of techniques, including conventional murine monoclonal antibody methodology e.g., the standard somatic cell hybridization technique of Kohler and Milstein, *Nature* 256: 495 (1975). See generally, Harlow, E. and Lane, D. (1988) *Antibodies: A Laboratory Manual*, Cold Spring Harbor Laboratory Press, Cold Spring Harbor, N.Y.

Immunization with protein, e.g., GCC or a soluble portion, or fusion protein comprising a portion of GCC (e.g., TOK107-hIg), or cells or membrane fractions therefrom, e.g., cells expressing surface-exposed GCC or a portion thereof (e.g., the pLKTOK4 product or the pLKTOK111 product), can be performed with the immunogen prepared for injection in a manner to induce a response, e.g., with adjuvant, e.g., complete Freund's adjuvant. Other suitable adjuvants include, TITERMAX GOLD® adjuvant (CYTRX Corporation, Los Angeles, Calif.) and alum. Small peptide immunogens can be linked to a larger molecule, such as keyhole limpet hemocyanin. Mice can be injected in a number of manners, e.g., subcutaneous, intravenous or intramuscular at a number of sites, e.g., in the peritoneum (i.p.), base of the tail, or foot pad, or a combination of sites, e.g., iP and base of tail (BIP). Booster injections can include the same or a different immunogen and can additionally include adjuvant, e.g., incomplete Freund's adjuvant Immunization with DNA, e.g., DNA encoding GCC or a portion thereof or fusion protein comprising GCC or a portion thereof (e.g., encoding TOK107-hIg) can be injected using gene gun technology. For example, DNA is loaded onto microscopic gold particles and injected into mice at frequent intervals over a brief period.

Generally, where a monoclonal antibody is desired, a hybridoma is produced by fusing a suitable cell from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans, human-antibody transgenic animals or other suitable animals immunized with the antigen of interest. Cells that produce antibodies of human origin (e.g., a human antibody) can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., *Hybridoma*, 17:299-304 (1998); Zanella et al., *J Immunol Methods*, 156:205-215 (1992); Gustafsson et al., *Hum Antibodies Hybridomas*, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA (e.g., with immunogen, e.g., TOK107-hIgG, immobilized on the microtiter well) or by FACS on a cell expressing GCC or a portion thereof, e.g., a cell expressing the pLKTOK111 product). For example, if the GCC-immunogen comprises a fusion moiety that is an affinity reagent, this moiety can allow the fusion protein comprising GCC or a portion thereof to be bound to a matrix, e.g., protein G-coated, streptavidin-coated, glutathione-derivatized or antibody-coated microtitre plates or assay chips, which are then combined with the immune serum or conditioned medium from a hybridoma or antibody-expressing recombinant cell, and the mixture incubated under conditions conducive to complex formation (e.g., at physiological conditions for salt and pH). Following incubation, the microtitre plate wells or chip cells are washed to remove any unbound components and binding by anti-GCC antibody is measured.

In embodiments, for therapeutic applications, the antibodies of the present invention are human or humanized antibodies. The advantage of human or humanized antibodies is that they potentially decrease or eliminate the immunogenicity of the antibody in a host recipient, thereby permitting an increase in the bioavailability and a reduction in the possibility of adverse immune reaction, thus potentially enabling multiple antibody administrations.

Modified antibodies include humanized, chimeric or CDR-grafted antibodies. Human anti-mouse antibody (HAMA) responses have led to development of chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. The presence of such murine or rat derived proteins can lead to the rapid clearance of the antibodies or can lead to the generation of an immune response against the antibody by a patient. In order to avoid the utilization of murine or rat derived antibodies, humanized antibodies where sequences are introduced to an antibody sequence to make it closer to human antibody sequence, or fully human antibodies generated by the introduction of human antibody function into a rodent have been developed so that the rodent would produce antibodies having fully human sequences. Human antibodies avoid certain of the problems associated with antibodies that possess murine, rabbit, or rat variable and/or constant regions.

Human Antibodies

Fully human antibody molecules can minimize the immunogenic and allergic responses intrinsic to mouse or mouse-derivatized mAbs and thus to increase the efficacy and safety of the administered antibodies. The use of fully human antibody molecules can provide a substantial advantage in the treatment of chronic and recurring human diseases, such as inflammation, autoimmunity, and cancer, which require repeated antibody administrations. Also, human antibody molecules can be produced using genetically engineered strains of animals in which the antibody gene expression of the animal is suppressed and functionally replaced with human antibody molecule gene expression.

Methods for making human antibodies are known in the art. One method for making human antibodies employs the use of transgenic animals, such as a transgenic mouse. These transgenic animals contain a substantial portion of the human antibody producing genome, e.g., a human immunoglobulin locus that can undergo functional rearrangement, inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference. Other transgenic human antibody-producing mice include HUMAB-MOUSE®, KIRIN TC MOUSE™ transchromosome mice, KM-MOUSE® (MEDAREX, Princeton, N.J.).

Using the human antibody transgenic animal technology, e.g., XENOMOUSE™ technology, human antibodies can be obtained by immunizing a XENOMOUSE™ mouse (Abgenix, Fremont, Calif.) with an antigen of interest. The lymphatic cells (such as B-cells) are recovered (e.g., isolated from spleen tissue) from the mice that express antibodies. These recovered cells can be fused with a myeloid-type cell line to prepare immortal hybridoma cell lines, using standard methodology. These hybridoma cell lines can be screened and selected to identify hybridoma cell lines that produce antibodies specific to the antigen of interest.

Human-antibody transgenic animals provide a source of nucleic acids that can be enriched in nucleic acids that encode antibodies having desired properties, such as specificity and affinity. For example, nucleic acids encoding antibodies or antibody variable regions can be isolated from human-antibody transgenic mice that have been immunized with a GCC protein or variant or portion thereof. The isolated nucleic acids or portions thereof (e.g., portions encoding variable regions, CDRs, framework regions) can be expressed using any suitable method (e.g., phage display) to produce a library of antibodies or antigen-binding fragments of antibodies (e.g., single chain antigen-binding fragments, double chain antigen-binding fragments) that is enriched for antibodies or antigen-binding fragments that bind a GCC protein. Such a library can exhibit enhanced diversity (e.g., combinatorial diversity through pairing of heavy chain variable regions and light chain variable regions) relative to the repertoire of antibodies produced in the immunized human-antibody transgenic animal. The library can be screened using any suitable assay (e.g., a GCC protein binding assay) to identify antibodies or antigen-binding fragments having desired properties (e.g., specificity, affinity). The nucleic acids encoding antibody or antigen-binding fragments having desired properties can be recovered using any suitable method. (See, e.g., U.S. Pat. No. 5,871,907 (Winter et al.) and U.S. Pat. No. 6,057,098 (Buechler et al.).)

Alternatively, the antibodies can be expressed in cell lines other than hybridoma cell lines. More specifically, sequences encoding particular antibodies can be cloned from cells producing the antibodies and used for transformation of a suitable mammalian host cell. In a preferred method, spleen and/or lymph node lymphocytes from immunized mice are isolated from the mice and plated in plaque assays as described previously in Babcook et al., Proc Natl Acad Sci USA. 93: 7843-8 (1996), which is incorporated herein by reference. Briefly, cells are plated in agar with sheep red blood cells, coated with GCC antigen and cells secreting mAb against the GCC antigen would fix complement and lyse the red blood cells immediately surrounding the mAb producing cells. Cells within the cleared plaques are lifted for sequencing of the immunoglobulin sequences and subcloning into expression vectors. Supernatants from transiently transfected cells containing GCC specific mAb are subsequently screened by ELISA and for binding to cells by flow cytometry. The variable sequences, or a portion thereof of the produced human antibodies comprising CDRs which bind particular epitopes may be utilized for production of modified antibodies. For example, the variable regions of the produced antibodies may be spliced into an expression cassette for ease of transfer of constructs, increased expression of constructs, and/or incorporation of constructs into vectors capable of expression of full length antibodies, see, e.g., US20060147445. In a particular embodiment, the expression cassette comprises the heavy chain constant region of the IgG1 isotype.

The Selected Lymphocyte Antibody Method (SLAM, see U.S. Pat. No. 5,627,052, Babcook et al. Proc. Natl. Acad. Sci. U.S.A. 93:7843-7848 (1996)) can also be used to identify cells which can provide the antibody of interest. In SLAM, B-cells are cultured directly, thus bypassing hybridoma technology, which typically captures only small percentage of the antibodies originally generated by a mouse. Using microplate-based assays, the B-cells are rapidly assayed over a period of several days. Typically, thousands of antigen-reactive cell-clones are identified, representing thousands of individual antigen-specific, e.g., GCC-specific, monoclonal antibodies. The number of different antigen-reactive monoclonal antibodies identified in a single experiment is typically increased many-fold. After applying additional rapid microplate-based assays to measure and rank antibodies by affinity and function, individual B-cell clones producing extremely high quality antibodies can be selected. In addition, by bypassing the hybridoma generation step, production can move rapidly into a recombinant manufacturing cell line. Individual B cells selected using the technology are isolated and the antibody genes can be directly introduced into a manufacturing cell line. The resulting cell line then can be developed for clinical trial testing over essentially the same timeline as that required for hybridoma cell line development.

Human mAb 5F9 (IgG2, kappa) can be produced by hybridoma 5F9, also referred to as hybridoma 46.5F9.8.2, which was deposited on Jan. 10, 2007, on behalf of Millennium Pharmaceuticals Inc., 40 Landsdowne Street, Cambridge, Mass., 02139, USA, at the American Type Culture Collection, 10801 University Boulevard, Manassas, Va. 20110, U.S.A., under Accession No. PTA-8132. (The deposit was made pursuant to, and in satisfaction of, the requirements of the Budapest Treaty on the International Recognition of the Deposit of Microorganisms for the Purposes of Patent Procedure.) The invention relates to hybridoma 5F9, to the antibody it produces, antigen-binding fragments thereof, and to nucleic acids encoding the antibody and portions thereof (e.g., heavy chain, heavy chain variable region, light chain, light chain variable region, CDRs). As described herein, hybridoma 5F9 produces an IgG2, kappa antibody.

Humanization and Display Technologies and Modifications to Antibodies

As discussed above, there are advantages to producing antibodies with reduced immunogenicity. This can be accomplished in connection with techniques of humanization and display techniques using appropriate libraries. It will be appreciated that murine antibodies or antibodies from other species can be humanized or primatized using techniques known in the art. See e.g., Winter and Harris *Immunol Today* 14:43-46 (1993) and Wright et al. *Crit. Reviews in Immunol.* 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *Proc Natl Acad Sci USA.* 84:3439 (1987) and *J. Immunol.* 139:3521 (1987)). mRNA is isolated from a hybridoma or other cell producing the antibody and used to produce cDNA: The cDNA of interest may be amplified by the polymerase chain reaction using specific primers (U.S. Pat. Nos. 4,683,195 and 4,683,202).

Alternatively, phage display technology (see, e.g., McCafferty et al, *Nature,* 348:552-553 (1990)) can be used to produce human antibodies and antibody fragments in vitro, from immunoglobulin variable (V) domain genes, e.g., from repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson and Chiswell, *Current Opinion in Structural Biology,* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.,* 222:581-597 (1991), or Griffith et al, *EMBO J.,* 12:725-734 (1993). See, also, U.S. Pat. Nos. 5,565,332 and 5,573,905. Display libraries can contain antibodies or antigen-binding fragments of antibodies that contain artificial amino acid sequences. For example, the library can contain Fab fragments which contain artificial CDRs (e.g., random amino acid sequences) and human framework regions. (See, for example, U.S. Pat. No. 6,300,064 (Knappik, et al.).)

Human antibodies may also be generated by in vitro activated B cells (see U.S. Pat. Nos. 5,567,610 and 5,229,275).

The sequences of human constant region genes may be found in Kabat et al. (1991) *Sequences of Proteins of Immunological Interest,* N.I.H. publication no. 91-3242. Human C region genes are readily available from known clones. The choice of isotype will be guided by the desired effector functions, such as complement fixation, or activity in antibody-dependent cellular cytotoxicity. Isotypes can be IgG1, IgG2, IgG3 or IgG4. In particular embodiments, antibody molecules of the invention are IgG1 and IgG2. Either of the human light chain constant regions, kappa or lambda, may be used. The chimeric, humanized antibody is then expressed by conventional methods.

In some embodiments, an anti-GCC antibody molecule of the invention can draw antibody-dependent cellular cytotoxicity (ADCC) to a cell expressing GCC, e.g., a tumor cell. Antibodies with the IgG1 and IgG3 isotypes are useful for eliciting effector function in an antibody-dependent cytotoxic capacity, due to their ability to bind the Fc receptor. Antibodies with the IgG2 and IgG4 isotypes are useful to minimize an ADCC response because of their low ability to bind the Fc receptor. In related embodiments substitutions in the Fc region or changes in the glycosylation composition of an antibody, e.g., by growth in a modified eukaryotic cell line, can be made to enhance the ability of Fc receptors to recognize, bind, and/or mediate cytotoxicity of cells to which anti-GCC antibodies bind (see, e.g., U.S. Pat. Nos. 7,317,091, 5,624,821 and publications including WO 00/42072, Shields, et al. *J. Biol. Chem.* 276:6591-6604 (2001), Lazar et al. *Proc. Natl. Acad. Sci. U.S.A.* 103:4005-4010 (2006), Satoh et al. *Expert Opin Biol. Ther.* 6:1161-1173 (2006)). In certain embodiments, the antibody or antigen-binding fragment (e.g., antibody of human origin, human antibody) can include amino acid substitutions or replacements that alter or tailor function (e.g., effector function). For example, a constant region of human origin (e.g., γ1 constant region, γ2 constant region) can be designed to reduce complement activation and/or Fc receptor binding. (See, for example, U.S. Pat. No. 5,648,260 (Winter et al.), U.S. Pat. No. 5,624,821 (Winter et al.) and U.S. Pat. No. 5,834,597 (Tso et al.), the entire teachings of which are incorporated herein by reference.) Preferably, the amino acid sequence of a constant region of human origin that contains such amino acid substitutions or replacements is at least about 95% identical over the full length to the amino acid sequence of the unaltered constant region of human origin, more preferably at least about 99% identical over the full length to the amino acid sequence of the unaltered constant region of human origin.

In still another embodiment, effector functions can also be altered by modulating the glycosylation pattern of the antibody. By altering is meant deleting one or more carbohydrate moieties found in the antibody, and/or adding one or more glycosylation sites that are not present in the antibody. For example, antibodies with enhanced ADCC activities with a mature carbohydrate structure that lacks fucose attached to an Fc region of the antibody are described in U.S. Patent Application Publication No. 2003/0157108 (Presta). See also U.S. Patent Application Publication No. 2004/0093621 (Kyowa Hakko Kogyo Co., Ltd). Glycofi has also developed yeast cell lines capable of producing specific glycoforms of antibodies.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which are engineered to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 *J. Biol. Chem.* 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 *Nat. Biotech.* 17:176-180).

Humanized antibodies can also be made using a CDR-grafted approach. Techniques of generation of such humanized antibodies are known in the art. Generally, humanized antibodies are produced by obtaining nucleic acid sequences that encode the variable heavy and variable light sequences of an antibody that binds to GCC, identifying the complementary determining region or "CDR" in the variable heavy and variable light sequences and grafting the CDR nucleic acid sequences on to human framework nucleic acid sequences. (See, for example, U.S. Pat. Nos. 4,816,567 and 5,225,539). The location of the CDRs and framework residues can be determined (see, Kabat, E. A., et al. (1991) *Sequences of Proteins of Immunological Interest*, Fifth Edition, U.S. Department of Health and Human Services, NIH Publication No. 91-3242, and Chothia, C. et al. *J. Mol. Biol.* 196:901-917 (1987)). Anti-GCC antibody molecules described herein have the CDR amino acid sequences and nucleic acid sequences encoding CDRs listed in Tables 5 and 6. In some embodiments sequences from Tables 5 and 6 can be incorporated into molecules which recognize GCC for use in the therapeutic or diagnostic methods described herein. The human framework that is selected is one that is suitable for in vivo administration, meaning that it does not exhibit immunogenicity. For example, such a determination can be made by prior experience with in vivo usage of such antibodies and studies of amino acid similarities. A suitable framework region can be selected from an antibody of human origin having at least about 65% amino acid sequence identity, and preferably at least about 70%, 80%, 90% or 95% amino acid sequence identity over the length of the framework region within the amino acid sequence of the equivalent portion (e.g., framework region) of the donor antibody, e.g., an anti-GCC antibody molecule (e.g., 3G1). Amino acid sequence identity can be determined using a suitable amino acid sequence alignment algorithm, such as CLUSTAL W, using the default parameters. (Thompson J. D. et al., *Nucleic Acids Res.* 22:4673-4680 (1994).)

Once the CDRs and FRs of the cloned antibody that are to be humanized are identified, the amino acid sequences encoding the CDRs are identified and the corresponding nucleic acid sequences grafted on to selected human FRs. This can be done using known primers and linkers, the selection of which are known in the art. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen. After the CDRs are grafted onto selected human FRs, the resulting "humanized" variable heavy and variable light sequences are expressed to produce a humanized Fv or humanized antibody that binds to GCC. Preferably, the CDR-grafted (e.g., humanized) antibody binds a GCC protein with an affinity similar to, substantially the same as, or better than that of the donor antibody. Typically, the humanized variable heavy and light sequences are expressed as a fusion protein with human constant domain sequences so an intact antibody that binds to GCC is obtained. However, a humanized Fv antibody can be produced that does not contain the constant sequences.

Also within the scope of the invention are humanized antibodies in which specific amino acids have been substituted, deleted or added. In particular, humanized antibodies can have amino acid substitutions in the framework region, such as to improve binding to the antigen. For example, a selected, small number of acceptor framework residues of the humanized immunoglobulin chain can be replaced by the corresponding donor amino acids. Locations of the substitutions include amino acid residues adjacent to the CDR, or which are capable of interacting with a CDR (see e.g., U.S. Pat. No. 5,585,089 or 5,859,205). The acceptor framework can be a mature human antibody framework sequence or a consensus sequence. As used herein, the term "consensus sequence" refers to the sequence found most frequently, or devised from the most common residues at each position in a sequence in a region among related family members. A number of human antibody consensus sequences are available, including consensus sequences for the different subgroups of human variable regions (see, Kabat, E. A., et al., *Sequences of Proteins of Immunological Interest*, Fifth Edition, U.S. Department of Health and Human Services, U.S. Government Printing Office (1991)). The Kabat database and its applications are freely available on line, e.g. via IgBLAST at the National Center for Biotechnology Information, Bethesda, Md. (also see, Johnson, G. and Wu, T. T., *Nucleic Acids Research* 29:205-206 (2001)).

Other techniques for humanizing antibodies are described in Padlan et al. EP 519596 A1, published on Dec. 23, 1992.

The anti-GCC antibody molecule includes other humanized antibodies which may also be modified by specific deletion of human T cell epitopes or "deimmunization" by the methods disclosed in PCT Publication Nos. WO 98/52976 and WO 00/34317, the contents of which are incorporated herein by reference. Briefly, the murine heavy and light chain variable regions of an anti-GCC antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the murine VH and VL sequences, as described in PCT Publication Nos. WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made, often but not exclusively, an amino acid common at this position in human germline antibody sequences may be used. Human germline sequences are disclosed in Tomlinson, I. A. et al., *J. Mol. Biol.* 227:776-798 (1992); Cook, G. P. et al., *Immunol. Today* Vol. 16 (5): 237-242 (1995); Chothia, D. et al., *J. Mol. Bio.* 227:799-817 (1992). The V BASE directory provides a comprehensive directory of human immunoglobulin variable region sequences (compiled by Tomlinson, I. A. et al. MRC Centre for Protein Engineering, Cambridge, UK). After the deimmunized VH and VL of an anti-GCC antibody are constructed by mutagenesis of the murine VH and VL genes, the mutagenized variable sequence can, optionally, be fused to a human constant region, e.g., human IgG1 or κ constant regions.

In other embodiments, reduction of an immunogenic response by a CDR-grafted antibody can be achieved by changes, e.g., deletions, substitutions, of amino acid residues in CDRs (Kashmiri et al. *Methods* 36:25-34 (2005), U.S. Pat. No. 6,818,749, Tan et al. *J. Immunol.* 169:1119-1125 (2006)). For example, residues at positions involved in contact with the antigen preferably would not be changed. Typically, such residues, the SDRs, are in positions which display high levels of variability among antibodies. Consensus sequences (e.g., SEQ ID NOs:302-307, Table 5) derived, e.g., by the Clustal method (Higgins D. G. et al., *Meth. Enzymol.* 266:383-402 (1996)), from anti-GCC antibody molecules, e.g., from antibodies described herein, aid in identifying SDRs. In the human anti-GCC antibody molecules described herein, the SDRs are the following, at least the first residue or in some embodiments, the first four residues of heavy chain CDR1; at least the N-terminal portion, e.g., the first seven, ten or 13 residues of heavy chain CDR2; nearly all of heavy chain CDR3; the C-terminal portion, e.g., after residue six, eight, or nine of light chain CDR1; about the first, middle and/or last residue of light chain CDR2; and most of light chain CDR3, or at least after residue two or three. Accordingly, to maintain binding to GCC protein after humanization or modification of an anti-GCC antibody molecule, such SDR residues in CDRs of the anti-GCC antibody molecules are less amenable to changes, e.g., from murine residues to human consensus residues than are residues in other residues of the CDRs or the framework regions. Conversely, it can be beneficial to change residues in non-human, e.g., murine CDRs to residues identified as consensus in human CDRs, e.g., CDRs of anti-GCC antibody molecules described herein (e.g., the sequences listed in Table 5). For example, a serine can represent a human residue for the C-terminus of heavy chain CDR1, and/or a tyrosine can represent a human residue for the second and/or third residues of heavy chain CDR1; heavy chain CDR2 can end in S-(L/V)-K-(S/G) (SEQ ID NO:312) to represent a human CDR; to represent a human CDR3, there can be a glycine after four to six residues and/or an aspartate six to nine residues in heavy chain CDR3; light chain CDR1 can begin with (K/R)-(A/S)-SQS-(V/L)-(S/L) (SEQ ID NO:313) to represent a human CDR; light chain CDR2 can have a serine in the third residue and/or an arginine in the fifth residue represent a human CDR; and/or light chain CDR3 can have a glutamine in the second residue and/or a tyrosine or serine in the third residue represent a human CDR.

Anti-GCC antibodies that are not intact antibodies are also useful in this invention. Such antibodies may be derived from any of the antibodies described above. Useful antibody molecules of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; (vii) a single domain functional heavy chain antibody, which consists of a VHH domain (known as a nanobody) see e.g., Cortez-Retamozo, et al., *Cancer Res.* 64: 2853-2857 (2004), and references cited therein; and (vii) an isolated CDR, e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. *Science* 242:423-426 (1988); and Huston et al. *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

In embodiments, some or all of the CDRs sequences, of one or both the heavy and light chain, can be used in another antibody molecule, e.g., in a CDR-grafted, humanized, or chimeric antibody molecule.

Embodiments include an antibody molecule that comprises sufficient CDRs, e.g., all six CDRs from one of the above-referenced human hybridoma, selected lymphocyte, or murine antibodies to allow binding to cell surface GCC.

In an embodiment the CDRs, e.g., all of the HCDRs, or all of the LCDRs, or all six, are embedded in human or human derived framework region(s). Examples of human framework regions include human germline framework sequences, human germline sequences that have been affinity matured (either in vivo or in vitro), or synthetic human sequences, e.g., consensus sequences. In an embodiment the heavy chain framework is an IgG1 or IgG2 framework. In an embodiment the light chain framework is a kappa framework.

In an embodiment the anti-GCC antibody molecule, e.g., a CDR-grafted or humanized antibody molecule, comprises sufficient CDRs, e.g., all six CDRs from one of the antibodies described herein, e.g., sequences listed in Table 5, to allow binding to GCC. (Exemplary nucleic acid sequences which can encode the CDR amino acid sequences listed in Table 5, are provided, in Table 6 herein). In particular embodiments, an anti-GCC antibody molecule can comprise CDRs from 5F9 or Abx-229.

Antibody fragments for in vivo therapeutic or diagnostic use can benefit from modifications which improve their serum half lives. Suitable organic moieties intended to increase the in vivo serum half-life of the antibody can include one, two or more linear or branched moiety selected from a hydrophilic polymeric group (e.g., a linear or a branched polymer (e.g., a polyalkane glycol such as polyethylene glycol, monomethoxy-polyethylene glycol and the like), a carbohydrate (e.g., a dextran, a cellulose, a polysaccharide and the like), a polymer of a hydrophilic amino acid (e.g., polylysine, polyaspartate and the like), a polyalkane oxide and polyvinyl pyrrolidone), a fatty acid group (e.g., a mono-carboxylic acid or a di-carboxylic acid), a fatty acid ester group, a lipid group (e.g., diacylglycerol group, sphingolipid group (e.g., ceramidyl)) or a phospholipid group (e.g., phosphatidyl ethanolamine group). Preferably, the organic moiety is bound to a predetermined site where the organic moiety does not impair the function (e.g., decrease the antigen binding affinity) of the resulting immunoconjugate compared to the non-conjugated antibody moiety. The organic moiety can have a molecular weight of about 500 Da to about 50,000 Da, preferably about 2000, 5000, 10,000 or 20,000 Da. Examples and methods for modifying polypeptides, e.g., antibodies, with organic moieties can be found, for example, in U.S. Pat. Nos. 4,179,337 and 5,612,460, PCT Publication Nos. WO 95/06058 and WO 00/26256, and U.S. Patent Application Publication No. 20030026805.

An anti-GCC antibody molecule can comprise all, or an antigen binding fragment of the variable region, of one or both, the heavy and light chain, of one of the above-referenced human hybridoma, selected lymphocyte, or murine antibodies.

In an embodiment the light chain amino acid sequence of (a) can differ from one of the reference amino acid sequence(s) referred to in (a)(i-ii) by as many as 1, 2, 3, 4, 5, 10, or 15 residues. In embodiments the differences are conservative substitutions. In embodiments, the differences are in the framework regions. In an embodiment the heavy chain amino acid sequence of (b) can differ from one of the reference amino acid sequence(s) referred to in (b)(i-ii) by as many as 1, 2, 3, 4, 5, 10, or 15 residues. In embodiments the differences are conservative substitutions. In embodiments the differences are in the framework regions.

In an embodiment the anti-GCC antibody molecule comprises one or both of:
  (a) a light chain amino acid sequence of all, or an antigen binding fragment of, either, (i) a light chain variable region amino acid sequence from Table 3, e.g., SEQ ID NO:20, or (ii) a light chain variable region amino acid encoded by a nucleotide sequence from Table 4, e.g., SEQ ID NO:19; and
  (b) a heavy chain amino acid sequence of all, or an antigen binding fragment of, either (i) a heavy chain variable region amino acid sequence from Table 3, e.g., SEQ ID NO:18, or (ii) a heavy chain amino acid sequence encoded by a nucleotide sequence from Table 4, e.g., SEQ ID NO:17.

In an embodiment the anti-GCC antibody molecule comprises one or both of:
  a) a light chain variable region, or an antigen binding fragment thereof, having at least 85, 90, 95, 97 or 99% homology with the light chain variable region of an anti-GCC antibody molecule of the invention, e.g., one of the above-referenced human hybridoma, selected lymphocyte, or murine antibodies; and
  (b) a heavy chain variable region, or an antigen binding fragment thereof, having at least 85, 90, 95, 97 or 99% homology with the heavy chain variable region of an anti-GCC antibody molecule of the invention, e.g., one of the above-referenced human hybridoma, selected lymphocyte, or murine antibodies.

Amino acid sequences of the variable regions of human hybridoma, selected lymphocyte, and murine antibodies can be found in Table 3.

In an embodiment, the anti-GCC antibody molecule is a 5F9 antibody molecule and includes one or both of: a) all or a fragment of the heavy chain constant region from SEQ ID NO: 231; and b) all or a fragment of the light chain constant region from SEQ ID NO: 233.

In another embodiment, the anti-GCC antibody molecule is an Abx-229 antibody molecule and includes one or both of: a) all or a GCC-binding fragment of the heavy chain variable region from SEQ ID NO: 46; and b) all or a GCC-binding fragment of the light chain variable region from SEQ ID NO: 48.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Polyadenylation and transcription termination occur at native chromosomal sites downstream of the coding regions. The resulting chimeric antibody may be joined to any strong promoter. Examples of suitable vectors that can be used include those that are suitable for mammalian hosts and based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CMV), and moloney murine leukemia virus (MMLV), native Ig promoters, etc. A variety of suitable vectors are known in the art, including vectors which are maintained in single copy or multiple copies, or which become integrated into the host cell chromosome, e.g., via LTRs, or via artificial chromosomes engineered with multiple integration sites (Lindenbaum et al. *Nucleic Acids Res*. 32:e172 (2004), Kennard et al. *Biotechnol. Bioeng.* Online May 20, 2009). Additional examples of suitable vectors are listed in a later section.

Thus, the invention provides an expression vector comprising a nucleic acid encoding an antibody, antigen-binding fragment of an antibody (e.g., a human, humanized, chimeric antibody or antigen-binding fragment of any of the foregoing), antibody chain (e.g., heavy chain, light chain) or antigen-binding portion of an antibody chain that binds a GCC protein.

Expression in eukaryotic host cells is useful because such cells are more likely than prokaryotic cells to assemble and secrete a properly folded and immunologically active antibody. However, any antibody produced that is inactive due to improper folding may be renaturable according to known methods (Kim and Baldwin, "Specific Intermediates in the Folding Reactions of Small Proteins and the Mechanism of Protein Folding", *Ann. Rev. Biochem.* 51, pp. 459-89 (1982)). It is possible that the host cells will produce portions of intact antibodies, such as light chain dimers or heavy chain dimers, which also are antibody homologs according to the present invention.

Further, as described elsewhere herein, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are known in the art. Winter and Harris *Immunol Today* 14:43-46 (1993) and Wright et al. *Crit. Reviews in Immunol.* 12125-168 (1992), Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. *Proc Natl Acad Sci USA* 87:6378-6382 (1990), Russel et al. *Nucl. Acids Research* 21:1081-1085 (1993), Hoganboom et al. *Immunol. Reviews* 130:43-68 (1992), Chiswell and McCafferty *TIBTECH* 10:80-84 (1992), and U.S. Pat. No. 5,733,743. If display technologies are utilized to produce antibodies that are not human, such antibodies can be humanized as described above.

It will be appreciated that antibodies that are generated need not initially possess a particular desired isotype but, rather, the antibody as generated can possess any isotype. For example, the antibody produced by the 5F9 hybridoma (ATCC deposit no. PTA-8132) has the IgG2 isotype. The isotype of the antibody can be switched thereafter, e.g., to IgG1 or IgG3 to elicit an ADCC response when the antibody binds GCC on a cell, using conventional techniques that are known in the art. Such techniques include the use of direct recombinant techniques (see e.g., U.S. Pat. No. 4,816,397), cell-cell fusion techniques (see e.g., U.S. Pat. No. 5,916,771), among others. In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

In certain embodiments, the GCC antibody molecule is a human anti-GCC IgG1 antibody. Since such antibodies possess desired binding to the GCC molecule, any one of such antibodies can be readily isotype-switched to generate a human IgG4 isotype, for example, while still possessing the same variable region (which defines the antibody's specificity and affinity, to a certain extent). Accordingly, as antibody candidates are generated that meet desired "structural" attributes as discussed above, they can generally be provided with at least certain additional "functional" attributes that are desired through isotype switching.

In an embodiment the variable region or antigen binding fragment thereof can be coupled to a constant region (or fragment thereof) other than the constant region it was generated with, e.g., a constant region (or fragment thereof) from another antibody or to a synthetic constant region (or fragment thereof). In embodiments the constant region is an IgG1 or IgG2 constant region (or fragment thereof). Sequence changes can be made in the variable or constant regions to modify effector activity of the antibody molecule.

Design and Generation of Other Therapeutics

The antibodies that are produced and characterized herein with respect to GCC provide for the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunoconjugates, and radiolabeled therapeutics, generation of peptide therapeutics, particularly intrabodies, and small molecules. Furthermore, as discussed above, the effector function of the antibodies of the invention may be changed by isotype switching to an IgG1, IgG2, IgG3, IgG4, IgD, IgA1, IgA2, IgE, or IgM for various therapeutic uses.

In connection with bispecific antibodies, bispecific antibodies can be generated that comprise (i) two antibodies, one with a specificity to GCC and another to a second molecule that are conjugated together, (ii) a single antibody that has one chain specific to GCC and a second chain specific to a second molecule, or (iii) a single chain antibody that has specificity to GCC and the other molecule. Such bispecific antibodies can be generated using techniques that are known. For example, bispecific antibodies may be produced by crosslinking two or more antibodies (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. See also, e.g., Fanger et al. *Immunomethods* 4:72-81 (1994) and Winter and Harris *Immunol Today* 14:43-46 (1993) and Wright et al. *Crit. Reviews in Immunol.* 12125-168 (1992) and in connection with (iii) see e.g., Traunecker et al. *Int. J. Cancer* (Suppl.) 7:51-52 (1992). Songsivilai & Lachmann Clin. *Exp. Immunol.* 79: 315-321 (1990), Kostelny et al. *J. Immunol.* 148:1547-1553 (1992).

In addition, "Kappabodies" (Ill. et al. "Design and construction of a hybrid immunoglobulin domain with properties of both heavy and light chain variable regions" *Protein Eng* 10:949-57 (1997)), "Minibodies" (Martin et al. *EMBO J* 13:5303-9 (1994), U.S. Pat. No. 5,837,821), "Diabodies" (Holliger et al. *Proc Natl Acad Sci USA* 90:6444-6448 (1993)), or "Janusins" (Traunecker et al. *EMBO J* 10:3655-3659 (1991) and Traunecker et al. *Int J Cancer* Suppl 7:51-52 (1992)) may also be prepared.

Nucleic Acid and Polypeptides

In another embodiment, the present invention relates to polynucleotide and polypeptide sequences that encode for or represent the antibody molecules described herein. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (antisense) strand. The coding sequence that encodes the polypeptide may be identical to the coding sequence provided herein or may be a different coding sequence which coding sequence, as a result of the redundancy or degeneracy of the genetic code, encodes the same polypeptide as the DNA provided herein.

In embodiments provided, polynucleotides encode at least one heavy chain variable region and at least one light chain variable region of the present invention, e.g., as summarized in Table 4.

The present invention also includes variant polynucleotides containing modifications such as polynucleotide deletions, substitutions or additions, and any polypeptide modification resulting from the variant polynucleotide sequence. A polynucleotide of the present invention may also have a coding sequence that is a variant of the coding sequence provided herein. For example, a variant polynucleotide can have at least 50%, 60%, 70%, 75%, 80%, 85%, 90%, 95% or 97% identity with a polynucleotide listed in Table 4. In embodiments, the variant polynucleotide encodes for an anti-GCC antibody molecule.

The present invention further relates to polypeptides that represent the antibodies of the present invention as well as fragments, analogs and derivatives of such polypeptides. The polypeptides of the present invention may be recombinant polypeptides, naturally produced polypeptides or synthetic polypeptides. The fragment, derivative or analogs of the polypeptides of the present invention may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention. In various aspects, the polypeptides of the invention may be partially purified, or purified product.

A polypeptide of the present invention can have an amino acid sequence that is identical to that of the antibodies described herein, e.g., summarized in Tables 2 or 3, or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine; replacement of lysine with arginine or histidine. In contrast, variations may include nonconservative changes, e.g., replacement of a glycine with a tryptophan. Similar minor variations may also include amino acid deletions or insertions or both. Guidance in determining which and how many amino acid residues may be substituted, inserted, or deleted without changing biological or immunological activity may be found using computer programs known in the art, for example DNASTAR software (DNASTAR, Inc., Madison, Wis.).

In another aspect, the invention features, isolated and/or recombinant nucleic acids encoding anti-GCC antibody molecules. In embodiments, the nucleic acids encode one or more of an antibody molecule, a heavy chain, a light chain, a light chain variable region, a heavy chain variable region, portions of the heavy chains and light chains of the antibody molecules described herein (e.g., a light chain variable region fragment which when paired with a full length heavy chain variable region is antigen binding, or a heavy chain variable region fragment which when paired with a full length light chain variable region is antigen binding), and CDRs. Embodiments include such nucleic acids disposed in vectors, e.g., expression vectors. In specific embodiments the invention includes plasmids pTOK58D-5F9LC and pTOK58D-5F9HC. Still further, the invention encompasses antibody molecules produced by host cells, e.g., expressing the antibody molecules encoded by plasmids pTOK58D-5F9LC and pTOK58D-5F9HC.

In an embodiment, is provided a vector, e.g., an expression vector, comprising one or both of:

sequences encoding a light chain variable region, e.g., sequences listed in Table 4, an antigen binding fragment thereof, or one, two or three CDRs from a light chain (and optionally a framework region), described herein, e.g., in Table 6; and sequences encoding a heavy chain variable region, e.g., sequences listed in Table 4, an antigen binding fragment thereof, or one, two or three CDRs from a heavy chain (and optionally a framework region), described herein, e.g., in Table 6.

In embodiments provided, polynucleotides encode at least one heavy chain variable region or at least one light chain variable region of the antibodies of the present invention. In embodiments provided, polypeptides can encode at least one heavy chain variable region and one light chain variable region of the antibodies of the present invention.

In an embodiment the anti-GCC antibody molecule comprises one or both of:

(a) a light chain variable region, or an antigen binding fragment thereof, encoded by a nucleic acid that hybridizes under selected stringency conditions with, (i) the complement of an anti-GCC antibody molecule-encoding-nucleic acid sequence described herein, e.g., in Table 4, or (ii) any nucleic acid sequence that encodes a light chain of an anti-GCC antibody molecule of the invention, e.g., one of the above-referenced human hybridoma, selected lymphocyte, or murine antibodies summarized in Tables 1 and 2; and (b) a heavy chain variable region, or an antigen binding fragment thereof, encoded by a nucleic acid that hybridizes under selected stringency conditions with, (i) the complement of an anti-GCC antibody molecule-encoding-nucleic acid sequence described herein, e.g., in Table 4, or (ii) any nucleic acid sequence that encodes a heavy chain of an anti-GCC antibody molecule of the invention, e.g., one of the above-referenced human hybridoma, selected lymphocyte, or murine antibodies summarized in Tables 1 and 2.

In an embodiment selected stringency conditions are high stringency or very high stringency conditions, e.g., as those conditions are described herein.

In additional aspects, the antibody or the antigen binding fragment comprises an amino acid sequence of the light chain variable region amino acid sequence of the antibody encoded by the DNA having ATCC Accession Number PTA-8132. In other additional aspects, the antibody or the antigen binding fragment comprises an amino acid sequence of the heavy chain variable region sequence of the antibody encoded by the DNA having ATCC Accession Number PTA-8132.

The present invention also provides vectors that include the polynucleotides of the present invention, host cells which are genetically engineered with vectors of the present invention and the production of the antibodies of the present invention by recombinant techniques.

The appropriate DNA sequence may be inserted into the vector by a variety of procedures. In general, the DNA sequence is inserted into appropriate restriction endonuclease sites by procedures known in the art. The polynucleotide sequence in the expression vector is operatively linked to an appropriate expression control sequence (i.e. promoter) to direct mRNA synthesis. Examples of such promoters include, but are not limited to, the Rous sarcoma virus LTR or the early or late SV40 promoter, the *E. coli* lac or trp, the phage lambda $P_L$ promoter and other promoters known to control expression of genes in prokaryotic (e.g., tac, T3, T7 promoters for *E. coli*) or eukaryotic (e.g., cytomegalovirus promoter, adenovirus late promoter, EF-1a promoter) cells or their viruses. The expression vector also contains a ribosome binding site for translation initiation and a transcription terminator. The vector may also include appropriate sequences for amplifying expression. For example, the vector can contain enhancers, which are transcription-stimulating DNA sequences of viral origin, such as those derived form simian virus such as SV40, polyoma virus, cytomegalovirus, bovine papilloma virus or Moloney sarcoma virus, or genomic, origin. The vector preferably also contains an origin of replication. The vector can be constructed to contain an exogenous origin of replication or, such an origin of replication can be derived from SV40 or another viral source, or by the host cell chromosomal replication mechanism.

In addition, the vectors optionally contain a marker gene for selection of transfected host cells such as dihydrofolate reductase marker genes to permit selection with methotrexate in a variety of hosts, or antibiotics, such as β-lactamase gene (ampicillin resistance), Tet gene (for tetracycline resistance) used in prokaryotic cells or neomycin, GA418 (geneticin, a neomycin-derivative) gpt (mycophenolic acid), ampicillin, or hygromycin resistance genes, or genes which complement a genetic lesion of the host cells such as the absence of thymidine kinase, hypoxanthine phosphoribosyl transferase, dihydrofolate reductase, etc. Genes encoding the gene product of auxotrophic markers of the host (e.g., LEU2, URA3, HISS) are often used as selectable markers in yeast.

In order to obtain the antibodies of the present invention, one or more polynucleotide sequences that encode for the light and heavy chain variable regions and light and heavy chain constant regions of the antibodies of the present invention should be incorporated into a vector. Polynucleotide sequences encoding the light and heavy chains of the antibodies of the present invention can be incorporated into one or multiple vectors and then incorporated into the host cells.

Suitable expression vectors for expression in mammalian cells include, for example, pCDM8, pCDNA1.1/amp, pcDNA3.1, pRc/RSV, pEF-1 (Invitrogen Life Technologies, Carlsbad, Calif.), pCMV-SCRIPT, pFB, pSG5, pXT1 (Stratagene, La Jolla, Calif.), pCDEF3 (Goldman, L. A., et al., *Biotechniques,* 21:1013-1015 (1996)), pSVSPORT (GIBCO division of Invitrogen Life Technologies, Carlsbad, Calif.), pEF-Bos (Mizushima, S., et al., *Nucleic Acids Res.,* 18:5322 (1990)), Bicistronic GPEX® Retrovector (Gala Biotech, Middleton, Wis.) and the like. Expression vectors which are suitable for use in various expression hosts, such as prokaryotic cells (*E. coli*), insect cells (*Drosophila* Schnieder S2 cells, Sf9) and yeast (*P. methanolica, P. pastoris, S. cerevisiae*) are also available. Exemplary vectors are pLKTOK58 (wild type IgG1 Fc sequence) and pLK-TOK59 (mutated IgG1 Fc sequence) (see U.S. Patent Application publication no. 20060147445).

As will be appreciated, antibodies in accordance with the present invention can be expressed in cell lines other than hybridoma cell lines. Sequences encoding the cDNAs or genomic clones for the particular antibodies can be used for a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, for introducing heterologous polynucleotides into mammalian cells, e.g., dextran-mediated transfection, calcium phosphate precipitation, polybrene mediated transfection, protoplast fusion, electroporation, encapsulation of the polynucleotide(s) into liposomes and direct microinjection of the DNA molecule. The transformation procedure used depends upon the host to be transformed. Methods for introduction of heterologous polynucleotides into mammalian cells are known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

In another aspect, the invention features, a host cell comprising a nucleic acid described herein. In embodiments the cell expresses an antibody molecule, or component thereof, described herein. Still further embodiment provides a method of producing an antibody molecule, e.g., an anti-GCC antibody molecule described herein, e.g. a human or humanized antibody molecule comprising maintaining the host cell under conditions appropriate for expression, whereby immunoglobulin chain(s) are expressed and an antibody molecule is produced. An additional embodiment provides a host cell comprising any of the foregoing expression vectors encoding heavy and light chain antibody sequences. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NS0), Chinese hamster ovary cells (CHO), COS cells. In a particular embodiment, the cultured host cell is a COS cell comprising nucleic acid sequences encoding a 5F9 antibody molecule. In another embodiment, the host cell is Hybridoma 5F9 (PTA-8132). Additionally cells include oocyte cells, and cells from a transgenic animal, e.g., mammary epithelial cell. For example, nucleic acids encoding an antibody molecule described herein can be expressed in a transgenic nonhuman animal.

Mammalian cell lines available as hosts for expression are known in the art and include many immortalized cell lines available from the American Type Culture Collection (ATCC), including but not limited to Chinese hamster ovary (CHO) cells, NSO cells, HeLa cells, baby hamster kidney (BHK) cells, monkey kidney cells (COS), human hepatocellular carcinoma cells (e.g., Hep G2), and a number of other cell lines. Nonmammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive GCC binding properties.

A still further embodiment provides a method of producing an anti-GCC antibody molecule, e.g., a human or humanized antibody molecule, comprising maintaining the host cell comprising nucleic acids described herein, e.g., one or more nucleic acid sequence listed in Table 4 or 6, under conditions appropriate for expression of an immunoglobulin, whereby immunoglobulin chains, are expressed and an antibody molecule, e.g., a human or humanized antibody molecule that binds GCC, or a fragment or variant thereof, is produced. For example, methods of expression of antibody molecules include the use of host cells wherein a first recombinant nucleic acid molecule encoding an antibody molecule, e.g., a human or humanized antibody light chain, and a second recombinant nucleic acid molecule encoding an antibody molecule, e.g., a human or humanized antibody heavy chain, are comprised in a single expression vector. In other embodiments, they are in separate vectors. The method can further comprise the step of isolating or recovering the antibody, antigen-binding fragment of an antibody, antibody chain or antigen-binding fragment of an antibody chain, if desired.

For example, a nucleic acid molecule (i.e., one or more nucleic acid molecules) encoding the heavy and light chains of a human antibody that binds a GCC protein, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable non-human animal, in suitable culture media supplemented with appropriate salts, growth factors, antibiotics, nutritional supplements, etc.), whereby the encoded polypeptide(s) are produced. If desired, the encoded protein can be isolated or recovered (e.g., from the animal, the host cell, medium, milk). This process encompasses expression in a host cell of a transgenic non-human animal (see, e.g., WO 92/03918, GenPharm International) or plant.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning, Microdrop technology, or any other methods known in the art. The GS system is discussed in whole or part in connection with European Patent Nos. 0 216 846, 0 256 055, and 0 323 997 and European Patent Application No. 89303964.4.

In an exemplary system for recombinant expression of a modified antibody, or antigen-binding portion thereof, of the invention, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

The antibodies, antigen-binding fragments, antibody chains and antigen-binding portions thereof described herein also can be produced in a suitable in vitro expression system, by chemical synthesis or by any other suitable method.

Fusion Proteins and Immunoconjugates

The anti-GCC antibodies described herein can be functionally linked by any suitable method (e.g., chemical coupling, genetic fusion, noncovalent association or otherwise) to one or more non-antibody molecular entities.

Fusion proteins can be produced in which an anti-GCC antibody molecule as described herein and a non-antibody moiety are components of a single continuous polypeptide chain. The non-antibody moiety can be located N-terminally, C-terminally, or internally, with respect to the antibody moiety. For example, some embodiments can be produced by the insertion of a nucleic acid encoding immunoglobulin sequences into a suitable expression vector, such as a pET vector (e.g., pET-15b, Novagen), a phage vector (e.g., pCNATAB 5 E, Pharmacia), or other vector, e.g., pRIT2T Protein A fusion vector, Pharmacia). The resulting construct can be expressed to produce antibody chains that comprise a non-antibody moiety (e.g., Histidine tag, E tag, or Protein A IgG binding domain). Fusion proteins can be isolated or recovered using any suitable technique, such as chromatography using a suitable affinity matrix (see, e.g., *Current Protocols in Molecular Biology* (Ausubel, F. M et al., eds., Vol. 2, Suppl. 26, pp. 16.4.1-16.7.8 (1991)).

The invention provides anti-GCC antibody molecules which are directed to and, in embodiments, are internalized into cells. They are capable of delivering therapeutic agents or detectable agents to or into cells expressing GCC, but not to or into cells where the target is not expressed. Thus, the invention also provides anti-GCC immunoconjugates comprising an anti-GCC antibody molecule as described herein, which is conjugated to a therapeutic agent or a detectable agent. In embodiments, the affinity for GCC of an anti-GCC immunoconjugate is at least 10, 25, 50, 75, 80, 90, or 95% of that for the unconjugated antibody. This can be determined using cell surface GCC or isolated GCC. In an embodiment the anti-GCC antibody molecule, e.g., an immunoconjugate, has an LD50, as determined by an assay described herein, of less than 1,000, 500, 250, 100, or 50 pM.

The anti-GCC antibody molecule can be modified to act as an immunoconjugate utilizing techniques that are known in the art. See e.g., Vitetta *Immunol Today* 14:252 (1993). See also U.S. Pat. No. 5,194,594. The preparation of radio-labeled antibodies can also be readily prepared utilizing techniques that are known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (U.S. Re. Pat. No. 35,500), U.S. Pat. Nos. 5,648,471, and 5,697,902.

In some embodiments, the antibody molecule and non-antibody moiety are connected by means of a linker. In such embodiments, the immunoconjugate is represented by formula (I):

Ab—(—X—Z)$_m$  (I)

wherein,

Ab is an anti-GCC antibody molecule described herein;

X is a moiety which connects Ab and Z, e.g., the residue of a linker described herein after covalent linkage to one or both of Ab and Z;

Z is a therapeutic agent or label; and m ranges from about 1 to about 15.

The variable m represents the number of —X—Z moieties per antibody molecule in an immunoconjugate of formula (I). In various embodiments, m ranges from 1 to 15, 1 to 10, 1 to 9, 1 to 8, 1 to 7, 1 to 6, 1 to 5, 1 to 4, 1 to 3, or 1 to 2. In some embodiments, m ranges from 2 to 10, 2 to 9, 2 to 8, 2 to 7, 2 to 6, 2 to 5, 2 to 4 or 2 to 3. In other embodiments, m is 1, 2, 3, 4, 5 or 6. In compositions comprising a plurality of immunoconjugates of formula (I), m is the average number of —X—Z moieties per Ab, also referred to as the average drug loading. Average drug loading may range from 1 to about 15 —X—Z moieties per Ab. In some embodiments, when m represents the average drug loading, m is about 1, about 2, about 3, about 4, about 5, about 6, about 7, or about 8. In exemplary embodiments, m is from about 2 to about 8. In one embodiment, m is about 8. In another embodiment, m is about 4. In another embodiment, m is about 2.

The average number of —X—Z moieties per Ab may be characterized by conventional means such as mass spectroscopy, ELISA assay, and HPLC. The quantitative distribution of immunoconjugates in terms of m may also be determined. In some instances, separation, purification, and characterization of homogeneous immunoconjugates where m is a certain value, as distinguished from immunoconjugates with other drug loadings, may be achieved by means such as reverse phase HPLC or electrophoresis.

The immunoconjugates of formula (I) may exist as mixtures, wherein each component of the mixture has a different m value. For example, an immunoconjugate of formula (I) may exist as a mixture of two separate immunoconjugate components: one immunoconjugate component wherein m is 7, and the other immunoconjugate component wherein m is 8.

In one embodiment, the immunoconjugate of formula (I) exists as a mixture of three separate immunoconjugates wherein m for the three separate immunoconjugates is 1, 2, and 3, respectively.

In one embodiment, the immunoconjugate of formula (I) exists as a mixture of three separate immunoconjugates wherein m for the three separate immunoconjugates is 3, 4, and 5, respectively.

In one embodiment, the immunoconjugate of formula (I) exists as a mixture of three separate immunoconjugates wherein m for the three separate immunoconjugates is 5, 6, and 7, respectively.

In one embodiment, the immunoconjugate of formula (I) exists as a mixture of three separate immunoconjugates wherein m for the three separate immunoconjugates is 7, 8, and 9, respectively.

In one embodiment, the immunoconjugate of formula (I) exists as a mixture of three separate immunoconjugates wherein m for the three separate immunoconjugates is 9, 10, and 11, respectively.

In one embodiment, the immunoconjugate of formula (I) exists as a mixture of three separate immunoconjugates wherein m for the three separate immunoconjugates is 11, 12, and 13, respectively.

In one embodiment, the immunoconjugate of formula (I) exists as a mixture of three separate immunoconjugates wherein m for the three separate immunoconjugates is 13, 14, and 15, respectively.

A variety of suitable linkers (e.g., heterobifunctional reagents for connecting an antibody molecule to a therapeutic agent or label) and methods for preparing immunoconjugates are known in the art. (See, for example, Chari et al., Cancer Research 52:127-131 (1992).) The linker can be cleavable, e.g., under physiological conditions, e.g., under intracellular conditions, such that cleavage of the linker releases the drug (therapeutic agent or label) in the intracellular environment. In other embodiments, the linker is not cleavable, and the drug is released, for example, by antibody degradation.

The linker can be bonded to a chemically reactive group on the antibody moiety, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound can be a natural residue in the amino acid sequence of the antibody moiety or it can be introduced into the antibody moiety, e.g., by DNA recombinant technology (e.g., by introducing a cysteine or protease cleavage site in the amino acid sequence) or by protein biochemistry (e.g., reduction, pH adjustment or proteolysis).

One of the most commonly used non-specific methods of covalent attachment is the carbodiimide reaction to link a carboxy (or amino) group of a compound to amino (or carboxy) groups of the antibody molecule. Additionally, bifunctional agents such as dialdehydes or imidoesters have been used to link the amino group of a compound to amino groups of an antibody molecule. Also available for attachment of drugs to antibody molecules is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibody molecule. Other techniques are known to the skilled artisan and within the scope of the present invention.

In certain embodiments, an intermediate, which is the precursor of the linker (X), is reacted with the drug (Z) under appropriate conditions. In certain embodiments, reactive groups are used on the drug and/or the intermediate. The product of the reaction between the drug and the intermediate, or the derivatized drug, is subsequently reacted with the antibody molecule under appropriate conditions.

The immunoconjugate can be purified from reactants by employing methodologies well known to those of skill in the art, e.g., column chromatography (e.g., affinity chromatography, ion exchange chromatography, gel filtration, hydrophobic interaction chromatography), dialysis, diafiltration or precipitation. The immunoconjugate can be evaluated by employing methodologies well known to those skilled in the art, e.g., SDS-PAGE, mass spectroscopy, or capillary electrophoresis.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in GCC-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO:319)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)-toluene), SPDB and SMPT (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg Med Chem.* 3(10):1299-1304), or a 3'-N-amide analog (Lau et al., 1995, *Bioorg-Med-Chem.* 3(10):1305-12).

In yet other embodiments, the linker unit is not cleavable and the drug is released by antibody degradation. (See for example U.S. Publication No. 20050238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of immunoconjugate, are cleaved when the immunoconjugate presents in an extracellular environment (e.g., in plasma). Whether a linker is not substantially sensitive to the extracellular environment can be determined, for example, by incubating with plasma the immunoconjugate for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent or label (Z). In yet other embodiments, the linker promotes cellular internalization when conjugated to both the Z moiety and the anti-GCC antibody molecule.

A variety of exemplary linkers that can be used with the present compositions and methods are described in WO 2004-010957, U.S. Publication No. 20060074008, U.S. Publication No. 20050238649, and U.S. Publication No. 20060024317 (each of which is incorporated by reference herein in its entirety and for all purposes).

Examples of linkers capable of being used to couple an antibody molecule to a therapeutic agent or label include, for example, maleimidocaproyl (mc); maleimidocaproyl-p-aminobenzylcarbamate; maleimidocaproyl-peptide-aminobenzylcarbamate linkers, e.g., maleimidocaproyl-L-phenylalanine-L-lysine-p-aminobenzylcarbamate and maleimidocaproyl-L-valine-L-citrulline-p-aminobenzylcarbamate (vc); N-succinimidyl 3-(2-pyridyldithio)proprionate (also known as N-succinimidyl 4-(2-pyridyldithio)pentanoate or SPP); 4-succinimidyl-oxycarbonyl-2-methyl-2-(2-pyridyldithio)-toluene (SMPT); N-succinimidyl 3-(2-pyridyldithio)propionate (SPDP); N-succinimidyl 4-(2-pyridyldithio)butyrate (SPDB); 2-iminothiolane; S-acetylsuccinic anhydride; disulfide benzyl carbamate; carbonate; hydrazone linkers; N-(α-Maleimidoacetoxy) succinimide ester; N-[4-(p-Azidosalicylamido) butyl]-3'-(2'-pyridyldithio)propionamide (AMAS); N-[β-Maleimidopropyloxy]succinimide ester (BMPS); [N-ε-Maleimidocaproyloxy]succinimide ester (EMCS); N-[γ-Maleimidobutyryloxy]succinimide ester (GMBS); Succinimidyl-4-[N-Maleimidomethyl]cyclohexane-1-carboxy-[6-amidocaproate] (LC-SMCC); Succinimidyl 6-(3-[2-pyridyldithio]-propionamido)hexanoate (LC-SPDP); m-Maleimidobenzoyl-N-hydroxysuccinimide ester (MB S); N-Succinimidyl[4-iodoacetyl]aminobenzoate (SIAB); Succinimidyl 4-[N-maleimidomethyl]cyclohexane-1-carboxylate (SMCC); N-Succinimidyl 3-[2-pyridyldithio]-propionamido (SPDP); [N-ε-Maleimidocaproyloxy]sulfosuccinimide ester (Sulfo-EMCS); N-[γ-Maleimidobutyryloxy]sulfosuccinimide ester (Sulfo-GMBS); 4-Sulfosuccinimidyl-6-methyl-α-(2-pyridyldithio)toluamido]hexanoate (Sulfo-LC-SMPT); Sulfosuccinimidyl 6-(3'-[2-pyridyldithio]-propionamido)hexanoate (Sulfo-LC-SPDP); m-Maleimidobenzoyl-N-hydroxysulfosuccinimide ester (Sulfo-MBS); N-Sulfosuccinimidyl[4-iodoacetyl]aminobenzoate (Sulfo-SIAB); Sulfosuccinimidyl 4-[AT-maleimidomethyl]cyclohexane-1-carboxylate (Sulfo-SMCC); Sulfosuccinimidyl 4-[p-maleimidophenyl]butyrate (Sulfo-SMPB); ethylene glycol-bis(succinic acid N-hydroxysuccinimide ester) (EGS); disuccinimidyl tartrate (DST); 1,4,7,10-tetraazacyclododecane-1,4,7,10-tetraacetic acid (DOTA); diethylenetriamine-pentaacetic acid (DTPA); and thiourea linkers.

In some embodiments, the linker —X— has the formula -$A_a$-$W_w$—$Y_y$—, and the immunoconjugate of formula (I) is characterized by formula (II):

Ab—($A_a$-$W_w$—$Y_y$—Z)$_m$  II wherein,
Ab is an anti-GCC antibody molecule described herein;
-A- is a Stretcher unit;
a is 0 or 1;
each —W— independently is an Amino Acid unit;
w is an integer ranging from 0 to 12;
—Y— is a self-immolative spacer unit;
y is 0, 1, or 2;
Z is a therapeutic agent or label; and
m ranges from about 1 to about 15.

The Stretcher unit (A), when present, is capable of linking an Ab unit to an Amino Acid unit (—W—), if present, to a Spacer unit (—Y—), if present; or to a therapeutic agent or label (Z). Useful functional groups that can be present on an anti-GCC antibody molecule, either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an anti-GCC antibody molecule. In another embodiment, sulfhydryl groups can be generated by reaction of an amino group of a lysine moiety of an anti-GCC antibody molecule with 2-iminothiolane (Traut's reagent) or other sulfhydryl generating reagents. In certain embodiments, the anti-GCC antibody molecule is a recombinant antibody and is engineered to carry one or more lysines. In certain other embodiments, the recombinant anti-GCC antibody molecule is engineered to carry additional sulfhydryl groups, e.g., additional cysteines.

In one embodiment, the Stretcher unit forms a bond with a sulfur atom of the Ab unit. The sulfur atom can be derived from a sulfhydryl group of an Ab. Representative Stretcher units of this embodiment are depicted within the square brackets of Formulas (IIIa) and (IIIb), wherein Ab-, —W—, —Y—, —Z, w and y are as defined above, and $R^a$ is selected from —$C_1$-$C_{10}$ alkylene-, —$C_2$-$C_{10}$ alkenylene-, —$C_2$-$C_{10}$ alkynylene-, -carbocyclo-, —O—($C_1$-$C_8$ alkylene)-, O—($C_2$-$C_8$ alkenylene)-, —O—($C_2$-$C_8$ alkynylene)-, -arylene-, —$C_1$-$C_1^0$ alkylene-arylene-, —$C_2$-$C_{10}$ alkenylene-arylene, —$C_2$-$C_{10}$ alkynylene-arylene, -arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, heterocyclo-, —$C_1$-$C_1^0$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_2$-$C_{10}$ alkynylene-, —($CH_2CH_2O)_r$—, or —($CH_2CH_2O)_rCH_2$—, and r is an integer ranging from 1-10, wherein said alkyl, alkenyl, alkynyl, alkylene, alkenylene, alkynylene, aryl, carbocyle, carbocyclo, heterocyclo, and arylene radicals, whether alone or as part of another group, are optionally substituted. In some embodiments, said alkyl, alkenyl, alkynyl, alkylene, alkenylene, alkynylene, aryl, carbocyle, carbocyclo, heterocyclo, and arylene radicals, whether alone or as part of another group, are unsubstituted. In some embodiments, $R^a$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, —$C_1$-$C_{10}$alkylene-(heterocyclo)-, -(heterocyclo)-$C_1$-$C_{10}$ alkylene-, —($CH_2CH_2O)_r$—, and —($CH_2CH_2O)_r$—$CH_2$—; and r is an integer ranging from 1-10, wherein said alkylene groups are unsubstituted and the remainder of the groups are optionally substituted.

It is to be understood from all the exemplary embodiments that even where not denoted expressly, from 1 to 15 drug moieties can be linked to an Ab (m=1-15).

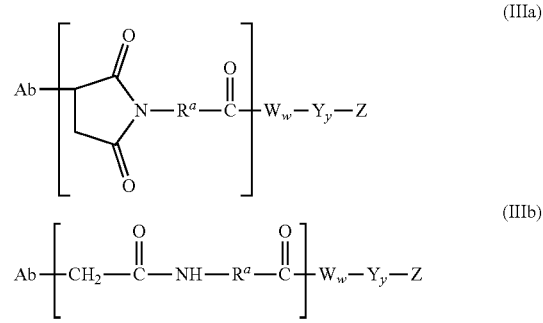

An illustrative Stretcher unit is that of Formula (IIIa) wherein $R^a$ is —$(CH_2)_5$—:

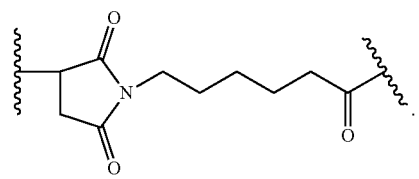 [SMILES: *C(=O)CCCCCN1C(=O)CC(*)C1=O]

Another illustrative Stretcher unit is that of Formula (IIIa) wherein $R^a$ is —$(CH_2CH_2O)_r$—$CH_2^-$; and r is 2:

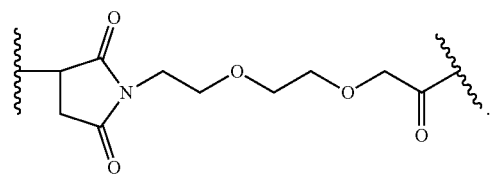 [SMILES: *C(=O)COCCOCCN1C(=O)CC(*)C1=O]

Another illustrative Stretcher unit is that of Formula (IIIa) wherein $R^a$ is -arylene- or arylene-$C_1$-$C_{10}$ alkylene-. In some embodiments, the aryl group is an unsubstituted phenyl group.

Still another illustrative Stretcher unit is that of Formula (IIIb) wherein $R^a$ is —(CH$_2$)$_5$—:

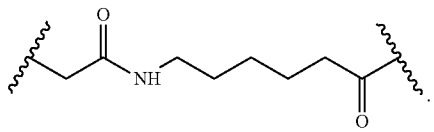 [SMILES: *CC(=O)NCCCCCC(*)=O]

In certain embodiments, the Stretcher unit is linked to the Ab unit via a disulfide bond between a sulfur atom of the Ab unit and a sulfur atom of the Stretcher unit. A representative Stretcher unit of this embodiment is depicted within the square brackets of Formula (IV), wherein $R^a$, Ab-, —W—, —Y—, —Z, w and y are as defined above.

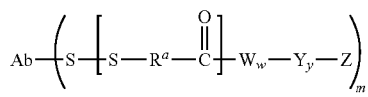
(IV)

It should be noted that throughout this application, the S moiety in the formula below refers to a sulfur atom of the Ab unit, unless otherwise indicated by context.

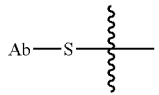

In yet other embodiments, the Stretcher, prior to attachment to Ab, contains a reactive site that can form a bond with a primary or secondary amino group of the Ab. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas (Va) and (Vb), wherein —$R^a$—, Ab-, —W—, —Y—, —Z, w and y are as defined above;

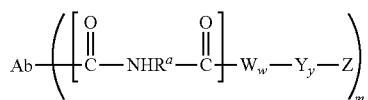
(Va)

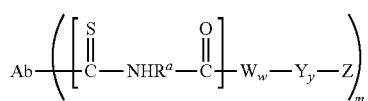
(Vb)

In some embodiments, the Stretcher contains a reactive site that is reactive to a modified carbohydrate's (—CHO) group that can be present on an Ab. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas (VIa), (VIb), and (VIc), wherein —$R^a$—, Ab-, —W—, —Y—, —Z, w and y are defined as above.

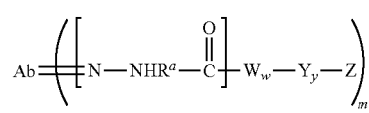
(VIa)

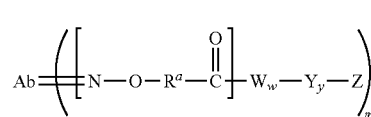
(VIb)

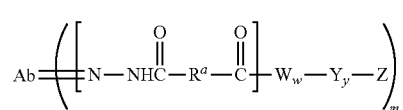
(VIc)

The Amino Acid unit (—W—), when present, links the Stretcher unit to the Spacer unit if the Spacer unit is present, links the Stretcher unit to the Drug moiety if the Spacer unit is absent, and links the Ab unit to the therapeutic agent or label moiety if the Stretcher unit and Spacer unit are absent. W$_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

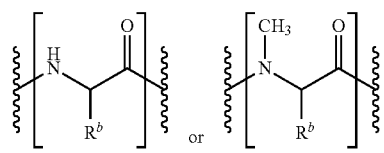

wherein $R^b$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

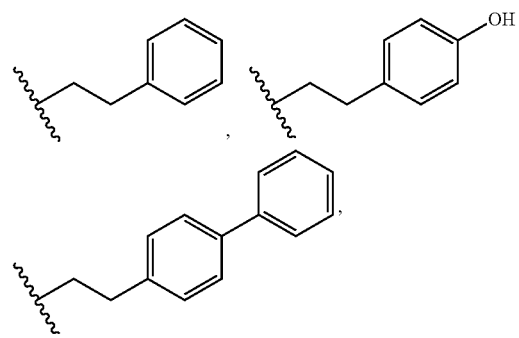

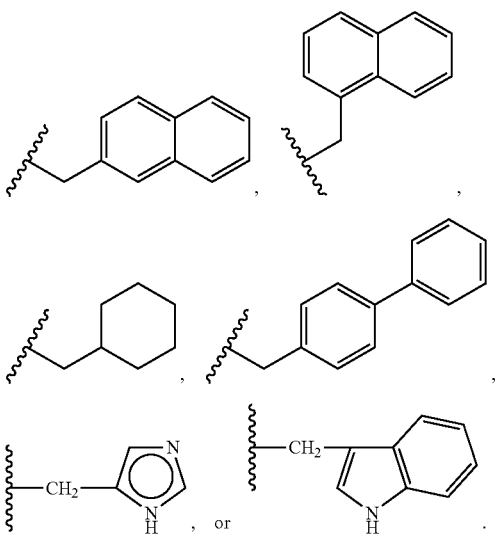

In some embodiments, the Amino Acid unit can be enzymatically cleaved by one or more enzymes, including a cancer or tumor-associated protease, to liberate the therapeutic agent or label moiety (—Z), which in one embodiment is protonated in vivo upon release to provide a therapeutic agent or label (Z).

In certain embodiments, the Amino Acid unit can comprise natural amino acids. In other embodiments, the Amino Acid unit can comprise non-natural amino acids. Illustrative $W_w$ units are represented by formulas (VII)-(IX):

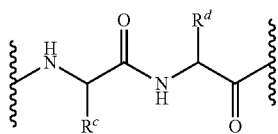

(VII)

wherein $R^c$ and $R^d$ are as follows:

| $R^c$ | $R^d$ |
|---|---|
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 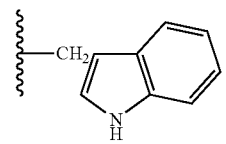 | $(CH_2)_3NHCONH_2$; |
| benzyl | methyl; |
| benzyl | $(CH_2)_3NHC(=NH)NH_2$; |

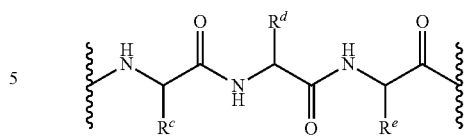

(VIII)

wherein $R^c$, $R^d$ and $R^e$ are as follows:

| $R^c$ | $R^d$ | $R^e$ |
|---|---|---|
| benzyl | Benzyl | $(CH_2)_4NH_2$; |
| isopropyl | Benzyl | $(CH_2)_4NH_2$; and |
| H | Benzyl | $(CH_2)_4NH_2$; |

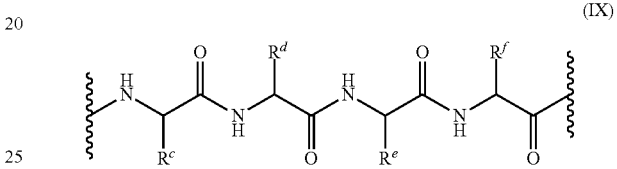

(IX)

wherein $R^c$, $R^d$, $R^e$ and $R^f$ are as follows:

| $R^c$ | $R^d$ | $R^e$ | $R^f$ |
|---|---|---|---|
| H | benzyl | isobutyl | H; and |
| methyl | isobutyl | methyl | isobutyl. |

Exemplary Amino Acid units include, but are not limited to, units of formula (VII) where: $R^c$ is benzyl and $R^d$ is —$(CH_2)_4NH_2$; $R^c$ is isopropyl and $R^d$ is —$(CH_2)_4NH_2$; or $R^c$ is isopropyl and $R^d$ is —$(CH_2)_3NHCONH_2$. Another exemplary Amino Acid unit is a unit of formula (VIII) wherein $R^c$ is benzyl, $R^d$ is benzyl, and $R^e$ is —$(CH_2)_4NH_2$.

Useful —$W_w$— units can be designed and optimized in their selectivity for enzymatic cleavage by a particular enzyme, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide. When $R^b$, $R^c$, $R^d$, $R^e$ or $R^f$ is other than hydrogen, the carbon atom to which $R^b$, $R^c$, $R^d$, $R^e$ or $R^f$ is attached is chiral.

Each carbon atom to which $R^b$, $R^c$, $R^d$, $R^e$ or $R^f$ is attached is independently in the (S) or (R) configuration.

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

The Spacer unit (—Y—), when present, links an Amino Acid unit to the therapeutic agent or label moiety (—Z—) when an Amino Acid unit is present. Alternatively, the Spacer unit links the Stretcher unit to the therapeutic agent or label moiety when the Amino Acid unit is absent. The Spacer unit also links the therapeutic agent or label moiety to the Ab unit when both the Amino Acid unit and Stretcher unit are absent.

Spacer units are of two general types: non self-immolative or self-immolative. A non self-immolative Spacer unit is one in which part or all of the Spacer unit remains bound to the therapeutic agent or label moiety after cleavage, particularly enzymatic, of an Amino Acid unit from the antibody-drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Z moiety or a glycine-Z moiety is cleaved from Ab-Aa-Ww-. In one embodiment, an independent hydrolysis reaction takes place within the target cell, cleaving the glycine-Z moiety bond and liberating the therapeutic agent or label.

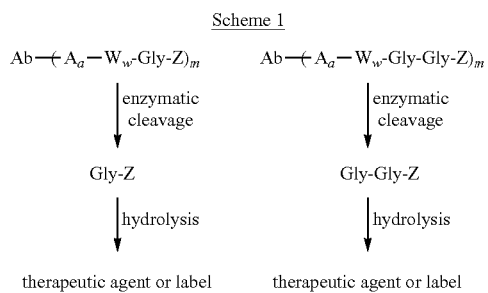

Scheme 1

In some embodiments, a non self-immolative Spacer unit (—Y—) is -Gly-. In some embodiments, a non self-immolative Spacer unit (—Y—) is -Gly-Gly-.

In one embodiment, the invention provides an immunoconjugate of formula (II) wherein the Spacer unit is absent (y=0), or a pharmaceutically acceptable salt thereof.

Alternatively, a conjugate containing a self-immolative Spacer unit can release —Z. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_r$— is a p-aminobenzyl alcohol (PAB) unit (see Schemes 2 and 3) whose phenylene portion is substituted with $Q_n$ wherein Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; and n is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to —Z via a carbonate, carbamate or ether group. Without being bound by any particular theory or mechanism, Scheme 2 depicts a possible mechanism of release of a therapeutic agent or label (—Z) from a PAB group that is attached directly to —Z via a carbamate or carbonate group as described by Toki et al., 2002, *J. Org. Chem.* 67:1866-1872.

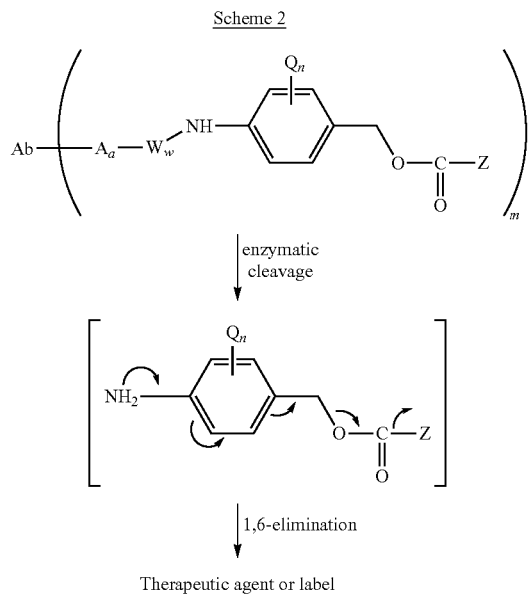

Scheme 2

In Scheme 2, Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; m is an integer ranging from 0-4; and m ranges from 1 to about 20. The alkyl, alkenyl and alkynyl groups, whether alone or as part of another group, can be optionally substituted.

Without being bound by any particular theory or mechanism, Scheme 3 depicts a possible mechanism of release of a therapeutic agent or label moiety (—Z) from a PAB group which is attached directly to —Z via an ether or amine linkage, wherein —Z includes the oxygen or nitrogen group that is part of the therapeutic agent or label moiety.

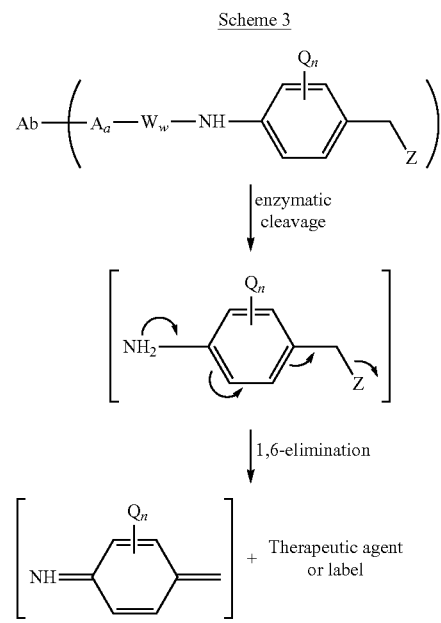

Scheme 3

In Scheme 3, Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; n is an integer ranging from 0-4; and m ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867) Elimination of amine-containing drugs that are substituted at the α-position of glycine (Kingsbury et al., 1984, *J. Med. Chem.* 27:1447) are also examples of self-immolative spacers.

In one embodiment, the Spacer unit is a branched bis(hydroxymethyl)-styrene (BHMS) unit as depicted in Scheme 4, which can be used to incorporate and release multiple drugs.

Scheme 4

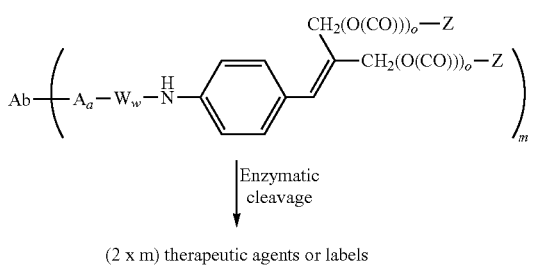

Enzymatic cleavage (2 × m) therapeutic agents or labels

In Scheme 4, Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; n is an integer ranging from 0-4; o is 0 or 1; and m is an integer of from 1 to about 20. The alkyl, alkenyl and alkynyl groups, whether alone or as part of another group, can be optionally substituted.

In some embodiments, the —Z moieties are the same. In yet another embodiment, the —Z moieties are different.

In one aspect, Spacer units (—$Y_y$—) are represented by Formulae (X)-(XII):

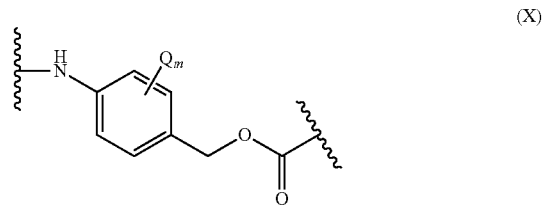

(X)

wherein Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; and m is an integer ranging from 0-4. The alkyl, alkenyl and alkynyl groups, whether alone or as part of another group, can be optionally substituted.

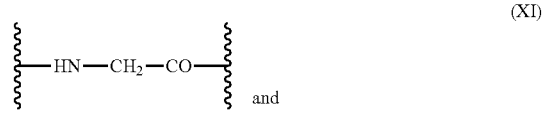

(XI)

and

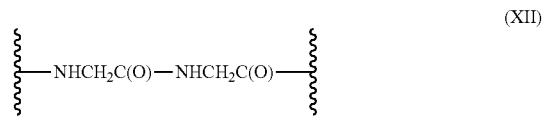

(XII)

In a group of selected embodiments, the conjugates of Formula (I) and (II) are:

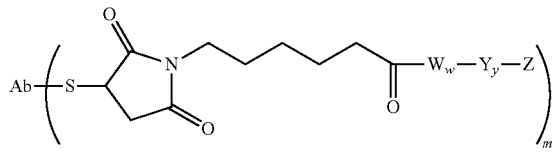

wherein w and y are each 0, 1 or 2:

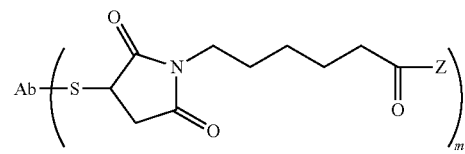

wherein w and y are each 0;

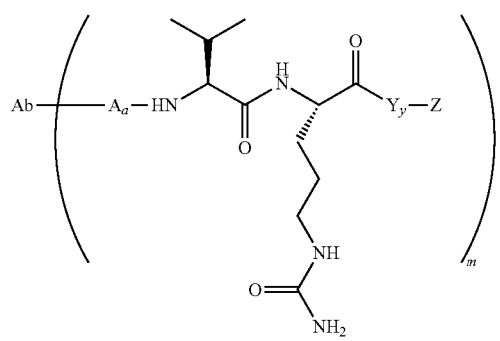

-continued

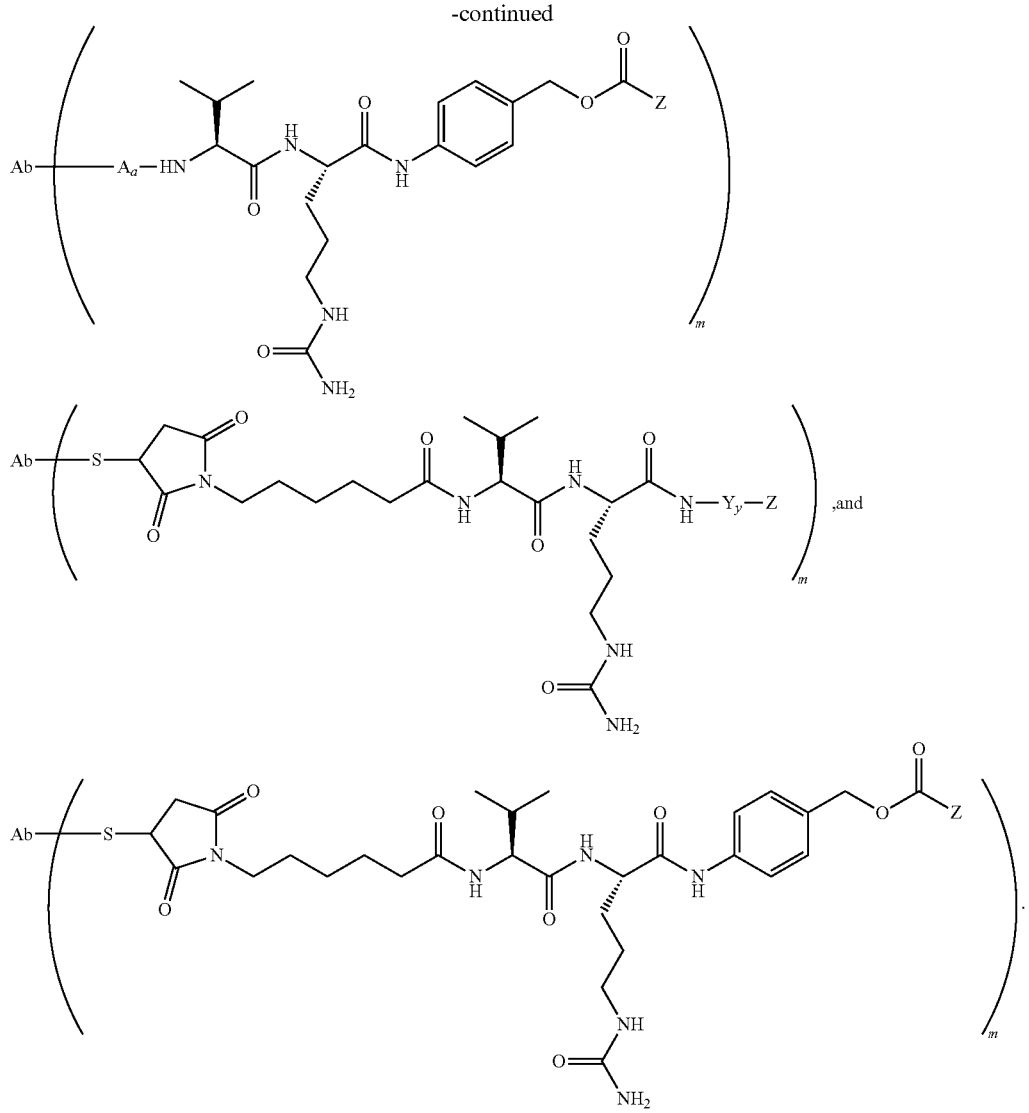

wherein $A_a$, $W_w$, $Y_y$, Z and Ab have the meanings provided above.

The variable Z in formula (I) is a therapeutic agent or label. The therapeutic agent can be any agent capable of exerting a desired biological effect. In some embodiments, the therapeutic agent sensitizes the cell to a second therapeutic modality, e.g., a chemotherapeutic agent, radiation therapy, immunotherapy.

In some embodiments, the therapeutic agent is a cytostatic or cytotoxic agent. Examples include, without limitation, antimetabolites (e.g., azathioprine, 6-mercaptopurine, 6-thioguanine, fludarabine, pentostatin, cladribine, 5-fluorouracil (5FU), floxuridine (FUDR), cytosine arabinoside (cytarabine), methotrexate, trimethoprim, pyrimethamine, pemetrexed); alkylating agents (e.g., cyclophosphamide, mechlorethamine, uramustine, melphalan, chlorambucil, thiotepa/chlorambucil, ifosfamide, carmustine, lomustine, streptozocin, busulfan, dibromomannitol, cisplatin, carboplatin, nedaplatin, oxaliplatin, satraplatin, triplatin tetranitrate, procarbazine, altretamine, dacarbazine, mitozolomide, temozolomide); anthracyclines (e.g., daunorubicin, doxorubicin, epirubicin, idarubicin, valrubicin); antibiotics (e.g., dactinomycin, bleomycin, mithramycin, anthramycin, streptozotocin, gramicidin D, mitomycins (e.g., mitomycin C), duocarmycins (e.g., CC-1065), calicheamicins); antimitotic agents (including, e.g., maytansinoids, auristatins, dolastatins, cryptophycins, vinca alkaloids (e.g., vincristine, vinblastine, vindesine, vinorelbine), taxanes (e.g., paclitaxel, docetaxel, or a novel taxane (see, e.g., International Patent Publication No. WO 01/38318, published May 31, 2001)), and colchicines; topoisomerase inhibitors (e.g., irinotecan, topotecan, amsacrine, etoposide, teniposide, mitoxantrone); and proteasome inhibitors (e.g., peptidyl boronic acids).

Maytansinoid Immunoconjugates

In some embodiments, the therapeutic agent is a maytansinoid. Maytansinoid compounds and methods for their conjugation to antibodies are described, for example, in Chari et al., *Cancer Res.,* 52: 127-131 (1992); Widdison et al., *J. Med. Chem.* 49: 4392-4408 (2006); and U.S. Pat. Nos. 5,208,020 and 6,333,410. Examples of maytansinoids include maytansine analogues having a modified aromatic ring (e.g., C-19-dechloro, C-20-demethoxy, C-20-acyloxy) and those having modifications at other positions (e.g., C-9-CH, C-14-alkoxymethyl, C-14-hydroxymethyl or acyloxymethyl, C-15-hydroxy/acyloxy, C-15-methoxy, C-18-N-demethyl, 4,5-deoxy). In certain embodiments, the maytansinoid is $N^{2'}$-deacetyl-$N^{2'}$-(4-mercapto-1-oxopentyl)maytansine (DM3), $N^{2'}$-deacetyl-$N^{2'}$-(3-mercapto-1-oxopropyl)-maytansine (DM1), or $N^{2'}$-deacetyl-$N^{2'}$-(4-mercapto-4-methyl-1-oxopentyl)maytansine (DM4).

Maytansinoid compounds that comprise a sulfhydryl group can be coupled to antibodies using a heterobifunctional linker that is connected to the maytansinoid compound by way of a thioether or disulfide linkage. In some such embodiments, the linker is coupled to an amino group on the antibody (e.g., a terminal amino group or the epsilon amino group of a lysine residue). In some embodiments, the heterobifunctional linker that is used to couple a maytansinoid compounds to an antibody is N-succinimidyl 3-(2-pyridyldithio)proprionate (also known as N-succinimidyl 4-(2-pyridyldithio)pentanoate, or SPP), 4-succinimidyl-oxycarbonyl-2-methyl-2-(2-pyridyldithio)-toluene (SMPT), N-succinimidyl 4-[N-maleimidomethyl]cyclohexane-1-carboxylate (SMCC), N-succinimidyl 3-(2-pyridyldithio)propionate (SPDP); N-succinimidyl 4-(2-pyridyldithio)butyrate (SPDB), 2-iminothiolane, or S-acetylsuccinic anhydride.

In certain embodiments, the immunoconjugate of formula (I) is characterized by the formula Ab-(SMCC-DM1)$_m$ (formula (I-1); Ab-(SPP-DM1)$_m$ (formula (I-2); or Ab-(SPDB-DM4)$_m$ (formula (I-3), wherein Ab is an anti-GCC antibody molecule as described herein, and m has the values and preferred values described above for formula (I).

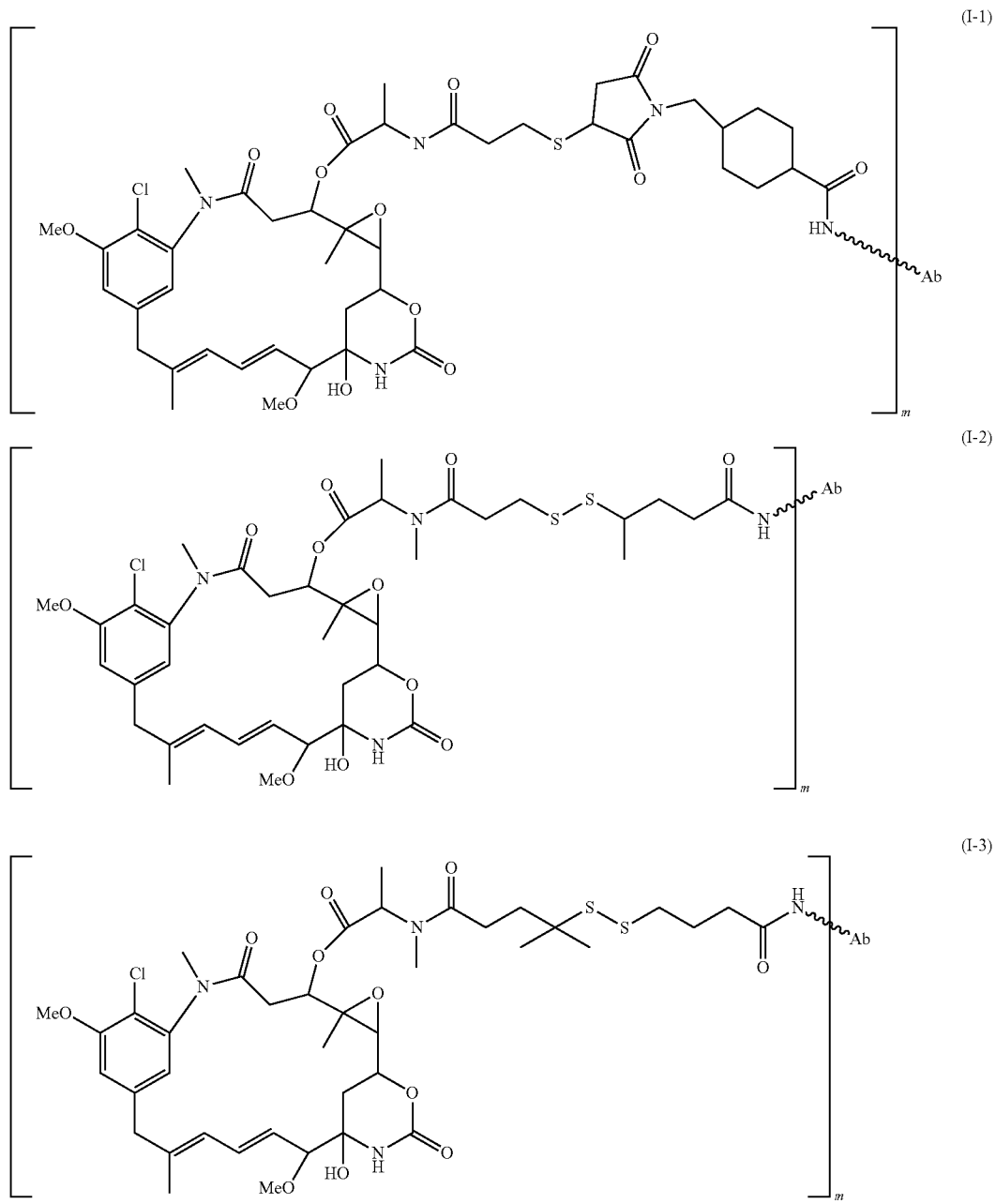

In some embodiments, the variable Ab in formula (I-1), (I-2), or (I-3) is an antibody molecule with features summarized in Tables 1 to 6. In certain embodiments, the variable Ab is a 5F9 antibody molecule or an Abx-229 antibody molecule.

In some embodiments, the variable m in formula (I-1), (I-2), or (I-3) ranges from about 1 to about 10, from about 3 to about 7, or from about 3 to about 5.

In certain particular embodiments, the invention relates to an immunoconjugate of formula (I-1), (I-2), or (I-3), wherein Ab is a 5F9 antibody molecule and m is about 4.

Dolastatin and Auristatin Immunoconjugates

In some other embodiments the therapeutic agent is a dolastatin. In some embodiments, the therapeutic agent is an auristatin, such as auristatin E (also known in the art as a derivative of dolastatin-10) or a derivative thereof. In some embodiments, the therapeutic agent is a compound selected from compounds of formulae (XIII)-(XXIII), or a pharmaceutically acceptable salt form thereof:

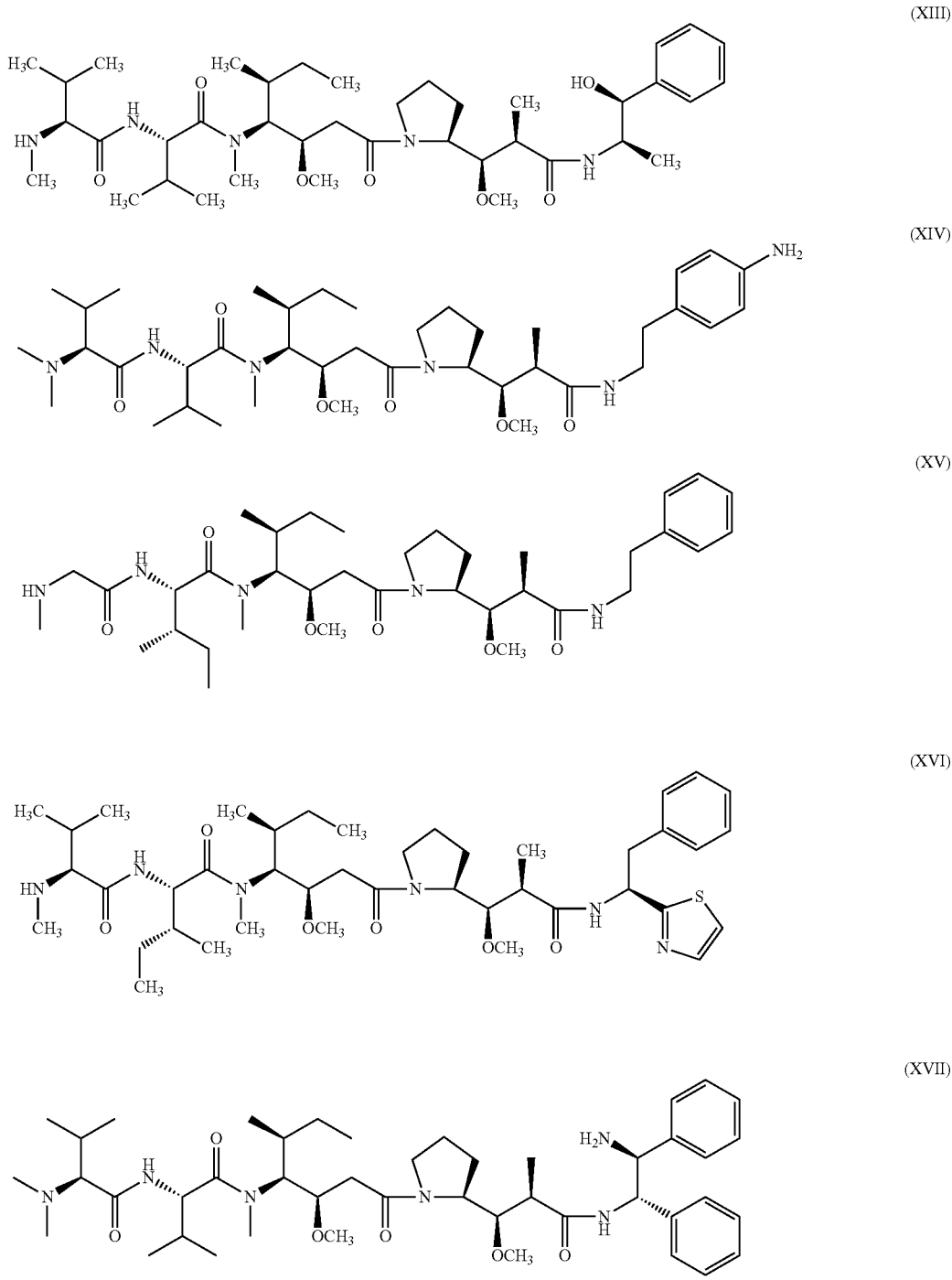

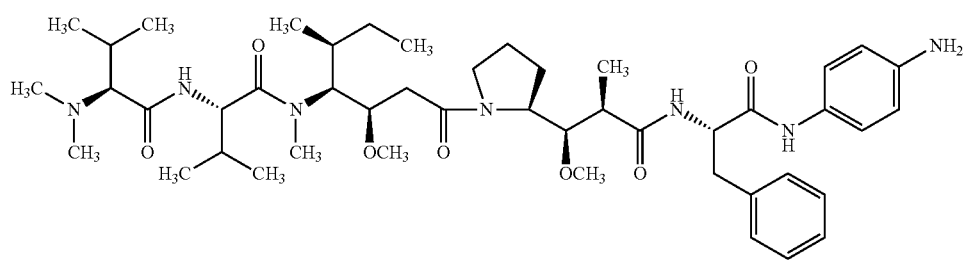
(XVIII)
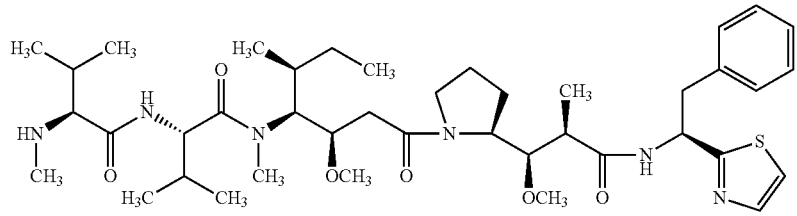
(XIX)
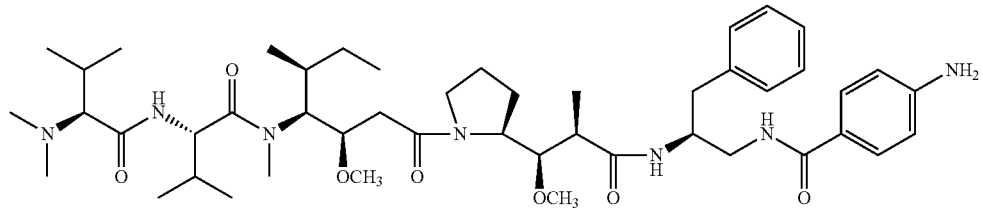
(XX)
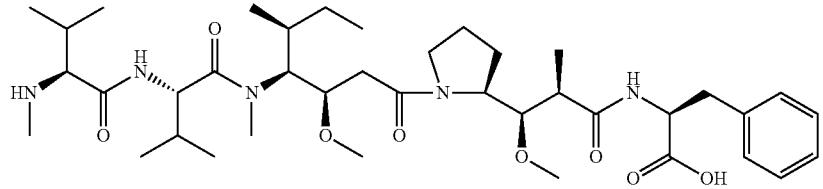
(XXI)
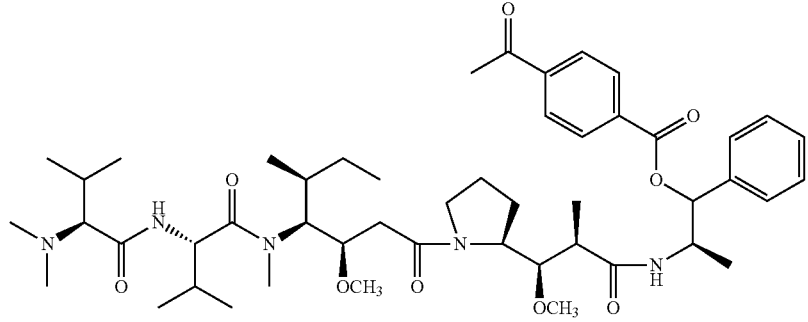
(XXII)
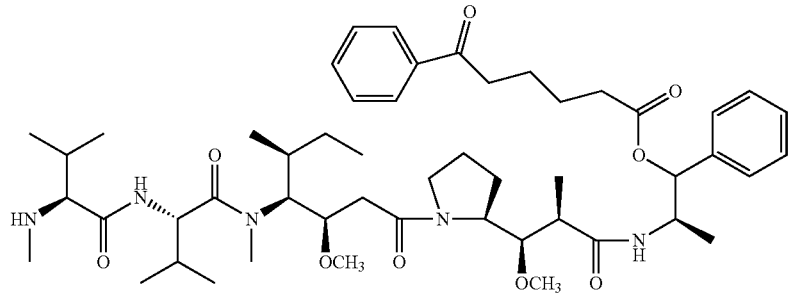
(XXIII)
Auristatin compounds and methods for their conjugation to antibodies are described, for example, in Doronina et al., *Nature Biotech.*, 21: 778-784 (2003); Hamblett at al, *Clin. Cancer Res.*, 10: 7063-7070 (2004); Carter and Senter, *Cancer J.*, 14 154-169 (2008); U.S. Pat. Nos. 7,498,298, 7,091,186, 6,884,869; 6,323,315; 6,239,104; 6,034,065;

5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414; U.S. Patent Publication Nos. 20090010945, 20060074008, 20080300192, 20050009751, 20050238649, and 20030083236; and International Patent Publication Nos. WO 04/010957 and WO 02/088172, each of which is incorporated by reference herein in its entirety and for all purposes.

The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include auristatin phenylalanine phenylenediamine (AFP; (XVIII)), monomethyl auristatin E (MMAE; (XIII)), and monomethyl auristatin F (MMAF; (XXI)).

Auristatins have been shown to interfere with microtubule dynamics and nuclear and cellular division and have anticancer activity. Auristatins for use in the present invention bind tubulin and can exert a cytotoxic or cytostatic effect on a GCC-expressing cell line. Methods for determining whether a compound binds tubulin are known in the art. See, for example, Muller et al., *Anal. Chem* 2006, 78, 4390-4397; Hamel et al., *Molecular Pharmacology*, 1995 47: 965-976; and Hamel et al., *The Journal of Biological Chemistry*, 1990 265:28, 17141-17149. For purposes of the present invention, the relative affinity of a compound to tubulin can be determined. Some preferred auristatins of the present invention bind tubulin with an affinity ranging from 10-fold lower (weaker affinity) than the binding affinity of MMAE to tubulin to 10-fold, 20-fold or even 100-fold higher (higher affinity) than the binding affinity of MMAE to tubulin.

There are a number of different assays, known in the art, that can be used for determining whether an auristatin or resultant immunoconjugate exerts a cytostatic or cytotoxic effect on a desired cell line. For example, the cytotoxic or cytostatic activity of an immunoconjugate can be measured by: exposing mammalian cells expressing a target protein of the immunoconjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the immunoconjugate.

For determining whether an immunoconjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the immunoconjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an immunoconjugate is useful in the treatment of cancers.

Cell viability can be measured by determining in a cell the uptake of a dye such as neutral red, trypan blue, or ALAMAR™ blue (see, e.g., Page et al., 1993, *Intl. J. Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., 1990, *J. Natl. Cancer Inst.* 82:1107-12).

Alternatively, a tetrazolium salt, such as MTT or WST, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, *Current Protocols in Immunology* (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

The effects of immunoconjugates can be tested or validated in animal models. A number of established animal models of cancers are known to the skilled artisan, any of which can be used to assay the efficacy of an immunoconjugate. Non-limiting examples of such models are described infra. Moreover, small animal models to examine the in vivo efficacies of immunoconjugates can be created by implanting human tumor cell lines into appropriate immunodeficient rodent strains, e.g., athymic nude mice or SCID mice.

In some embodiments, the variable —Z in formula (I) is an auristatin moiety of the formula (X-A) or formula (X-B):

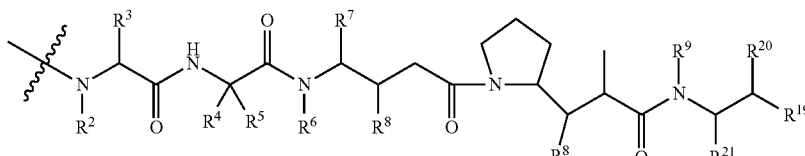

(X-A)

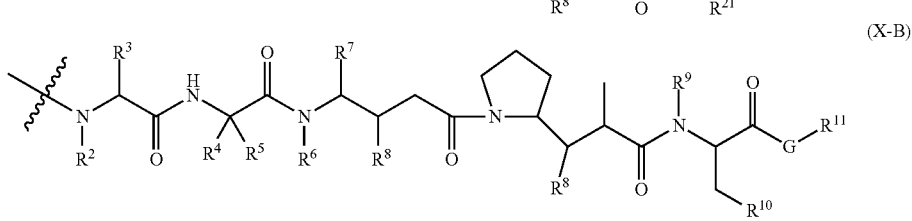

(X-B)

wherein, independently at each location:
the wavy line indicates a bond;
$R^2$ is —$C_1$-$C_{20}$ alkyl, —$C_2$-$C_{20}$ alkenyl, or —$C_2$-$C_{20}$ alkynyl;
$R^3$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);
$R^4$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);
$R^5$ is —H or —$C_1$-$C_8$ alkyl;
or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or -carbocycle and s is 2, 3, 4, 5 or 6,
$R^6$ is —H, —$C_1$-$C_{20}$ alkyl, —$C_2$-$C_{20}$ alkenyl, or —$C_2$-$C_{20}$ alkynyl;
$R^7$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle);
each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;
$R^9$ is —H, —$C_1$-$C_{20}$ alkyl, —$C_2$-$C_{20}$ alkenyl, or —$C_2$-$C_{20}$ alkynyl;
$R^{19}$ is -aryl, -heterocycle, or -carbocycle;
$R^{20}$ is —H, —$C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^{18}$ represents =O;
$R^{21}$ is —H, —$C_1$-$C_{20}$ alkyl, —$C_2$-$C_{20}$ alkenyl, or —$C_2$-$C_{20}$ alkynyl, -aryl, -heterocycle, or -carbocycle;
$R^{10}$ is -aryl or -heterocycle;
G is —O—, —S—, —NH—, or —$NR^{12}$—, wherein $R^{12}$ is —$C_1$-$C_{20}$ alkyl, —$C_2$-$C_{20}$ alkenyl, —$C_2$-$C_{20}$ alkynyl;
$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_s$—$R^{14}$, or —$(R^{13}O)_s$—CH$(R^{15})_2$;
s is an integer ranging from 0-1000;
$R^{13}$ is —$C_2$-$C_{20}$ alkylene, —$C_2$-$C_{20}$ alkenylene, or —$C_2$-$C_{20}$ alkynylene;
$R^{14}$ is —H, —$C_1$-$C_{20}$ alkyl, —$C_2$-$C_{20}$ alkenyl, or —$C_2$-$C_{20}$ alkynyl;
each occurrence of $R^{15}$ is independently —H, —COOH, —$(CH_2)_t$—N$(R^{16})_2$, —$(CH_2)_t$—$SO_3$H, —$(CH_2)_t$—$SO_3$—$C_1$-$C_{20}$ alkyl, —$(CH_2)_t$—$SO_3$—$C_2$-$C_{20}$ alkenyl, or —$(CH_2)_t$—$SO_3$—$C_2$-$C_{20}$ alkynyl;
each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_t$—COOH; and
t is an integer ranging from 0 to 6; wherein said alkyl, alkenyl, alkynyl, alkylene, alkenylene, alkynyklene, aryl, carbocyle, and heterocycle radicals, whether alone or as part of another group, are optionally substituted.

Auristatins of the formula (X-A) include those wherein said alkyl, alkenyl, alkynyl, alkylene, alkenylene, alkynyklene, aryl, carbocyle, and heterocycle radicals are unsubstituted.

Auristatins of the formula (X-A) include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula (X-A) include those wherein
$R^2$ is —$C_1$-$C_8$ alkyl;
$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocycle, aryl, and heterocycle radicals are optionally substituted;
$R^5$ is -hydrogen;
$R^6$ is —$C_1$-$C_8$ alkyl;
each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted;

$R^9$ is -hydrogen or —$C_1$-$C_8$ alkyl;

$R^{19}$ is optionally substituted phenyl;

$R^{20}$ is $OR^{18}$; wherein $R^{18}$ is H, a hydroxyl protecting group, or a direct bond where $OR^{18}$ represents =O;

$R^{21}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, alkynyl, and carbocycle radicals are optionally substituted; or a pharmaceutically acceptable salt form thereof.

Auristatins of the formula (X-A) include those wherein $R^2$ is methyl;

$R^3$ is —H, —$C_1$-$C_8$ alkyl, —$C_2$-$C_8$ alkenyl, or —$C_2$-$C_8$ alkynyl, wherein said alkyl, alkenyl and alkynyl radicals are optionally substituted;

$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene ($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, alkynylene, aryl, and carbocycle radicals whether alone or as part of another group are optionally substituted;

$R^5$ is H; $R^6$ is methyl;

$R^7$ is —$C_1$-$C_8$ alkyl, —$C_2$-$C_8$ alkenyl or —$C_2$-$C_8$ alkynyl;

each $R^8$ is methoxy;

$R^9$ is -hydrogen or —$C_1$-$C_8$ alkyl;

$R^{19}$ is phenyl;

$R^{20}$ is $OR^{18}$; wherein $R^{18}$ is —H, a hydroxyl protecting group, or a direct bond where $OR^{18}$ represents =O;

$R^{21}$ is methyl; or a pharmaceutically acceptable salt form thereof.

Auristatins of the formula (X-A) include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{19}$ is phenyl; $R^{29}$ is $OR^{18}$; wherein $R^{18}$ is H, a hydroxyl protecting group, or a direct bond where $OR^{18}$ represents =O; and $R^{21}$ is methyl; or a pharmaceutically acceptable salt form thereof.

Auristatins of the formula (X-A) include those wherein $R^2$ is methyl or $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{19}$ is phenyl; $R^{20}$ is $OR^{18}$; wherein $R^{18}$ is H, a hydroxyl protecting group, or a direct bond where $OR^{18}$ represents =O; and $R^{21}$ is $C_1$-$C_3$ alkyl; or a pharmaceutically acceptable salt form thereof.

Auristatins of the formula (X-B) include those wherein $R^2$ is methyl;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocyle, aryl, and heterocyclic radicals whether alone or as part of another group are optionally substituted;

$R^5$ is —H;

$R^6$ is methyl;

each $R^8$ is methoxy;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted;

$R^{10}$ is optionally substituted aryl or optionally substituted heterocycle;

G is —O—, —S—, —NH—, or —$NR^{12}$—, wherein $R^{12}$ is —$C_1$-$C_{20}$ alkyl, —$C_2$-$C_{20}$ alkenyl, or —$C_2$-$C_{20}$ alkynyl, each of which is optionally substituted;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_s$—$R^{14}$, or —$(R^{13}O)_s$—$CH(R^{15})_2$, wherein said alkyl, alkenyl, alkynyl, aryl, and heterocycle radicals are optionally substituted;

s is an integer ranging from 0-1000;

$R^{13}$ is —$C_2$-$C_{20}$ alkylene, —$C_2$-$C_{20}$ alkenylene, or —$C_2$-$C_{20}$ alkynylene, each of which is optionally substituted;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted;

each occurrence of $R^{15}$ is independently —H, —COOH, —$(CH_2)_t$—$N(R^{16})_2$, —$(CH_2)_t$—$SO_3H$, —$(CH_2)_t$—$SO_3$—$C_1$-$C_{20}$ alkyl, —$(CH_2)_t$—$SO_3$—$C_2$-$C_{20}$ alkenyl, or —$(CH_2)_t$—$SO_3$—$C_2$-$C_{20}$ alkynyl wherein said alkyl, alkenyl and alkynyl radicals are optionally substituted;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_t$—COOH wherein said alkyl, alkenyl and alkynyl radicals are optionally substituted;

t is an integer ranging from 0 to 6; or a pharmaceutically acceptable salt form thereof.

In certain of these embodiments, $R^{10}$ is optionally substituted phenyl;

Auristatins of the formula (X-B) include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula (X-B) include those wherein said alkyl, alkenyl, alkynyl, alkylene, alkenylene, alkynyklene, aryl, carbocyle, and heterocycle radicals are unsubstituted.

Auristatins of the formula (X-B) include those wherein $R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is optionally substituted phenyl; G is O, S, or NH; and $R^{11}$ is as defined herein; or a pharmaceutically acceptable salt form thereof.

Auristatins of the formula (X-B) include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is optionally substituted phenyl; G is O, S, or NH; and $R^{11}$ is as defined herein; or a pharmaceutically acceptable salt form thereof.

Auristatins of the formula (X-B) include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{11}$ is phenyl; and G is O or NH and $R^{11}$ is as defined herein, preferably hydrogen; or a pharmaceutically acceptable salt form thereof.

Auristatins of the formula (X-B) include those wherein $R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is phenyl; and G is O or NH and $R^{11}$ is as defined herein, preferably hydrogen; or a pharmaceutically acceptable salt form thereof.

Auristatins of the formula (X-A) or (X-B) include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainder of the substituents are as defined herein.

Auristatins of the formula (X-A) or (X-B) include those wherein $R^2$ and $R^6$ are each methyl, and $R^9$ is H. The remainder of the substituents are as defined herein.

Auristatins of the formula (X-A) or (X-B) include those wherein each occurrence of $R^8$ is —$OCH_3$. The remainder of the substituents are as defined herein.

Auristatins of the formula (X-A) or (X-B) include those wherein $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H. The remainder of the substituents are as defined herein.

Auristatins of the formula (X-B) include those wherein G is —O— or —NH—. The remainder of the substituents are as defined herein.

Auristatins of the formula (X-B) include those wherein $R^{10}$ is aryl. The remainder of the substituents are as defined herein.

Auristatins of the formula (X-B) include those where $R^{10}$ is -phenyl. The remainder of the substituents are as defined herein.

Auristatins of the formula (X-B) include those wherein G is —O—, and $R^{11}$ is H, methyl or t-butyl. The remainder of the substituents are as defined herein.

Auristatins of the formula (X-B) include those wherein, when G is —NH, $R^{11}$ is —$(R^{13}O)_s$—$CH(R^{15})_2$, wherein $R^{15}$ is —$(CH_2)_t$—$N(R^{16})_2$, and $R^{16}$ is —$C_1$-$C_8$ alkyl or —$(CH_2)_t$—COOH. The remainder of the substituents are as defined herein.

Auristatins of the formula (X-B) include those wherein when G is —NH, $R^{11}$ is —$(R^{13}O)_s$—$CH(R^{15})_2$, wherein $R^{15}$ is H or —$(CH_2)_t$—$SO_3H$. The remainder of the substituents are as defined herein.

In preferred embodiments of the immunoconjugates of formula (II), when Z is an auristatin molecule of formula (X-A), w is an integer ranging from 1 to 12, preferably 2 to 12, y is 1 or 2, and a is preferably 1.

In some embodiments of the immunoconjugates of formula (II), when Z is an auristatin molecule of formula (X-B), a is 1 and w and y are 0.

Illustrative therapeutic agents (—Z) include those having the following structures:

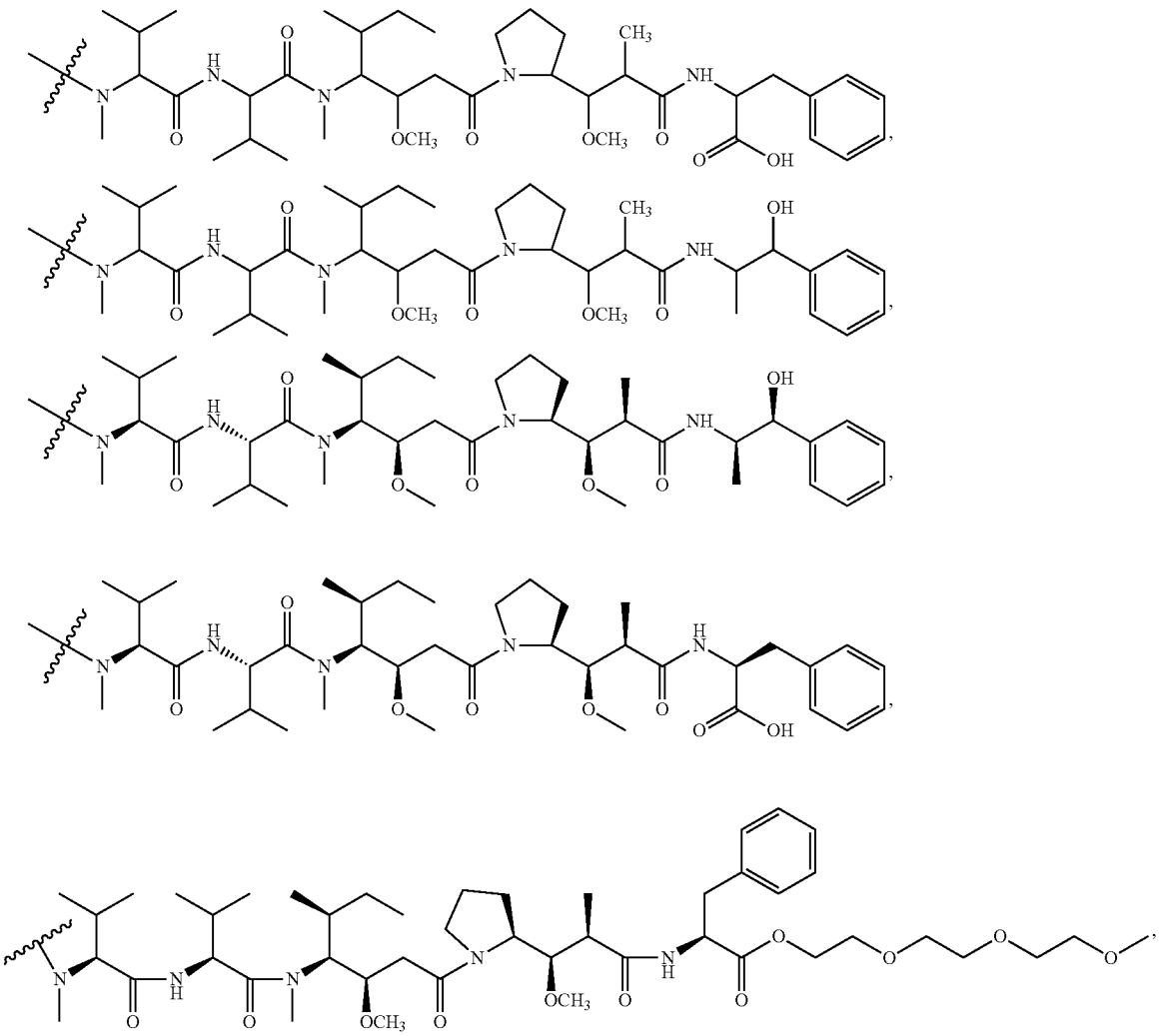

-continued
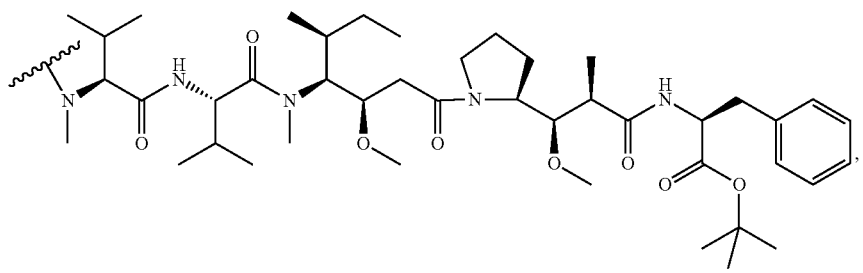
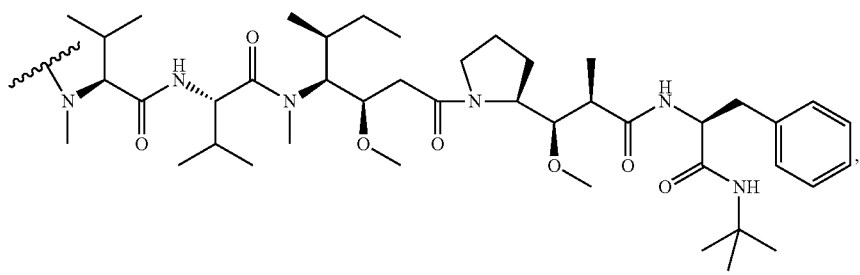
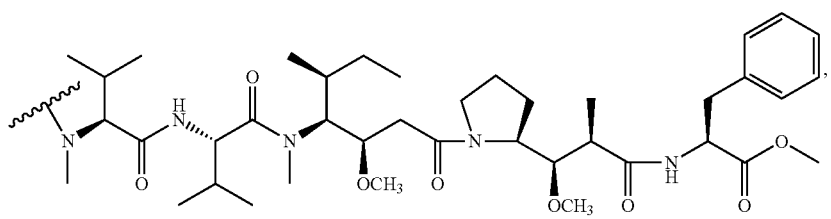
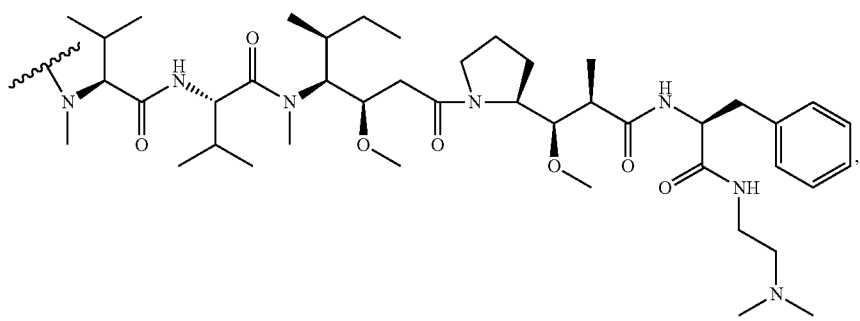
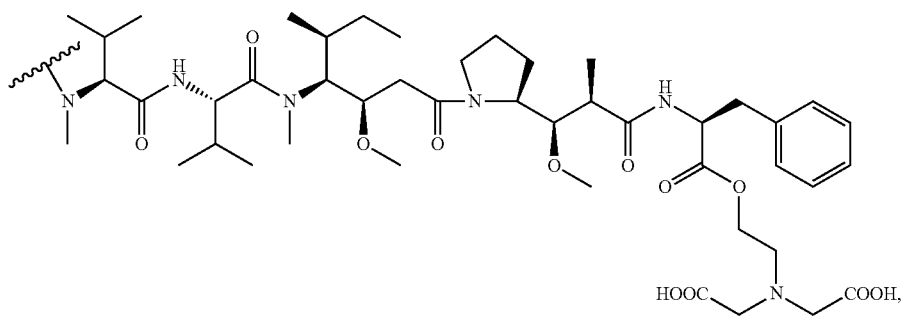
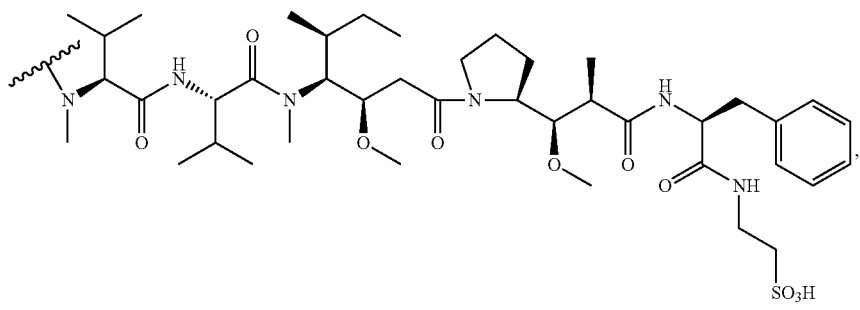

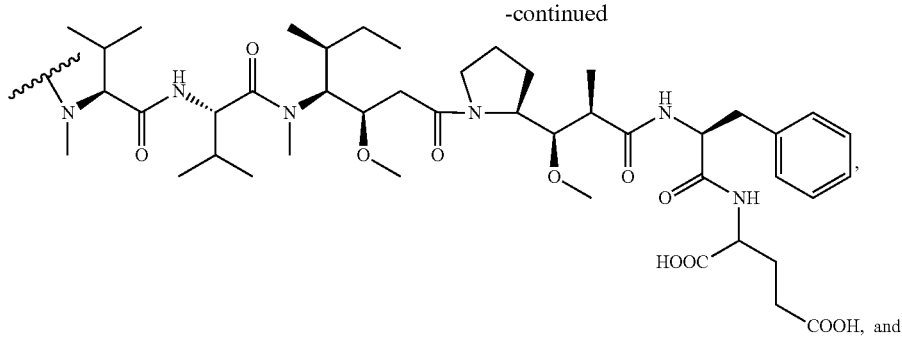

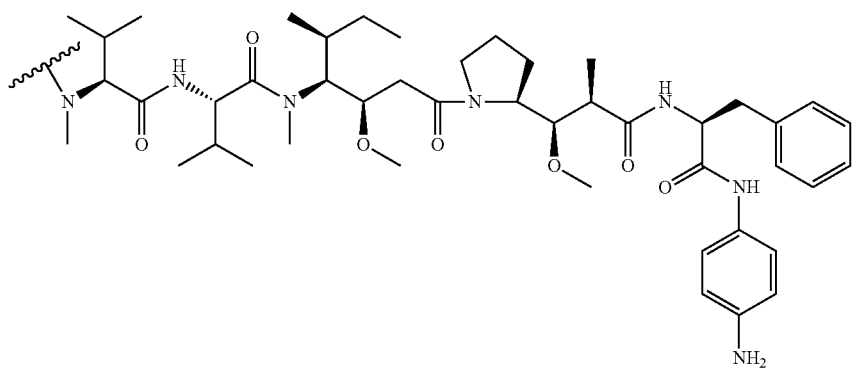

In one aspect, hydrophilic groups, such as but not limited to triethylene glycol esters (TEG) can be attached to the auristatin molecule of formula (X-B) at $R^{11}$. Without being bound by theory, the hydrophilic groups assist in the internalization and non-agglomeration of the therapeutic agent.

In some embodiments, the therapeutic agent is not TZT-1027. In some embodiments, the therapeutic agent is not auristatin E, dolastatin 10, or auristatin PE.

In some embodiments, the auristatin molecule is linked to a cysteine moiety on the antibody molecule by way of a linker containing a maleimide moiety, e.g., a maleimidocaproyl moiety.

In some embodiments, the auristatin molecule is coupled to the antibody molecule using a heterobifunctional linker that is connected to a hydroxyl group on the auristatin molecule. In some such embodiments, the linker comprises a hydrazone. In some embodiments, the linker is a hydrazone compound formed by reaction of maleimidocaproyl-hydrazide and a ketocarboxylic acid, e.g., 5-benzoylvaleric acid. In particular embodiments, the linker is (Z)-6-(2-(6-(2,5-dioxo-2,5-dihydro-1H-pyrrol-1-yl)-hexanoyl)hydrazono)-6-phenylhexanoic acid.

In some other embodiments the auristatin molecule is coupled to the antibody using a heterobifunctional linker that is connected to a monomethyl amino group on the auristatin molecule. In some embodiments, the linker comprises a cleavable moiety, e.g., a peptide moiety, and a self-immolative p-aminobenzylcarbamate spacer. Exemplary linkers include maleimidocaproyl (mc), maleimidocaproyl-L-phenylalanine-L-lysine-p-aminobenzylcarbamate, and maleimidocaproyl-L-valine-L-citrulline-p-aminobenzylcarbamate (vc).

In certain embodiments, the immunoconjugate of formula (I) is characterized by the formula Ab-(vc-MMAF)$_m$, (formula (I-4)); Ab-(vc-MMAE)$_m$, (formula (I-5)); Ab-(mc-MMAE)$_m$, (formula (I-6)); or Ab-(mc-MMAF)$_m$, (formula (I-7)), wherein Ab is an anti-GCC antibody molecule as described herein, S is a sulfur atom of the antibody, and m has the values and preferred values described above for formula (I). In certain embodiments, m is an integer from 1 to about 5.

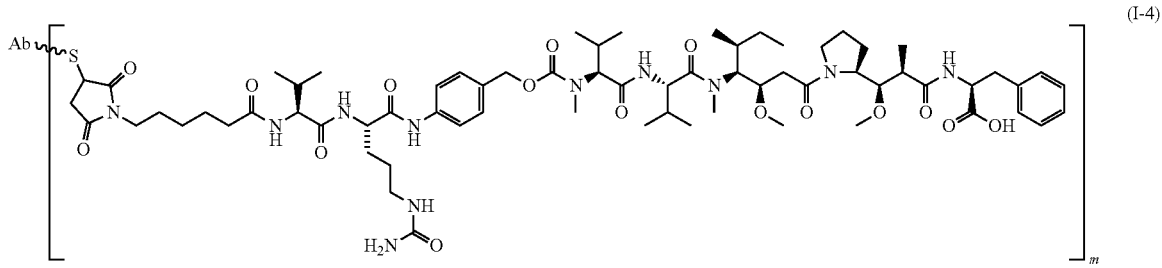

(I-4)

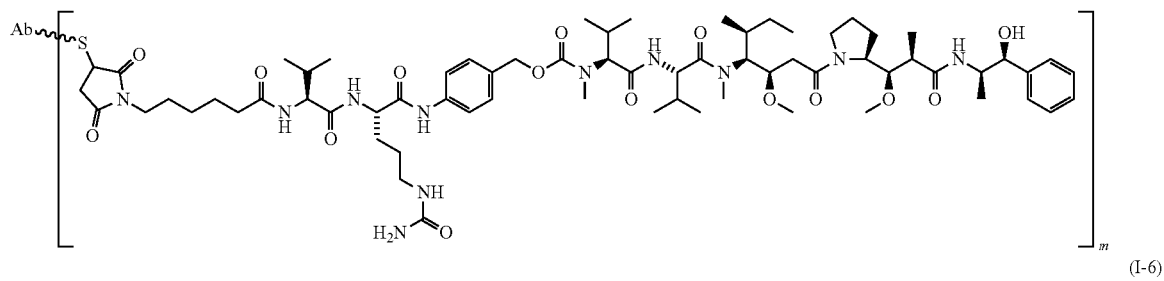

(I-5)

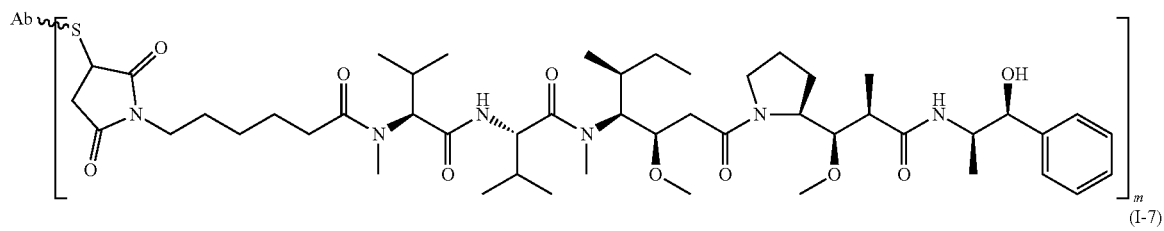

(I-6)

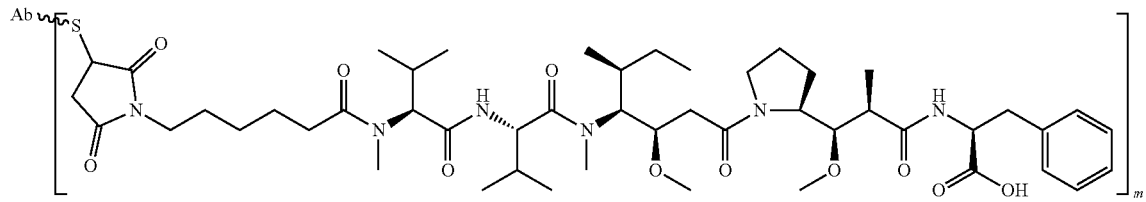

(I-7)

In some embodiments, the variable Ab in formula (I-4), (I-5), (I-6), or (I-7) is an antibody molecule with features summarized in Tables 1 to 6. In certain embodiments, the variable Ab is a 5F9 antibody molecule or an Abx-229 antibody molecule.

In some embodiments, the variable m in formula (I-4), (I-5), (I-6), or (I-7) ranges from about 2 to about 10, from about 6 to about 8, or from about 4 to about 6.

In certain particular embodiments, the invention relates to an immunoconjugate of formula (I-4), (I-5), (I-6), or (I-7), wherein Ab is a 5F9 antibody molecule and m is about 4.

The immunoconjugates disclosed herein can be used for modifying a given biological response. The therapeutic agent is not to be construed as limited to classical chemical therapeutic agents. For example, the therapeutic agent may be a nucleic acid, protein, or polypeptide possessing a desired biological activity. For example, the antibody molecule can be conjugated to an antisense molecule, an siRNA molecule, shRNA molecule or miRNA molecule that can interfere with expression of a gene, thereby producing a desired biological effect.

Proteins and polypeptides that can be conjugated to the antibody molecules of the invention include, for example, toxins and components thereof, such as abrin, abrin A chain, ricin, ricin A chain, modeccin, modeccin A chain, alpha-sarcin, exotoxin A (from *Pseudomonas aeruginosa*), PE38 (truncated *pseudomonas* exotoxin), gelonin, diphtheria toxin, diphtheria toxin A fragment, certain *Aleurites fordii* proteins, certain *Dianthus caryophyllus* proteins (e.g., dianthin 30 and dianthin 32), certain *Phytolacca Americana* proteins (e.g., PAP, PAPII, and PAP-S), certain *Saponaria officinlis* proteins (e.g., saporin 6), *Momordica charantia* inhibitor, curcin, crotin, mitogillin, restrictocin, phenomycin, and enomycin; proteins to engage the immune system at the tumor or induce an effector function at the tumor, such as tumor necrosis factor, interferon, nerve growth factor, platelet derived growth factor, and tissue plasminogen activator; and biological response modifiers such as, for example, cytokines and lymphokines (e.g., interleukin-1 ("IL-1"), interleukin-2 ("IL-2"), interleukin-6 ("IL-6"), granulocyte macrophase colony stimulating factor ("GM-CSF"), and granulocyte colony stimulating factor ("G-CSF")), and other growth factors.

The antibodies of the invention can also be conjugated or fused to viral surface proteins present on viral particles. For example, a single-chain anti-GCC antibody of the present invention could be fused (e.g., to form a fusion protein) to a viral surface protein. Alternatively, a whole anti-GCC antibody of the present invention, or a fragment thereof, could be chemically conjugated (e.g., via a chemical linker) to a viral surface protein. Preferably, the virus is one that fuses with endocytic membranes, e.g., an influenza virus, such that the virus is internalized along with the anti-GCC antibody and thereby infects GCC-expressing cells. The virus can be genetically engineered as a cellular toxin. For example, the virus could express or induce the expression of genes that are toxic to cells, e.g., cell death promoting genes. Preferably, such viruses would be incapable of viral replication.

An anti-GCC antibody molecule described herein can also be conjugated to a prodrug or prodrug activator. In a method to kill or suppress tumor cells, a first anti-GCC antibody molecule of the invention is conjugated with a prodrug that is activated only when in close proximity with a prodrug activator. The prodrug activator is conjugated with a second antibody molecule, preferably one that binds to a non-competing site on the GCC molecule. Whether two antibodies bind to competing or non-competing binding sites can be determined by conventional competitive binding assays. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," (1996) *Cancer Research,* 56:3287-3292.

Therapeutically active radioisotopes can also be coupled to anti-GCC antibodies, or antigen binding fragments, or derivatives thereof. Radioactive isotopes can be used in diagnostic or therapeutic applications. Radioactive isotopes that can be coupled to the anti-GCC antibodies include, but are not limited to α-, β-, or γ-emitters, or β- and γ-emitters. See, e.g., S.E. Order, "Analysis, Results, and Future Prospective of the Therapeutic Use of Radiolabeled Antibody in Cancer Therapy," *Monoclonal Antibodies for Cancer Detection and Therapy,* R. W. Baldwin et al. (eds.), pp 303-316 (Academic Press 1985. Such radioactive isotopes include, but are not limited to copper ($^{64}Cu$), iodine ($^{131}I$ or $^{125}I$), yttrium ($^{90}Y$), lutetium ($^{177}Lu$), actinium ($^{225}Ac$), praseodymium, astatine ($^{211}At$) rhenium ($^{186}Re$), bismuth ($^{212}Bi$ or $^{213}Bi$) indium ($^{111}In$), technetium ($^{99m}Tc$), phosphorus ($^{32}P$), rhodium ($^{188}Rh$), sulfur ($^{35}S$), carbon ($^{14}C$), tritium ($^{3}H$), chromium ($^{51}Cr$), chlorine ($^{36}Cl$), cobalt ($^{57}Co$ or $^{58}Co$), iron ($^{59}Fe$), selenium ($^{75}Se$), or gallium ($^{67}Ga$). Radioisotopes useful as therapeutic agents include yttrium ($^{90}Y$), lutetium ($^{177}Lu$), actinium ($^{225}Ac$), praseodymium, astatine ($^{211}At$) rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$), technetium ($^{99m}Tc$), phosphorus ($^{32}P$), carbon ($^{14}C$), and tritium ($^{3}H$), or one or more of the therapeutic isotopes listed above.

Radioimmunotherapy (RIT) using antibodies labeled with $^{131}I$, $^{90}Y$, and $^{177}Lu$ is under intense clinical investigation. There are significant differences in the physical characteristics of these three nuclides and as a result, the choice of radionuclide can be important in order to deliver maximum radiation dose to the tumor. The higher beta energy particles of $^{90}Y$ may be good for bulky tumors, but it may not be necessary for small tumors and especially bone metastases. The relatively low energy beta particles of $^{131}I$ are ideal, but in vivo dehalogenation of radioiodinated molecules is a major disadvantage for internalizing antibody. In contrast, $^{177}Lu$ has low energy beta particle with only 0.2-0.3 mm range and delivers much lower radiation dose to bone marrow compared to $^{90}Y$. In addition, due to longer physical half-life (compared to $^{90}Y$), the tumor residence times are higher. As a result, higher activities (more mCi amounts) of $^{177}Lu$ labeled agents can be administered with comparatively less radiation dose to marrow. There have been several clinical studies investigating the use of $^{177}Lu$ labeled antibodies in the treatment of various cancers. (Mulligan T et al. *Clin Cancer Res.* 1: 1447-1454 (1995); Meredith R F, et al. *J Nucl Med* 37:1491-1496 (1996); Alvarez R D, et al. *Gynecologic Oncology* 65: 94-101 (1997)).

Useful detectable agents with which an antibody or an antibody portion of the invention may be derivatized (or labeled) include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Pharmaceutical Compositions

In another aspect, the invention features compositions, e.g., pharmaceutically acceptable compositions, which include an anti-GCC antibody molecule or immunoconjugate thereof, as described herein, formulated together with a pharmaceutically acceptable carrier. In embodiments, the anti-GCC antibody molecule is one with exemplary features summarized in Tables 1 and 2.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). The pharmaceutical composition can include one or more additional excipients, e.g., salts, buffers, tonicity modifiers, lyoprotectants, nonionic detergents, surfactants, and preservatives.

The compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Some typical compositions are in the form of injectable or infusible solutions, intended for parenteral administration (e.g., intravenous, subcutaneous, intraperitoneal, intramuscular). In some embodiments, the antibody is administered by intravenous infusion or injection. In other embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In some embodiments, the pharmaceutical composition is sterile and stable under the conditions of manufacture and storage. The composition can be formulated as a solution, microemulsion, dispersion, liposome, microsphere, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by sterilization, e.g., by filtration. Generally, dispersions are prepared by incorporating the active compound into a sterile vehicle that contains a basic dispersion medium and the required other ingredients from those enumerated above. In the case of sterile powders for the preparation of sterile injectable solutions, the provided methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antigen binding fragments of the present invention can be administered by a variety of methods known in the art, although for many therapeutic applications, the route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an anti-GCC antibody molecule or immunoconjugate described herein may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixirs, suspensions, syrups, wafers, and the like. To administer an antibody or an antibody fragment of the invention by other than parenteral administration, it may be necessary to coat the compound with, or co-administer the compound with, a material to prevent its inactivation.

Therapeutic compositions can be administered with medical devices known in the art. For example, pharmaceutical preparations can be disposed within a device, e.g., an air- or liquid-tight container, which contains one or more dosages. Examples of delivery devices include, without limitation, vials, cannulas, needles, drip bags, and lines. The invention also provides methods of placing an antibody molecule or immunoconjugate described herein into such a device.

In some embodiments, the invention provides an anti-GCC antibody molecule or immunoconjugate described herein, which is formulated in a liposome composition. In some embodiments, the liposome is coated with antibody molecule. In some such embodiments, the liposome is filled with a therapeutic agent. Liposomic delivery can allow for the delivery of an agent, e.g., a therapeutic agent, that is not linked to the antibody. This approach can be used to deliver an agent, e.g., a therapeutic agent, that is not amenable to cross-linking to the antibody molecule or an agent, e.g., a therapeutic agent, which is to be sequestered, or which contact with non-target cells should be minimized. In particular embodiments, the liposome is filled with a cytostatic or cytotoxic agent. In certain particular embodiments, the therapeutic agent is selected from the group consisting of maytansinoids, an auristatins, dolastatins, duocarmycins, cryptophycins, taxanes, DNA alkylating agents calicheamicins, and derivatives of the foregoing. In other embodiments, the liposome is filled with nucleic acid sequence comprising RNA interference molecules, e.g., antisense molecules, siRNA, hsRNA or miRNA molecules, which are capable of diminishing GCC expression or the expression of another gene, e.g., an oncogene, in cells expressing GCC. In some other embodiments, the liposome is coated or filled with an immunoconjugate comprising an anti-GCC antibody molecule and a therapeutic agent or label.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The term "dosage unit form," as used herein, refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or an antigen binding fragment of the invention is 0.1-20 mg/kg, or 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective" amount of an antibody or an antigen binding fragment of the invention. A "therapeutically effective" amount refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter (e.g., tumor growth rate) in treated subjects by at least about 20%, at least about 40%, at least about 60%, and in some embodiments at least about 80%, relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

Also within the scope of the invention are kits comprising an anti-GCC antibody molecule or immunoconjugate as described herein. Further included are kits comprising liposome compositions comprising an anti-GCC antibody molecule or immunoconjugate. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the anti-GCC antibody molecule or immunoconjugate to detect GCC, in vitro, e.g., in a sample, e.g., a biopsy or cells from a patient having a cancer, or in vivo. The instructions can include guidance for therapeutic application including suggested dosages and/or modes of administration, e.g., in a patient with a cancer (e.g., a cancer of gastrointestinal origin, such as, for example, colon cancer, stomach cancer, esophageal cancer). Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. In some applications the antibody will be reacted with other components, e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-GCC antibody molecules or immunoconjugates, formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody. The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers (phenol, sulfites, glutathione, cysteine, gentisic acid, nicotinic acid, ascorbyl palmitate, HOP(:O)H$_2$I glycerol, sodium formaldehyde sulfoxylate, Na$_2$S$_2$O, Na$_2$S$_2$O$_3$, and SO$_2$, etc.).

A provided kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient with or without further purification. The chelator-conjugated antibody may be supplied in lyophilized form.

Uses

The anti-GCC antibody molecules described herein have in vitro and in vivo diagnostic, prognostic, imaging, therapeutic and prophylactic utilities. For example, these antibody molecules can be administered to cells in culture, e.g. in vitro or ex vivo, or administered in a subject, e.g., in vivo, to treat, prevent, and/or diagnose a variety of disorders.

The antibody molecules, immunoconjugates, and fusion proteins described herein can be used can modulate an activity or function of a GCC protein, such as ligand binding (e.g., binding of ST or guanylin), GCC-mediated signal transduction, maintenance of intestinal fluid, electrolyte homeostasis, intracellular calcium release (calcium flux), cell differentiation, cell proliferation, or cell activation.

In one aspect, the invention features a method of killing, inhibiting or modulating the growth of, or interfering with the metabolism of, a GCC-expressing cell. In one embodiment, the invention provides a method of inhibiting GCC-mediated cell signaling or a method of killing a cell. The method may be used with any cell or tissue which expresses GCC, such as a cancerous cell (e.g., a cell from a cancer of the gastrointestinal system, such as, for example, a cancer of the colon, stomach, or esophagus, or a pancreatic cell), or a metastatic lesion. Nonlimiting examples of GCC-expressing cells include T84 human colonic adenocarcinoma cells, fresh or frozen colonic tumor cells, and cells comprising a recombinant nucleic acid encoding GCC or a portion thereof.

Methods of the invention include the steps of contacting the cell with an anti-GCC antibody molecule or immunoconjugate thereof, as described herein, in an effective amount, i.e., amount sufficient to inhibit GCC-mediated cell signaling or an amount sufficient to kill the cell. The method can be used on cells in culture, e.g. in vitro, in vivo, ex vivo, or in situ. For example, cells that express GCC (e.g., cells collected by biopsy of a tumor or metastatic lesion; cells from an established cancer cell line; or recombinant cells), can be cultured in vitro in culture medium and the contacting step can be effected by adding the anti-GCC antibody molecule or immunoconjugate to the culture medium. In methods of killing a cell, the method comprises using a naked anti-GCC antibody molecule, or an immunoconjugate comprising an anti-GCC antibody molecule and a cytotoxic agent. The method will result in killing of cells expressing GCC, including in particular tumor cells expressing GCC (e.g., colonic tumor cells).

Reference to Table 7 can serve as a guide to select an antibody(ies) to use for various methods. For example, Table 7 indicates which antibodies were confirmed to internalize after binding GCC. Such antibodies would be useful when linked to a cytotoxic moiety or a moiety for cell imaging. Antibodies which do not internalize can be used for diagnostic purposes or therapeutic methods using naked antibody designed to elicit an antibody-dependent cell-mediated cytotoxic response, or perhaps for liposome delivery methods.

Anti-GCC antibody molecules of the present invention bind to extracellular domains of GCC or portions thereof in cells expressing the antigen. As a result, when practicing the methods of the present invention to kill, suppress, or detect cancerous cells, the antibodies or antigen binding fragments, bind to all such cells, not only to cells which are fixed or cells whose intracellular antigenic domains are otherwise exposed to the extracellular environment. Consequently, binding of the antibodies or antigen binding fragments, is concentrated in areas where there are cells expressing GCC, irrespective of whether these cells are fixed or unfixed, viable or necrotic. Additionally or alternatively, the anti-GCC antibody molecules, bind to and are internalized with GCC upon binding cells expressing the antigen.

The method also can be performed on cells present in a subject, as part of an in vivo protocol. In one embodiment, the subject is a human subject. Alternatively, the subject can be a mammal expressing a GCC antigen with which an anti-GCC antibody molecule disclosed herein cross-reacts. An anti-GCC antibody molecule or immunoconjugate thereof can be administered to a human subject for therapeutic purposes. An anti-GCC antibody molecule or immunoconjugate also can be administered to a non-human mammal expressing the GCC-like antigen with which the antibody cross-reacts (e.g., a primate, pig or mouse) for veterinary purposes or as an animal model of human disease. Animal models may be useful for evaluating the therapeutic efficacy of antibodies of the invention (e.g., testing of dosages and time courses of administration). For in vivo embodiments, the contacting step is effected in a subject and includes administering an anti-GCC antibody molecule or immunoconjugate thereof to the subject under conditions effective to permit both binding of the antibody molecule to the extracellular domain of GCC expressed on the cell, and the treating of the cell.

In one embodiment, the invention provides a method of treating cancer by administering an anti-GCC antibody molecule or an immunoconjugate comprising an anti-GCC antibody molecule and a cytotoxic agent to a patient in need of such treatment. The method can be used for the treatment of any cancerous disorder which includes at least some cells that express the GCC antigen. As used herein, the term "cancer" is meant to include all types of cancerous growths or oncogenic processes, metastatic tissues or malignantly transformed cells, tissues, or organs, irrespective of histopathologic type or stage of invasiveness. The terms "cancer" and "tumor" may be used interchangeably (e.g., when used in the context of treatment methods, "treatment of a cancer" and "treatment of a tumor" have the same meaning).

In embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting colon. Adenocarcinomas include malignancies such as non-small cell carcinoma of the lung. Metastatic lesions of the aforementioned cancers can also be treated or prevented using the methods and compositions of the invention. In some embodiments, the cancer to be treated is a cancer of the gastrointestinal system (e.g., colorectal cancer, esophageal cancer, or stomach cancer). In some embodiments, the cancer is pancreatic cancer.

In one embodiment, the cancer is a colorectal cancer, e.g., colorectal adenocarcinoma, colorectal leiomyosarcoma, colorectal lymphoma, colorectal melanoma, or a colorectal neuroendocrine tumor. In a particular embodiment, the cancer is metastatic colon cancer. In another embodiment, the cancer is a stomach cancer (e.g., gastric adenocarcinoma, lymphoma, or sarcoma), or metastasis thereof. In another embodiment, the cancer is an esophageal cancer (e.g., a squamous cell carcinoma or adenocarcinoma of the esophagus).

The method can be useful in treating a relevant disorder at any stage or subclassification. For example, method can be used to treat early or late stage colon cancer, or colon cancer of any of stages 0, I, IIA, IIB, IIIA, IIIB, IIIC, and IV.

In some embodiments, the method for treating cancer (e.g., a cancer described herein, e.g., colorectal, esophageal, or stomach cancer) comprises administering to a patient in need of such treatment a naked anti-GCC antibody molecule described herein. In other embodiments, the method comprises administering an immunoconjugate comprising an anti-GCC antibody molecule described herein and a cytotoxic agent. In some such embodiments, the immunoconjugate is characterized by formula (I), as described herein. In certain embodiments, the immunoconjugate is characterized by formula (I-1), (I-2), (I-3), (I-4), (I-5), (I-6), or (I-7) as described herein. In particular embodiments, the immunoconjugate is characterized by formula (I), (I-1), (I-2), (I-3), (I-4), (I-5), (I-6), or (I-7), wherein the variable Ab is an antibody molecule with features summarized in Tables 1 to 6. In certain embodiments, the variable Ab is a 5F9 antibody molecule or an Abx-229 antibody molecule. In certain particular embodiments, the immunoconjugate is characterized by formula (I-5) or (I-7), wherein the variable Ab is a 5F9 antibody molecule.

Methods of administering antibody molecules and immunoconjugates are described above. Suitable dosages of the molecules used will depend on the age and weight of the subject and the particular compound used.

In some embodiments, the anti-GCC antibody molecule or immunoconjugate is administered in treatment cycles. A "treatment cycle" consists of a treatment period, during which the anti-GCC antibody molecule or immunoconjugate is administered as described above, followed by a rest period, during which no anti-GCC antibody molecule or immunoconjugate is administered. The treatment cycle can be repeated as necessary to achieve the desired effect.

The anti-GCC antibodies described herein (e.g., naked anti-GCC antibody molecules or immunoconjugates comprising an anti-GCC antibody molecule and a therapeutic agent) may be used in combination with other therapies. For example, the combination therapy can include a composition of the present invention co-formulated with, and/or co-administered with, one or more additional therapeutic agents, e.g., one or more anti-cancer agents, e.g., cytotoxic or cytostatic agents, hormone treatment, vaccines, and/or other immunotherapies. In other embodiments, the anti-GCC antibodies are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the anti-GCC antibody molecule or immunoconjugate thereof is used in combination with a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The selection of therapeutic agent(s) or treatment modality to be combined with an anti-GCC antibody molecule or immunoconjugate of the invention will depend on the disorder to be treated. The additional agent(s) or treatment modality may include, for example, standard approved therapies for the indication being treated. For example, when the anti-GCC antibody molecule or immunoconjugate thereof is used to treat colon cancer, it may be used in combination with, e.g., surgery; radiation therapy; 5-fluorouricil (5-FU), capecitibine, leucovorin, irinotecan, oxaliplatin, bevacizumab, cetuximab, panitumum, or combinations thereof (e.g., oxaliplatin/capecitibine (XELOX), 5-fluorouricil/leucovorin/oxaliplatin (FOLFOX), 5-fluorouricil/leucovorinfirinotecan (FOLFIRI), FOLFOX plus bevacizumab, or FOLFIRI plus bevacizumab).

In another aspect, the invention features the use of an anti-GCC antibody molecule or immunoconjugate as described herein in the manufacture of a medicament. In an embodiment, the medicament is for treating cancer, e.g., a gastrointestinal cancer. In some embodiments, the medicament comprises an anti-GCC antibody molecule having features summarized in Tables 1-6. In some embodiments, the medicament comprises a 5F9 antibody molecule or Abx-229 antibody molecule.

Anti-GCC antibodies and immunoconjugates described herein can be used to detect the presence of GCC, e.g., to detect the presence of GCC in a biological sample, or to detect the presence or distribution of GCC in a subject. The term "detecting" as used herein encompasses quantitative or qualitative detection. Detecting GCC or GCC protein, as used herein, means detecting intact GCC protein or detecting a portion of the GCC protein that comprises the epitope to which the anti-GCC antibody molecule binds.

Accordingly, in another aspect, the invention features, a method of detecting GCC protein, e.g., detecting a GCC expressing cell or tissue, e.g., a tumor cell, or a tumor having cells, that express GCC. The method comprises: contacting a material, e.g., a cell or tissue, e.g., a sample of a tumor which expresses GCC, with an anti-GCC antibody molecule, e.g., an anti-GCC antibody molecule described herein, under conditions which allow formation of a complex between the anti-GCC antibody molecule and GCC protein; and detecting formation of a complex between antibody molecule and GCC protein, to thereby detect the presence of GCC protein, e.g., to detect a GCC expressing cell or tumor.

In an embodiment the anti-GCC antibody molecule is an immunoconjugate comprising a detectable label.

In certain embodiments, the tissues include normal and/or cancerous tissues that express GCC at higher levels relative to other tissues, for example other tissue such as B cells and/or B cell associated tissues.

Methods of detection described herein, whether in vitro or in vivo, can be used to evaluate a subject. In an embodiment the method is performed in vivo, and can be used, e.g., for imaging, staging, evaluation or diagnosis of a patient. In certain embodiments, the disorder is a cell proliferative disorder, such as a cancer or a tumor, e.g., colon cancer.

Thus, in another aspect, the invention provides, a method for detecting the presence of GCC protein in vitro (e.g., in a biological sample, such as a tissue biopsy, e.g., from a tumor tissue, from a subject) or in vivo (e.g., by in vivo imaging in a subject). The method comprises: (i) contacting a sample with an anti-GCC antibody molecule or immunoconjugate thereof, or administering to a subject, an anti-GCC antibody molecule or immunoconjugate thereof; and (ii) detecting formation of a complex between the anti-GCC antibody molecule and GCC protein. Complex formation is indicative of the presence or level of GCC.

In embodiments the level of complex detected in the sample or subject is compared with a reference value, e.g., a value for complex formation or level of GCC. In an embodiment a level of GCC which exceeds a reference value is indicative of a GCC-mediated disorder.

In an embodiment the method comprises contacting a reference sample, e.g., a control sample (e.g., a control biological sample, such as plasma, tissue, biopsy) or a control subject) with an anti-GCC antibody molecule or immunoconjugate thereof and comparing the level of complex detected therein with the level detected in the sample or subject.

In certain embodiments, a test cell or tissue is obtained from an individual suspected of having a disorder associated with increased expression of GCC.

In an embodiment the level of GCC, in a sample from the subject, or in the subject, is compared with a reference level, e.g., the level of GCC in a control material, e.g., a normal cell of the same tissue origin as the subject's cell or a cell having GCC at levels comparable to such a normal cell. The method can comprise, e.g., responsive to the detected level of GCC, providing a diagnosis, a prognosis, an evaluation of the efficacy of treatment, or the staging of a disorder. A higher level of GCC in the sample or subject, as compared to the control material, indicates the presence of a disorder associated with increased expression of GCC. A higher level of GCC in the sample or subject, as compared to the control material, can also indicate, the relative lack of efficacy of a treatment, a relatively poorer prognosis, or a later stage of disease. The level of GCC can also be used to evaluate or select future treatment, e.g., the need for more or less aggressive treatment, or the need to switch from one treatment regimen to another.

The level of GCC can also be used to select or evaluate patients. E.g., in embodiments patients whose tumor cells express high amounts of GCC on their surfaces would be considered good candidates for treatment with toxin-conjugated anti-GCC antibody molecules. In embodiments patients whose tumor cells express low amounts of GCC on their surfaces would not be as good candidates for this or might be candidates for combining the anti-GCC antibody molecule with an additional treatment method, or be candidates for naked antibody therapy. In another example, the dose of the toxin-conjugated anti-GCC antibody molecule could be adjusted to reflect the number of GCC molecules expressed on the surfaces of tumor cells. Patients with high numbers of GCC molecules on their tumor cell surfaces might be treated with lower doses than patients with low numbers of GCC molecules. Detecting the presence of GCC-expressing tumor cells in vivo can allow identification of tissues into the primary GCC-expressing tumor has metastasized. Knowledge of which tissues have metastases can lead to targeted application of tumor therapy.

As discussed above, the antibody molecules described herein permit assessment of the presence of a GCC protein in normal versus neoplastic tissues, through which the presence or severity of disease, disease progress and/or the efficacy of therapy can be assessed. For example, therapy can be monitored and efficacy assessed. In one example, a GCC protein can be detected and/or measured in a first sample obtained from a subject having an inflammatory disease and therapy can be initiated. Later, a second sample can be obtained from the subject and GCC protein in the sample can be detected and/or measured. A decrease in the quantity of GCC protein detected or measured in the second sample can be indicative of therapeutic efficacy.

Exemplary cell proliferative disorders that may be evaluated, e.g., diagnosed, using an antibody disclosed herein include a proliferative disorder including, but not limited to, colon cancer, stomach cancer, esophageal cancer.

In certain embodiments, a method, such as those described above, comprises detecting binding of an anti-GCC antibody to GCC expressed on the surface of a cell or in a membrane preparation obtained from a cell expressing GCC on its surface. In certain embodiments, the method comprises contacting a cell with an anti-GCC antibody under conditions permissive for binding of the anti-GCC antibody to GCC, and detecting whether a complex is formed between the anti-GCC antibody and GCC on the cell surface. An exemplary assay for detecting binding of an anti-GCC antibody to GCC expressed on the surface of a cell is a "FACS" assay.

Exemplary samples for methods described herein comprise tissue or body fluid, such as an inflammatory exudate, blood, serum, bowel fluid, stool sample, or biopsy. In one example, a sample (e.g., tissue and/or body fluid) can be obtained from an individual and a suitable immunological method can be used to detect and/or measure GCC protein expression. Suitable immunological methods for detecting or measuring GCC protein expression include enzyme-linked immunosorbent assays (ELISA), radioimmunoassay, immunohistology, flow cytometry, and the like.

Anti-GCC antibody molecules used in methods described herein, e.g., in the in vivo and in vitro detection, e.g., diagnostic, staging, or imaging methods, can be directly or indirectly labeled with a detectable substance to facilitate detection of the bound or unbound binding agent. Suitable detectable substances include various biologically active enzymes, ligands, prosthetic groups, fluorescent materials, luminescent materials, chemiluminescent materials, bioluminescent materials, chromophoric materials, electron dense materials, paramagnetic (e.g., nuclear magnetic resonance active) materials, and radioactive materials. In some embodiments, the anti-GCC antibody molecule is coupled to a radioactive ion, e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^3$H), rhodium ($^{188}$Rh), technetium ($^{99}$mTc), praseodymium, or phosphorous ($^{32}$P); or a positron-emitting radionuclide, e.g., carbon-11 ($^{11}$C), potassium-40 ($^{40}$K), nitrogen-13 ($^{13}$N), oxygen-15 ($^{15}$O), fluorine-18 ($^{18}$F), and iodine-121 ($^{121}$I).

Exemplary labels include fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, and 2,3-dihydrophthalazinediones Other exemplary labels include horseradish peroxidase (HRP), alkaline phosphatase, galactosidase, glucoamylase, lysozyme, saccharide oxidases, e.g., glucose oxidase, galactose oxidase, and glucose 6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Fluorophore and chromophore labeled antibody molecules can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer Science, 162:526 (1968) and Brand, L. et al. Annual Review of Biochemistry, 41:843-868 (1972). The antibodies can be labeled with fluorescent chromophore groups by conventional procedures such as those disclosed in U.S. Pat. Nos. 3,940,475, 4,289,747, and 4,376,110.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthhydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen Certain other methods can be used to detect binding of anti-GCC antibodies to GCC. Such methods include, but are not limited to, antigen-binding assays that are known in the art, such as western blots, radioimmunoassays, ELISA (enzyme linked immunosorbent assay), "sandwich" Immunoassays, immunoprecipitation assays, fluorescent immunoassays, protein A immunoassays, and immunohistochemistry (IHC).

Complex formation between the anti-GCC antibody molecule and GCC can be detected by measuring or visualizing either the antibody (or antibody fragment) bound to the GCC antigen or unbound antibody molecule. Conventional detection assays can be used, e.g., western blots, radioimmunoassays, ELISA (enzyme linked immunosorbent assay), "sandwich" immunoassays, immunoprecipitation assays, fluorescent immunoassays, protein A immunoassays, and immunohistochemistry (IHC) or radioimmunoassay (RIA).

Alternative to labeling the anti-GCC antibody molecule, the presence of GCC can be assayed in a sample by a competition immunoassay utilizing standards labeled with a detectable substance and an unlabeled anti-GCC antibody molecule. In this assay, the biological sample, the labeled standards and the GCC binding agent are combined and the amount of labeled standard bound to the unlabeled antibody is determined. The amount of GCC in the sample is inversely proportional to the amount of labeled standard bound to the GCC binding agent.

It is also possible to directly detect GCC to anti-GCC antibody molecule complex formation without further manipulation or labeling of either component (GCC or antibody molecule), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another example, determination of the ability of an antibody molecule to recognize GCC can be accomplished without labeling either assay component (GCC or antibody molecule) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In still another embodiment, the invention provides a method for detecting the presence of GCC-expressing tumor tissues in vivo. The method includes (i) administering to a subject (e.g., a patient having a cancer) an anti-GCC antibody or antigen binding fragment thereof, preferably a antibody or antigen binding fragment thereof conjugated to a detectable label or marker; (ii) exposing the subject to a means for detecting said detectable label or marker to the GCC-expressing tissues or cells.

Examples of labels useful for diagnostic imaging in accordance with the present invention are radiolabels such as $^{131}I$, $^{111}In$, $^{68}Ga$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a single photon emission computed tomography ("SPECT") detector or positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares (1983) *Radioimmunoimaging and Radioimmunotherapy*, Elsevier, New York, for techniques relating to the radiolabeling of antibodies. See also, D. Colcher et al. *Meth. Enzymol.* 121: 802-816 (1986.

In the case of a radiolabeled antibody, the antibody is administered to the patient, is localized to the tumor bearing the antigen with which the antibody reacts, and is detected or "imaged" in vivo using known techniques such as radionuclear scanning using e.g., a gamma camera or emission tomography or computed tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

In other embodiments, the invention provides methods for determining the dose, e.g., radiation dose, that different tissues are exposed to when a subject, e.g., a human subject, is administered an anti-GCC antibody molecule that is conjugated to a radioactive isotope. The method includes: (i) administering an anti-GCC antibody molecule as described herein, e.g., a anti-GCC antibody molecule, that is labeled with a radioactive isotope to a subject; (ii) measuring the amount of radioactive isotope located in different tissues, e.g., tumor, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled anti-GCC antibody molecule to the subject. The concentration of radioisotope present in a given tissue, integrated over time, and multiplied by the specific activity of the radioisotope can be used to calculate the dose that a given tissue receives. Pharmacological information generated using anti-GCC antibody molecules labeled with one radioactive isotope, e.g., a gamma-emitter, e.g., $^{111}$In, can be used to calculate the expected dose that the same tissue would receive from a different radioactive isotope which cannot be easily measured, e.g., a beta-emitter, e.g., $^{90}$Y.

Anti-GCC Antibody Sequences

Anti-GCC antibodies were generated by several methods, as is discussed in more detail in the Examples. Briefly, mouse monoclonal antibodies 3G1 8F1 and 10B8 were generated by traditional immunization technology in conventional mice. Human monoclonal antibodies 1D2, 5F9, 5H3, 6H8, 8C2, and 10C10 were generated using transgenic mice that generate fully human IgG2 antibodies, utilizing Abgenix XENOMOUSE transgenic technology, and isolated using hybridoma technology. Human mAb Abx-012, mAb Abx-020, mAb Abx-106, mAb Abx-198, mAb Abx-221, mAb Abx-229, mAb Abx-338 and mAb Abx-393 were generated using transgenic mice that generate fully human IgG2 antibodies. Single antibodies were isolated using Abgenix SLAM technology. These were used to make fully human IgG1 antibodies. Specificity of the antibodies against GCC was tested by ELISA and flow cytometry (FCM). A subset of the generated antibodies was selected for further characterization.

Table 1 below summarizes for several anti-GCC antibodies the antibody designation, the immunogen used to generate the antibody, the animal used, the source, the species and the isotype isolates.

variable region of mAb 5F9 (SEQ ID NO:18); and the nucleic acid sequence encoding the mature heavy chain variable region of mAb 5F9 (SEQ ID NO:17) is depicted in Table 4, row 9. The encoded amino acid sequences of mAb 5F9 heavy chain CDR (CDR) 1 (SEQ ID NO:106), CDR2 (SEQ ID NO:108) and CDR3 (SEQ ID NO:110) are depicted in Table 5, rows 25-27, respectively; and the nucleic acid sequences of mAb 5F9 heavy chain CDR1 (SEQ ID NO:105), CDR2 (SEQ ID NO:107) and CDR3 (SEQ ID NO:109) are shown in Table 6, rows 25-27, respectively.

Table 3, row 10 is an illustration of the encoded amino acid sequence of the mature light chain variable region of mAb 5F9 (SEQ ID NO:20); and the nucleic acid sequence encoding the mature kappa light chain variable region of mAb 5F9 (SEQ ID NO:19) is depicted in Table 4, row 10. The encoded amino acid sequences of mAb 5F9 light chain CDR (CDR) 1 (SEQ ID NO:112), CDR2 (SEQ ID NO:114) and CDR3 (SEQ ID NO:116) are depicted in Table 5, rows 28-30, respectively; and the nucleic acid sequences of mAb 5F9 light chain CDR1 (SEQ ID NO:111), CDR2 (SEQ ID NO:113) and CDR3 (SEQ ID NO:115) are shown in Table 6, rows 28-30, respectively.

Sequencing of the CDRs allowed determination of the abundance of residues that might serve as toxin conjugation sites. An unpaired free cysteine in the antigen binding region could be a site for auristatin conjugation and a lysine could be a site for maytansine conjugation. Toxin conjugation to an amino acid of the CDR would raise the concern of altering the binding affinity of the antibody to GCC. Thus, in embodiments the CDRs lack an amino acid which can be conjugated to a therapeutic agent.

TABLE 1

| Ab | Immunogen | Animal | Source | Species | Isotype |
|---|---|---|---|---|---|
| 3G1 | TOK107-hIg | C57 conventional mouse | Hybridoma | Mouse | IgG1, k |
| 8F1 | TOK107-hIg | C57 conventional mouse | Hybridoma | Mouse | IgG1, k |
| 10B8 | TOK107-hIg | C57 conventional mouse | Hybridoma | Mouse | IgG1, k |
| 1D3 | TOK107-hIg | C57 conventional mouse | Hybridoma | Mouse | IgG1, k |
| 8E12 | TOK107-hIg | C57 conventional mouse | Hybridoma | Mouse | IgG1, k |
| 5F9 | TOK107-hIg | XenoMouse | Hybridoma | Human | IgG2, k |
| 1D2 | TOK107-hIg | XenoMouse | Hybridoma | Human | IgG2, k |
| 5H3 | CHO-GC-C#27 cells | XenoMouse | Hybridoma | Human | IgG2, k |
| 6H8 | CHO-GC-C#27 cells | XenoMouse | Hybridoma | Human | IgG2, k |
| 8C2 | CHO-GC-C#27 cells | XenoMouse | Hybridoma | Human | IgG2, k |
| 10C10 | CHO-GC-C#27 cells | XenoMouse | Hybridoma | Human | IgG2, k |
| 10D3 | CHO-GC-C#27 cells | XenoMouse | Hybridoma | Human | IgG2, k |
| 1C9 | CHO-GC-C#27 cells | XenoMouse | Hybridoma | Human | IgG2, k |
| 229 | TOK107-hIg | XenoMouse | SLAM | Human | IgG1, k |
| 012 | TOK107-hIg | XenoMouse | SLAM | Human | IgG1, k |
| 221 | TOK107-hIg | XenoMouse | SLAM | Human | IgG1, k |
| 020 | TOK107-hIg | XenoMouse | SLAM | Human | IgG1, k |
| 338 | TOK107-hIg | XenoMouse | SLAM | Human | IgG1, k |
| 106 | TOK107-hIg | XenoMouse | SLAM | Human | IgG1, k |
| 198 | TOK107-hIg | XenoMouse | SLAM | Human | IgG1, k |
| 393 | TOK107-hIg | XenoMouse | SLAM | Human | IgG1, k |

The sequences of the light and heavy chain variable regions were determined. Table 2 below is a summary of the SEQ ID NOs for the variable regions of several antibodies. The amino acid and nucleic acid sequences for the variable regions of each of the heavy and light chains for murine and human anti-GCC antibodies are shown in Tables 3 and 4, respectively.

The amino acid and nucleic acid sequences for each of the CDRs of the heavy and light chains for anti-GCC antibodies are shown in Tables 5 and 6, respectively.

For example, Table 3, row 9 is an illustration of the encoded amino acid sequence of the mature heavy chain

TABLE 2

Summary of SEQ ID NOs for the variable regions of monoclonal antibodies.

| mAb | IgG chain | NA SEQ ID | AA SEQ ID |
|---|---|---|---|
| 3G1 | Heavy chain | 1 | 2 |
|  | Light chain | 3 | 4 |
| 8E12 | Heavy chain | 5 | 6 |
|  | Light chain | 7 | 8 |

TABLE 2-continued

Summary of SEQ ID NOs for the variable regions of monoclonal antibodies.

| mAb | IgG chain | NA SEQ ID | AA SEQ ID |
|---|---|---|---|
| 8F1 | Heavy chain | 9 | 10 |
|  | Light chain | 11 | 12 |
| 1D3 | Heavy chain | 13 | 14 |
|  | Light chain | 15 | 16 |
| 5F9 | Heavy chain | 17 | 18 |
|  | Light chain | 19 | 20 |
| 5H3 | Heavy chain | 21 | 22 |
|  | Light chain | 23 | 24 |
| 6H8 | Heavy chain | 25 | 26 |
|  | Light chain | 27 | 28 |
| 8C2 | Heavy chain | 29 | 30 |
|  | Light chain | 31 | 32 |
| 10C10 | Heavy chain | 33 | 34 |
|  | Light chain | 35 | 36 |
| 10D3 | Heavy chain | 286 | 287 |
|  | Light chain | 288 | 289 |
| Abx-012 | Heavy chain | 238 | 239 |
|  | Light chain | 240 | 241 |
| Abx-020 | Heavy chain | 37 | 38 |
|  | Light chain | 39 | 40 |
| Abx-106 | Heavy chain | 242 | 243 |
|  | Light chain | 244 | 245 |
| Abx-198 | Heavy chain | 41 | 42 |
|  | Light chain | 43 | 44 |
| Abx-221 | Heavy chain | 246 | 247 |
|  | Light chain | 248 | 249 |
| Abx-229 | Heavy chain | 45 | 46 |
|  | Light chain | 47 | 48 |
| Abx-338 | Heavy chain | 49 | 50 |
|  | Light chain | 51 | 52 |
| Abx-393 | Heavy chain | 53 | 54 |
|  | Light chain | 55 | 56 |

TABLE 3

Amino acid sequence of mAb variable region

|  | mAb | IgG chain | SEQ ID NO: | Amino Acid Sequence |
|---|---|---|---|---|
| 1 | 3G1 | Heavy chain | 2 | QVQLKESGPGLVAPSQSLSITCTVSGFSLS<u>RNAIS</u>WVRQP PGKGLEWLG<u>VIWTGGGTNYNSALKS</u>RLSIRKENSKSQVF LKMNSLQTEDTARYFCAR<u>SGYDGFD</u>YWGQGTLVTVSA |
| 2 | 3G1 | Light chain | 4 | QIVLTQSPAIMSASPGEKVTMTC<u>SASSSVNYMH</u>WYQQK SGTSPKRWIY<u>DTSKLAS</u>GVPARFSGSGSGTSYSLTITSME AEDAATYYC<u>QQWSGNPYT</u>FGGGTKLEIK |
| 3 | 8E12 | Heavy chain | 6 | QVQLKQSGAELVKPGASVKISCKASGYTFT<u>DYYIN</u>WVK QRPGQGLEWIG<u>KIGPRSGNTYYNEKFKG</u>KATLTADKSSS TAYMQLSSLTSEDSAVYFCAR<u>WDAY</u>WGQGTLVTVS |
| 4 | 8E12 | Light chain | 8 | DVVMTQTPLSLSVTIGQPASISC<u>KSSQSLLYSNGKTYLN</u> WLQQRPGQAPKHLMY<u>QVSKLDP</u>GIPDRFSGSGSETDFTL KISRVEAEDLGVYYC<u>LQGTYYPYT</u>FGGGTKLEIK |
| 5 | 8F1 | Heavy chain | 10 | QVQLQQPGAELVKPGASVQMSCKASGYIFT<u>GYWMY</u>WV KQRPGQGLEWIG<u>RIHPSDSNTNYNQKFKG</u>KATLTVDKSS STAYMQLSSLTSEDSAVYYCTH<u>ALAY</u>WGQGTLVTVS |
| 6 | 8F1 | Light chain | 12 | DVVLTQTPLTLSITIGQPASISC<u>KSSQSLLYSNGKTYLS</u>WL LQRPGQSPKRLIY<u>LVSQLDS</u>GVPDRFTGSGSGTDFTLKIS RVEAEDLGVYYC<u>VQGTHLFT</u>FGSGTKLEIK |
| 7 | 1D3 | Heavy chain | 14 | QVQLKQSGAELVKPGASVKMSCKASGYTFTDYYINWV KQRPGQGLEWIGKIGPRSGSTYYNEKFKGKATLTADKSS STAYMQLSSLTSEDSAVYFCARWDAYWGQGTLVTVSA |
| 8 | 1D3 | Light chain | 16 | DVVMTQTPLSLSVTIGQPASISCKSSQSLLYSNGKTYLN WLQQRPGQAPKHLMYQVSKLDPGIPDRFSGSGSETDFTL KISRVEAEDLGVYYCLQGTYYPYTFGGGTKLEIK |
| 9 | 5F9 | Heavy chain | 18 | QVQLQQWGAGLLKPSETLSLTCAVFGGSFSGYYWSWIR QPPGKGLEWIGEINHRGNTNDNPSLKSRVTISVDTSKNQF ALKLSSVTAADTAVYYCARERGYTYGNFDHWGQGTLV TVSS |
| 10 | 5F9 | Light chain | 20 | EIVMTQSPATLSVSPGERATLSCRASQSVSRNLAWYQQK PGQAPRLLIYGASTRATGIPARFSGSGSGTEFTLTIGSLQS EDFAVYYCQQYKTWPRTFGQGTNVEIK |
| 11 | 5H3 | Heavy chain | 22 | QVQLVESGGGLVKPGGSLRLSCAASGFTFSDCYMSWIR QSPGKGLEWVSYITTSGNTIYYADSVKGRFTISRDNAKN SLYLQMNSLRAEDTAVYYCARDWGWFYGMDVWGQGT TVTVSS |

TABLE 3-continued

Amino acid sequence of mAb variable region

| mAb | IgG chain | SEQ ID NO: | Amino Acid Sequence |
|---|---|---|---|
| 12 5H3 | Light chain | 24 | DIVMTQTPLSLSVTPGQPASISCKSSQSLLHNDGKTYLYWYLQKPGQPPQLLIYEVSNRFSGVPDRFSSSGSXTDFTLKISRVEAEDVGVYYCMQSIQLPRTFGQGTKVEIK |
| 13 6H8 | Heavy chain | 26 | QVQLVESGGGVVQPGRSLRLSCAASGFTFSSYGMHWVRQAPGKGLEWVAAIWYDGSNKYYADSVKGRFTISRDNSKNTLYLQMNSLRAEDTAVYYCARGRSSSYFDYWGQGTLVTVSS |
| 14 6H8 | Light chain | 28 | DIVMTQTPLSSPVTLGQPASISCRSSQSLVHSDGNTYLSWLQQRPGQPPRLLIYKTSNRFSGVPDRFSGSGAGTDFTLKISRVGAEDVGVYYCMQATQFPTFGQGTRLEIK |
| 15 8C2 | Heavy chain | 30 | QVQLVESGGGVVQPGRSLRLSCVASGFTFSSYGMHWVRQAPGKGLEWVGAIWYDGSNKYYAASVKGRFTISRDNSKNTLYLQMNSLRAEDTAVFYCARGRSSSYFDYWGQGTLVTVSS |
| 16 8C2 | Light chain | 32 | DIVMTQTPLSSPVTLGQPASISCRSSQSLVHSDGNTYLSWLQQRPGQPPRLLIYKTSNRFSGVPDRFSGSGAGTDFTLKISRVGAEDVGVYYCMQATQFPTFGQGTRLEIK |
| 17 10C10 | Heavy chain | 34 | QVQLVESGGGVVQPGRSLRLSCAASGFTFSSYGMHWVRQAPGKGLEWVAAIWYDGSNKYYADSVKGRFTISRDNSKNTLYLQMNSLRAEDTAVYYCARGRSSSYFDYWGQGTLVTVSS |
| 18 10C10 | Light chain | 36 | DIVMTQTPLSSPVTLGQPASFSCRSSQSLVHSDGNTYLSWLQQRPGQPPRLLIYKISNRFSGVPDRFSGSGAGTDFTLKISRVEAEDVGVYYCMQATQFPTFGQGTRLEIK |
| 35 10D3 | Heavy chain | 287 | QVQLQQWGAGLLKPSETLSLTCAVFGGSFSGYYWSWIRQPPGKGLEWIGEINHRGNTNDNPSLKSRVTISVDTSKNQFALKLSSVTAADTAVYYCARERGYTYGNFDHWGQGTLVTVSS |
| 36 10D3 | Light chain | 289 | EIVLTQSPGTLSLSPGERATLSCRASQSVSSRYLAWYQQKPGQAPRLLIYGASSRATGTPDRFSGSGSGTDFTLTISRLEPEDFAVYFCQQYERSFTFGPGTKVD |
| 19 Abx-012 | Heavy chain | 239 | QVQLQESGPGLVKPSETLSLTCTVSGASISHYYWSWIRQPAGKGLEWIGRIYISGRTSYNPSLKSRVTVSVDTSKNQFSLKLSSVTAADTAVYYCARDRLTGYFDYWGQGTLVTVSS |
| 20 Abx-012 | Light chain | 241 | EIVLTQSPGTLSLSPGERATLSCRASQSVSSSYLAWYQQKPGQAPRLLIYGASSRAAGIPDRFSGSGSGTDFTLTISRLEPEDFAVYYCQQYGSSLTFGGGTKVEIK |
| 21 Abx-020 | Heavy chain | 38 | QVQLVESGGGLVKPGGSLRLSCAASGFTFSDYYMSWIRQAPGKGLEWISYITSSGSTIYYSASVKGRFTISRDNAKNSLYLQMNSLRAEDTAVYYCARDFSGWFGVHFDYWGQGTLVTVSS |
| 22 Abx-020 | Light chain | 40 | DIVMTQTPLSLSVTPGQPASISCKSSQSLLHSDGKTYLYWYLQKPGQPPQLLIYEVSNRFSGVPNRFSGSGSGTDFTLKISRVEAEDVGVYYCMQSIQLTWTFGQGTKVEIK |
| 23 Abx-106 | Heavy chain | 243 | QVQLQESGPGLVKPSETLSLTCTVSGASISHYYWSWIRQPAGKGLEWIGRIYISGRTSYNPSLKSRVTVSVDTSKNQFSLKLSSVTAADTAVYYCARDRLTGYFDYWGQGTLVTVSS |
| 24 Abx-106 | Light chain | 245 | EIVLTQSPGTLSLSPGERATLSCRASQSVSSSYLAWYQQKPGQAPRLLIYGTSSRATGIPDRFSGSGSGTDFTLTISRLEPEDFAVYYCQQYGSSPMCSFGQGTKLEIK |
| 25 Abx-198 | Heavy chain | 42 | EVQLLESGGGLVQPGGSLRLSCAASGFTFSSYAMSWVRQAPGKGLDWVSDISGSGGSTYYADSVKGRFTISRDNSKNTLYLQMHSLSAEDTAIYYCAKRRWQGYFDLWGRGTLVTVSS |
| 26 Abx-198 | Light chain | 44 | EIVLTQSPGTLSLSPGERATLSCRARQRVDSRYLAWYQQKPGQAPRLLIYGASSRATGIPDRFSGSGSGTDFTLTISRLEPEDFAVYYCQQYGSSPLTFGGGTKVEIK |

TABLE 3-continued

Amino acid sequence of mAb variable region

| mAb | IgG chain | SEQ ID NO: | Amino Acid Sequence |
|---|---|---|---|
| 27 Abx-221 | Heavy chain | 247 | EVQLLESGGGLVQPGGSLRLSCAASGFTFSRYAMNWVRQAPGKGLEWVSGISGSGGSTYYADSVKGRFTISRDNSKNTLYLQMNSLRAEDTAVYYCAKDRDFWSGPFDYWGQGTLVTVSS |
| 28 Abx-221 | Light chain | 249 | EIVMTPSSATLSVSPGERATLSCRASQSVSRSLAWYQQKPGQAPRLLIYGASTRATGIPARFSGSGSGTEFTLTISSLQSEDVAVYYCQQYNNWMCSFGQGTKLEIK |
| 29 Abx-229 | Heavy chain | 46 | EVQLLESGGGLVQPGGSLRLSCAASGFTFSRYAMNWVRQAPGKGLEWVSGISGSGGRTYYADSVKGRFTISRDNSKNTLYLQMNSLRAEDTAVYYCAKDRDFWSGPFDYWGQGTLVTVSS |
| 30 Abx-229 | Light chain | 48 | EIVMTPSSATLSVSPGERATLSCRASQSVSRNLAWYQQKPGQAPRLLIYGASTRATGIPARFSGSGSGTEFTLTISSLQSEDFAVYYCHQYSNWMCSFGQGTKLEIK |
| 31 Abx-338 | Heavy chain | 50 | QVQLQESGPGLVKPSETLSLTCTVSGGSIRSYYWSWIRQPAGKGLEWIGRIYISGRTTFNPSLKSRVTISVDTSKNQFSLKLSSVTAADTAVYFCARDRYYGYLDYWGQGTLVTVSS |
| 32 Abx-338 | Light chain | 52 | EIVLTQSPGTLSLSPGERATLSCRASQSVSRSYLAWYQQKPGQAPRLLIYDASSRATGIPDRFSGSGSGTDFTLTISRLEPEDFAVYYCQQYGSSPSTFGQGTRLEIK |
| 33 Abx-393 | Heavy chain | 54 | QVQLQESGPGLVKPSETLSLTCTVSGGSIRHYYWSWIRQPPGKGLEWIGYIYYSGSTNYNLSLKSRVTISRDTSKNQVSLKLSSVTAADTAVYYCAAGMGFDYWGQGTLVTVSS |
| 34 Abx-393 | Light chain | 56 | DIQMTQSPSSLSASIGDRVTITCRASQAIRNDLGWYQLKPGKAPKRLIYSASSLQSGVPSRFSGSGSGTEFTLTISSLQPEDSATYYCLQHNSFPPTFGQGTKVEIK |

TABLE 4

Nucleic acid sequence of mAb variable region

| mAb | IgG chain | SEQ ID NO: | Nucleic Acid Sequence |
|---|---|---|---|
| 1 3G1 | Heavy chain | 1 | CAGGTGCAGCTGAAGGAGTCAGGACCTGGCCTGGTGGCGCCCTCACAGAGCCTGTCCATCACATGCACTGTCTCTGGGTTCTCATTAAGCAGAAATGCTATAAGCTGGGTTCGCCAGCCACCAGGAAAGGGTCTGGAGTGGCTTGGAGTAATATGGACTGGTGGAGGCACAAATTATAATTCAGCTCTCAAATCCAGACTGAGCATCCGCAAAGAGAACTCCAAGAGTCAAGTTTTCTTAAAAATGAACAGTCTACAAACTGAAGACACAGCCAGGTACTTCTGTGCCAGAAGTGGTTACGACGGGTTTGATTACTGGGGCCAAGGGACTCTGGTCACTGTCTCTGCA |
| 2 3G1 | Light chain | 3 | CAGATTGTTCTCACCCAGTCTCCAGCAATCATGTCTGCATCTCCAGGGGAGAAGGTCACCATGACCTGCAGTGCCAGCTCAAGTGTAAATTACATGCACTGGTACCAGCAGAAGTCAGGCACCTCCCCCAAAAGATGGATTTATGACACATCCAAACTGGCTTCTGGAGTCCCTGCTCGCTTCAGTGGCAGTGGGTCTGGGACCTCTTACTCTCTCACAATCACCAGCATGGAGGCTGAAGATGCTGCCACTTATTACTGCCAGCAGTGGAGTGGTAACCCGTACACGTTCGGAGGGGGGACCAAACTGGAAATAAAA |
| 3 8E12 | Heavy chain | 5 | CAGGTCCAGTTGAAGCAGTCTGGAGCTGAACTGGTGAAGCCTGGGGCTTCAGTGAAGATATCCTGCAAGGCTTCTGGCTACACCTTCACTGACTACTATATAAACTGGGTGAAGCAGAGGCCTGGACAGGGCCTTGAGTGGATTGGAAAGATTGGTCCTCGAAGTGGTAATACTTACTACAATGAGAAGTTCAAGGGCAAGGCCACACTGACTGCAGACAAATCGTCCAGCACAGCCTACATGCAGCTCAGC |

TABLE 4-continued

Nucleic acid sequence of mAb variable region

| | mAb | IgG chain | SEQ ID NO: | Nucleic Acid Sequence |
|---|---|---|---|---|
| | | | | AGCCTGACATCTGAGGACTCTGCAGTCTATTTCTGTG<br>CAAGATGGGATGCTTACTGGGGCCAAGGGACTCTGG<br>TCACTGTCTCT |
| 4 | 8E12 | Light chain | 7 | GATGTTGTGATGACCCAGACTCCACTGTCTTTGTCGG<br>TTACCATTGGACAACCAGCCTCTATCTCTTGCAAGTC<br>AAGTCAGAGCCTCTTATATAGTAATGGAAAGACATA<br>TTTGAATTGGTTACAACAGAGGCCTGGCCAGGCTCC<br>AAAGCACCTAATGTATCAGGTGTCCAAACTGGACCC<br>TGGCATCCCTGACAGGTTCAGTGGCAGTGGATCAGA<br>AACAGATTTTACACTTAAAATCAGCAGAGTGGAGGC<br>TGAAGATTTGGGAGTTTATTACTGCTTGCAAGGTAC<br>ATATTATCCGTACACGTTCGGAGGGGGGACCAAGCT<br>GGAAATAAAG |
| 5 | 8F1 | Heavy chain | 9 | CAGGTCCAACTGCAGCAGCCTGGGGCTGAACTGGTG<br>AAGCCTGGGGCTTCAGTGCAGATGTCCTGTAAGGCT<br>TCTGGCTATATTTTCACCGGCTACTGGATGTACTGGG<br>TGAAGCAGAGGCCTGGCCAAGGCCTTGAGTGGATTG<br>GAAGGATTCATCCTTCTGATAGTAATACTAACTACA<br>ATCAAAAGTTCAAGGGCAAGGCCACATTGACTGTAG<br>ACAAATCCTCCAGCACAGCCTACATGCAACTCAGCA<br>GCCTGACATCTGAGGACTCTGCGGTCTATTACTGTAC<br>CCATGCCCTTGCTTACTGGGGCCAAGGGACTCTGGT<br>CACTGTCTCT |
| 6 | 8F1 | Light chain | 11 | GATGTTGTGTTGACCCAGACTCCACTCACTTTGTCGA<br>TTACCATTGGACAACCAGCCTCTATCTCTTGCAAGTC<br>AAGTCAGAGCCTCTTATATAGTAATGGAAAAACCTA<br>TTTGAGTTGGTTATTACAGAGGCCAGGCCAGTCTCC<br>AAAGCGCCTAATCTATCTGGTGTCTCAACTGGACTCT<br>GGAGTCCCTGACAGGTTCACTGGCAGTGGATCAGGA<br>ACAGATTTTACACTGAAGATCAGCAGAGTGGAGGCT<br>GAGGATTTGGGAGTGTATTACTGCGTGCAAGGTACA<br>CATTTATTCACGTTCGGCTCGGGGACAAAGTTGGAA<br>ATAAAA |
| 7 | 1D3 | Heavy chain | 13 | CAGGTCCAGCTGAAGCAGTCTGGAGCTGAGCTGGTG<br>AAGCCTGGGGCTTCAGTGAAGATGTCCTGCAAGGCT<br>TCTGGCTACACCTTCACAGACTACTATATAAACTGG<br>GTGAAGCAGAGGCCTGGACAGGGCCTTGAGTGGATT<br>GGAAAGATTGGTCCTAGAAGTGGTAGTACTTACTAC<br>AATGAGAAGTTCAAGGGCAAGGCCACACTGACTGC<br>AGACAAATCCTCCAGCACAGCCTACATGCAGCTCAG<br>CAGCCTGACATCTGAGGACTCTGCAGTCTATTTCTGT<br>GCAAGATGGGATGCTTACTGGGGCCAAGGGACTCTG<br>GTCACTGTCTCTGCA |
| 8 | 1D3 | Light chain | 15 | GATGTTGTGATGACCCAGACTCCACTGTCTTTGTCGG<br>TTACCATTGGACAACCAGCCTCTATCTCTTGCAAGTC<br>AAGTCAGAGCCTCTTATATAGTAATGGAAAGACATA<br>TTTGAATTGGTTACAACAGAGGCCTGGCCAGGCTCC<br>AAAGCACCTAATGTATCAGGTGTCCAAACTGGACCC<br>TGGCATCCCTGACAGGTTCAGTGGCAGTGGATCAGA<br>AACAGATTTTACACTTAAAATCAGCAGAGTGGAGGC<br>TGAAGATTTGGGAGTTTATTACTGCTTGCAAGGTAC<br>ATATTATCCGTACACGTTCGGAGGGGGGACCAAGCT<br>GGAAATAAAA |
| 9 | 5F9 | Heavy chain | 17 | CAGGTGCAGCTACAGCAGTGGGGCGCAGGACTGTTG<br>AAGCCTTCGGAGACCCTGTCCCTCACCTGCGCTGTCT<br>TTGGTGGGTCCTTCAGTGGTTACTACTGGAGCTGGAT<br>CCGCCAGCCCCCAGGGAAGGGGCTGGAGTGGATTG<br>GGGAAATCAATCATCGTGGAAACACCAACGACAAC<br>CCGTCCCTCAAGAGTCGAGTCACCATATCAGTAGAC<br>ACGTCCAAGAACCAGTTCGCCCTGAAGCTGAGTTCT<br>GTGACCGCCGCGGACACGGCTGTTTATTACTGTGCG<br>AGAGAACGTGGATACACCTATGGTAACTTTGACCAC<br>TGGGGCCAGGGAACCCTGGTCACCGTCTCCTCA |
| 10 | 5F9 | Light chain | 19 | GAAATAGTGATGACGCAGTCTCCAGCCACCCTGTCT<br>GTGTCTCCAGGGGAAAGAGCCACCCTCTCCTGCAGG<br>GCCAGTCAGAGTGTTAGCAGAAACTTAGCCTGGTAT<br>CAGCAGAAACCTGGCCAGGCTCCCAGGCTCCTCATC |

TABLE 4-continued

Nucleic acid sequence of mAb variable region

| | mAb | IgG chain | SEQ ID NO: | Nucleic Acid Sequence |
|---|---|---|---|---|
| | | | | TATGGTGCATCCACCAGGGCCACTGGAATCCCAGCC AGGTTCAGTGGCAGTGGGTCTGGGACAGAGTTCACT CTCACCATCGGCAGCCTGCAGTCTGAAGATTTTGCA GTTTATTACTGTCAGCAGTATAAAACCTGGCCTCGG ACGTTCGGCCAAGGGACCAACGTGGAAATCAAA |
| 11 | 5H3 | Heavy chain | 21 | CAGGTGCAGCTGGTGGAGTCTGGGGGAGGCTTGGTC AAGCCTGGAGGGTCCCTGAGACTCTCCTGTGCAGCC TCTGGATTCACCTTCAGTGACTGCTACATGAGCTGG ATCCGCCAGTCTCCAGGGAAGGGGCTGGAGTGGGTT TCATACATTACTACTAGTGGTAATACCATTTACTACG CAGACTCTGTGAAGGGCCGATTCACCATCTCCAGGG ACAACGCCAAGAACTCACTGTATCTGCAAATGAACA GCCTGAGAGCCGAGGACACGGCCGTGTATTACTGTG CGAGAGACTGGGGATGGTTCTACGGTATGGACGTCT GGGGCCAAGGGACCACGGTCACCGTCTCCTCA |
| 12 | 5H3 | Light chain | 23 | GATATTGTGATGACCCAGACTCCACTCTCTCTGTCCG TCACCCCTGGACAGCCGGCCTCCATCTCCTGCAAGT CTAGTCAGAGCCTCCTGCATAATGATGGAAAGACCT ATTTGTATTGGTACCTGCAGAAGCCAGGCCAGCCTC CACAACTCCTGATCTATGAAGTTTCCAACCGGTTCTC TGGAGTGCCAGATAGGTTCAGTAGCAGCGGGTCNNG GACAGATTTCACACTGAAAATCAGCCGGGTGGAGGC TGAGGATGTTGGGGTTTATTACTGCATGCAAAGTAT ACAGCTTCCTCGGACGTTCGGCCAAGGGACCAAGGT GGAAATCAAA |
| 13 | 6H8 | Heavy chain | 25 | CAGGTGCAGCTGGTGGAGTCTGGGGGAGGCGTGGTC CAGCCTGGGAGGTCCCTGAGACTCTCCTGTGCAGCG TCTGGATTCACCTTCAGTAGCTATGGCATGCACTGG GTCCGCCAGGCTCCAGGCAAGGGGCTGGAGTGGGTG GCAGCTATATGGTATGATGGAAGTAATAAATACTAT GCAGACTCCGTGAAGGGCCGATTCACCATCTCCAGA GACAATTCCAAGAACACGCTGTATCTGCAAATGAAC AGCCTGAGAGCCGAGGACACGGCTGTGTATTACTGT GCGAGAGGGAGGAGCAGCTCGTACTTTGACTATTGG GGCCAGGGAACCCTGGTCACCGTCTCCTCA |
| 14 | 6H8 | Light chain | 27 | GATATTGTGATGACCCAGACTCCACTCTCCTCACCTG TCACCCTTGGACAGCCGGCCTCCATCTCCTGCAGGTC TAGTCAAAGCCTCGTACACAGTGATGGAAACACCTA CTTGAGTTGGCTTCAGCAGAGGCCAGGCCAGCCTCC AAGACTCCTAATTTATAAGACTTCTAACCGCTTCTCT GGGGTCCCAGACAGATTCAGTGGCAGTGGGGCAGG GACAGATTTCACACTGAAAATCAGCAGGGTGGGAGC TGAGGATGTCGGGGTTTATTACTGCATGCAAGCTAC GCAATTTCCAACCTTCGGCCAAGGGACACGACTGGA GATTAAA |
| 15 | 8C2 | Heavy chain | 29 | caggtgcagctggtggagtctgggg gaggcgtggtccagcctgggaggTCCCTGAGA CTCTCCTGTGTAGCGTCTGGATTCACCTTCAGT AGCTATGGCATGCACTGGGTCCGCCAGGCTCCAGGC AAGGGGCTGGAGTGGGTGGGAGCTATATGGTATGAT GGAAGTAATAAATACTATGCAGCCTCCGTGAAGGGC CGATTCACCATCTCCAGAGACAATTCCAAGAACACG CTGTATCTGCAAATGAACAGCCTGAGAGCCGAGGAC ACGGCTGTATTTTACTGTGCGAGAGGGAGGAGCAGC TCGTATTTTGACTACTGGGGCCAGGGAACCCTGGTC ACCGTCTCCTCA |
| 16 | 8C2 | Light chain | 31 | GATATTGTGATGACCCAGACTCCACTCTCCTCACCTG TCACCCTTGGACAGCCGGCCTCCATCTCCTGCAGGTC TAGTCAAAGCCTCGTACACAGTGATGGAAACACCTA CTTGAGTTGGCTTCAGCAGAGGCCAGGCCAGCCTCC AAGACTCCTAATTTATAAGACTTCTAACCGCTTCTCT GGGGTCCCAGACAGATTCAGTGGCAGTGGGGCAGG GACAGATTTCACACTGAAAATCAGCAGGGTGGGAGC TGAGGATGTCGGGGTTTATTACTGCATGCAAGCTAC GCAATTTCCAACCTTCGGCCAAGGGACACGACTGGA GATTAAA |

TABLE 4-continued

Nucleic acid sequence of mAb variable region

| | mAb | IgG chain | SEQ ID NO: | Nucleic Acid Sequence |
|---|---|---|---|---|
| 17 | 10C10 | Heavy chain | 33 | CAGGTGCAGCTGGTGGAGTCTGGGGGAGGCGTGGTC CAGCCTGGGAGGTCCCTGAGACTCTCCTGTGCAGCG TCTGGATTCACCTTCAGTAGCTATGGCATGCACTGG GTCCGCCAGGCTCCAGGCAAGGGGCTGGAGTGGGTG GCAGCTATATGGTATGATGGAAGTAATAAATACTAT GCAGACTCCGTGAAGGGCCGATTCACCATCTCCAGA GACAATTCCAAGAACACGCTGTATCTGCAAATGAAC AGCCTGAGAGCCGAGGACACGGCTGTGTATTACTGT GCGAGAGGGAGGAGCAGCTCGTACTTTGACTATTGG GGCCAGGGAACCCTGGTCACCGTCTCCTCA |
| 18 | 10C10 | Light chain | 35 | GATATTGTGATGACCCAGACTCCACTCTCCTCACCTG TCACCCTTGGACAGCCGGCCTCCTTCTCCTGCAGGTC TAGTCAAAGCCTCGTACACAGTGATGGAAACACGTA CTTGAGTTGGCTTCAGCAGAGGCCAGGCCAGCCTCC AAGACTCCTAATTTATAAGATTTCTAACCGGTTCTCT GGGGTCCCAGACAGATTCAGTGGCAGTGGGGCAGG GACAGATTTCACACTGAAAATCAGCAGGGTGGAAGC TGAGGATGTCGGGGTTTATTACTGCATGCAAGCTAC ACAATTTCCAACCTTCGGCCAAGGGACACGACTGGA GATTAAA |
| 35 | 10D3 | Heavy Chain | 286 | CAGGTGCA GCTACAGCAGTGGGGCGCAGGACTGTTGAAGCCTTC GGAGACCCTGTCCC TCACCTGCGCTGTCTTTGGTGGGTCCTTCAGTGGTTA CTACTGGAGCTGG ATCCGCCAGCCCCCAGGGAAGGGGCTGGAGTGGATT GGGGAAATCAATCA TCGTGGAAACACCAACGACAACCCGTCCCTCAAGAG TCGAGTCACCATAT CAGTAGACACGTCCAAGAACCAGTTCGCCCTGAAGC TGAGTTCTGTGACC GCCGCGGACACGGCTGTTTATTACTGTGCGAGAGAA CGTGGATACACCTA TGGTAACTTTGACCACTGGGGCCAGGGAACCCTGGT CACCGTCTCCTCA |
| 36 | 10D3 | Light chain | 288 | GAAATTGTGTTGACGCAGTCTCCAGGCACCCTGTCTT TGTCTCCAGGGGA AAGAGCCACCCTCTCCTGCAGGGCCAGTCAGAGTGT TAGCAGCAGGTACT TAGCCTGGTACCAGCAGAAACCTGGCCAGGCTCCCA GGCTCCTCATCTAT GGTGCATCCAGCAGGGCCACTGGCACCCCAGACAGG TTCAGTGGCAGTGG GTCTGGGACAGACTTCACTCTCACCATCAGCAGACT GGAGCCTGAAGATT TTGCAGTGTATTTCTGTCAGCAGTATGAAAGGTCATT CACTTTCGGCCCT GGGACCAAAGTGGAT |
| 19 | Abx-012 | Heavy chain | 238 | CAGGTGCAGTTGCAGGAGTCGGGCCCAGGACTGGTG AAGCCTTCGGAGACCCTGTCCCTCACCTGCACTGTCT CTGGTGC CTCCATCAGTCATTACTACTGGAGCTGGATCCGGCA GCCCGCCGGGAAGGGACTGGAATGGATTGGGCGTAT CTATATCA GTGGGAGGACCAGCTACAACCCCTCCCTCAAGAGTC GAGTCACCGTGTCAGTAGACACGTCCAAGAACCAGT TCTCCCTG AAGCTGAGCTCTGTGACCGCCGCGGACACGGCCGTG TATTACTGTGCGAGAGATCGGCTAACTGGGTACTTT GACTACTG GGGCCAGGGAACCCTGGTCACCGTCTCCTCAG |
| 20 | Abx-012 | Light chain | 240 | GAAATTGTGTTGACGCAGTCTCCAGGCACCCTGTCTT TGTCTCCAGGGGAAAGAGCCACCCTCTCCTGCAGGG CCAGTCA GAGTGTTAGCAGCAGCTACTTAGCCTGGTACCAGCA GAAACCTGGCCAGGCTCCCAGGCTCCTCATCTATGG TGCATCCA GCAGGGCCGCTGGCATCCCAGACAGGTTCAGTGGCA |

TABLE 4-continued

Nucleic acid sequence of mAb variable region

| | mAb | IgG chain | SEQ ID NO: | Nucleic Acid Sequence |
|---|---|---|---|---|
| | | | | GTGGGTCTGGGACAGACTTCACTCTCACCATCAGCAGACTGGAG<br>CCTGAAGATTTTGCAGTGTATTACTGTCAGCAGTATGGTAGCTCCCTCACTTTCGGCGGAGGGACCAAGGTGGAGATCAAAC |
| 21 | Abx-020 | Heavy chain | 37 | CAGGTGCAGCTGGTGGAGTCTGGGGGAGGCTTGGTCAAGCCTGGAGGGTCCCTGAGACTCTCCTGTGCAGCCTCTGGATTCACCTTCAGTGACTACTACATGAGCTGGATCCGCCAGGCTCCAGGGAAGGGGCTGGAGTGGATTTCATACATTACTAGTAGTGGTAGTACCATATACTACTCAGCCTCTGTGAAGGGCCGATTCACCATCTCCAGGGACAACGCCAAGAACTCACTGTATCTGCAAATGAACAGCCTGAGAGCCGAGGACACGGCCGTGTATTACTGTGCGAGAGATTTCAGTGGCTGGTTCGGAGTCCACTTTGACTACTGGGGCCAGGGAACCCTGGTCACCGTCTCCTCG |
| 22 | Abx-020 | Light chain | 39 | GATATTGTGATGACCCAGACTCCACTCTCTCTGTCCGTCACCCCTGGACAGCCGGCCTCCATCTCCTGTAAGTCTAGTCAGAGCCTCCTGCATAGTGATGGAAAGACCTATTTGTATTGGTACCTGCAGAAGCCAGGCCAGCCTCCACAGCTCCTGATCTATGAAGTTTCCAACCGGTTCTCTGGAGTGCCAAATAGGTTCAGTGGCAGCGGGTCAGGGACAGATTTCACACTGAAAATCAGCGGGTGGAGGCTGAGGATGTTGGGGTTTATTACTGCATGCAAAGTATACAACTTACGTGGACGTTCGGCCAAGGGACCAAGGTGGAAATCAAA |
| 23 | Abx-106 | Heavy chain | 242 | CAGGTGCAGTTGCAGGAGTCGGGCCCAGGACTGGTGAAGCCTTCGGAGACCCTGTCCCTCACCTGCACTGTCTCTGGTGCCTCCATCAGTCATTACTACTGGAGCTGGATCCGGCAGCCCGCCGGGAAGGGACTGGAATGGATTGGGCGTATCTATATCAGTGGGAGGACCAGCTACAACCCCTCCCTCAAGAGTCGAGTCACCGTGTCAGTAGACACGTCCAAGAACCAGTTCTCCCTGAAGCTGAGCTCTGTGACCGCCGCGGACACGGCCGTGTATTACTGTGCGAGAGATCGGCTAACTGGGTACTTTGACTACTGGGGCCAGGGAACCCTGGTCACCGTCTCCTCAGC |
| 24 | Abx-106 | Light chain | 244 | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCAGCTACTTAGCCTGGTACCAGCAGAAACCTGGCCAGGCTCCCAGGCTCCTCATCTATGGTACATCCAGCAGGGCCACTGGCATCCCAGACAGGTTCAGTGGCAGTGGGTCTGGGACAGACTTCACTCTCACCATCAGCAGACTGGAGCCTGAAGACTTTGCAGTGTATTACTGTCAGCAGTATGGTAGCTCACCCATGTGCAGTTTTGGCCAGGGGACCAAGCTGGAGATCAAACG |
| 25 | Abx-198 | Heavy chain | 41 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGACTGGGTCTCAGATATTAGTGGTAGTGGTGGTAGCACATACTACGCAGACTCCGTGAAGGGCCGGTTCACCATCTCCAGAGACAATTCCAAGAACACGCTGTATCTGCAAATGCACAGCCTGAGCGCCGAGGACACGGCCATATATTACTGTGCGAAACGGCGGTGGCAGGGGTACTTCGATCTCTGGGGCCGTGGCACCCTGGTCACTGTCTCCTCA |
| 26 | Abx-198 | Light chain | 43 | GAAATTGTGTTGACGCAGTCTCCAGGCACCCTGTCTTTGTCTCCAGGGGAAAGAGCCACCCTCTCCTGCAGGGCCAGGCAGCGTGTTGACAGCAGGTACTTAGCCTGGTACCAGCAGAAACCTGGCCAGGCTCCCAGGCTCCTCATCTATGGTGCATCCAGCAGGGCCACTGGCATCCCAG |

TABLE 4-continued

Nucleic acid sequence of mAb variable region

| mAb | IgG chain | SEQ ID NO: | Nucleic Acid Sequence |
|---|---|---|---|
| | | | ACAGGTTCAGTGGCAGTGGGTCTGGGACAGACTTCA CTCTCACCATCAGCAGACTGGAGCCTGAAGATTTTG CAGTGTATTACTGTCAGCAGTATGGTAGCTCACCGC TCACTTTCGGCGGAGGGACCAAGGTGGAGATCAAA |
| 27 Abx-221 | Heavy chain | 246 | GAGGTGCAGCTGTTGGAGTCTGGGGGAGGCTTGGTA CAGCCTGGGGGGTCCCTGAGACTCTCCTGTGCAGCC TCTGGATT CACCTTTAGCCGCTATGCCATGAACTGGGTCCGCCA GGCTCCAGGGAAGGGGCTGGAGTGGGTCTCAGGTAT TAGTGGTA GTGGTGGTAGCACATACTACGCAGACTCCGTGAAGG GCCGGTTCACCATCTCCAGAGACAATTCCAAGAACA CGCTGTAT CTGCAAATGAACAGCCTGAGAGCCGAGGACACGGC CGTATATTACTGTGCGAAAGATCGCGATTTTTGGAG TGGTCCATT TGACTACTGGGGCCAGGGAACCCTGGTCACCGTCTC CTCAGC |
| 28 Abx-221 | Light chain | 248 | GAAATAGTGATGACGCCGTCTTCAGCCACCCTGTCT GTGTCTCCAGGGGAAAGAGCCACCCTCTCCTGTAGG GCCAGTCA GAGTGTTAGTAGAAGCTTAGCCTGGTACCAGCAGAA ACCTGGCCAGGCTCCCAGGCTCCTCATCTACGGTGC ATCCACCA GGGCCACTGGGATCCCAGCCAGGTTCAGTGGCAGTG GGTCTGGGACAGAATTCACTCTCACCATCAGCAGCC TGCAGTCT GAAGATGTTGCAGTTTATTACTGTCAGCAGTATAAT AACTGGATGTGCAGTTTTGGCCAGGGGACCAAGCTG GAGATCAA ACG |
| 29 Abx-229 | Heavy chain | 45 | GAGGTGCAGCTGTTGGAGTCTGGGGGAGGCTTGGTA CAGCCTGGGGGGTCCCTGAGACTCTCCTGTGCAGCC TCTGGATTCACCTTTAGCCGCTATGCCATGAACTGGG TCCGCCAGGCTCCAGGGAAGGGGCTGGAGTGGGTCT CAGGTATTAGTGGGAGTGGTGGTAGGACATACTACG CAGACTCCGTGAAGGGCCGGTTCACCATCTCCAGAG ACAATTCCAAGAACACACTATATCTGCAAATGAACA GCCTGAGAGCCGAGGACACGGCCGTATATTACTGTG CGAAAGATCGCGATTTTTGGAGTGGTCCATTTGACT ACTGGGGCCAGGGAACCCTGGTCACCGTCTCCTCA |
| 30 Abx-229 | Light chain | 47 | GAAATAGTGATGACGCCGTCTTCAGCCACCCTGTCT GTGTCTCCAGGGGAGAGAGCCACCCTCTCCTGCAGG GCCAGTCAGAGTGTTAGTAGAAACTTAGCCTGGTAC CAGCAGAAACCTGGCCAGGCTCCCAGGCTCCTCATC TATGGTGCATCCACCAGGGCCACTGGTATCCCAGCC AGGTTCAGTGGCAGTGGGTCTGGGACAGAATTCACT CTCACCATCAGCAGCCTGCAGTCTGAAGATTTTGCA GTTTATTACTGTCACCAGTATAGTAACTGGATGTGCA GTTTTGGCCAGGGGACCAAGCTGGAGATCAAA |
| 31 Abx-338 | Heavy chain | 49 | CAGGTGCAGCTGCAGGAGTCGGGCCCAGGACTGGTG AAGCCTTCGGAGACCCTGTCCCTCACCTGCACTGTCT CTGGTGGCTCCATCAGAAGTTACTACTGGAGCTGGA TCCGGCAGCCCGCCGGGAAGGGACTGGAGTGGATTG GACGTATTTATATCAGTGGGAGGACCACCTTCAACC CCTCCCTCAAGAGTCGAGTCACCATATCAGTGGACA CGTCCAAGAACCAGTTCTCCCTGAAGCTGAGCTCTG TGACCGCCGCGGACACGGCCGTGTATTTCTGTGCGA GAGATAGATATTATGGCTACCTTGACTACTGGGGCC AGGGAACCCTGGTCACCGTCTCCTCA |
| 32 Abx-338 | Light chain | 51 | GAAATTGTGTTGACGCAGTCTCCAGGCACCCTGTCTT TGTCTCCAGGGGAAAGAGCCACCCTCTCCTGCAGGG CCAGTCAGAGTGTTAGCCGCAGTTACTTAGCCTGGT ACCAACAGAAACCTGGCCAGGCTCCCAGGCTCCTCA TCTATGATGCATCCAGCAGGGCCACTGGCATCCCAG ACAGGTTCAGTGGCAGTGGGTCTGGGACAGACTTCA |

TABLE 4-continued

Nucleic acid sequence of mAb variable region

| mAb | IgG chain | SEQ ID NO: | Nucleic Acid Sequence |
|---|---|---|---|
| | | | CTCTCACCATCAGCAGACTGGAGCCTGAAGATTTTG CAGTGTATTACTGTCAGCAGTATGGTAGTTCACCGA GCACCTTCGGCCAAGGGACACGACTGGAGATTAAA |
| 33 Abx-393 | Heavy chain | 53 | CAGGTGCAGCTGCAGGAGTCGGGCCCAGGACTGGTG AAGCCTTCGGAGACCCTGTCCCTCACCTGCACTGTCT CTGGCGGCTCCATCCGTCATTACTACTGGAGCTGGA TCCGGCAGCCCCCAGGGAAGGGACTGGAGTGGATTG GGTATATCTATTACAGTGGGAGCACCAACTACAACC TCTCCCTCAAGAGTCGAGTCACCATATCAAGAGACA CGTCCAAGAATCAGGTCTCCCTG AAGCTGAGTTCTGTGACCGCTGCGGACACGGCCGTG TATTATTGTGCGGCGGGTATGGGCTTTGACTACTGG GGCCAGGGAACCCTGGTCACCGTCTCCTCA |
| 34 Abx-393 | Light chain | 55 | GACATCCAGATGACCCAGTCTCCTTCCTCCCTGTCTG CATCTATAGGAGACAGAGTCACCATCACTTGCCGGG CAAGTCAGGCCATTAGAAATGATTTAGGCTGGTATC AGCTGAAACGGGGAAAGCCCCTAAGCGCCTGATCT ATTCTGCATCCAGTTTGCAAAGTGGGGTCCCATCAA GGTTCAGCGGCAGTGGATCTGGGACAGAATTCACTC TCACAATCAGCAGCCTGCAGCCTGAGGATTCTGCAA CTTATTACTGTCTACAGCATAATAGTTTCCCTCCGAC GTTCGGCCAAGGGACCAAGGTGGAAATCAAA |

TABLE 5

Amino acid sequence of CDRs

| | mAb | IgG chain | SEQ ID NO: | Amino Acid Sequence |
|---|---|---|---|---|
| 1 | 3G1 | VH CDR1 | 58 | RNAIS |
| 2 | 3G1 | VH CDR2 | 60 | VIWTGGGTNYNSALKS |
| 3 | 3G1 | VH CDR3 | 62 | SGYDGFDY |
| 4 | 3G1 | VL CDR1 | 64 | SASSSVNYMH |
| 5 | 3G1 | VL CDR2 | 66 | DTSKLAS |
| 6 | 3G1 | VL CDR3 | 68 | QQWSGNPYT |
| 7 | 8E12 | VH CDR1 | 70 | DYYIN |
| 8 | 8E12 | VH CDR2 | 72 | KIGPRSGNTYYNEKFKG |
| 9 | 8E12 | VH CDR3 | 74 | WDAY |
| 10 | 8E12 | VL CDR1 | 76 | KSSQSLLYSNGKTYLN |
| 11 | 8E12 | VL CDR2 | 78 | QVSKLDP |
| 12 | 8E12 | VL CDR3 | 80 | LQGTYYPYT |
| 13 | 8F1 | VH CDR1 | 82 | GYWMY |
| 14 | 8F1 | VH CDR2 | 84 | RIHPSDSNTNYNQKFKG |
| 15 | 8F1 | VH CDR3 | 86 | ALAY |
| 16 | 8F1 | VL CDR1 | 88 | KSSQSLLYSNGKTYLS |
| 17 | 8F1 | VL CDR2 | 90 | LVSQLDS |
| 18 | 8F1 | VL CDR3 | 92 | VQGTHLFT |
| 19 | 1D3 | VH CDR1 | 94 | DYYIN |
| 20 | 1D3 | VH CDR2 | 96 | KIGPRSGSTYYNEKFKG |
| 21 | 1D3 | VH CDR3 | 98 | WDAY |
| 22 | 1D3 | VL CDR1 | 100 | KSSQSLLYSNGKTYL |
| 23 | 1D3 | VL CDR2 | 102 | QVSKLDP |
| 24 | 1D3 | VL CDR3 | 104 | LQGTYYPYT |
| 25 | 5F9 | VH CDR1 | 106 | GYYWS |

TABLE 5-continued

Amino acid sequence of CDRs

| mAb | IgG chain | SEQ ID NO: Amino Acid Sequence |
|---|---|---|
| 26 5F9 | VH CDR2 | 108 EINHRGNTNDNPSLKS |
| 27 5F9 | VH CDR3 | 110 ERGYTYGNFDH |
| 28 5F9 | VL CDR1 | 112 RASQSVSRNLA |
| 29 5F9 | VL CDR2 | 114 GASTRAT |
| 30 5F9 | VL CDR3 | 116 QQYKTWPRT |
| 31 5H3 | VH CDR1 | 118 DCYMS |
| 32 5H3 | VH CDR2 | 120 YITTSGNTIYYADSVKG |
| 33 5H3 | VH CDR3 | 122 DWGWFYGMDV |
| 34 5H3 | VL CDR1 | 124 KSSQSLLHNDGKTYLY |
| 35 5H3 | VL CDR2 | 126 EVSNRFS |
| 36 5H3 | VL CDR3 | 128 MQSIQLPRT |
| 37 6H8 | VH CDR1 | 130 SYGMH |
| 38 6H8 | VH CDR2 | 132 AIWYDGSNKYYADSVKG |
| 39 6H8 | VH CDR3 | 134 GRSSSYFDY |
| 40 6H8 | VL CDR1 | 136 RSSQSLVHSDGNTYLS |
| 41 6H8 | VL CDR2 | 138 KTSNRFS |
| 42 6H8 | VL CDR3 | 140 MQATQFPT |
| 43 8C2 | VH CDR1 | 142 SYGMH |
| 44 8C2 | VH CDR2 | 144 AIWYDGSNKYYAASVKG |
| 45 8C2 | VH CDR3 | 146 GRSSSYFDY |
| 46 8C2 | VL CDR1 | 148 RSSQSLVHSDGNTYLS |
| 47 8C2 | VL CDR2 | 150 KTSNRFS |
| 48 8C2 | VL CDR3 | 152 MQATQFPT |
| 49 10C10 | VH CDR1 | 154 SYGMH |
| 50 10C10 | VH CDR2 | 156 AIWYDGSNKYYADSVKG |
| 51 10C10 | VH CDR3 | 158 GRSSSYFDY |
| 52 10C10 | VL CDR1 | 160 RSSQSLVHSDGNTYLS |
| 53 10C10 | VL CDR2 | 162 KISNRFS |
| 54 10C10 | VL CDR3 | 164 MQATQFPT |
| 103 10D3 | VH CDR1 | 291 GYYWS |
| 104 10D3 | VH CDR2 | 293 EINHRGNTNDNPSLKS |
| 105 10D3 | VH CDR3 | 295 ERGYTYGNFDH |
| 106 10D3 | VL CDR1 | 297 RASQSVSSRYLA |
| 107 10D3 | VL CDR2 | 299 GASSRAT |
| 108 10D3 | VL CDR3 | 301 QQYERSFT |
| 55 Abx-012 | VH CDR1 | 251 HYYWS |
| 56 Abx-012 | VH CDR2 | 253 RIYISGRTSYNPSLKS |
| 57 Abx-012 | VH CDR3 | 255 DRLTGYFDY |
| 58 Abx-012 | VL CDR1 | 257 RASQSVSSSYLA |
| 59 Abx-012 | VL CDR2 | 259 GASSRAA |
| 60 Abx-012 | VL CDR3 | 261 QQYGSSLT |
| 61 Abx-020 | VH CDR1 | 166 DYYMS |
| 62 Abx-020 | VH CDR2 | 168 YITSSGSTIYYSASVKG |
| 63 Abx-020 | VH CDR3 | 170 DFSGWFGVHFDY |
| 64 Abx-020 | VL CDR1 | 172 KSSQSLLHSDGKTYLY |
| 65 Abx-020 | VL CDR2 | 174 EVSNRFS |
| 66 Abx-020 | VL CDR3 | 176 MQSIQLTWT |
| 67 Abx-0106 | VH CDR1 | 263 HYYWS |

TABLE 5-continued

Amino acid sequence of CDRs

| mAb | IgG chain | SEQ ID NO: | Amino Acid Sequence |
|---|---|---|---|
| 68 Abx-106 | VH CDR2 | 265 | RIYISGRTSYNPSLKS |
| 69 Abx-106 | VH CDR3 | 267 | DRLTGYFDY |
| 70 Abx-106 | VL CDR1 | 269 | RASQSVSSSYLA |
| 71 Abx-106 | VL CDR2 | 271 | GTSSRAT |
| 72 Abx-106 | VL CDR3 | 273 | QQYGSSPMCS |
| 73 Abx-198 | VH CDR1 | 178 | SYAMS |
| 74 Abx-198 | VH CDR2 | 180 | DISGSGGSTYYADSVKG |
| 75 Abx-198 | VH CDR3 | 182 | RRWQGYFDL |
| 76 Abx-198 | VL CDR1 | 184 | RARQRVDSRYLA |
| 77 Abx-198 | VL CDR2 | 186 | GASSRAT |
| 78 Abx-198 | VL CDR3 | 188 | QQYGSSPLT |
| 79 Abx-221 | VH CDR1 | 275 | RYAMN |
| 80 Abx-221 | VH CDR2 | 277 | GISGSGGSTYYADSVKG |
| 81 Abx-221 | VH CDR3 | 279 | DRDFWSGPFDY |
| 82 Abx-221 | VL CDR1 | 281 | RASQSVSRSLA |
| 83 Abx-221 | VL CDR2 | 283 | GASTRAT |
| 84 Abx-221 | VL CDR3 | 285 | QQYNNWMCS |
| 85 Abx-229 | VH CDR1 | 190 | RYAMN |
| 86 Abx-229 | VH CDR2 | 192 | GISGSGGRTYYADSVKG |
| 87 Abx-229 | VH CDR3 | 194 | DRDFWSGPFDY |
| 88 Abx-229 | VL CDR1 | 196 | RASQSVSRNLA |
| 89 Abx-229 | VL CDR2 | 198 | GASTRAT |
| 90 Abx-229 | VL CDR3 | 200 | HQYSNWMCS |
| 91 Abx-338 | VH CDR1 | 202 | SYYWS |
| 92 Abx-338 | VH CDR2 | 204 | RIYISGRTTFNPSLKS |
| 93 Abx-338 | VH CDR3 | 206 | DRYYGYLDY |
| 94 Abx-338 | VL CDR1 | 208 | RASQSVSRSYLA |
| 95 Abx-338 | VL CDR2 | 210 | DASSRAT |
| 96 Abx-338 | VL CDR3 | 212 | QQYGSSPST |
| 97 Abx-393 | VH CDR1 | 214 | HYYWS |
| 98 Abx-393 | VH CDR2 | 216 | YIYYSGSTNYNLSLKS |
| 99 Abx-393 | VH CDR3 | 218 | GMGFDY |
| 100 Abx-393 | VL CDR1 | 220 | RASQAIRNDLG |
| 101 Abx-393 | VL CDR2 | 222 | SASSLQS |
| 102 Abx-393 | VL CDR3 | 224 | LQHNSFPPT |
| 109 consensus | VH CDR1 | 302 | x-x/Y-x/Y-M/W-S/N |
| 110 consensus | VH CDR2 | 303 | x-I-x-x-SG-[x or none]-x-T/I-[y/T/S]-x-x-L/V-K-s/G |
| 111 consensus | VH CDR3 | 304 | [4-6x]-G-[2-3x]-D-Y |
| 112 consensus | VL CDR1 | 305 | R/K-A/S-SQS-V/L-S/L-[5-9x] |
| 113 consensus | VL CDR2 | 306 | x-x-S-x-R-x-x |
| 114 consensus | VL CDR3 | 307 | Q/H/M-Q-Y/S-[5-7x] |

TABLE 6

Nucleic acid sequence of CDRs

| mAb | IgG chain | SEQ ID NO: | Nucleic Acid Sequence |
|---|---|---|---|
| 1 3G1 | VH CDR1 | 57 | AGAAATGCTATAAGC |
| 2 3G1 | VH CDR2 | 59 | GTAATATGGACTGGTGGAGGCACAAATTATAATTCAGCTCTCAAATCC |
| 3 3G1 | VH CDR3 | 61 | AGTGGTTACGACGGGTTTGATTAC |
| 4 3G1 | VL ACCDR1 | 63 | AGTGCCAGCTCAAGTGTAAATTACATGC |

TABLE 6-continued

Nucleic acid sequence of CDRs

| | mAb | IgG chain | SEQ ID NO: Nucleic Acid Sequence |
|---|---|---|---|
| 5 | 3G1 | VL CDR2 | 65 GACACATCCAAACTGGCTTCT |
| 6 | 3G1 | VL CDR3 | 67 CAGCAGTGGAGTGGTAACCCGTACACG |
| 7 | 8E12 | VH CDR1 | 69 GACTACTATATAAAC |
| 8 | 8E12 | VH CDR2 | 71 AAGATTGGTCCTCGAAGTGGTAATACTTACTACAATGAGAAGTTCAAGGGC |
| 9 | 8E12 | VH CDR3 | 73 TGGGATGCTTAC |
| 10 | 8E12 | VL CDR1 | 75 AAGTCAAGTCAGAGCCTCTTATATAGTAATGGAAAGACATATTTGAAT |
| 11 | 8E12 | VL CDR2 | 77 CAGGTGTCCAAACTGGACCCT |
| 12 | 8E12 | VL CDR3 | 79 TTGCAAGGTACATATTATCCGTACACG |
| 13 | 8F1 | VH CDR1 | 81 GGCTACTGGATGTAC |
| 14 | 8F1 | VH CDR2 | 83 AGGATTCATCCTTCTGATAGTAATACTAACTACAATCAAAAGTTCAAGGGC |
| 15 | 8F1 | VH CDR3 | 85 GCCCTTGCTTAC |
| 16 | 8F1 | VL CDR1 | 87 AAGTCAAGTCAGAGCCTCTTATATAGTAATGGAAAAACCTATTTGAGT |
| 17 | 8F1 | VL CDR2 | 89 CTGGTGTCTCAACTGGACTCT |
| 18 | 8F1 | VL CDR3 | 91 GTGCAAGGTACACATTTATTCACG |
| 19 | 1D3 | VH CDR1 | 93 GACTACTATATAAAC |
| 20 | 1D3 | VH CDR2 | 95 AAGATTGGTCCTAGAAGTGGTAGTACTTACTACAATGAGAAGTTCAAGGGC |
| 21 | 1D3 | VH CDR3 | 97 TGGGATGCTTAC |
| 22 | 1D3 | VL CDR1 | 99 AAGTCAAGTCAGAGCCTCTTATATAGTAATGGAAAGACATATTTGAAT |
| 23 | 1D3 | VL CDR2 | 101 CAGGTGTCCAAACTGGACCCT |
| 24 | 1D3 | VL CDR3 | 103 TTGCAAGGTACATATTATCCGTACACG |
| 25 | 5F9 | VH CDR1 | 105 GGTTACTACTGGAGC |
| 26 | 5F9 | VH CDR2 | 107 GAAATCAATCATCGTGGAAACACCAACGACAACCCGTCCCTCAAG |
| 27 | 5F9 | VH CDR3 | 109 GAACGTGGATACACCTATGGTAACTTTGACCAC |
| 28 | 5F9 | VL CDR1 | 111 AGGGCCAGTCAGAGTGTTAGCAGAAACTTAGCC |
| 29 | 5F9 | VL CDR2 | 113 GGTGCATCCACCAGGGCCACT |
| 30 | 5F9 | VL CDR3 | 115 CAGCAGTATAAAACCTGGCCTCGGACG |
| 31 | 5H3 | VH CDR1 | 117 GACTGCTACATGAGC |
| 32 | 5H3 | VH CDR2 | 119 TACATTACTACTAGTGGTAATACCATTTACTACGCAGACTCTGTGAAGGGC |
| 33 | 5H3 | VH CDR3 | 121 GACTGGGGATGGTTCTACGGTATGGACGTC |
| 34 | 5H3 | VL CDR1 | 123 AAGTCTAGTCAGAGCCTCCTGCATAATGATGGAAAGACCTATTTG |
| 35 | 5H3 | VL CDR2 | 125 GAAGTTTCCAACCGGTTCTCT |
| 36 | 5H3 | VL CDR3 | 127 ATGCAAAGTATACAGCTTCCTCGGACG |
| 37 | 6H8 | VH CDR1 | 129 AGCTATGGCATGCAC |
| 38 | 6H8 | VH CDR2 | 131 GCTATATGGTATGATGGAAGTAATAAATACTATGCAGACTCCGTGAAGGGC |
| 39 | 6H8 | VH CDR3 | 133 GGGAGGAGCAGCTCGTACTTTGACTAT |
| 40 | 6H8 | VL CDR1 | 135 AGGTCTAGTCAAAGCCTCGTACACAGTGATGGAAACACCTACTTGAGT |
| 41 | 6H8 | VL CDR2 | 137 AAGACTTCTAACCGCTTCTCT |
| 42 | 6H8 | VL CDR3 | 139 ATGCAAGCTACGCAATTTCCAACC |
| 43 | 8C2 | VH CDR1 | 141 AGCTATGGCATGCAC |
| 44 | 8C2 | VH CDR2 | 143 GCTATATGGTATGATGGAAGTAATAAATACTATGCAGCCTCCGTGAAGGGC |
| 45 | 8C2 | VH CDR3 | 145 GGGAGGAGCAGCTCGTATTTTGACTAC |
| 46 | 8C2 | VL CDR1 | 147 AGGTCTAGTCAAAGCCTCGTACACAGTGATGGAAACACCTACTTGAGT |
| 47 | 8C2 | VL CDR2 | 149 AAGACTTCTAACCGCTTCTCT |
| 48 | 8C2 | VL CDR3 | 151 ATGCAAGCTACGCAATTTCCA |
| 49 | 10C10 | VH CDR1 | 153 AGCTATGGCATGCAC |
| 50 | 10C10 | VH CDR2 | 155 GCTATATGGTATGATGGAAGTAATAAATACTATGCAGACTCCGTGAAGGGC |
| 51 | 10C10 | VH CDR3 | 157 GGGAGGAGCAGCTCGTACTTTGACTAT |
| 52 | 10C10 | VL CDR1 | 159 AGGTCTAGTCAAAGCCTCGTACACAGTGATGGAAACACGTACTTGAGT |

TABLE 6-continued

Nucleic acid sequence of CDRs

| mAb | IgG chain | SEQ ID NO: | Nucleic Acid Sequence |
|---|---|---|---|
| 53 10C10 | VL CDR2 | 161 | AAGATTTCTAACCGGTTCTCT |
| 54 10C10 | VL CDR3 | 163 | ATGCAAGCTACACAATTTCCAACC |
| 103 10D3 | VH CDR1 | 290 | GGTTACTACTGGAGC |
| 104 10D3 | VH CDR2 | 292 | GAAATCAATCATCGTGGAAACACCAACGACAACCCGTCCCTCAAG |
| 105 10D3 | VH CDR3 | 294 | GAACGTGGATACACCTATGGTAACTTTGACCAC |
| 106 10D3 | VL CDR1 | 296 | AGGGCCAGTCAGAGTGTTAGCAGCAGGTACTTAGCCT |
| 107 10D3 | VL CDR2 | 298 | GGTGCATCCAGCAGGGCCACTG |
| 108 10D3 | VL CDR3 | 300 | CAGCAGTATGAAAGGTCATTCACTT |
| 55 Abx-012 | VH CDR1 | 250 | CATTACTACTGGAGC |
| 56 Abx-012 | VH CDR2 | 252 | CGTATCTATATCAGTGGGAGGACCAGCTACAACCCCTCCCTCAAGAGT |
| 57 Abx-012 | VH CDR3 | 254 | GATCGGCTAACTGGGTACTTTGACTAC |
| 58 Abx-012 | VL CDR1 | 256 | AGGGCCAGTCAGAGTGTTAGCAGCAGCTACTTAGCC |
| 59 Abx-012 | VL CDR2 | 258 | GGTGCATCCAGCAGGGCCGCT |
| 60 Abx-012 | VL CDR3 | 260 | CAGCAGTATGGTAGCTCCCTCACT |
| 61 Abx-020 | VH CDR1 | 165 | GACTACTACATGAGC |
| 62 Abx-020 | VH CDR2 | 167 | TACATTACTAGTAGTGGTAGTACCATATACTACTCAGCCTCTGTGAAGGGC |
| 63 Abx-020 | VH CDR3 | 169 | GATTTCAGTGGCTGGTTCGGAGTCCACTTTGACTAC |
| 64 Abx-020 | VL CDR1 | 171 | AAGTCTAGTCAGAGCCTCCTGCATAGTGATGGAAAGACCTATTTGTAT |
| 65 Abx-020 | VL CDR2 | 173 | GAAGTTTCCAACCGGTTCTCT |
| 66 Abx-020 | VL CDR3 | 175 | ATGCAAAGTATACAACTTACGTGGACG |
| 67 Abx-106 | VH CDR1 | 262 | CATTACTACTGGAGC |
| 68 Abx-106 | VH CDR2 | 264 | CGTATCTATATCAGTGGGAGGACCAGCTACAACCCCTCCCTCAAGAGT |
| 69 Abx-106 | VH CDR3 | 266 | GATCGGCTAACTGGGTACTTTGACTAC |
| 70 Abx-106 | VL CDR1 | 268 | AGGGCCAGTCAGAGTGTTAGCAGCAGCTACTTAGCC |
| 71 Abx-106 | VL CDR2 | 270 | GGTACATCCAGCAGGGCCACT |
| 72 Abx-106 | VL CDR3 | 272 | CAGCAGTATGGTAGCTCACCCATGTGCAGT |
| 73 Abx-198 | VH CDR1 | 177 | AGCTATGCCATGAGC |
| 74 Abx-198 | VH CDR2 | 179 | GATATTAGTGGTAGTGGTGGTAGCACATACTACGCAGACTCCGTGAAGGGC |
| 75 Abx-198 | VH CDR3 | 181 | CGGCGGTGGCAGGGGTACTTCGATCTC |
| 76 Abx-198 | VL CDR1 | 183 | AGGGCCAGGCAGCGTGTTGACAGCAGGTACTTAGCC |
| 77 Abx-198 | VL CDR2 | 185 | GGTGCATCCAGCAGGGCCACT |
| 78 Abx-198 | VL CDR3 | 187 | CAGCAGTATGGTAGCTCACCGCTCACT |
| 79 Abx-221 | VH CDR1 | 274 | CGCTATGCCATGAAC |
| 80 Abx-221 | VH CDR2 | 276 | GGTATTAGTGGTAGTGGTGGTAGCACATACTACGCAGACTCCGTGAAGGGC |
| 81 Abx-221 | VH CDR3 | 278 | GATCGCGATTTTGGAGTGGTCCATTTGACTAC |
| 82 Abx-221 | VL CDR1 | 280 | AGGGCCAGTCAGAGTGTTAGTAGAAGCTTAGCC |
| 83 Abx-221 | VL CDR2 | 282 | GGTGCATCCACCAGGGCCACT |
| 84 Abx-221 | VL CDR3 | 284 | CAGCAGTATAATAACTGGATGTGCAGT |
| 85 Abx-229 | VH CDR1 | 189 | CGCTATGCCATGAAC |
| 86 Abx-229 | VH CDR2 | 191 | GGTATTAGTGGGAGTGGTGGTAGGACATACTACGCAGACTCCGTGAAGGGC |
| 87 Abx-229 | VH CDR3 | 193 | GATCGCGATTTTGGAGTGGTCCATTTGACTAC |
| 88 Abx-229 | VL CDR1 | 195 | AGGGCCAGTCAGAGTGTTAGTAGAAACTTAGCC |
| 89 Abx-229 | VL CDR2 | 197 | GGTGCATCCACCAGGGCCACT |
| 90 Abx-229 | VL CDR3 | 199 | CACCAGTATAGTAACTGGATGTGCAGT |
| 91 Abx-338 | VH CDR1 | 201 | AGTTACTACTGGAGC |
| 92 Abx-338 | VH CDR2 | 203 | CGTATTTATATCAGTGGGAGGACCACCTTCAACCCCTCCCTCAAGAGT |
| 93 Abx-338 | VH CDR3 | 205 | GATAGATATTATGGCTACCTTGACTAC |
| 94 Abx-338 | VL CDR1 | 207 | AGGGCCAGTCAGAGTGTTAGCCGCAGTTACTTAGCC |

TABLE 6-continued

Nucleic acid sequence of CDRs

| mAb | IgG chain | SEQ ID NO: | Nucleic Acid Sequence |
|---|---|---|---|
| 95Abx-338 | VL CDR2 | 209 | GATGCATCCAGCAGGGCCACT |
| 96Abx-338 | VL CDR3 | 211 | CAGCAGTATGGTAGTTCACCGAGCACC |
| 97Abx-393 | VH CDR1 | 213 | CATTACTACTGGAGC |
| 98Abx-393 | VH CDR2 | 215 | TATATCTATTACAGTGGGAGCACCAACTACAACCTCTCCCTCAAGAGT |
| 99Abx-393 | VH CDR3 | 217 | GGTATGGGCTTTGACTAC |
| 100Abx-393 | VL CDR1 | 219 | CGGGCAAGTCAGGCCATTAGAAATGATTTAGGC |
| 101Abx-393 | VL CDR2 | 221 | TCTGCATCCAGTTTGCAAAGT |
| 102Abx-393 | VL CDR3 | 223 | CTACAGCATAATAGTTTCCCTCCGACG |

Expression vectors were created as described above which contain coding sequence for both the heavy and light chain of each of mAb 5F9 and Abx-229.

The invention is illustrated by the following examples, which should not be construed as further limiting.

EXAMPLES

Example 1: Generation of Anti-GCC Antibodies and Characterization

The generation of GCC protein for immunization and screening was performed as follows. GCC antigen was prepared by subcloning a portion of the GCC gene encoding a sequence comprising the following GCC sequence (signal sequence and extracellular domain) into an expression vector.

```
                                           (SEQ ID NO: 229)
MKTLLLDLALWSLLFQPGWLSFSSQVSQNCHNGSYEISVLMMGNSAFAEP

LKNLEDAVNEGLEIVRGRLQNAGLNVTVNATFMYSDGLIHNSGDCRSSTC

EGLDLLRKISNAQRMGCVLIGPSCTYSTFQMYLDTELSYPMISAGSFGLS

CDYKETLTRLMSPARKLMYFLVNFWKTNDLPFKTYSWSTSYVYKNGTETE

DCFWYLNALEASVSYFSHELGFKVVLRQDKEFQDILMDHNRKSNVIIMCG

GPEFLYKLKGDRAVAEDIVIILVDLFNDQYFEDNVTAPDYMKNVLVLTLS

PGNSLLNSSFSRNLSPTKRDFALAYLNGILLFGHMLKIFLENGENITTPK

FAHAFRNLTFEGYDGPVTLDDWGDVDSTMVLLYTSVDTKKYKVLLTYDTH

VNKTYPVDMSPTFTWKNSKL
```

The expression vector (pLKTOK107) provided a C-terminal IgG1Fc region to fuse with the GCC sequence. This vector comprised an exon with the IgG1 hinge, CH2 and CH3 domains, mutated to eliminate an unpaired cysteine from the CH1 fragment in the exon. This IgG1Fc region was further mutated at lysine 235 and glycine 237 to alanines. The construct was expressed recombinantly in human embryonic kidney (HEK) 293 cells transfected with the gene for SV40 T-antigen as secreted GCC sequence (amino acid residues 24 to 430 of SEQ ID NO:228) fused to a C-terminal human IgG1 Fc. The protein, named TOK107-hIg (alt. name hGCC-ECD/hIgG1 Fc, SEQ ID NO:317), was purified by protein A chromatography and size exclusion chromatography.

GCC antigen was also prepared by subcloning the above fusion protein into an expression vector such as pLK-TOK111, which allows for fusion of the murine IgG2a transmembrane region onto the C-terminus. When this construct is expressed recombinantly in CHO cells, the GCC extracellular domain is detected on the cell surface. High cell surface expression of the GCC-Ig fusion protein (SEQ ID NO:318) is achieved when the pLKTOK111 vector is co-transfected with pLKTOK123, which comprises murine CD79a (MB-1) and CD79b (B29). Clone #27 from this transfection (CHO-GCC #27) was used as immunogen. HT-29-GCC #2 cells also were used as immunogen.

For screening of hybridoma supernatants and purified mAbs by ELISA, the nucleic acid encoding a GCC fusion construct was cloned into a pCMV1 expression vector (Sigma). Purification tags: FLAG-tag (in the N-terminus) and His-tag (in the C-terminus) were cloned into the construct as well. The fusion protein construct was transfected into 293 cells, expressed, and recombinant protein was purified over and Anti-FLAG® M2-Agarose Affinity column (Sigma).

Reagents and Cell Lines.

HEK293 cells, CHO, and T84 human colon cancer cells and were obtained from ATCC and maintained according to ATCC protocols.

Mice:

Female C57BL/6 mice, 4-6 weeks old, were purchased from Taconic Farms, Inc. (Germantown, N.Y.) for the generation of the murine hybridomas. Xenomice, bred in-house until 4-6 weeks old, producing human IgG2 antibodies were obtained from Abgenix, Inc. (Fremont, Calif.) for the generation of the human hybridomas. All animals were acquired and maintained according to the guidelines of the Institutional Animal Care and Use Committee of Millennium Pharmaceuticals, Inc.

Cell Lines:

The cell lines used for functional assays were cell pairs of GCC transfected cells and vector control HEK293 or HT29 cells. HT29 cells were transfected with the full length GCC under control of the EF-1α promoter or empty vector (pLKTOK4) and selected in G418. The GCC in these cells was confirmed to have a cGMP response when contacted with the ST peptide (1-18 or 5-18). HEK293 cells were transfected full length GCC under control of the CMV promoter or empty vector (pN8mycSV40) and selected in blasticidin. The GCC in these cells has a myc tag. The clones selected for highest GCC expression were 293-GCC #2, HT29-GCC #2 and HT29-GCC #5. The HT29-GCC #2 also were used as immunogens for generating anti-GCC antibody molecules. Additional GCC-expressing cells are CT26 cells. To develop the GCC-expressing CT26 cell line, pTOK58D vector was used. Full length GCC was cloned into the site normally used for heavy chain cloning and luciferase was cloned into the site normally used for light chain cloning. After transfection into CT26 cells, independent expression of both GCC and luciferase was confirmed. Surface expression of GCC was confirmed by flow cytometry using the 5F9 antibody. Clone #32 was selected for further studies.

The T84 colon cancer cell line endogenously expresses GCC. Taqman analysis of GCC in a broad cell line panel revealed that T84 was the only cell line that express mRNA for GCC. Staining for GCC with a GCC selective mAb on cell pellets of T84 cells showed significant GCC protein expression.

Quantitation of GCC receptor levels with radiolabeled ligand (ST-toxin) suggested that the 293-GCC #2 cell expressed more GCC than T84 cells while the HT29-GCC #2 or #5 expressed the fewest GCC molecules per cell.

| Cell line | Whole cell binding assay (receptor/cell) |
|---|---|
| HT-29-GCC#2/#5 | 100,000 |
| T84 endogenous GCC | 300,000 |
| 293-GCC | 600,000 |

Generation of Murine mAbs by Protein Immunization:

Human GCC extracellular domain/human Ig fusion protein (TOK107-hIg, 50 µg) was suspended in Dulbecco's phosphate buffered saline (PBS; GIBCO, Grand Island, N.Y.) and emulsified with an equal volume of complete Freund's adjuvant (Sigma Chemical Co., St. Louis, Mo.). C57BL/6 mice were immunized by injection of the emulsion at three subcutaneous sites and one intraperitoneal (i.p.) site. Two weeks after the initial immunization, the mice were given a booster immunization i.p. with 25 µg TOK107-hIg in incomplete Freund's adjuvant. One week later, a small amount of blood was collected from the tail vein and the serum binding activity against TOK107-Ig was titered by ELISA. Mice were selected for fusion when their titer exceeded 1:24,300 by ELISA or 1:500 by FACS. The selected mice were boosted by injection of 25 µg TOK107-hIg in PBS. Four days later, one mouse was euthanized and a spleen cell suspension was prepared and washed with PBS for fusion with P3 cells. One month later, spleen cells from another mouse were prepared for fusion with P3 cells. The fused cells were tested for production of antibodies which specifically bound to GCC by ELISA for binding TOK107-hIg compared to a nonGCC antigen or to the Fc region of IgG and by FACS for binding to T84 cells, or Caco-2 cells or HT-29 clone #2 cells compared to vector control and compared to non-GCC-expressing MCF-7 cells. Isotype was determined using ISOSTRIP® mouse monoclonal antibody isotyping kit (Roche Diagnostics Mannheim Germany). These immunization schemes and hybridoma fusions produced the 1D3, 8E12, 3G1 and 10B8 murine anti-GCC antibody molecules.

Generation of Human mAbs.

XENOMOUSE genetically engineered mice (Abgenix, Fremont, Calif.) (8 to 10 weeks old) were immunized for production of human monoclonal antibodies. See, Mendez et al. *Nature Genetics* 15:146-156 (1997), Green and Jakobovits *J. Exp. Med.* 188:483-495 (1998). Several immunization schemes were employed. In one scheme, one hundred micrograms of human GC-C extracellular domain/human Ig fusion protein (TOK107-hIg) were suspended in Dulbecco's phosphate buffered saline (PBS; GIBCO, Grand Island, N.Y.) and emulsified with an equal volume of complete Freund's adjuvant (Sigma Chemical Co., St. Louis, Mo.). XENOMOUSE™ were immunized by injection of the emulsion at three subcutaneous sites, base of tail and one intraperitoneal (i.p.) site. Fourteen days after the initial immunization, the mice were given a booster immunization with 50 µg TOK107-hIg in incomplete Freund's adjuvant. Sera testing indicated insufficient titer so after a few weeks rest, a second booster of 50 µg human TOK107-hIg was given. Two weeks later, a small amount of blood was collected from the tail vein and the serum activity against TOK107-Ig was titered by ELISA and against HT29-GCC #2 cells by FACS. Mice were selected for fusion when their titer exceeded 1:24,300 by ELISA or 1:500 by FACS. Nearly three months after that boost, mice were boosted with $10^7$ HT-29 #2 cells and the next day boosted with 50 µg TOK107-hIg, both in incomplete Freund's adjuvant. A mouse immunized with this scheme produced the 5F9 and the 1D2 human anti-GCC antibody molecules. A mouse immunized with this scheme produced the 5F9 and the 1D2 human anti-GCC antibody molecules.

Four days later, the mice were euthanized and spleen cell suspensions were prepared and washed with PBS for the fusion. The fused cells were tested for production of antibodies which specifically bound to GCC by ELISA for binding TOK107-hIg compared to a nonGCC antigen or to the Fc region of IgG and by FACS for binding to T84 cells or HT-29 clone #2 cells compared to vector control and compared to non-GCC-expressing MCF-7 cells. Isotype was determined using ELISA or by FACS using IgG or IgM specific secondary antibodies. A mouse immunized with this scheme produced the 5F9 and the 1D2 human anti-GCC antibody molecules.

In another scheme, CHO-GCC #27 cells ($5\times10^6$) comprising the pkTOK111 vector and expressing the GCC extracellular domain on their surfaces were used as the immunogen two times with two weeks between BIP (base of tail+intraperitoneal) immunizations. After sampling blood to identify anti-GCC reactivity by ELISA against TOK107-hIg, the mice were boosted with HT-29 GCC #2 cells (either three weeks or more than two months since the previous boost). Four days after the last boost, the respective spleen was harvested for cell fusion. The fused cells were tested for production of antibodies which specifically bound to GCC by ELISA for binding TOK107-hIg compared to a nonGCC antigen or to the Fc region of IgG and by FACS for binding to HT-29 clone #2 cells compared to vector control, T84 cells or non-GCC-expressing MCF-7 cells. Isotype was determined using ELISA. These immunization schemes and hybridoma fusions produced the 5H3, 6H8, 8C2, 10C10, 10D3 and 1C9 human anti-GCC antibody molecules.

Hybridomas that Produce Human mAb:

Spleen cells were counted and mixed with SP 2/0 myeloma cells (ATCC No. CRL8-006, Rockville, Md.) that are incapable of secreting either heavy or light chain immunoglobulin chains at a spleen:myeloma ratio of 2:1. Cells were fused with polyethylene glycol 1450 (ATCC) in 12 96-well tissue culture plates in HAT selection medium according to standard procedures. Between 10 and 21 days after fusion, hybridoma colonies became visible and culture supernatants were harvested then screened by ELISA and FACS.

SLAM Technology-Based Antibody Generation:

Monoclonal antibodies were also isolated by Abgenix's SLAM technology (Babcook et al *PNAS* 93:7843-7848 (1996)). The initial step in this method was to immunize XENOMOUSE mice were immunized with GCC antigen by a scheme among those described below. Then the SLAM (Selected Lymphocyte Antibody Method) step involves first identifying within a large population of lymphoid cells a single lymphocyte that is producing an antibody with a desired specificity or function, and then rescuing from that lymphocyte the genetic information that encodes the specificity of the antibody. The variable region of such a lymphocyte (initially producing an IgG2 or IgG4 antibody) is amplified and transferred to a vector bearing the IgG1 isotype.

Immunization schemes for the SLAM antibodies (e.g., Abx-229, -012, -221, -020, -338, -106, -198 or -393) included using TOK-hIg or TOK-hIg conjugated to keyhole limpet hemocyanin Immunizations were either through the foot pad or a combination of the base of the tail and intraperitoneal. The initial immunization of 10 µg immunogen included either TITERMAX® gold adjuvant or complete Freund's adjuvant. Six to eight boosts with 5 µg of immunogen were performed, using either Alum, TITERMAX® gold adjuvant or incomplete Freund's adjuvant. If TITERMAX gold was the initial adjuvant, alum was the boost adjuvant and boosts were performed at 3 to 4 day intervals. If the initial immunization and boosts employed complete then incomplete Freund's adjuvants, intervals between boosts were performed at about two week intervals. Sera tests of titers at the fourth to sixth boost sometimes were followed by additional boosts. The final boost prior to harvest four days later employed the immunogen in PBS.

Analysis of mAb by ELISA.

High-protein binding 96-well EIA plates (Costar/Corning, Inc. Corning, N.Y.) were coated with 50 µl/well of a 2 µg/ml solution (0.1 µg/well) of TOK107-hIg and incubated overnight at 4° C. The excess solution was aspirated and the plates were washed with PBS/0.05% Tween-20 (three times), then blocked with 1% bovine serum albumin (BSA, fraction V, Sigma Chemical Co., MO) for 1 hr at room temperature (RT) to inhibit non-specific binding. The BSA solution was removed and 50 µl/well of hybridoma supernatant from each fusion plate well were added. The plates were then incubated for 45 min. at 37° C. and washed three times with PBS/0.05% Tween-20. Horseradish peroxidase (HRP)-conjugated goat anti-mouse or anti-human IgG F(ab)2 (H&L) (Jackson Research Laboratories, Inc., West Grove, Pa.) diluted 1:4000 in 1% BSA/PBS was added to each well and then the plates were incubated for 45 min. at 37° C. After washing, 50 µl/well of ABTS solution (Zymed, South San Francisco, Calif.) was added. The intensity of the green color of positive wells at 405 nm was assessed on a Vmax microtitre plate reader (Molecular Devices Corp., Sunnyvale, Calif.). All hybridoma wells that gave a positive response were then expanded to 24-well cultures, subcloned by limiting dilution and analyzed by ELISA and FACS. The three best producing subclones were expanded further.

Analysis of mAb by Flow Cytometry.

Flow cytometry (FACS) screening was done on all the fusion plate supernatants in parallel to the ELISA screening. HT-29 clone #2 or untransfected HT-29 cells were grown in T225 flasks (Costar/Corning, Inc., Corning, N.Y.) in DMEM (GIBCO) supplemented 10% fetal bovine serum (GIBCO). Cells were detached from the flask surface using Versene (GIBCO), collected and washed twice with DMEM, then once with 1% BSA/PBS solution. The cells were re-suspended in 1% BSA/PBS and 2×10$^6$ cells were added to each well of V-bottomed 96-well plates (Costar) and centrifuged for 5 min at 2500 RPM (wash). The wash solution was discarded and 50 µl/well of supernatant from each fusion plate well wash added. A plate sealer (Linbro/MP Biomedicals, LLC, Solon, Ohio) was applied and the plates were then gently vortexed to resuspend and mix the cells with the supernatants and incubated at 4° C. (on ice) for 30 min. The plates were then washed with cold 1% BSA/PBS (three times) and 50111/well FITC-conjugated donkey anti-mouse IgG F(Ab)2 (H&L) or FITC-conjugated goat anti-human IgG F(Ab)2 (H&L) (Jackson) diluted 1:50 was added to each well for 30 min. at 4° C. (on ice in dark). The plates were again washed three times in cold 1% BSA/PBS and fixed in cold 1% paraformaldehyde (Sigma)/PBS. The cells were transferred to cluster tubes (Costar) and analyzed on a FACScalibur flow cytometer (Becton Dickenson, San Jose, Calif.). Any hybridoma wells that showed a positive shift were then expanded to 24-well cultures, subcloned by limiting dilution.

Internalization assay.

Internalization of anti-GCC antibody molecules was tested in both GCC-expressing cells and vector control cells, using immunofluorescence microscopy. Cells were grown on coverslips and placed on ice for 10 minutes prior to incubation with 10 µg/ml antibody in cold culture medium for 20 minutes on ice. For internalization, antibody-containing medium was replaced with fresh culture medium and the cells were shifted to 37° C. for 2-3 hours or maintained on ice. After rinsing in PBS and a brief fixation in 4% paraformaldehyde at room temperature, cells were permeabilized for 15 min in 0/5% TRITON X-100. The localization of the test antibody was determined using a fluorescently labeled anti-IgG antibody by laser scanning confocal microscopy. Antibody molecules localized to the cell surface of GCC-expressing cells when on ice. Upon incubation at 37° C., 5F9 showed punctuate staining within the cell membrane, indicative of internalization. No internalization was detected with vector cells.

Summary of Properties of Anti-GCC Antibody Molecules.

Most of the antibodies generated herein were tested in a number of the assays described above. Table 7 summarizes the in vitro properties for each. (T84=human colon tumor cells, MCF7=human breast tumor cells, WB=western blot, IP=immunoprecipitation, IHC=immunohistochemistry; internalization used T84 cells compared to MCF-7 cells)

TABLE 7

Properties of anti-GCC antibody molecules

| Ab | ELISA | | FACS | | | | WB | IP | IHC | Internalization |
|---|---|---|---|---|---|---|---|---|---|---|
|  | TOK107-hIg | TOK82-hIg | HT-29#2 | HT-29 | T84 | MCF7 |  |  |  |  |
| 8F1 | + | +/− | + | +/− | + | +/− | + |  | + |  |
| 3G1 | + | − | + | − | + | − | − | + | + | + |
| 10B8 | + | − | + | − | + | − | − | + | + |  |
| 5H3 | + | − | + | − | + | − | − | + | + | + |
| 6H8 | + | − | + | − | + | − | − | + |  | + |
| 8C2 | + | − | + | − | + | − | − | + | + | + |
| 10C10 | − | − | + | − | + | − | − | + |  |  |
| 10D3 | + | − | + | − | + | − | + | + |  |  |
| 1D2 | + | − | + | − | + | − | − | + |  |  |

TABLE 7-continued

Properties of anti-GCC antibody molecules

| | ELISA | | FACS | | | | | | | |
|---|---|---|---|---|---|---|---|---|---|---|
| Ab | TOK107-hIg | TOK82-hIg | HT-29#2 | HT-29 | T84 | MCF7 | WB | IP | IHC | Internalization |
| 4A12 | + | − | + | − | + | − | − | + | | |
| 5F9 | + | − | + | − | + | − | + | + | + | + |
| 1C9 | + | − | + | − | + | − | − | + | | |
| Abx-012 | + | | + | | | | − | + | + | + |
| Abx-015 | + | | − | | | | + | + | | |
| Abx-020 | + | | + | | | | − | + | | + |
| Abx-106 | + | | + | | | | | + | | − |
| Abx-198 | + | | + | | | | | + | | + |
| Abx-221 | + | | + | | | | | + | | + |
| Abx-229 | + | | + | | | | | + | | + |
| Abx-252 | + | | + | | | | | + | | + |
| Abx-338 | + | | + | | | | | + | | + |
| Abx-393 | + | | + | | | | | − | | + |

Additionally, some antibodies were tested for their ability to inhibit the ST peptide-induced calcium ion flux in GCC-expressing cells. The cGMP assay was performed in HT29-GCC #18 cells in the presence of 50 nM ST in the presence or absence of anti-GCC antibody molecules. There was dose-dependent inhibition of the calcium ion flux by 5F9. Other antibodies, 5H3 and Abx-338 also inhibited the calcium ion flux induced by ST.

Estimate of Relative Affinity of Anti-GCC Antibody Molecules.

The relative affinities (EC50; antibody concentration for half maximal binding) of some anti-GCC antibody molecules were estimated from ELISA measurements against TOK107-hIg and by FACS measurements with GCC-expressing cells. The following table displays some results.

TABLE 8

EC50 of anti-GCC antibody molecules

| Antibody | EC50, TOK107-hIg, M | EC50, Cells, M |
|---|---|---|
| 5F9 | $3.65 \times 10^{-8}$ | $1.24 \times 10^{-9}$ |
| 5H3 | $4.16 \times 10^{-9}$ | $4.7 \times 10^{-7}$ |
| Abx-338 | $4.9 \times 10^{-12}$ | $9.0 \times 10^{-8}$ |
| 3G1 | $2.28 \times 10^{-8}$ | $5.8 \times 10^{-10}$ |
| Abx-229 | $2.95 \times 10^{-8}$ | |
| Abx-221 | $6.55 \times 10^{-9}$ | |
| Abx-020 | $4.58 \times 10^{-9}$ | |
| Abx-012 | $5.55 \times 10^{-10}$ | |
| Abx-198 | $4.77 \times 10^{-8}$ | |

Measurement of Affinity of Anti-GCC Antibody Molecules.

A BIACORE™ T100 system (GE Healthcare, Piscataway, N.J.) was used to measure the affinity of anti-GCC 5F9 antibody at 22° C.

Step 1: MAb 5F9 (Prep A) was diluted to 20 μg/mL in 10 mM sodium acetate, pH 4.0 and Reference 5F9 MAb (Prep B) was diluted to 10 μg/mL in 10 mM sodium acetate, pH 4.0. Each mAb was covalently immobilized to several CM4 BIACORE chips using standard amine coupling. For each CM4 chip prepared, Prep A 5F9 was immobilized over two flow cells at around 75-100 RU while Prep B 5F9 was immobilized to one flow cell at around 70-80 RU. The remaining fourth flow cell of each CM4 chip was used as the reference flow cell.

Step 2: The stock concentration of GCC-ECD-Fc (TOK107-hIg) was determined using the methods detailed by Pace et al. in *Protein Science*, 4:2411 (1995), and Pace and Grimsley in *Current Protocols in Protein Science* 3.1.1-3.1.9 (2003).

Step 3: For each prepared CM4 chip described in Step 1, GCC-ECD-Fc was injected for 2 minutes at a concentration range of 202 nM-1.6 nM (2× serial dilution) followed by a 7 minute dissociation. Samples were randomly injected in triplicate with several buffer inject cycles interspersed for double referencing. To obtain more significant off-rate decay data, three additional 101 nM GCC-ECD-Fc injections and three additional buffer injections were performed with a 2 minute injection and a 4 hour dissociation time. A flow rate of 100 μL/min was used for all experiments and all surfaces were regenerated with a 20 second pulse of 10 mM Glycine-HCl (pH 2.0). All samples were prepared in the running buffer which was Hepes-buffered saline, 0.005% polysorbate 20, pH 7.4 (HBS-P) with 100 μg/mL of BSA added.

Step 4: All sensorgram (plot of surface plasmon resonance vs time) data were processed with Scrubber 2.0 software (BioLogic Software, Campbell, Australia) and globally fit to a 1:1 interaction model including a term for the mass transport constant $k_m$ using CLAMP™ software (Myszka and Morton *Trends Biochem. Sci.* 23:149-150 (1998)).

The 1:1 model provided a very good fit to the data as long as the mAb immobilization levels were kept low enough so that the $R_{max}$ resulting from the global analysis of the sensorgram data was at least below 12 RU for each surface. In most cases, one of the two Prep A 5F9 surfaces had an $R_{max}$ too low (below 2 RU) for reliable kinetic measurements. Data from two flow cells of GCC-ECD-Fc binding to Prep A 5F9 from the same CM4 chip were simultaneously fit whenever possible, however. When mAb surfaces were prepared resulting in a higher $R_{max}$ (>12 RU), sensorgrams clearly showed complex kinetics and thus a 1:1 model fit the data poorly. This isn't surprising due to the fact that GCC-ECD-Fc is a bivalent construct and a higher surface density of immobilized mAb most likely increases the probability that the GCC-ECD-Fc binds avidly to the surface. Replicates reported for this study include only those data that fit well to the 1:1 interaction model. The resulting $K_D$'s and rate constants of all replicates for Prep A 5F9 and the Prep B reference mAb are listed in Table 9 and Table 10, respectively.

TABLE 9

GCC-Fc binding to immobilized Prep A 5F9 mAb

| Replicate | $R_{max}$ (RU) | $k_a$ (M$^{-1}$s$^{-1}$) | $k_d$ (s$^{-1}$) | $K_D$ (pM) |
|---|---|---|---|---|
| A | 11 | 1.06 × 10$^5$ | 1.19 × 10$^{-5}$ | 112 |
| B | 8 | 1.20 × 10$^5$ | 1.10 × 10$^{-5}$ | 91.7 |
| C | 5 | 1.07 × 10$^5$ | 2.15 × 10$^{-5}$ | 201 |
| D | 9 | 1.22 × 10$^5$ | 1.11 × 10$^{-5}$ | 91.0 |
| E | 6.4 | 9.64 × 10$^4$ | 1.77 × 10$^{-5}$ | 184 |
| Avg. (95% Conf. Int.) | | 1.10 (0.13) × 10$^5$ | 1.46 (0.59) × 10$^{-5}$ | 136 (65) |

TABLE 10

GCC-Fc binding to immobilized Prep B 5F9 mAb

| Replicate | $R_{max}$ (RU) | $k_a$ (M$^{-1}$s$^{-1}$) | $k_d$ (s$^{-1}$) | $K_D$ (pM) |
|---|---|---|---|---|
| F | 9 | 9.68 × 10$^4$ | 7.64 × 10$^{-6}$ | 78.9 |
| G | 8 | 1.20 × 10$^5$ | 1.24 × 10$^{-5}$ | 103 |
| H | 7 | 9.09 × 10$^4$ | 9.57 × 10$^{-6}$ | 105 |
| I | 12 | 1.21 × 10$^5$ | 1.54 × 10$^{-5}$ | 127 |
| Avg. (95% Conf. Int.) | | 1.07 (0.25) × 10$^5$ | 1.13 (0.54) × 10$^{-5}$ | 103 (31) |

Conjugation of Toxins to Antibodies

Maytansines.

Mouse anti-human (MAH)-IgG-DM1, and anti-GCC-DM1 were generated according to a one-step process for the production of cytotoxic conjugates of maytansinoids as described in U.S. Pat. No. 6,441,163.

Briefly, maytansinoids were conjugated to antibodies using published procedures. DM1 was conjugated to antibodies using SMCC heterobifunctional crosslinker (succinimidyl-4-(N-maleimidomethyl)cyclohexane-1-carboxylate; Chari et al. *Cancer Research* 52:127-131 (1992). DM4 was conjugated to antibodies using SPDB heterobifunctional crosslinker (Widdison et al. *J. Med. Chem.* 49:4392-4408 (2006)). Conjugated antibody is separated from unreacted reaction by-products by gel filtration chromatography using a SEPHADEX™ G-25 column.

Auristatins.

Conjugation by auristatins can be performed using published procedures (e.g., Doronina et al., *Nature Biotech.*, 21: 778-784 (2003)). In general, auristatins are linked to cysteines of antibody chains. Linkage to cysteines is accomplished first by reduction of disulfide bonds in the antibody molecule. Control of the reduction process seeks to limit the reduction to some, but not necessarily all, interchain disulfide bonds. Consequently, auristatins are able to bind at the free cysteines. Quenching of the conjugation reaction is followed by removal of reaction by-products and buffer exchange to the desired formulation.

In brief, an anti-GCC antibody molecule at 7.6 mg/mL is pre-equilibrated at 37° C., and then a 15% volume of 500 mM sodium borate, pH 8.0 is added to raise the pH to 7.5-8.0. The solution also contains 1 mM DTPA. The antibody is partially reduced by adding 2.6 equivalents of tris(2-carboxyethyl)phosphine (TCEP) per mole of anti-GCC antibody molecule and stirring at 37° C. After 28 minutes, the solution of reduced anti-GCC antibody molecule is placed on ice, then treated immediately with 4.8-4.9 molar equivalents (relative to anti-GCC antibody molecule) of drug linker (e.g., mc-vc-MMAF or mc-vc-MMAE or mc-MMAF) as a 20.5 mM solution in DMSO. Additional DMSO is introduced to bring the mixture to 10% DMSO by volume. The reaction mixture is stirred on ice for ~90 minutes before treatment with a 5-fold molar excess of N-acetyl cysteine (relative to mc-vc-MMAF). The conjugate is isolated by tangential flow filtration, first being concentrated to ~10 mg/mL, then diafiltered with ~10 diavolumes of PBS. The resulting antibody drug conjugates had an average drug loading of about four drug-linker units per antibody. For convenience, in the following Examples and attached Figures, auristatin immunoconjugates are referred to in the following abbreviated format, irrespective of drug loading: "Ab-vc-MMAF" refers to an anti-GCC antibody molecule conjugated with mc-vc-MMAF; "Ab-vc-MMAE" refers to an anti-GCC antibody molecule conjugated with mc-vc-MMAE; and "Ab-mc-MMAF" refers to an anti-GCC antibody molecule conjugated with mc-MMAF Immunoconjugates comprising specific anti-GCC antibody molecules are referred to in the same format, e.g., 5F9-vc-MMAF, 5F9-vc-MMAE, and 5F9-mc-MMAF.

To prepare antibody drug conjugates with an average drug loading of about two drug-linker units per antibody, the protocol (above) is modified by reducing the amount of TCEP by 50%. The amount of drug linker is also reduced by 50%. The corresponding antibody drug conjugate is abbreviated as Ab-vc-MMAF(2).

Preparation of 5F9 vcMMAE

Using a method similar to the general method set forth above, the 5F9 mAb was conjugated to an auristatin derivative designated MMAE (Formula (XIII)) using a vc (Val-Cit) linker described herein to create the immunoconjugate designated 5F9 vcMMAE. The conjugation of the vc linker to MMAE (Seattle Genetics, Inc., Bothell, Wash.) was completed as previously described (see, e.g., US 2006/0074008).

Briefly, a 17.8 mg/mL solution of the 5F9 mAb in 100 mM acetate at pH 5.8 was adjusted to pH 8 with 0.3 M sodium phosphate dibasic, yielding a final mAb concentration of 11.3 mg/ml. Then, DTPA was added for a 1 mM final concentration in the reaction mixture. The mAb was then partially reduced by adding 2.28 molar equivalents of TCEP (relative to moles of mAb), and then stirred at 37° C. for 1.5 hours. The partially reduced mAb solution was then cooled to 4° C., and 4.4 molar equivalents of vcMMAE (relative to moles of antibody) were added as a 20.3 mM solution in DMSO. The mixture was stirred for 30 minutes at 22° C., then for 15 additional minutes following the addition of 5 molar equivalents of N-acetylcysteine (relative to moles of vcMMAE). Excess quenched vcMMAE and other reaction components were removed by ultrafiltration/diafiltration of the immunoconjugate with 10 diavolumes of PBS, pH 7.4. The resulting immunoconjugate was designated 5F9 vcM-MAE and has the following formula:

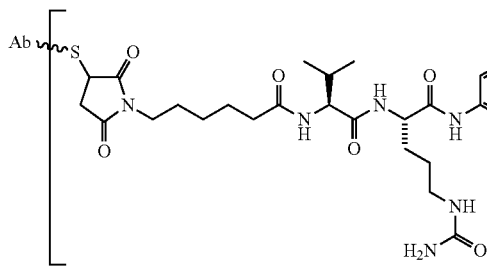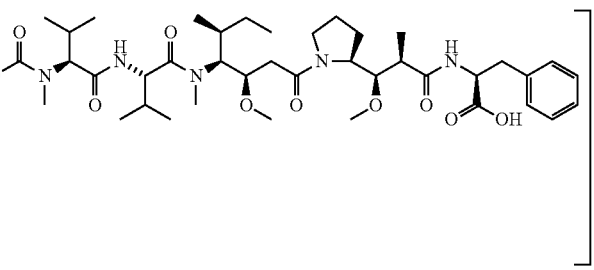

where Ab is the 5F9 mAb, and m is from 1 to 8. The average drug loading (m) was about 3.6.

Cytotoxicity Assays.

To measure each antibody's ability to bind, internalize and kill target expressing cells, cytotoxicity assays were performed. In this assay, cells were incubated with various concentrations of the unconjugated primary anti-GCC antibody and a fixed non-toxic concentration of DM1-conjugated anti-human Fc secondary antibody (indirect cytotoxicity) or with various concentrations of toxin conjugated anti-GCC mAb (direct cytotoxicity). Cell viability was measured by WST assay after 4 days incubation. The relative potency of human anti-GCC antibodies on 293-GCC #2 cells is shown in Table 8 and was determined using a DM1 conjugated mouse anti-human IgG mAb (MAH-IgG was purified from clone HP607 (CRL1753, ATCC). 5F9 and 229 are the most potent anti-GCC mAb with LD50's of 26 and 78 pM. Although not shown here, the error is generally within 20% of these averages, as measured by range of replicates or standard deviation of >2 replicates.

TABLE 11

Cytotoxicity assay results for anti-GCC antibodies on 293-GCC#2 cells

| Anti-GCC Ab | LD50 (pM) |
|---|---|
| 5F9 | 26 |
| 229 | 78 |
| 106 | 166 |
| 221 | 207 |
| 338 | 267 |
| 12 | 279 |
| 20 | 569 |
| 5H3 | 722 |
| 10D3 | 1596 |
| 8C2 | 2038 |
| 10C10 | 2443 |
| 1D2 | >3055 |
| 6H8 | >4818 |
| 393 | >5400 |
| 198 | >5400 |

Cell Surface Binding.

Binding of unconjugated 5F9 or 5F9 conjugated to auristatins, was evaluated by in indirect immunofluorescence assay using flow cytometry. $1 \times 10^6$ cells/well were plated in a V-bottom 96 well plate and incubated on ice for 1 hour with serial antibody dilutions of 1-0.001 µg/ml. Cells were washed twice with 3% FBS in ice cold PBS and incubated with 1:200 mouse anti-human PE IgG (Southern Biotech 2043-09) for 1 hour on ice. Cells were washed again and analyzed by flow cytometry on a BD FACS Canto II flow cytometer. Data was analyzed using FACS Canto II system software and mean fluorescence intensities were determined.

Epitope Mapping.

Multiple strategies were initiated to identify epitopes. Peptide array. 20-mer peptides, with 15 aa overlap were generated, covering the extracellular domain (ECD) into the transmembrane domain of GCC (aa 1-440). Peptides were synthesized and provided as arrays, immobilized on glass slides. Arrays were hybridized with each of the anti-GCC antibodies to determine if linear peptides were sufficient for binding. Abx-198 bound peptides 55 and 56, while 3G1, 8F1 and 10B8 antibodies bound peptides 55, 56 and 57. The sequence, ILVDLFNDQYLEDNVTAPDYMKNVLVLTLS (SEQ ID NO:225) is spanned by these peptides. A region of overlap among the peptides is LEDNVTAPDY (SEQ ID NO:314). Abx-012, Abx-338 and Abx-106 bound peptides 71 and 72. The sequence, FAHAFRNLTFEGYDGPVTLDDWGDV (SEQ ID NO:226), and the sequence RNLTFEGYDGPVTLD (SEQ ID NO:315) overlaps the two peptides.

Cell Surface Binding to GCC Truncation Mutants.

Truncation mutants of the GCC ECD were generated (FL mature peptide and 8 truncations (Δ1-32, Δ1-49, Δ1-94, Δ1-128, Δ1-177, Δ1-226, Δ1-279, Δ1-229 and Δ1-379), as FLAG tagged constructs (pFLAG-CMV-3), representing approximately 50 aa deletion increments. Constructs were expressed in 293 cells, followed by immunoprecipitation by the anti-GCC antibody molecule and Western blotting for the FLAG epitope in lysates of 293 cells transfected with the GCC ECD mutants. Antibody 5F9 binds cells with the A1-32 mutation, but not cells with the Δ1-49 mutation. The binding of 5F9 to GCC was lost when the protein is truncated between aa 33-50 suggesting that this region is involved in the recognition of 5F9 to its binding epitope on GCC. However, since the rat and mouse GCC sequences are identical to human GCC in this region, and 5F9 does not bind mouse or rat GCC, 5F9 antibody likely binds a conformational epitope formed by the presence of amino acids 33 to 50 of human GCC.

Example 2. Toxin-Linker Selection/ADC Characterization

In an antibody drug conjugate (ADC) strategy, the conjugation of highly potent toxins to antibodies, the cytotoxicity of the toxin can be directed to tumors in a target-specific manner, delivering the toxin to antigen expressing tumor cells without affecting antigen negative cells in normal tissues thus reducing systemic toxicity. Auristatin (analog of dolastatin 10) and maytansine class toxins were evaluated as ADCs with anti-GCC mAb. These toxins are all inhibitors of microtubule polymerization, acting as antimitotics. Tests in which cells were contacted with free toxins indicated that the cytotoxicity of free toxins did not distinguish between cells with GCC expression and control cells without GCC. These free toxins were potent against the 293-vector, 293-GCC #2 cells, in HT29-vector vs. HT29-GCC #5 cells as shown in Table 9.

TABLE 12

Cytotoxicity of free toxins

| Cell line | MMAE | | MMAF | | DM1 | | DM4 | |
|---|---|---|---|---|---|---|---|---|
| | LD50 | SD | LD50 | SD | LD50 | SD | LD50 | SD |
| 293 vector | 0.07 | 6 | 3.37 | 2.34 | 2.83 | 2.00 | 0.79 | 0.79 |
| 293 GCC#2 | 4 | 3 | 2.07 | 1.48 | 2.96 | 2.23 | 0.83 | 1.03 |
| HT29 | 4 | 1 | 5.21 | 1.91 | 2.69 | 1.09 | 0.57 | 0.27 |
| HT29 GCC#5 | 7 | 4 | 7.65 | 3.32 | 1.00 | 0.14 | 0.40 | 0.17 |

The chemistry by which the different toxins are conjugated to antibodies differs and affects linker stability. Linker stability affects the therapeutic window by impacting drug release in the blood or nontarget tissues vs. drug release at the tumor. The ideal ADC linker has high stability while in the blood, but efficient release upon target mediated cell entry.

Auristatins

Three auristatin-linker pairs were evaluated. To first evaluate these conjugates in vitro and then determine which toxin-linker for large scale in vivo studies, 5F9 was conjugated to vcMMAE, vcMMAF and mcMMAF (20 mgs per conjugate).

Auristatins are synthetic toxins related to the natural product dolastatin 10. MMAE and MMAF differ subtly, with the MMAF form having a carboxylic acid group in the R2 position, reducing cell permeability and potency as free toxin. MMAE is a Pgp drug pump substrate, while MMAF is not.

Auristatins are conjugated to interchain cysteines through a process of partial antibody reduction, reaction with a maleimido drug derivative, quenching with excess cysteine, concentration and buffer exchange into PBS. The auristatins can be attached with a cathepsin B sensitive dipeptide linker, which is cleaved upon cellular uptake, or with a noncleavable linker.

In the vcMonoMethylAuristatin linker, a valine citrulline dipeptide linkage is attached to the drug through a p-amino benzyl carbamate (PAB) group and to the antibody through a maleimido caproyl conjugation group. Upon internalization, the dipeptide linker is cleaved by the lysosomal protease cathepsin B, the PAB group self destructs, and free toxin is released. This linker was designed to maintain serum stability while maximizing intracellular drug release by cathepsin B.

Auristatins can also be linked to antibodies through noncleavable linkers such as MMAF directly attached to the maleimido conjugation group, with no peptidase sensitive linker. MC conjugated ADC's are also effective at target mediated cell kill.

The mechanism of drug release for noncleavable auristatin conjugates is thought to be through general antibody degradation in lysosomes. Through LC/MS studies it has been reported that Ab-mcMMAF conjugates release toxin in the form of a single cysteine-adduct.

Binding of Antibody Drug Conjugates

All of the 5F9 antibody drug conjugates bound to 293-GCC #2 cells equally well. Table 10 shows the mean fluorescence intensity of 5F9 conjugates at increasing concentrations 293-GCC #2 cells. Other studies determined that the 5F9-SPDB-DM4 conjugate bound 293-GCC #2 cells in a concentration-dependent manner, whereas the 209-SPDB-DM4 antibody did not bind.

TABLE 13

Chart of MFIs from binding assay of 5F9 and 5F9 conjugates in 293 GCC #2 cells:

| | μg/ml of 5F9 or 5F9 conjugate | | | | | |
|---|---|---|---|---|---|---|
| | 0.001 | 0.004 | 0.016 | 0.063 | 0.25 | 1 |
| 5F9 | 500 | 937 | 2465 | 6615 | 7816 | 8026 |
| vcMMAE | 445 | 696 | 1787 | 4854 | 7296 | 7416 |
| vcMMAF | 440 | 707 | 1502 | 4830 | 7563 | 7779 |
| mcMMAF | 483 | 776 | 2106 | 5353 | 7398 | 7585 |

The 5F9-auristatin toxin conjugates were tested in direct cytotoxicity assays of a variety of cells which been transfected with GCC nucleic acid and selected for expression of GCC. A survey of the level of surface expression of GCC found that 293 GCC #2 cells express high amounts of GCC; HT 29 #2 and CT 26 #2.5 cells express GCC at intermediate to low levels; CT 26 #32 cells express GCC at high levels; and HT 29 GCC #5 and HT 29 GCC #18 express low amounts of GCC. Table 11 shows a compilation of multiple studies yielding cytotoxicity data for the three auristatin conjugates in cells expressing target, or in wild-type cells or vector control cells. Target enhanced killing is observed in all cases of 5F9-conjugated toxins on 293 GCC #2 cells, with a greatly increased window when using MMAF vs. MMAE. Both the cleavable and noncleavable forms of MMAF were similarly potent. As a negative control, antibody drug conjugates were also made with sc209 antibody, which is a human IgG1 monoclonal antibody raised against an unrelated target, with no reactivity to GCC. Direct cytotoxicity assays with 209 ADCs vs. 5F9 vcMMAF ADC showed target enhanced cell kill in the 293 cell model and the HT29 cell model. A comparison of 5F9-conjugated toxin activity among the cell lines indicates that the level of cytotoxicity has some correlation with the amount of GCC expressed by the cells. These data suggest that at least some cell lines expressing the most GCC were more susceptible to the cytotoxic activity of the conjugate than were cells expressing lower amounts of GCC. See Example 1 for relative GCC numbers per cell. Another factor in differences of cytotoxicity levels may be differences in internalization or intracellular processing of the conjugates, which may vary among wild type cell lines.

TABLE 14

Cytotoxicity of anti-GCC auristatin ADCs.

| Cell line | LD 50 (nM) of 5F9 conjugates | | | LD50 (nM) of 209 conjugates |
|---|---|---|---|---|
| | vcMMAE | vcMMAF | mcMMAF | |
| 293 Vector | 128 | >10 | >10 | |
| 293 GCC # 2 | 0.37 | 0.001 | 0.002 | |
| 293 Vector | 1.8 | >10 | >10 | |
| 293 GCC # 2 | 0.13 | 0.005 | 0.007 | |
| 293 Vector | | >10 | | >10 |
| 293 GCC # 2 | | 0.0004 | | >10 |
| HT 29 WT | 84 | >10 | >10 | |
| HT 29 GCC #2 | 24.1 | 0.127 | 3.1 | |
| CT 26 WT | >500 | >10 | >10 | |
| CT 26 GCC #2.5 | >500 | >10 | >10 | |
| CT 26 GCC #32 | 267 | 0.004 | 0.064 | |
| HT 29 vector | 520.6 | >10,000 | >10,000 | |
| HT 29 GCC #5 | 653.5 | 563.2 | >10,000 | |
| HT 29 GCC #18 | 554.6 | >10,000 | >10,000 | |
| HT29 | 0.93 | >10 | >10 | |
| HT29 GCC#5 | 0.59 | 0.32 | >10 | |
| HT29 | | >10 | | >10 |
| HT29 GCC#5 | | 0.035 | | >10 |

If these potencies translate in vivo, with equal efficacy between mc and vcMMAF, the higher predicted MTD for mcMMAF would suggest a larger therapeutic window for this conjugate.

Maytansines

The 5F9-maytansine ADCs showed potent target enhanced killing in the 293-GCC #2 cells (Table 12). Interestingly, the 5F9-maytansine conjugates both showed target enhanced killing in the 293 model, however no target enhanced killing was observed in the HT29 model, raising concern about the utility of this model for in vivo evaluation of the maytansine conjugates. Again, the reasons for this difference are not readily explicable, but may be attributed to different receptor densities and/or differences in the internalization or processing of the conjugates within cells. As a negative control, antibody drug conjugates were also made with sc209 antibody, which is a human IgG1 monoclonal antibody to an unrelated target, with no reactivity to GCC. Direct cytotoxicity assays with 209 ADCs vs. 5F9 ADCs show target enhanced cell kill in the 293 cell model with all 5F9 conjugates. In the HT29 cell model, 5F9-DMx conjugates and 209-DMx conjugates kill equally well, indicating a non-target specific mechanism of killing in those cells.

Example 3: In Vivo Evaluation

Tumor Models:

In vivo cytotoxicity of 5F9 ADCs were evaluated in mouse xenograft models. The initial in vivo work was done with the HT29-GCC #5 and #18 cell lines. The 293-GCC #2 cell line also was tested for in vivo growth and was developed as a serially transplantable trocar model.

To address the question of whether the GCC expression level in the xenograft model was relevant to the level of GCC expression in patients with metastatic colon cancer, GCC expression levels were compared by IHC analyses of xenograft tissue, human primary colon tumors and metastases. A panel of fresh frozen cell lines and tissues were utilized for GCC quantitation by rIHC with a mouse mAb to GCC 3G1. For IHC quantitation, scoring was done using a semi-quantitative 0-3 score system. If tumor model GCC levels≤clinical GCC levels, modeling will likely be accurate or overestimate the exposure needed clinically. If tumor model GCC levels>clinical GCC levels, modeling may underestimate the exposure needed clinically.

While there was some variability in the expression of GCC in metastatic samples, expression by the HT29-GCC #5 and #18 cells was in the range of many of the metastatic samples. By IHC, the staining of GCC on the HT29-GCC #5 and #18 cells was equivalent or lower than on the metastatic

TABLE 15

Cytotoxicity of anti-GCC maytansine ADCs

| Cell line | LD50 (nM) | | | |
|---|---|---|---|---|
| | 5F9-SMCC-DM1 | 209-SMCC-DM1 | 5F9-SPDB-DM4 | 209-SPDB-DM4 |
| 293 vector | 25.3 | | 10.4 | |
| 293 GCC#2 | <0.004 | | <0.004 | |
| 293 vector | 32 | 11 | 13 | 7.4 |
| 293 GCC#2 | <0.000004 | 6.7 | <0.000004 | 4.8 |
| HT29 | 22.4 | | 7.7 | |
| HT29 GCC#5 | 20.8 | | 9.1 | |
| HT29 | 22 | 12 | 4.8 | 2.1 |
| HT29 GCC#5 | 30 | 22 | 5.8 | 4.2 | cells. This data suggests that our tumor models express GCC at levels comparable to the levels found in clinical samples of metCRC.

Table 16 represents the scintillation counts for various tissues harvested at the 192 hour timepoint with averages for three animals represented. 5F9 preferentially accumulated in HT29-GCC #5 tumors vs. HT29-vector tumors, while 209 did not show much differential accumulation. This result provided support that a 5F9 antibody drug conjugates could be expected to accumulate in GCC expressing tumors. In all other tissues evaluated, there was little difference in the levels of 5F9 vs. mAb 209 antibody accumulation.

In Vivo Distribution of Radiolabeled 5F9 in HT29-GCC #5 & HT29-Vector Tumor-Bearing Mice A radioimaging study in tumor bearing mice was performed to evaluate tumor targeting and in vivo biodistribution of the anti-GCC antibody 5F9 and a negative control antibody sc209 (human IgG1 monoclonal antibody targeting an unrelated cell surface target). The antibodies were radiolabeled with $^{111}$In using DTPA as a bifunctional chelator. The in vivo behavior, including tumor targeting and biodistribution in normal tissues over time, was investigated with a murine dual-tumor model with both GCC(−) and GCC(+) tumors. In vivo images (SPECT/CT) were acquired, and tissue radioactivity counting was used to supplement the spatial resolution.

Subcutaneous tumors were grown in nude mice, with HT29-vector tumors on the right and HT29-GCC #5 tumors on the left. Antibodies were dosed at 0.3 mCi=15 μg per animal. There were three animals per group, and groups were harvested at 1 h, 24 h, 48 h, 72 h, 120 h and 192 h.

A survey of tissues from animals in the 192 h group indicated that both 5F9 and 209 accumulated to a similar degree in most normal tissues (e.g., blood, heart, stomach, small intestine, large intestine, muscle and skin) and in HT29-vector control tumors. Ab 209 accumulated to slightly higher levels than 5F9 in liver and 5F9 accumulated to slightly higher levels than 209 in lungs, spleen and kidneys. In the HT29-GCC #5 tumors, 5F9 preferentially accumulated at levels more than two-fold higher than the 209 levels. This result provided support that a 5F9 antibody drug conjugates could be expected to accumulate in GCC expressing tumors.

To understand the kinetics of antibody accumulation in tumors, tumor data for each antibody was obtained for all time points throughout the study. The only tissue that showed accumulation is the 5F9 antibody in the GCC expressing tumor. The radioactivity level in all other tissues remained relatively flat, with little difference between the 5F9 levels and 209 levels. 5F9 preferentially accumulated in HT29-GCC #5 tumors, while 209 did not show any accumulation. This result provided support that a 5F9 antibody drug conjugate could be expected to accumulate in GCC expressing tumors.

TABLE 16

Accumulation of $^{111}$ In-labeled GCC specific mAb but not control mAb to tumors expressing GCC.

|  | Mean % ID 5F9 | Mean % ID ctr IgG |
|---|---|---|
| 1 hr | 2.816 +/− 0.133 | 2.494 +/− 0.167 |
| 24 hr | 3.057 +/− 0.107 | 3.010 +/− 0.630 |
| 72 hr | 4.485 +/− 1.029 | 3.564 +/− 0.152 |
| 120 hr | 5.162 +/− 1.012 | 3.412 +/− 0.048 |
| 192 hr | 6.550 +/− 1.015 | 2.782 +/− 0.085 |

Accumulation of radiolabeled 5F9 in GCC expressing tumors over 7 days supported a once weekly dosing schedule.

Pilot Efficacy Studies in HT29-GCC #5 s.c. Tumors

Studies were performed to determine efficacious conjugates and dosage regimens in mice bearing HT29-GCC #5 tumors. Mice were dosed with single or multiple doses. These studies determined that there was toxicity at too frequent dosing at higher levels of toxin conjugate (e.g., 150 μg/kg 5F9vcMMAF on a q3d×5 schedule). Another study determined that q14d×5 schedule was too infrequent in this model to allow some toxin conjugates to show significant efficacy vs. controls. Additionally, a PD study with maytansinoid-antibody conjugates in this model demonstrated dose-dependent phosphohistone accumulation only with the DM4 toxin, not the DM1 toxin. Another study in this model showed some tumor growth inhibition by the non-specific 209-toxin conjugate. These results suggested that other in vivo models needed to be evaluated.

PK/PD Study with 5F9 ADCs in Mice Carrying 293-GCC #2 Tumors.

An alternative tumor model used 293-GCC #2 cells. A PD study for 5F9 ADCs in 293-GCC #2 tumor bearing mice was performed. Mice were dosed with single doses of 5F9vcMMAF at 75 ug/kg or 150 ug/kg and serum was taken at timepoints from 1 hr through 4 days for PD analysis of phosphohistone H3 to test antimitotic effects of the toxin on tumor cells. Phospho-histone H3 was detected by antibody (Upstate Biotechnology, now Millipore, Billerica, Mass.) staining of paraffin embedded sections of tumors. The data in Table 17 shows that each of the ADCs caused a significant increase in the pH3 positive cell population in the tumors indicating that each of them at both 75 and 150 μg/kg toxin dose equivalents was able to reach the tumors and have the desired anti-mitotic effect on the tumor cells.

TABLE 17

The PD response as assessed by arrest of cells in mitosis (% pH 3 positive tumor cells) following a single iv dose of 5F9 ADCs.

|  |  | Average % Tumor cells pH 3 positive | SD |
|---|---|---|---|
| Vehicle control |  | 2.556801 | 2.37707 |
| 5F9-vcMMAE 75 μg/kg | 1 hr | 4.525187 | 0.178882 |
|  | 4 hr | 2.551616 | 1.688255 |
|  | 8 hr | 4.243988 | 0.352938 |
|  | 24 hr | 9.8199 | 4.82057 |
|  | 48 hr | 8.692061 | 4.756786 |
|  | 96 hr | 8.628345 | 1.065456 |
| 5F9-vcMMAE 150 μg/kg | 1 hr | 3.334943 | 1.351667 |
|  | 4 hr | 2.78543 | 1.690216 |
|  | 8 hr | 4.575611 | 1.130484 |
|  | 24 hr | 13.78776 | 3.343155 |
|  | 48 hr | 14.26067 | 5.448921 |
|  | 96 hr | 14.67942 | 1.827724 |
| 5F9-vcMMAF 75 μg/kg | 1 hr | 4.235245 | 0.617585 |
|  | 4 hr | 4.18364 | 0.846752 |
|  | 8 hr | 4.930098 | 0.54746 |
|  | 24 hr | 20.22484 | 2.453935 |
|  | 48 hr | 9.920771 | 3.788795 |
|  | 96 hr | 10.38187 | 1.896461 |
| 5F9-vcMMAF 150 μg/kg | 1 hr | 3.465674 | 1.341187 |
|  | 4 hr | 4.416646 | 0.807636 |
|  | 8 hr | 8.594385 | 4.005021 |
|  | 24 hr | 21.53718 | 7.25212 |
|  | 48 hr | 15.15814 | 4.28407 |
|  | 96 hr | 11.12288 | 2.150476 |
| 5F9-mcMMAF 75 μg/kg | 1 hr | 5.365582 | 1.14198 |
|  | 4 hr | 4.044478 | 0.992449 |
|  | 8 hr | 8.228597 | 3.098222 |

TABLE 17-continued

The PD response as assessed by arrest of cells in mitosis (% pH 3 positive tumor cells) following a single iv dose of 5F9 ADCs.

|  |  | Average % Tumor cells pH 3 positive | SD |
|---|---|---|---|
|  | 24 hr | 14.10734 | 1.611093 |
|  | 48 hr | 19.37223 | 8.146504 |
|  | 96 hr | 7.749388 | 1.180759 |
| 5F9-mcMMAF 150 µg/kg | 1 hr | 3.212482 | 0.509604 |
|  | 4 hr | 4.722554 | 1.577531 |
|  | 8 hr | 9.105349 | 5.963128 |
|  | 24 hr | 27.51416 | 10.96057 |
|  | 48 hr | 13.34043 | 3.414961 |
|  | 96 hr | 15.60917 | 3.386154 |

Similar studies measured the phosphohistone levels in 293-GCC #2 tumor-bearing mice treated with 5F9vcMMAF, 5F9-SPDB-DM4 and 5F9-SMCC-DM1. Mice were dosed with single doses at 150 ug/kg and serum was taken at timepoints from 1 hr through 21 days for PK analysis of both total antibody and toxin-conjugated antibody. The percentage of phosphohistone H3 positive cells in 293-GCC #2 tumors increased in response to all three ADCS: 5F9vcMMAF, 5F9-SMCC-DM1 and 5F9-SPDB-DM4. Maximal phosphohistone H3 levels were 3- to 5-fold increased over baseline, with peaks at 24 hours post-injection.

Efficacy Study with 5F9vcMMAF and 5F9-DMx in 293-GCC #2 s.c. Tumors

5F9-SPDB-DM4, 5F9-SMCC-DM1 and 5F9vcMMAF were tested for efficacy in the 293-GCC #2 tumor model at two doses (75 µg/kg and 150 µg/kg toxin), on a q14dx5 schedule. Specifically, this study included vehicle-treated control, Sc209-DM1 (150 µg/kg DM1 eq), Sc209-DM4 (150 µg/kg DM4 eq), Sc209-vcMMAF (150 µg/kg MMAF eq), 5F9-DM1 (150 µg/kg DM1 eq), 5F9-DM1 (75 µg/kg DM1 eq), 5F9-DM4 (150 µg/kg DM4 eg), 5F9-DM4 (75 µg/kg DM4 eq), 5F9-vcMMAF (150 µg/kg MMAF eq), and 5F9-vcMMAF (75 µg/kg MMAF eq). Taconic females mice bearing 293-GCC #2 cells (10 mice per group) were used.

FIG. 1 depicts tumor growth in 293-GCC #2 bearing SCID mice treated with 5F9vc-MMAF, -DM1, and -DM4 on a q14d schedule. Dose-dependent efficacy was observed with 5F9-SPDB-DM4 in the 293-GCC #2 model, while the 209-SPDB-DM4 control had no effect. 5F9-SMCC-DM1 was also efficacious, however less so than 5F9-SPDB-DM4 at 150 ug/kg. 5F9vcMMAF (75 ug/kg and 150 ug/kg) was the most efficacious, however 209vcMMAF also had some activity. Therefore at these doses and schedules, 5F9-SPDB-DM4 had the greatest efficacious differential from its control conjugate.

Efficacy Study with 5F9vcMMAF and 5F9-DMx in 293-GCC #2 s.c. Tumors

5F9-SPDB-DM4 and 5F9-SMCC-DM1 were tested for efficacy in the 293-GCC #2 tumor model at two doses (75 ug/kg and 150 ug/kg toxin) on a q7dx5 schedule. Specifically, this study included vehicle-treated control, 5F9 alone (15 mg/kg), DM1 (300 µg/kg), DM4 (300 µg/kg), Sc209-DM1 (150 µg/kg DM1 eq), Sc209-DM4 (150 µg/kg DM4 eq), Sc209-vcMMAF (150 µg/kg MMAF eq), 5F9-DM1 (150 µg/kg DM1 eq), 5F9-DM1 (75 µg/kg DM1 eq), 5F9-DM4 (150 µg/kg DM4 eq), and 5F9-DM4 (75 µg/kg DM4 eq). Taconic females mice bearing 293-GCC #2 cells (10 mice per group) were used.

Efficacy Study with Auristatin Conjugates in 293 GCC #2 Tumors

293 GCC #2 tumor-bearing SCID mice were treated with 5F9 conjugates with vc MMAE, vcMMAF or mcMMAF at three doses in comparison with 209 conjugates of these toxins or with free toxins or vehicle control. Doses were administered iv on a q7dx4 schedule. Tumors were harvested at days 3, 7, 10, 13 and 17. The tumors in mice treated with control reagents demonstrated a continual increase in volume. Tumors treated with 5F9 auristatin conjugates showed dose- and time-dependent inhibition of this tumor growth. Table 18 provides a summary of the results (TGI=tumor growth inhibition, T/C=treatment/control, TGD=tumor growth delay, CR/PR=complete response/partial response; p value=measure to judge statistical significance, NS=not significant).

TABLE 18

Analysis of Auristatin ADCs in 293 GCC#2 tumor-bearing mice.

| Groups | TGI | T/C | TGD | CR/PR | P value |
|---|---|---|---|---|---|
| 209-vcMMAE 300 µg/kg | 24.5 | 0.76 | 0.9 | 0 | 0.38 > 0.05 NS |
| 209-vcMMAF 150 µg/kg | 29.4 | 0.71 | 1.4 | 0 | 0.27 > 0.05 NS |
| 209-mcMMAE 150 µg/kg | 36.5 | 0.63 | 1.4 | 0 | 0.15 > 0.05 NS |
| Free MMAE 300 µg/kg | 35.6 | 0.64 | 2 | 0 | 0.18 > 0.05 NS |
| Free mcMMAF 150 µg/kg | −3.4 | 1.03 | −1.3 | 0 | 0.73 > 0.05 NS |
| 5F9-vcMMAE 300 µg/kg | 96.9 | 0.03 |  | 9/10 PR | <0.001 |
| 5F9-vcMMAE 150 µg/kg | 83.5 | 0.17 |  | 2/10 PR | <0.01 |
| 5F9-vcMMAF 150 µg/kg | 97 | 0.03 |  | 9/10 PR | <0.001 |
| 5F9-mcMMAF 150 µg/kg | 97 | 0.03 |  | 9/10 PR | <0.001 |
| 5F9-vcMMAE 75 µg/kg | 54.5 | 0.45 | 4.4 |  | 0.01 < p < 0.05 |
| 5F9-vcMMAF 75 µg/kg | 88.5 | 0.12 |  | 6/10 PR | <0.001 |
| 5F9-mcMMAF 75 µg/kg | 87.5 | 0.13 |  | 7/10 PR | =0.001 |
| 5F9-vcMMAF 37.5 µg/kg | 65.2 | 0.35 | 7.1 |  | =0.01 |
| 5F9-mcMMAF 37.5 µg/kg | 63.6 | 0.36 | 5.8 |  | =0.01 |

All three of these ADCs were efficacious in the 293 GCC #2 model on a q7d schedule. 5F9-vcMMAF and 5F9-mcMMAF are more potent than 5F9-vcMMAE, which correlates with in vivo PD (pHisH3) and in vitro cytotoxicity data.

Efficacy Study with 5F9vcMMAF and 5F9-DMx in T84 s.c. Tumors

5F9-SPDB-DM4 and 5F9-SMCC-DM1 were tested for efficacy in the T84 tumor model at two doses (75 ug/kg and 150 ug/kg toxin) on a q7dx5 schedule. Specifically, this study included vehicle-treated control, 5F9 alone (15 mg/kg), DM1 (300 µg/kg), DM4 (300 µg/kg), Sc209-DM1 (150 µg/kg DM1 eq), Sc209-DM4 (150 µg/kg DM4 eq), Sc209-vcMMAF (150 µg/kg MMAF eq), 5F9-DM1 (150 µg/kg DM1 eq), 5F9-DM1 (75 µg/kg DM1 eq), 5F9-DM4 (150 µg/kg DM4 eq), and 5F9-DM4 (75 µg/kg DM4 eq). Taconic females mice bearing T84 cells (10 mice per group) were used.

Immunohistochemistry

Detection and measurement of relative amounts of GCC in tissues such as biopsies and xenografts can be performed by immunohistochemistry. Frozen tissue sections are fixed in a 1:1 solution of acetone and methanol for 20 min at room temperature. Slides are washed in 1×PBS for 5 minutes. Slides are processed with an automatic staining device, such as Ventana Discovery XT automated stainer (Ventana Medical Systems, Tucson, Ariz.) using manufacturers suggested reaction buffer. Anti-GCC antibodies are diluted to 5 µg/ml in 5% goat serum. For human anti-GCC antibodies, e.g., 5F9, detecting secondary antibody is a 1:500 solution of goat anti-human biotinylated antibody in Dako Protein block (Dako, Carpinteria, Calif.). After autostainer process the antibody reaction, the slides are removed from the autostainer, rinsed in reaction buffer, dehydrated through standard series until xylene and given coverslips with a xylene-based mounting media.

Efficacy Study of ADCs in a Primary Tumor Model

Models of primary colorectal carcinoma and gastric cancer are developed as subcutaneous tumors in mice. 5F9-vcMMAE and 5F9-mcMMAF ADCs are tested in PHTX-11c primary tumor-bearing mice. Doses are administered iv on a q7d×4 schedule. Conjugates of toxins with 209 are administered to control mice.

Antitumor Activity of ADCs in a Primary Tumor Model

Two similar studies were conducted to determine the in vivo antitumor activity of 5F9-vcMMAE and to compare the antitumor activity of 5F9-vcMMAE to free toxin MMAE and to non-immune vcMMAE antibody toxin conjugate (209-vcMMAE) in PHTX-9c primary human colon tumor xenograft mice at various doses and dosing schedules and to determine the re-growth kinetics following treatment. Female CB-17 SCID mice (eight weeks old) were inoculated subcutaneously (SC) into the flank with PHTX-9c tumor fragments (2 mm×2 mm). Tumor growth was monitored twice per week using vernier calipers and the mean tumor volume was calculated using the formula (0.5×[length× width$^2$]). When the mean tumor volume reached approximately 150 mm$^3$ (Study A) or 160 mm$^3$ (Study B), animals were randomized into treatment groups (n=10/group for Study A and n=9/group for Study B).

Mice were treated (Study A) on a once weekly (QW) dosing schedule (3 doses) with 0.938, 1.875, 3.75, or 7.5 mg/kg 5F9-vcMMAE intravenously (IV) for 20 days or controls, which included vehicle (0.9% saline), 0.075 or 0.15 mg/kg MMAE IV on a QW schedule, or 1.875 or 3.75 mg/kg 209-vcMMAE IV on QW dosing schedules for 20 Days. In the second study (Study B), mice were treated with 0.938, 1.875, 3.75, 7.5, or 10.0 mg/kg 5F9-vcMMAE IV on a QW schedule (3 doses) or 3.75 mg/kg IV on a twice weekly (BIW) schedule (6 doses), or controls including vehicle, 7.5 or 10 mg/kg 209-vcMMAE, or 0.135 or 0.18 mg/kg MMAE administered IV on a QW schedule for 20 days. Doses were administered on Days 1, 8, and 15 for the QW schedule and Days 1, 4, 8, 11, 15, and 18 for the BIW schedule. The dose of free MMAE was calculated to match the amount of MMAE in the immunoconjugate doses by the following rationale: The equivalent dose of MMAE is 1.8% of the MLN0264 dose. The equivalent dose of linker+ MMAE is 4% of the 5F9-vcMMAE dose. These calculations are based on a mean 3.9 MMAE molecules per antibody and a free antibody molecular weight of 150 kD. Actual antibody molecular weight will vary slightly due to degree of glycosylation.

Tumor volume and body weight were measured twice weekly and were continued beyond the treatment period to measure regrwoth kinetics, as evidenced by tumor growth delay (TGD). Tumor volume measurements were continued until tumor volume reached 10% of the body weight in a single mouse within a treatment group, at which time the group was terminated. The percentage of tumor growth inhibition (TGI) ([mean tumor volume of the control group−mean tumor volume of a treated group]/mean tumor volume of the control group; a T/C ratio) was determined on Day 20. The T/C ratios across a treatment group were compared to the T/C ratios of the control group using a two-tailed Welch's t-test. Because the entire group was terminated if one tumor reached the size limit (approx. 1000 mm$^3$), TGD could not be calculated for groups where the average regrowth was slow.

The differences in the tumor growth trends over time between pairs of treatment groups were assessed using linear mixed effects regression models. These models account for the fact that each animal was measured at multiple time points. A separate model was fit for each comparison, and the areas under the curve (AUC) for each treatment group were calculated using the predicted values from the model. The percent decrease in AUC (dAUC) relative to the reference group was then calculated. A statistically significant P value ($<0.05$) suggests that the trends over time for the two treatment groups were different. Results are summarized in Tables 19 and 20, below.

Antitumor activity was observed in all 5F9-vcMMAE-treated groups in both studies and the effect was shown to be dose-dependent. The results of the two studies were comparable. In mice treated with 5F9-vcMMAE at 0.938 mg/kg, IV on a QW schedule, TGI was 20.7-21.4%, p value was $<0.05$ compared with vehicle group. In the 1.875 mg/kg treated group administered IV, on a QW schedule TGI was 41.3-44.7%, p value was $<0.001$. In 3.75 mg/kg treated group administered IV, on a QW schedule TGI was 65.3-65.7% ($p<0.001$) compared with vehicle group. 5F9-vcMMAE administered at 7.5 mg/kg IV QW yielded a TGI of 84.1-84.3% ($p<0.001$) and 10 mg/kg IV QW (Study B only) yielded a TGI of 91.2% ($p<0.001$). When 3.75 mg/kg was administered IV on a BIW schedule (S), significant inhibition was observed with a TGI of 84.9% ($p<0.001$).

Moderate antitumor activity was observed at the higher doses of 209-vcMMAE of 7.5 and 10.0 mg/kg with TGI of 35.7 and 45.4%, respectively ($p<0.001$) but low doses of 209-vcMMAE (1.875 and 3.75 mg/kg) exhibited no inhibition ($p>0.05$). The antitumor activity observed by the high 209-vcMMAE is likely due to nonspecific activity by the MMAE portion of the immunoconjugate.

Administration of free toxin MMAE yielded mixed results: 0.075, 0.135, and 0.15 mg/kg administered IV QW yielded no tumor growth inhibition ($p>0.05$) but administration of 0.18 mg/kg IV QW resulted in TGI of 50.4% ($p<0.001$).

The greatest maximum body weight loss observed during treatment period was 2.3% on day 7 in the free toxin 0.18 mg/kg MMAE group of Study B and the 0.938 mg/kg 5F9-vcMMAE group of the same study. This indicates the drug was well-tolerated.

Tumor volume measurements were continued beyond the treatment period until tumor volume reached 10% of the body weight in a single mouse within a treatment group and then the treatment group was terminated. In these studies, tumor re-growth appeared to be dose-dependent.

TABLE 19

Study A results of treatment of primary human colon tumor Xenograft in SCID mice.

| Treatment | Dose (mg/kg) | Method of Administration/ frequency | TGI | BW change (mean maximum percent) | TGD (days)/(or days until first tumor > 1000 mm³) |
|---|---|---|---|---|---|
| Vehicle | 0 | IV QW × 3 doses | N/A | −0.2 | 0 |
| 209-vcMMAE | 1.875 | IV QW × 3 doses | −2.0 (p > 0.05) | 8.3 | 0.6 |
| 209-vcMMAE | 3.75 | IV QW × 3 doses | 4.5 (p > 0.05) | 6.9 | 0.4 |
| MMAE | 0.075 | IV QW × 3 doses | 5.0 (p > 0.05) | 8.3 | 1.0 |
| MMAE | 0.15 | IV QW × 3 doses | 11.1 (p > 0.05) | 10.8 | 2.0 |
| 5F9-vcMMAE | 0.938 | IV QW × 3 doses | 21.4 (p > 0.05) | 9.0 | 3.3 |
| 5F9-vcMMAE | 1.875 | IV QW × 3 doses | 44.7 (p > 0.001) | 10.6 | 8.2 |
| 5F9-vcMMAE | 3.75 | IV QW × 3 doses | 65.3 (p > 0.001) | 9.0 | 17.8 |
| 5F9-vcMMAE | 7.5 | IV QW × 3 doses | 84.1 (p > 0.001) | 7.5 | (>58 days first tumor) |

TABLE 20

Study B results of treatment of primary human colon tumor Xenograft in SCID mice.

| Treatment | Dose (mg/kg) | Method of Administration/ frequency | TGI | BW change (mean maximum percent) | TGD (days)/(or days until first tumor > 1000 mm³) |
|---|---|---|---|---|---|
| Vehicle | 0 | IV QW × 3 doses | N/A | −1.8 | 0 |
| 209-vcMMAE | 7.5 | IV QW × 3 doses | 35.7 (p > 0.001) | 4.2 | 4.2 |
| 209-vcMMAE | 10.0 | IV QW × 3 doses | 45.4 (p > 0.001) | 2.6 | 11.3 |
| MMAE | 0.135 | IV QW × 3 doses | 2.2 (p > 0.05) | 9.3 | 0.2 |
| MMAE | 0.18 | IV QW × 3 doses | 50.4 (p > 0.001) | −2.3 | 8.6 |
| 5F9-vcMMAE | 0.938 | IV QW × 3 doses | 20.7 (p > 0.001) | −2.3 | 3.8 |
| 5F9-vcMMAE | 1.875 | IV QW × 3 doses | 41.3 (p > 0.001) | 5.6 | 6.6 |
| 5F9-vcMMAE | 3.75 | IV QW × 3 doses | 65.7 (p > 0.001) | −2.2 | 16 |
| 5F9-vcMMAE | 3.75 | IV BIW × 6 doses | 84.9 (p > 0.001) | −1.8 | 31.9 |
| 5F9-vcMMAE | 7.5 | IV QW × 3 doses | 84.3 (p > 0.001) | 6.5 | (>47 days first tumor) |
| 5F9-vcMMAE | 10.0 | IV QW × 3 doses | 91.2 (p > 0.001) | 7.2 | (>56 days first tumor) |

Pilot Efficacy Study with Naked 5F9 Anti hGCC Antibody in CT26 hGCC/Luc #32 Disseminated Model (Balb/c Mice)

This model tests the ability of naked antibodies to bind to GCC-expressing tumor cells in the circulation and prevent establishment of new tumors. Female balb/c mice were inoculated by i.v. with CT26 hGCC/luc #32 cells at $1 \times 10^5$/mouse and $5 \times 10^5$/mouse. Vehicle 0.9% NaCl and non-specific antibody (naked 209) were administered to control groups for comparison to administration of naked 5F9. Both antibodies were engineered (in the pLKTOK58 vector) to have the IgG1 isotype, so their Fc regions could elicit an antibody-dependent cell-mediated cytotoxic response after binding to cell surface antigens (i.e., GCC for 5F9 and an unrelated target for 209). Dosing was started one day before inoculation by i.v, with a dosing schedule of once/week i.v×4 (q7d×4). Tumor growth was monitored by Xenogen imaging system twice a week. Body weight and survival were monitored twice a week as well. Lung weight and images including MRI images were taken at the end of this study.

Figure 2:
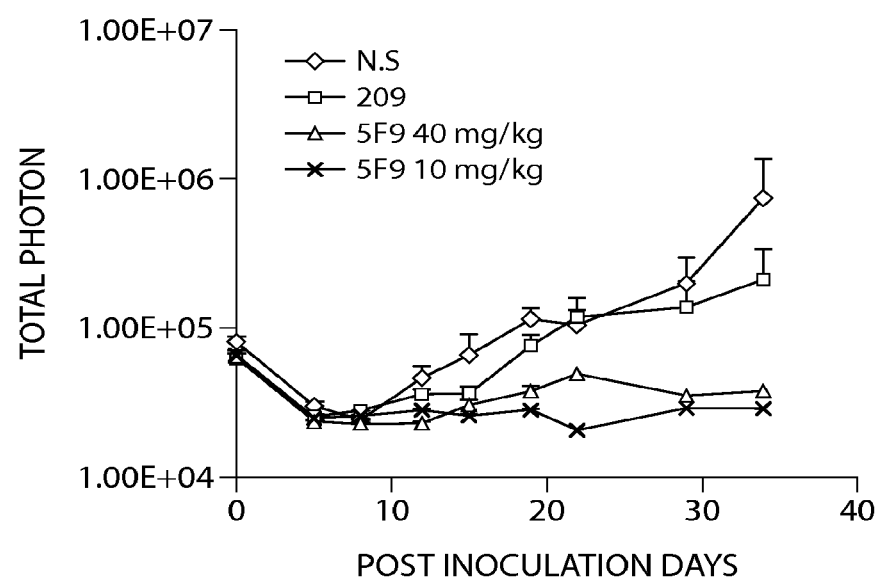
FIG. 2 depicts lung weight of mice treated with 0.9% NaCl; 209 antibody at 40 mg/kg; or 5F9 antibody at 10 or 40 mg/kg on day 41 p.i.

As shown in FIG. 2, both 5F9 groups (40 mg/kg and 10 mg/kg; $1 \times 10^5$/mouse) show efficacy (on day 34p.i: T/C (treatment/control) is 0.04 to 0.05). T/C for the 5F9 group is 0.18 to 0.14 on day 34p.i compared to the 209 group. T/C for the 209 40 mg/kg group is 0.64 compared to 0.9% NaCl (Normal Saline) group. No benefit was seen with 5F9 in $5 \times 10^5$ groups.

Figure 3:
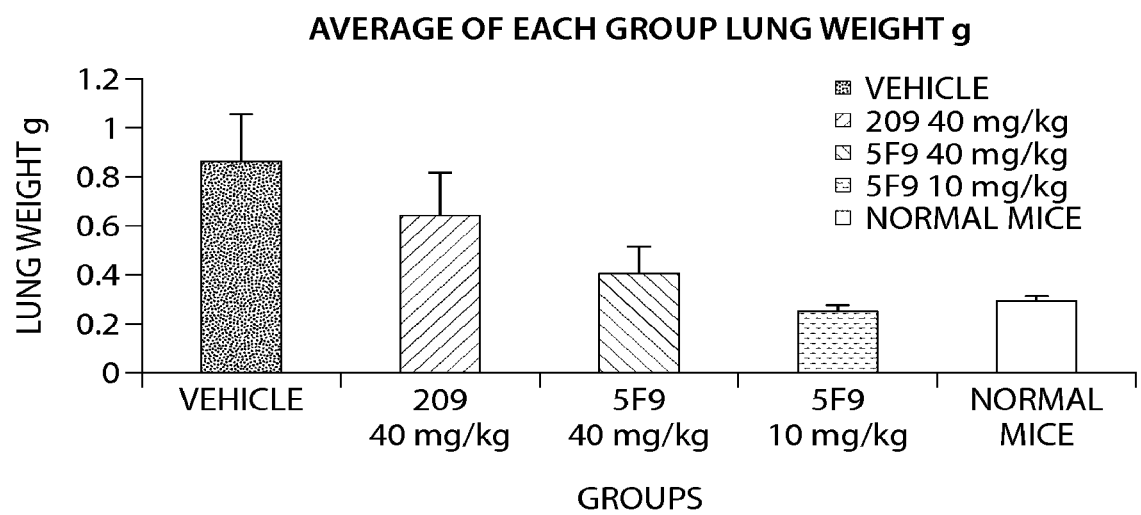
FIG. 3 depicts the survival curve of CT26-hGCC tumor-bearing mice treated with 5F9 antibody.

Lung weight of each group at the end of this study was shown in FIG. 3. T test: vehicle vs. 209 40 mg/kg P=0.4; vehicle vs. 5F9 40 mg/kg P<0.05; vehicle vs. 5F9 10 mg/kg P<0.01. Visual inspection of lungs confirmed fewer tumor nodules in the 5F9-treated groups than in the vehicle or 209-treated groups. In vivo MRI of the mice showed massive lung tumor exfiltration to surrounding tissues and heart displacement in vehicle-treated mice. In a 5F9 40 mg/kg-treated mouse, normal lung presentation was seen without evidence of tumor.

Figure 4:
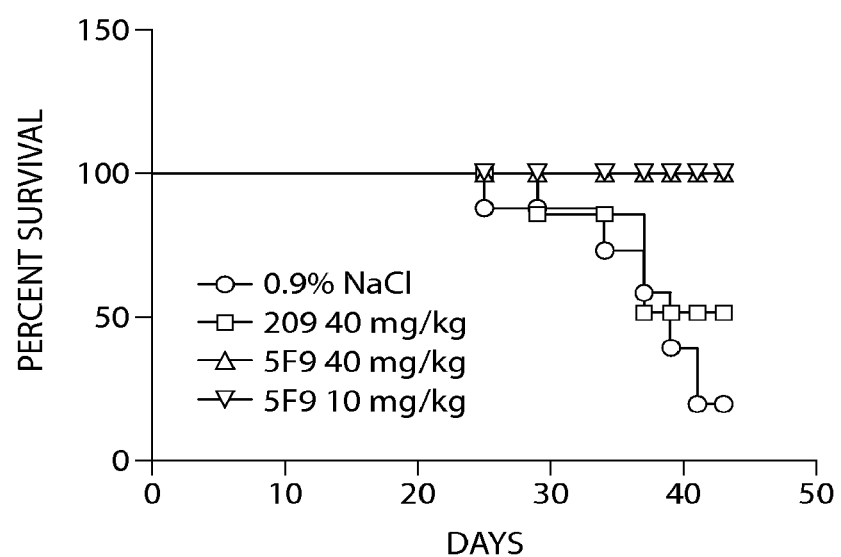
FIG. 4 depicts ELISA binding assays to test antibody cross-reactivity of GCC orthologs.

A survival curve is shown in FIG. 4. Significant increase in survival with 5F9 treated groups ($1 \times 10^5$) was observed and there was no difference between 5F9 10 and 40 mg/kg groups.

Example 4: Generating an Antibody Production Cell Line

To generate a stable CHO cell line clone expressing 5F9 with a productivity of >600 mg/L, expression vectors for 5F9 were generated by subcloning light chain variable region (SEQ ID NO:19) and heavy chain variable region (SEQ ID NO:17) into the pLKTOK58 expression vector, containing WT human IgG1 Fc and the neomycin resistance gene. Expression of the 5F9 variable region-IgG1 fusion product is under control of the EF-1a promoter.

Cloning and Sequencing of the Anti-GCC Human Monoclonal Antibody 5F9 Variable Regions Total RNA was isolated (Qiagen's RNeasy kit) from human hybridoma 46.5F9 subclone 8.2. This hybridoma carries the "standard" published Kappa constant region of the light chain (GenBank accession #AW383625, or BM918539) and the "standard" published IgG2 constant region of the heavy chain (GenBank accession #BX640623, or AJ294731). 5' race-ready, poly-G tailed cDNA was synthesized by traditional methods (Nature Methods 2, 629-630 (2005)). The light chain variable region was PCR amplified from cDNA by 5' race using a poly-C anchor oligo in combination with a reverse primer specific for the Kappa constant region. The heavy chain variable region was amplified with a reverse primer specific for the IgG2 constant region in multiple combinations with forward primers specific to the known heavy chain leader sequences. PCR products were TOPO® cloned (Invitrogen™, Life Technologies, Inc.) and sequenced with M13F and M13R primers.

Construction of Mammalian Expression Vectors Carrying Anti-GCC Human Monoclonal Antibody 5F9

Mammalian expression vectors carrying the 5F9 light and heavy variable regions were constructed to generate production CHO cell lines. For the native construct, the variable regions of the 5F9 light and heavy chains were sub-cloned into pLKTOK58D (US Patent Application #20040033561). This vector carries two mammalian selection markers: neomycin resistance and DHFR/methotrexate (for amplification). The vector allows co-expression of both light and heavy chains from tandem EF1alpha promoters, each located upstream of the vector's leader-Kappa constant and leader-IgG1 (wild type Fc) constant regions. For sub-cloning, the variable regions of the light and heavy chains were PCR amplified from sequence-confirmed TOPO clones with gene-specific primers containing unique restriction sites for directional cloning into the junctions of the respective leader-Kappa and leader-IgG1 regions of the vector. The sequences of the primers are as follows (5F9 variable region-specific sequences in bold font):

```
Native 5F9 light chain leader-variable primers:
forward NotI
                                    (SEQ ID NO: 234)
5'ataagaatGCGGCCGCCTCACCATGGGATGGAGCTGTATCATCCTCT

TCTTGGTAGCAACAGCTACAGGTGTCCACTCCGAAATAGTGATGACGCAG

TCTCCAGCCACCCTG-3' reverse BsiWI
                                    (SEQ ID NO: 235)
5'-GCCACCGTACGTTTGATTTCCACGTTGGTCCCTTGGCCGAACGTC-

3'

Native 5F9 heavy chain leader-variable primers
forward EcoRI
                                    (SEQ ID NO: 236)
5'ccgGAATTCCTCACCATGGGATGGAGCTGTATCATCCTCTTCTTGGT

AGCAACAGCTACAGGTGTCCACTCCCAGGTGCAGCTACAGCAGTGGGG

CGCAGGAC-3' reverse Blpl
                                    (SEQ ID NO: 237)
5'-GGAGGCTGAGCTGACGGTGACCAGGGTTCCCTGGCCCCAGTGGTC-

3'
```

Clones were confirmed by double stranded DNA sequencing of both the light and heavy chains.

Two transfection methods were used to introduce the constructs into CHO cells: the traditional MPI process and the Crucell process. CHO cell transfections were initiated with the native 5F9 construct using the traditional MPI process. Linearized and nonlinearized DNAs were used, with either electroporation or Lipopfectamine 2000 CD transfection. Approximately 30 stable pools were generated through selection in G418, non nucleoside medium and 5 nM methotrexate. Based on FMAT analysis of antibody production levels, three stable pools were chosen for cloning. The pool with the highest production secreted antibody at 12.2 ug/ml. These three pools have been frozen down.

Crucell STAR elements can be evaluated to make 5F9 expression vectors containing a STAR element.

```
5F9/hIgG1 heavy chain nucleotide sequence is:
                                    (SEQ ID NO: 230)
GAATTCCTCACCATGGGATGGAGCTGTATCATCCTCTTCTTGGTAGCAAC

AGCTACAGGTGTCCACTCCCAGGTGCAGCTACAGCAGTGGGGCGCAGGAC

TGTTGAAGCCTTCGGAGACCCTGTCCCTCACCTGCGCTGTCTTTGGTGGG

TCTTTCAGTGGTTACTACTGGAGCTGGATCCGCCAGCCCCCAGGGAAGGG

GCTGGAGTGGATTGGGGAAATCAATCATCGTGGAAACACCAACGACAACC

CGTCCCTCAAGAGTCGAGTCACCATATCAGTAGACACGTCCAAGAACCAG

TTCGCCCTGAAGCTGAGTTCTGTGACCGCCGCGGACACGGCTGTTTATTA

CTGTGCGAGAGAACGTGGATACACCTATGGTAACTTTGACCACTGGGGCC

AGGGAACCCTGGTCACCGTCAGCTCAGCCTCCACCAAGGGCCCATCGGTC

TTCCCCCTGGCACCCTCCTCCAAGAGCACCTCTGGGGGCACAGCGGCCCT

GGGCTGCCTGGTCAAGGACTACTTCCCCGAACCGGTGACGGTGTCGTGGA

ACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAG

CTTGGGCACCCAGACCTACATCTGCAACGTGAATCACAAGCCCAGCAACA

CCAAGGTGGACAAGAAAGTTGAGCCCAAATCTTGTGACAAAACTCACACA

TGCCCACCGTGCCCAGCACCTGAACTCCTGGGGGGACCGTCAGTCTTCCT

CTTCCCCCCAAAACCCAAGGACACCCTCATGATCTCCCGGACCCCTGAGG

TCACATGCGTGGTGGTGGACGTGAGCCACGAAGACCCTGAGGTCAAGTTC

AACTGGTACGTGGACGGCGTGGAGGTGCATAATGCCAAGACAAAGCCGCG

GGAGGAGCAGTACAACAGCACGTACCGTGTGGTCAGCGTCCTCACCGTCC

TGCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGCA

GCCCCGAGAACCACAGGTGTACACCCTGCCCCCATCCCGGGATGAGCTGA

CCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAA

GACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGC

TCCGTGATGCATGAGGCTCTGCACAACCACTACACGCAGAAGAGCCTCTC

CCTGTCTCCGGGTAAATAATAGGGATAACAGGGTAATACTAGAG

5F9/hIgG1 heavy chain protein sequence is;
                                    (SEQ ID NO: 231)
MGWSCIILFLVATATGVHSQVQLQQWGAGLLKPSETLSLTCAVFGGSFSG

YYWSWIRQPPGKGLEWIGEINHRGNTNDNPSLKSRVTISVDTSKNQFALK

LSSVTAADTAVYYCARERGYTYGNFDHWGQGTLVTVSSASTKGPSVFPLA

PSSKSTSGGTAALGCLVKDYFPEPVTVSWNSGALTSGVHTFPAVLQSSGL
```

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK

5F9/hKappa light chain nucleotide sequence is:
(SEQ ID NO: 232)
GCGGCCGCCTCACCATGGGATGGAGCTGTATCATCCTCTTCTTGGTAGCA

ACAGCTACAGGTGTCCACTCCGAAATAGTGATGACGCAGTCTCCAGCCAC

CCTGTCTGTGTCTCCAGGGGAAAGAGCCACCCTCTCCTGCAGGGCCAGTC

AGAGTGTTAGCAGAAACTTAGCCTGGTATCAGCAGAAACCTGGCCAGGCT

CCCAGGCTCCTCATCTATGGTGCATCCACCAGGGCCACTGGAATCCCAGC

CAGGTTCAGTGGCAGTGGGTCTGGGACAGAGTTCACTCTCACCATCGGCA

GCCTGCAGTCTGAAGATTTTGCAGTTTATTACTGTCAGCAGTATAAAACC

TGGCCTCGGACGTTCGGCCAAGGGACCAACGTGGAAATCAAACGTACGGT

GGCTGCACCATCTGTCTTCATCTTCCCGCCATCTGATGAGCAGTTGAAAT

CTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCA

GGAGAGTGTCACAGAGCAGGACAGCAAGGACAGCACCTACGCCCTCAGCA

GCACCCTGACCCTGAGCAAAGCAGACTACGAGAAACACAAAGTCTACGCC

TGCGAAGTCACCCATCAGGGCCTGAGCTCGCCCGTCACAAAGAGCTTCAA

CAGGGGAGAGTGTTAGTCTAGA

5F9/hKappa light chain protein sequence is:
(SEQ ID NO: 233)
MGWSCIILFLVATATGVHSEIVMTQSPATLSVSPGERATLSCRASQSVSR

NLAWYQQKPGQAPRLLIYGASTRATGIPARFSGSGSGTEFTLTIGSLQSE

DFAVYYCQQYKTWPRTFGQGTNVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

The heavy and light chain nucleic acid sequences for 5F9 listed below were inserted into pTOK58D vector:

(SEQ ID NO: 308)
atgggatggagctgtatcatcctcttcttggtagcaacagctacaggtgt ccactccgaaatagtgatgacgcagtctccagccaccctgtctgtgtctc caggggaaagagccaccctctcctgcagggccagtcagagtgttagcaga aacttagcctggtatcagcagaaacctggccaggctcccaggctcctcat ctatggtgcatccaccagggccactggaatcccagccaggttcagtggca gtgggtctgggacagagttcactctcaccatcggcagcctgcagtctgaa gattttgcagtttattactgtcagcagtataaaacctggcctcggacgtt cggccaagggaccaacgtggaaatcaaacgtacggtggctgcaccatctg tcttcatcacccgccatctgatgagcagttgaaatctggaactgcctctg ttgtgtgcctgctgaataacttctatcccagagaggccaaagtacagtgg aaggtggataacgccctccaatcgggtaactcccaggagagtgtcacaga gcaggacagcaaggacagcacctacgcctcagcagcaccctgaccctga gcaaagcagactacgagaaacacaaagtctacgcctgcgaagtcacccat cagggcctgagctcgcccgtcacaaagagcttcaacaggggagagtgtta g (SEQ ID NO: 309)
atgggatggagctgtatcatcctcttcttggtagcaacagctacaggtgt ccactcccaggtgcagctacagcagtggggcgcaggactgttgaagcctt cggagaccctgtccctcacctgcgctgtctttggtgggtctttcagtggt tactactggagctggatccgccagcccccagggaaggggctggagtggat tgggaaatcaatcatcgtggaaacaccaacgacaacccgtccctcaaga gtcgagtcaccatatcagtagacacgtccaagaaccagttcgccctgaag ctgagttctgtgaccgccgcggacacggctgtttattactgtgcgagaga acgtggatacacctatggtaactttgaccactggggccagggaaccctgg tcaccgtcagctcagcctccaccaagggcccatcggtcttccccctggca ccctcctccaagagcacctctgggggcacagcggccctgggctgcctggt caaggactacttccccgaaccggtgacggtgtcgtggaactcaggcgccc tgaccagcggcgtgcacaccttcccggctgtcctacagtcctcaggactc tactccctcagcagcgtggtgaccgtgccctccagcagcttgggcaccca gacctacatctgcaacgtgaatcacaagcccagcaacaccaaggtggaca agaaagttgagcccaaatcagtgacaaaactcacacatgcccaccgtgcc cagcacctgaactcctggggggaccgtcagtcttcctcttccccccaaaa cccaaggacaccctcatgatctcccggacccctgaggtcacatgcgtggt ggtggacgtgagccacgaagaccctgaggtcaagttcaactggtacgtgg acggcgtggaggtgcataatgccaagacaaagccgcgggaggagcagtac aacagcacgtaccgtgtggtcagcgtcctcaccgtcctgcaccaggactg gctgaatggcaaggagtacaagtgcaaggtctccaacaaagccctcccag cccccatcgagaaaaccatctccaaagccaaagggcagccccgagaacca caggtgtacaccctgcccccatcccgggatgagctgaccaagaaccaggt cagcctgacctgcctggtcaaaggcttctatcccagcgacatcgccgtgg agtgggagagcaatgggcagccggagaacaactacaagaccacgcctccc gtgctggactccgacggctccttcttcctctacagcaagctcaccgtgga caagagcaggtggcagcaggggaacgtcttctcatgctccgtgatgcatg aggctctgcacaaccactacacgcagaagagcctctccctgtctccgggt aaataa The sequences encoding the Abx-229 heavy and light chains sequence below were inserted into pTOK58D vector:

(SEQ ID NO: 310)
atggagtttgggctgagctggcttttttcttgtggctattttaaaaggtgt ccagtgtgaggtgcagctgttggagtctgggggaggcttggtacagcctg gggggtccctgagactctcctgtgcagcctctggattcacctttagccgc tatgccatgaactgggtccgccaggctccagggaaggggctggagtgggt ctcaggtattagtgggagtggtggtaggacatactacgcagactccgtga agggccggttcaccatctccagagacaattccaagaacacactatatctg caaatgaacagcctgagagccgaggacacggccgtatattactgtgcgaa agatcgcgattttggagtggtccatttgactactggggccagggaaccc tggtcaccgtcagctcagcctccaccaagggcccatcggtcttccccctg gcaccctcctccaagagcacctctgggggcacagcggccctgggctgcct ggtcaaggactacttccccgaaccggtgacggtgtcgtggaactcaggcg ccctgaccagcggcgtgcacaccttcccggctgtcctacagtcctcagga ctctactccctcagcagcgtggtgaccgtgccctccagcagcttgggcac ccagacctacatctgcaacgtgaatcacaagcccagcaacaccaaggtgg acaagaaagttgagcccaaatcagtgacaaaactcacacatgccaccgt gcccagcacctgaactcctgggggaccgtcagtcttcctcttccccca aaacccaaggacacccctcatgatctcccgacccctgaggtcacatgcgt ggtggtggacgtgagccacgaagaccctgaggtcaagttcaactggtacg tggacggcgtggaggtgcataatgccaagacaaagccgcgggaggagcag tacaacagcacgtaccgtgtggtcagcgtcctcaccgtcctgcaccagga ctggctgaatggcaaggagtacaagtgcaaggtctccaacaaagccctcc cagcccccatcgagaaaaccatctccaaagccaaagggcagccccgagaa ccacaggtgtacaccctgcccccatcccgggatgagctgaccaagaacca ggtcagcctgacctgcctggtcaaaggcttctatcccagcgacatcgccg tggagtgggagagcaatgggcagccggagaacaactacaagaccacgcct cccgtgctggactccgacggctccttcttcctctacagcaagctcaccgt ggacaagagcaggtggcagcaggggaacgtcttctcatgctccgtgatgc atgaggctctgcacaaccactacacgcagaagagcctctccctgtctccg ggtaaataa (SEQ ID NO: 311)

atgaggctccctgctcagcttctcttcctcctgctactctggctcccaga taccactggagaaatagtgatgacgccgtcttcagccacccctgtctgtgt ctccaggggagagagccaccctctcctgcagggccagtcagagtgttagt agaaacttagcctggtaccagcagaaacctggccaggctcccaggctcct catctatggtgcatccaccagggccactggtatcccagccaggttcagtg gcagtgggtctgggacagaattcactctcaccatcagcagcctgcagtct gaagattttgcagtttattactgtcaccagtatagtaactggatgtgcag ttttggccaggggaccaagctggagatcaaacgtacggtggctgcaccat ctgtcttcatcttcccgccatctgatgagcagttgaaatctggaactgcc tctgttgtgtgcctgctgaataacttctatcccagagaggccaaagtaca gtggaaggtggataacgccctccaatcgggtaactcccaggagagtgtca cagagcaggacagcaaggacagcacctacagcctcagcagcaccctgacc ctgagcaaagcagactacgagaaacacaaagtctacgcctgcgaagtcac ccatcagggcctgagctcgcccgtcacaaagagcttcaacaggggagagt gttag While this invention has been shown and described with references to provided embodiments thereof, it will be understood by those skilled in the art that various changes in form and details may be made therein without departing from the scope of the invention encompassed by the appended claims.

---

What is claimed is:

1. An anti-guanylyl cyclase C (GCC) antibody molecule comprising:
   three heavy chain complementarity determining regions (HCDR1, HCDR2, and HCDR3) comprising amino acid sequences of SEQ ID NO: 190 (HCDR1), SEQ ID NO: 192 (HCDR2), and SEQ ID NO: 194 (HCDR3); and three light chain complementarity determining regions (LCDR1, LCDR2, and LCDR3) comprising amino acid sequences of SEQ ID NO: 196 (LCDR1), SEQ ID NO: 198 (LCDR2), and SEQ ID NO: 200 (LCDR3).

2. The anti-GCC antibody molecule of claim 1, wherein the anti-GCC antibody molecule comprises human or human derived heavy and light chain variable region frameworks.

3. The anti-GCC antibody molecule of claim 1, wherein the anti-GCC antibody molecule comprises a heavy chain variable region comprising an amino acid sequence of SEQ ID NO: 46; and a light chain variable region comprising an amino acid sequence of SEQ ID NO: 48.

4. The anti-GCC antibody molecule of claim 1, wherein the anti-GCC antibody molecule comprises a human IgG1 heavy chain constant region.

5. The anti-GCC antibody molecule of claim 1, wherein the anti-GCC antibody molecule comprises a human Ig kappa light chain constant region.

6. The anti-GCC antibody molecule of claim 1, wherein the anti-GCC antibody molecule is conjugated to a therapeutic agent or a detectable label.

7. An immunoconjugate of formula (I):

or a pharmaceutically acceptable salt thereof, wherein:
Ab is the anti-GCC antibody molecule of claim 1;
X is a linker moiety which connects Ab and Z;
Z is a therapeutic agent or a detectable label; and
m is an integer from 1 to 15.

8. The immunoconjugate of claim 7, wherein the therapeutic agent is a cytostatic or cytotoxic agent.

9. A pharmaceutical composition comprising the anti-GCC antibody molecule of claim 1 and a pharmaceutically acceptable carrier.

10. A pharmaceutical composition comprising the immunoconjugate of claim 7 and a pharmaceutically acceptable carrier.

11. A container comprising the pharmaceutical composition of claim 9.

12. A kit comprising the anti-GCC antibody molecule of claim 1.

* * * * *